US010725055B1

(12) United States Patent
Pluth et al.

(10) Patent No.: US 10,725,055 B1
(45) Date of Patent: Jul. 28, 2020

(54) COMPOUNDS FOR CARBONYL SULFIDE/CARBON DISULFIDE/HYDROGEN SULFIDE RELEASE AND METHODS OF MAKING AND USING THE SAME

(71) Applicant: University of Oregon, Eugene, OR (US)

(72) Inventors: Michael D. Pluth, Eugene, OR (US); Andrea Steiger, Eugene, OR (US); Yu Zhao, Eugene, OR (US)

(73) Assignee: University of Oregon, Eugene, OR (US)

( * ) Notice: Subject to any disclaimer, the term of this patent is extended or adjusted under 35 U.S.C. 154(b) by 127 days.

(21) Appl. No.: 15/484,023

(22) Filed: Apr. 10, 2017

Related U.S. Application Data

(60) Provisional application No. 62/323,309, filed on Apr. 15, 2016.

(51) Int. Cl.
G01N 33/84 (2006.01)
C07C 333/08 (2006.01)
C07C 275/70 (2006.01)
C12Q 1/527 (2006.01)
G01N 33/52 (2006.01)

(52) U.S. Cl.
CPC ........... *G01N 33/84* (2013.01); *C07C 275/70* (2013.01); *C07C 333/08* (2013.01); *C12Q 1/527* (2013.01); *C12Y 402/01001* (2013.01); *G01N 33/52* (2013.01); *G01N 2800/7009* (2013.01)

(58) Field of Classification Search
None
See application file for complete search history.

(56) References Cited

U.S. PATENT DOCUMENTS

| 2002/0143202 A1 | 10/2002 | Zhuang et al. |
| 2007/0202198 A1 | 8/2007 | Purcell |
| 2008/0004245 A1 | 1/2008 | Wallace et al. |
| 2009/0184005 A1 | 7/2009 | Zhang et al. |
| 2010/0099683 A1 | 4/2010 | Tomkinson et al. |

FOREIGN PATENT DOCUMENTS

| BE | 666778 A | * | 1/1966 | ........... C07C 329/00 |
| CN | 1256270 A | * | 6/2000 | ........... C07D 235/28 |
| JP | 2737717 B2 | * | 4/1998 | |
| WO | WO 2006/111791 | | 10/2006 | |
| WO | WO 2012/075242 | | 6/2012 | |
| WO | WO 2012/154126 | | 11/2012 | |
| WO | WO 2013/045951 | | 4/2013 | |
| WO | WO 2014/124208 | | 8/2014 | |

OTHER PUBLICATIONS

Cesarini et al. Biorg. Med. Chem. (2008) 16: 4173-4185 (Year: 2008).*
Machine translation of JP 2737717 B2 (dated Apr. 1998) downloaded from ProQuest Sep. 25, 2018. (Year: 1998).*
Juby et al. J. Med. Chem. (1967) 1093): 491-5 (Year: 1967).*
Zakhari et al. Bioorg. Med. Chem. (2011) 19: 6203-6209 (Year: 2011).*
CHEMCATS file in Registry of STN (May 11, 2006), RN of 883807-46-3, downloaded Oct. 25, 2019 (Year: 2006).*
Sun et al.(Chenn. Commun. (2015) 51: 5721-5724 (Year: 2015).*
Verrinder et al. (Can. J. Chem. (1978) 56: 2582-2589 (Year: 1978).*
Sato et al. Science of Synthesis (2005) 18: 821-968 (Year: 2005).*
DeMilo et al. (in Synthesis Chem. Agrochemicals, ACS Symposium Series (1987) (American Chemical Soc.: Washington, D.C.) pp. 260-262 (Year: 1987).*
Wakamori et al. Agr. Biol. Chem. (1969) 33(10): 1367-1376 (Year: 1969).*
Amin et al. Chemosphere (2008) 70: 511-515 (Year: 2008).*
Machine trnaslation of Hengda et al. (CN 1256270A; published 2000) downloaded from ESPACENET on Oct. 26, 2019 (Year: 2000).*
Krutosikova et al. Collection Czechoslov. Chem. Commun. (1975) 40: 2529-2535 (Year: 1975).*
Zhu et al. (Chem. Eur. J. (2013) 19: 12800-12805 (Year: 2013).*
Neves et al. Tetrahedron (1979) 35(17): 2053-2059 (Year: 1979).*
RN: 501359-88-2 in Chemical Library in the Registry Database, entered in STN Apr. 2, 2003; downloaded Oct. 26, 2019 (Year: 2003).*
MacLellan et al. Chem. Commun. (2011) 47: 3395-3397 (Year: 2011).*
Steiger et al. J. Am. Chem. Soc. (May 24, 2016) 138: 7526-7529 (Year: 2016).*
Alajarin et al., "Benzylic Newman-Kwart rearrangement of O-azidobenzyl thiocarbamates triggered by phosphines: pseudopericyclic [1,3] shifts via uncoupled concerted mechanisms," *Tetrahedron*, 65(12): pp. 2579-2590, Jan. 20, 2009.
Alajarin et al., "Intramolecular addition of benzylic radicals onto ketenimines. Synthesis of 2-alkylindoles," *Organic and Biomolecular Chemistry*, 1(23): 4282-4292, Oct. 23, 2003.
Bailey et al., "Chemiluminescent Detection of Enzymatically Produced Hydrogen Sulfide: Substrate Hydrogen Bonding Influences Selectivity for $H_2S$ over Biological Thiols," *J. Am. Chem. Soc.*, 135(44):16697-16704, Oct. 4, 2013.

(Continued)

*Primary Examiner* — Susan M Hanley

(74) *Attorney, Agent, or Firm* — Klarquist Sparkman, LLP

(57) ABSTRACT

Disclosed herein are embodiments of donor compounds that can be used to produce $H_2S$ from COS or $CS_2$ released from the donor compounds. In some embodiments, the donor compounds can indirectly produce $H_2S$ after being exposed to a reactive component in a triggering event. In other embodiments, the donor compounds can indirectly regenerate $H_2S$ after reacting with an $H_2S$ analyte. The donor compounds disclosed herein can be used for analytical techniques, disease diagnostics, and/or therapeutic applications. Methods of making and using the donor compounds also are provided herein.

21 Claims, 25 Drawing Sheets

(56) References Cited

OTHER PUBLICATIONS

Benavides et al., "Hydrogen sulfide mediates the vasoactivity of garlic," *Proceedings of the National Academy of Sciences of the United States of America*, 104(46): 17977-17982, Nov. 13, 2007.

Braverman et al. "The Rearrangement of Furfuryl Dimethylthionocarbamates," *International Journal of Sulfur Chemistry*, 8(55), 1973.

Chauhan et al. "Esterase Activated Carbonyl Sulfide/Hydrogen Sulfide ($H_2S$) Donors," *Org. Lett.*, 19(1): 62-65, Dec. 20, 2016.

Chitnis et al., "Pharmacological actions of the slow release hydrogen sulfide donor GYY4137 on phenylephrine-induced tong in isolated bovine ciliary artery," *Experimental Eye Research*, vol. 116, pp. 350-354, Nov. 2013.

Devarie-Baez et al., "Light-Induced Hydrogen Sulfide Release from 'Caged' gem-Dithiols," *Organic Letters*, 15(11): 2786-2789, May 22, 2013.

Gu et al., "Development of a boron-dipyrromethene-$Cu^{2+}$ensemble based colorimetric probe toward hydrogen sulfide in aqueous media," *Tetrahedron Letters* 52:5000-5003, Sep. 2011.

Jarosz et al., "Microplate-Based Colorimetric Detection of Free Hydrogen Sulfide," *Analytical Chemistry*, 85(7):3638-3643, Mar. 11, 2013.

Jensen et al., "Studies of Thioacids and Their Derivatives. IX. Thiosemicarbizides," *Acta Chemica Scandinavica*, vol. 22, pp. 1-50, 1968.

Jensen et al., "Studies of Thioacids and Their Derivatives. XV. (Alkoxythiocarbonyl)hydrazines and [(Alkylthio)thiocarbonyl]hydrazines," *Acta Chemica Scandinavica*, vol. 23, pp. 1916-1934, 1969.

Kashfi et al., "Biology and therapeutic potential of hydrogen sulfide and hydrogen sulfide-releasing chimeras," *Biochemical Pharmacology*, 85(5): 689-703, Mar. 1, 2013.

Kawanaka et al., "Design and Synthesis of Orally Bioavailable Inhibitors of Inducible Nitric Oxide Synthase. Part 1: Synthesis and Biological Evaluation of Dihydropyridin-2-imines," *Bioorganic & Medicinal Chemistry Letters*, vol. 12, pp. 2291-2294, 2002.

Kim et al., "Synthesis of Novel N-(2-Hydrophenyl)arylsulfonamides as Selective HDAC Inhibitory and Cytotoxic Agents," *Bulletin of the Korean Chemical Society*, 34(5):1487-1493, 2013.

Lee et al., "Analysis of structure-activity relationships for the 'B-region' of N-(4-t-butylbenzyl)-N'-[4-(methylsulfonylamino)benzyl]-thiourea analogues as TRPV1 antagonists," *Bioorganic and Medicinal Chemistry Letters*, 15(18): 4143-4150, Sep. 15, 2005.

Lee et al., "Detection of hydrogen peroxide with chemiluminescent micelles," *International Journal of Nanomedicine* 3(4):471-476, Dec. 2008.

Li et al., "Characterization of a novel, water-soluble hydrogen sulfide-releasing molecule (GYY4137): New insights into the biology of hydrogen sulfide," *Circulation*, 117(18): 2351-2360, May 6, 2008.

Lippert et al., "Reaction-Based Fluorescent Probes for Selective Imaging of Hydrogen Sulfide in Living Cells," *Journal of the American Chemical Society*, 133(26): 10078-10080, Jun. 15, 2011.

Liu et al., "A visible light excitable colorimetric and fluorescent ESIPT probe for rapid and selective detection of hydrogen sulfide," *Organic & Biomolecular Chemistry*, 12:438-445, Nov. 6, 2013.

Liu et al., "Capture and Visualization of Hydrogen Sulfide by a Fluorescent Probe," *Angew. Chem. Int. Ed.*, 123(44):10327-10329, Sep. 6, 2011.

Maity et al., "A probe for ratiometric near-infrared fluorescence and colorimetric hydrogen sulfide detection and imaging in living cells," *RSC Advances* vol. 4, pp. 11147-11151, Feb. 10, 2014.

Martelli et al., "Arylthioamides as $H_2S$ Donors: L-Cysteine-Activated Releasing Properties and Vascular Effects in Vitro and in Vivo," *ACS Medicinal Chemistry Letters*, 4(10): 904-908, Aug. 8, 2013.

Montoya et al., "Selective turn-on fluorescent probes for imaging hydrogen sulfide in living cells," *Chemical Communications*, vol. 48, pp. 4767-4769, Mar. 16, 2012.

Montoya et al., "Development of Selective Colorimetric Probes for Hydrogen Sulfide Based on Nucleophilic Aromatic Substitution," *J. Org. Chem.*, 78(13): 6550-6557, Jun. 4, 2013.

Nishiyama et al., "Addition Reaction of Deoxygenation of Alcohols Using Isothiocyanates and Triethylsilane-DTBP," *Tetrahedron Letters*, 34(23): 3745-374, Feb. 22, 1993.

Olson et al., "A Practical Look at the Chemistry and Biology of Hydrogen Sulfide," *Antioxidants & Redox Signaling*, 17(1): 32-44, Jan. 16, 2012.

Peng et al., "A Fluorescent Probe for Fast and Quantitative Detection of Hydrogen Sulfide in Blood," *Angew. Chem. Int. Ed.*, 50(41): 9672-9675, Oct. 4, 2011.

Qian et al., "Selective fluorescent probes for live-cell monitoring of sulphide," *Nature Communications* 2(495): 1-7, Oct. 11, 2011.

Roda et al., "Analytical chemiluminescence and bioluminescence: latest achievements and new horizons," *Analytical and Bioanalytical Chemistry*, 402(1) :69-76, Oct. 16, 2011.

Saha et al., "A colorimetric and fluorometric BODIPY probe for rapid, selective selection of $H_2S$ and its application in live cell imaging," *Organic & Biomolecular Chemistry*, vol. 11, pp. 8166-8170, Oct. 22, 2013.

Sasakura et al., "Development of a Highly Selective Fluorescence Probe for Hydrogen Sulfide," *Journal of the American Chemical Society*, 133(45): 18003-18005, Oct. 14, 2011.

Seletsky et al., "Structurally simplified macrolactone analogues of halichondrin B," *Bioorganic and Medicinal Chemistry Letters*, 14(22): 5547-5550, Sep. 21, 2004.

Shen et al., "Measurement of plasma hydrogen sulfide in vivo and in vitro," *Free Radical Biology & Medicine*, 50(9): 1021-1031, Jan. 27, 2011.

Tomasova et al., "Effects of AP39, a novel triphenylphosphonium derivatised anethole dithioethione hydrogen sulfide donor, on rat haemodynamic parameters and chloride and calcium Ca(v)3 and RyR2 channels," *Nitric Oxide-Biology and Chemistry*, vol. 46, pp. 131-144, Dec. 30, 2014.

Van De Bittner et al., "In vivo imaging of hydrogen peroxide production in a murine tumor model with a chemoselective bioluminescent reporter," *PNAS* 107(50):21316-21321, Dec. 14, 2010.

Wei et al., "NBD-based colorimetric and fluorescent turn-on probes for hydrogen sulfide," *Organic & Biomolecular Chemistry*, vol. 12, pp. 479-485, Oct. 29, 2013.

Whiteman et al., "Emerging role of hydrogen sulfide in health and disease: critical appraisal of biomarkers and pharmacological tools," *Clinical Science*, 121(11): 459-488, Aug. 9, 2011.

Wu et al., "A selective colorimetric and ratiometric fluorescent probe for hydrogen sulfide," *Organic & Biomolecular Chemistry* vol. 10, pp. 8342-8347, Aug. 8, 2012.

Yamaguchi et al., "Evaluation of chemiluminescence reagents for selective detection of reactive oxygen species," *Analytica Chimica Acta*, 665(1): 74-78, Mar. 19, 2010.

Yu et al., Study on Cyclometalated Palladium-azo Complexes as Colorimetric Probes for Hazardous Gas in Water, *Chinese J. Chem.*, 25(6): 797-801, Jun. 14, 2007.

Zhang et al., "A dicopper complex chemiluminescence probe for the determination of thiols in the extracts of murine P388 lymphocytic leukemia cell," *Chem. Comm.*, No. 37, pp. 5624-5626, Aug. 18, 2009.

Zhang et al., "Highly selective and sensitive colorimetric probe for hydrogen sulfide by a copper (II) complex of azo-dye based on chemosensing ensemble approach," *Spectrochimica Acta Part A: Molecular and Biomolecular Spectroscopy*, vol. 90, pp. 35-39, Jan. 16, 2012.

Zhang et al., "On-Site Visual Detection of Hydrogen Sulfide in Air Based on Enhancing the Stability of Gold Nanoparticles," *ACS Applied Materials & Interfaces*, 6(9):6300-6307, Apr. 22, 2014.

Zhao et al., "A highly selective colorimetric chemodosimeter for fast and quantitative detection of hydrogen sulfide," *Analyst*, 137(23):5576-5580, Sep. 25, 2012.

Zhao et al., "Cysteine-Activated Hydrogen Sulfide ($H_2S$) Donors," *Journal of the American Chemical Society*, 133(1):15-17, Jan. 12, 2011.

(56) References Cited

OTHER PUBLICATIONS

Zhou et al., "Thioglycine and L-thiovaline: Biologically active $H_2S$-donors," *Bioorganic & Medicinal Chemistry*, 20(8): 2675-2678, Feb. 27, 2012.

* cited by examiner

COMPOUNDS FOR CARBONYL SULFIDE/CARBON DISULFIDE/HYDROGEN SULFIDE RELEASE AND METHODS OF MAKING AND USING THE SAME

CROSS REFERENCE TO RELATED APPLICATION

This application claims the benefit of and priority to U.S. Provisional Patent Application No. 62/323,309, filed on Apr. 15, 2016, the entirety of which is incorporated herein by reference.

ACKNOWLEDGMENT OF GOVERNMENT SUPPORT

The claimed invention was made with government support under RO1GM113030 awarded by The National Institutes of Health (NIH). The government has certain rights in the invention.

FIELD

The present disclosure is directed to embodiments of compounds capable of producing carbonyl sulfide (COS) or carbon disulfide ($CS_2$) and/or producing/regenerating hydrogen sulfide ($H_2S$), as well as methods of making and using such compounds.

BACKGROUND

Hydrogen sulfide ($H_2S$) has been recognized as an important biological molecule and plays important biological and pharmacological roles in different conditions associated with human health. For example, $H_2S$ has been implicated in hypertension, diabetes, diseases of mental deficiency, asthma, stroke, and other conditions. Slow releasing $H_2S$ donating molecules have been used both as research tools and in clinical trials to abate different disease states. For example, administration of $H_2S$ results in reduction in blood pressure in hypertensive mice. Additionally, the negative GI trauma that is caused by popular NSAIDs appears to be abated by sulfide-donating molecules during drug-delivery.

Although convenient, direct administration of $H_2S$ or sulfide-containing salts leads to a large burst of released $H_2S$, which is quickly metabolized/oxidized by cellular components as part of a toxicological response, and merely results in a disruption of redox homeostasis rather than elevated $H_2S$ levels. Motivated by these limitations, researchers have developed "slow-releasing" $H_2S$ donors that deliver $H_2S$ at a sustained, slow rate, more consistent with enzymatic production. One major limitation of these donor constructs is that they do not allow for $H_2S$ to be triggered by a biological response. For example, $H_2S$ is well established to provide protection against oxidative stress damage, such as that incurred during myocardial infarction (MI) or ischemia reperfusion injury. There exists a need in the art for an $H_2S$ delivery platform that does not release $H_2S$ until challenged with reactive components.

SUMMARY

Disclosed herein are embodiments of donor compounds capable of producing (or releasing) carbonyl sulfide or carbon disulfide, which can be further converted to hydrogen sulfide. Donor compounds contemplated by the present disclosure are discussed herein.

Also disclosed are embodiments of methods of using the disclosed donor compounds. In some embodiments, the methods can comprise administering to a sample a donor compound disclosed herein, or a composition thereof, and exposing the donor compound to a reactive component to release COS, $CS_2$, $H_2S$, or a combination thereof. In some embodiments, the reactive component is selected from an oxidant, a reductant, an enzyme, a nucleophile, light an acid, a base, or a combination thereof. Some embodiments can further comprise exposing the sample, released COS, released $CS_2$, or a combination thereof to carbonic anhydrase, nitrogenase, RuBisCO, CO dehydrogenase, COSase, $CS_2$ hydrolase, water, or a combination thereof. In yet additional embodiments, the method can further comprise analyzing the sample to detect a reaction between the donor compound and the reactive component, measuring an amount of COS, $CS_2$, or $H_2S$ produced, or a combination thereof. Analyzing the sample can comprise detecting a color change or fluorescence change produced by a reaction product of the reaction between the donor compound and the reactive component. In some embodiments, the sample is biological sample selected from a cell, tissue, and/or bodily fluid.

Additional methods can include administering to a sample a donor compound disclosed herein; exposing the sample to $H_2S$ or reactive oxygen, sulfur, or nitrogen species, to form a composition comprising an amine-terminated compound, COS, $CS_2$, a cyclic by-product having a formula selected from those described, or any combination of the amine-terminated compound, the COS, the $CS_2$, and the cyclic by-product; and exposing the composition to $H_2O$, carbonic anhydrase, nitrogenase, RuBisCO, CO dehydrogenase, COSase, $CS_2$ hydrolase, or a combination thereof, to regenerate $H_2S$. The methods can further comprise analyzing the sample to detect a reaction between the donor compound and the reactive component, measuring an amount of COS, $CS_2$, or $H_2S$ produced, or a combination thereof. In such embodiments, analyzing the sample can comprise detecting a color change or fluorescence change produced by a reaction product obtained from reaction between the donor compound and the $H_2S$ or other reactive oxygen, sulfur, or nitrogen species.

Also disclosed herein are embodiments of methods for diagnosing a disease, which can comprise administering or providing a donor compound disclosed herein. In some embodiments, the donor compound can be administered to biological sample or a subject. In some embodiments, the method can further comprise analyzing the sample to detect a reaction between the donor compound and the reactive component, measuring an amount of COS, $CS_2$, or $H_2S$ produced, or a combination thereof. In some embodiments, the method can further comprise determining if a subject has a disease associated with $H_2S$ misregulation or a disease associated with carbonic anhydrase overexpression.

Also disclosed herein are compositions comprising two or more of the following: an amine-terminated compound selected from an amine-terminated phenyl group, an amine-terminated alkyl group, an amine-terminated saccharide, an amine-terminated targeting group, an amine-terminated detectable moiety, or an amine-terminated drug molecule; COS, $CS_2$, $H_2S$, or a combination thereof; and a cyclic by-product compound having a structure satisfying a formula disclosed herein. In some embodiments, the composition comprises an amine-terminated fluorophore or amine-terminated phenyl group; COS, $CS_2$, $H_2S$, or a combination thereof; and a cyclic by-product as disclosed herein.

Also disclosed herein are embodiments of kits comprising one or more of the donor compounds described herein and one or more of a filter, a multi-well plate, a test strip, a slide, a disc, or a container. In some embodiments, the kit can further comprise an enzyme, carbonic anhydrase, nitrogenase, RuBisCO, CO dehydrogenase, COSase, $CS_2$ hydrolase, water, a solubilizing agent, or a combination thereof.

The foregoing and other objects, features, and advantages of the disclosure will become more apparent from the following detailed description, which proceeds with reference to the accompanying figures.

BRIEF DESCRIPTION OF THE DRAWINGS

FIG. 1A shows triggered release of a caged analyte; FIG. 1B shows an embodiment where irreversible probe activation occurs with analyte consumption; and FIG. 1C shows an embodiment where irreversible probe activation occurs with analyte replacement.

FIG. 2 shows rates of: $H_2S$ production from COS hydrolysis by carbonic anhydrase (CA) with varying concentrations of a CA inhibitor (acetazolamide, or AAA) (left graph); $H_2S$ release after reduction by TCEP in the presence of CA (middle graph); and quantification of total sulfide in whole mouse blood after treatment with donor compounds 3 and 4 after 30 minutes of incubation time in the presence of excess TCEP (right graph).

FIG. 3A is an $^1$H-NMR spectrum before (top) and after (bottom) TCEP addition; FIG. 3B is a $^{13}C\{^1H\}$-NMR spectrum of donor compound 1 before (top) and after (bottom) TCEP addition; and FIG. 3C is a $^{19}$F-NMR spectrum of donor compound 1 before (top) and after (bottom) TCEP addition.

FIG. 8A is graph of fluorescence intensity as a function of wavelength, showing the fluorescence response of a representative fluorophore-containing donor compound to $H_2S$, wherein the inlet shows integrated fluorescence over time by comparison to the donor compound in the absence of NaSH; and FIG. 8B is a graph of relative fluorescence that shows the selectivity of a representative donor compound for $H_2S$ over other reactive sulfur, oxygen, and nitrogen species.

FIG. 11A is graph of the $H_2S$ release (micromolar) as a function of time (minutes) for a representative donor compound compared to control compounds, in the presence of UV light, an enzyme, and an enzyme and an inhibitor of that enzyme; FIG. 11B is a graph of the $H_2S$ release (micromolar) as a function of time (minutes) for a representative donor compound in the presence of cellular nucleophiles.

FIG. 12A is an $^1$H-NMR spectrum before (top) and after (bottom) PLE addition; FIG. 12B is a $^{13}C\{^1H\}$-NMR spectrum of the representative donor compound before (top) and after (bottom) PLE addition.

FIG. 13A is a graph of response (nA) as a function of time (minutes) showing $H_2S$ release from a control compound and a representative donor compound in the absence of an enzyme, and in the presence of an enzyme and an enzyme and an inhibitor of that enzyme;

FIG. 13B is a graph of the fluorescence of an $H_2S$-responsive probe as a function of wavelength for a representative donor compound in an enzyme.

FIG. 14A is a graph of the reduction of MTT (as a percentage of DMSO control) for two control compounds in a cell line; FIG. 14B is a graph of the reduction of LDH (normalized to a DMSO control) for two control compounds in a cell line; FIG. 14C is a graph of the reduction of MTT (as a percentage of DMSO control) of a representative donor compound (5) and two control compounds (6 and 7); and FIG. 14D is a graph of the reduction of LDH (normalized to a DMSO control) for a representative donor compound (5) and two control compounds (6 and 7).

FIGS. 15A-15C are graphs of basal cell respiration (FIG. 15A), maximal respiration (FIG. 15B) and ATP synthesis (FIG. 15C) as a percentage of DMSO control as a function of concentration (1, 3, and 10 micromolar) of a representative donor compound (5) and two control compounds (6 and 7); FIGS. 15D-15F are graphs of cellular oxygen consumption (in pM/min/microgram) as a function of time (minutes) for a representative donor compound (5) and two control compounds (6 and 7) present at 1 micromolar (FIG. 15D), 3 micromolar (FIG. 15E) and 10 micromolar (FIG. 15F) concentrations; and FIGS. 15G-15I are graphs of the basal cell respiration (FIG. 15G), maximal respiration (FIG. 15H) and ATP synthesis (FIG. 15I) as a percentage of DMSO control as a function of concentration (1, 3, and 10 micromolar) of two control donor compounds; for FIGS. 15A-C, bars labeled "1502" are controls, bars labeled "1504" are donor compound 5, bars labeled "1506"

Figure 15A:
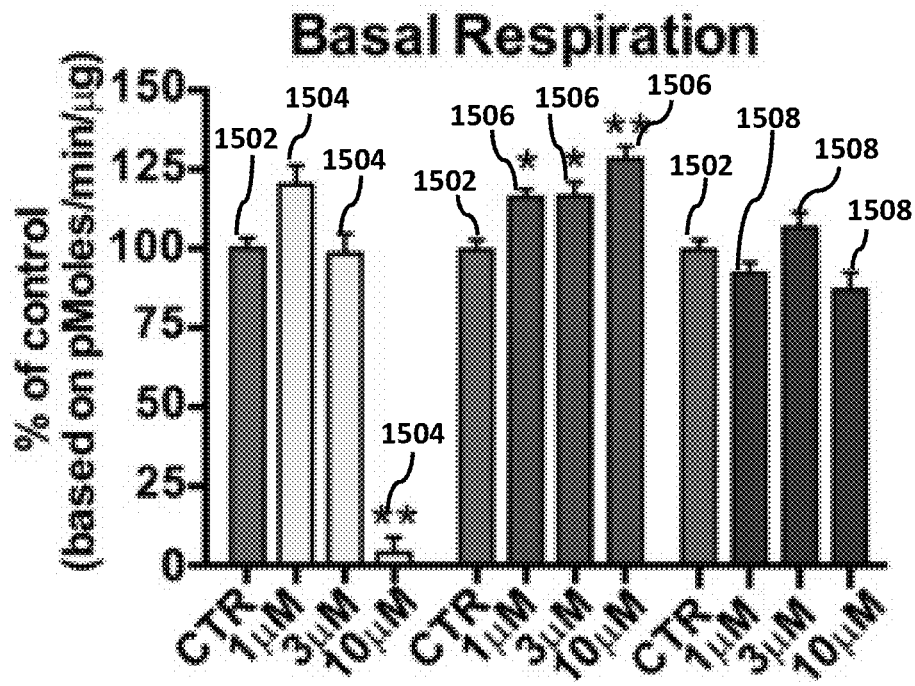
FIGS. 15A-15I show the results of cellular bioenergetics studies of cells in the presence of varying concentrations of a representative donor compound disclosed herein and/or control compounds.
Figure 15B:
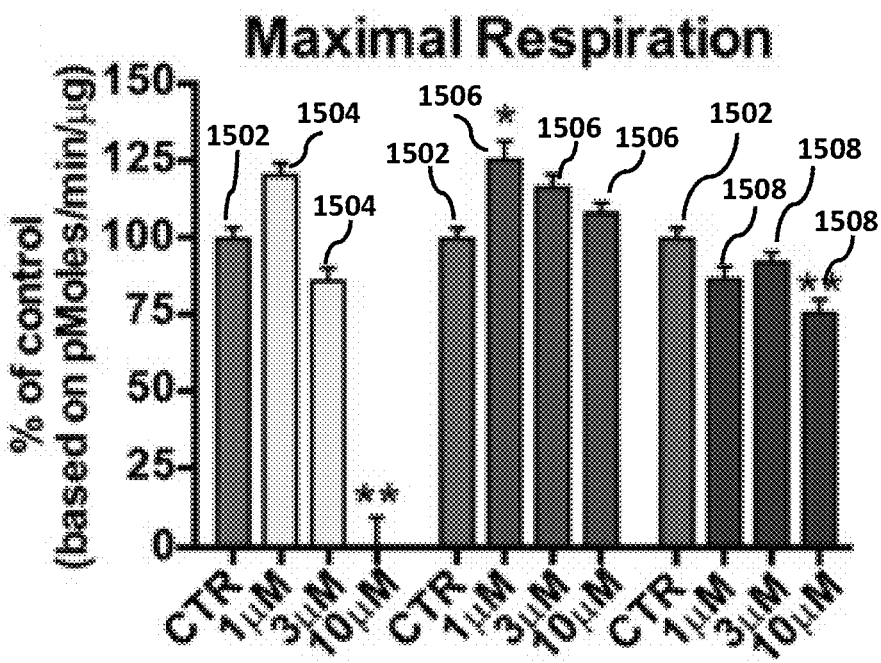
Figure 15C:
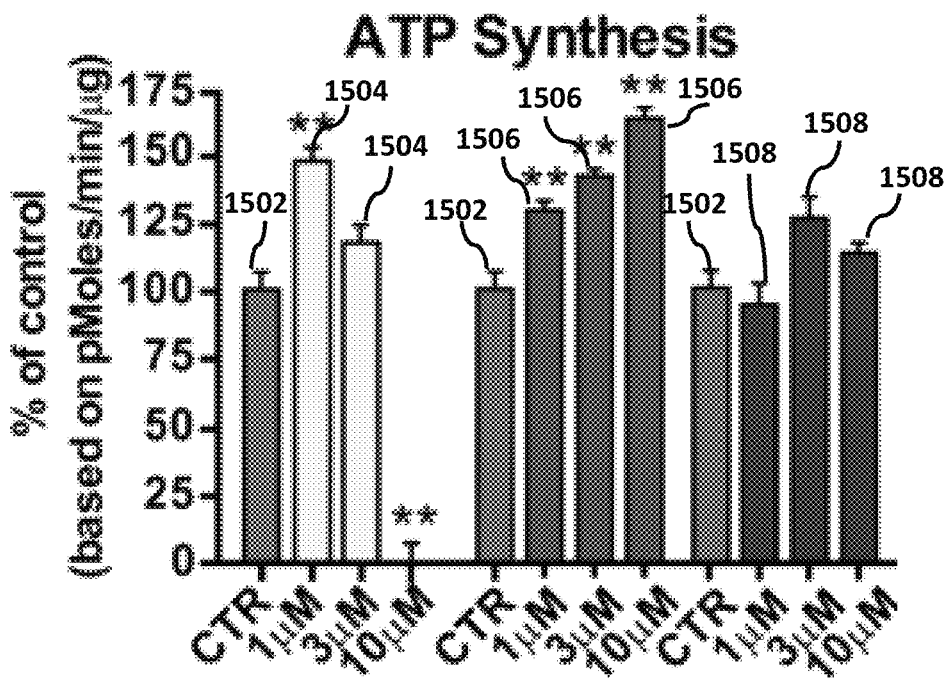
Figure 15D:
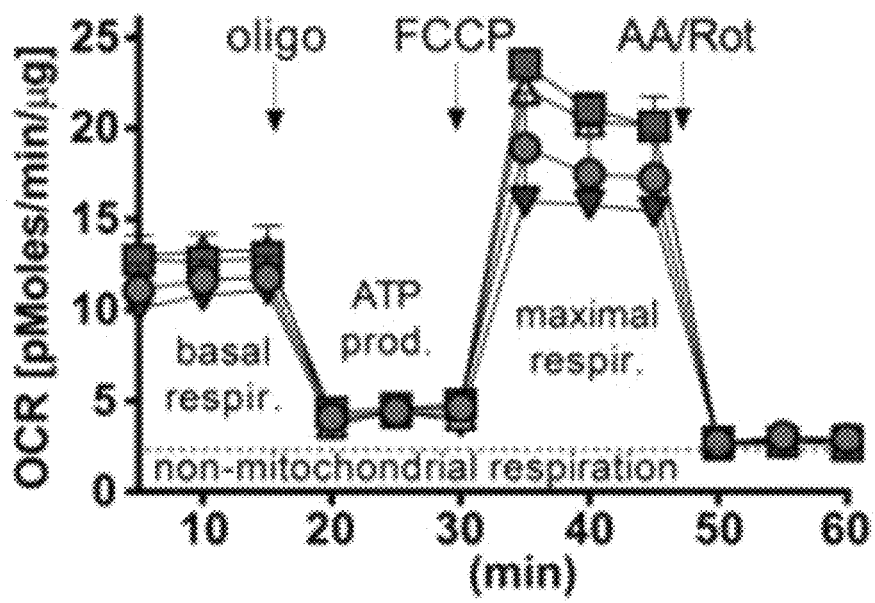
Figure 15E:
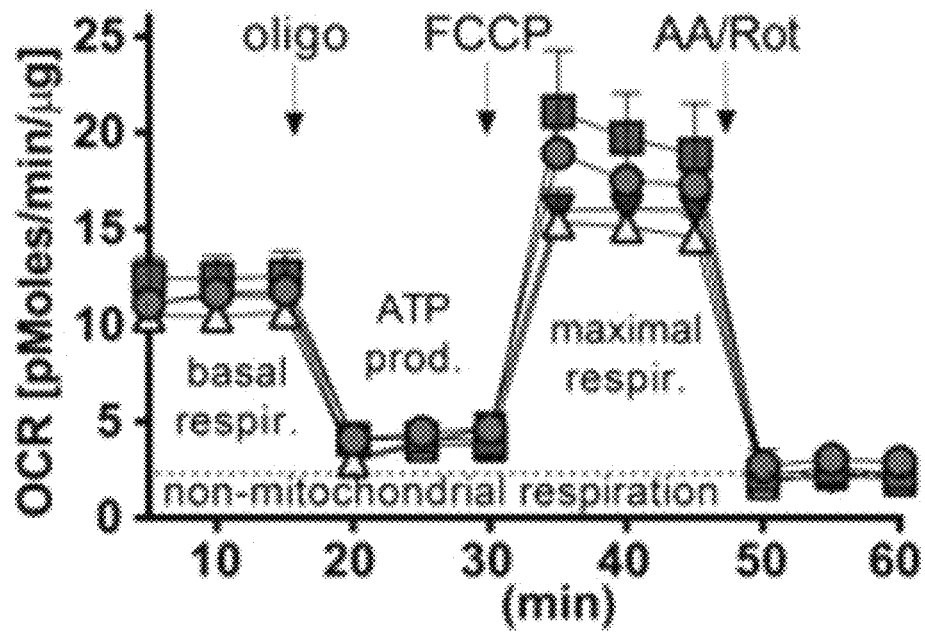
Figure 15F:
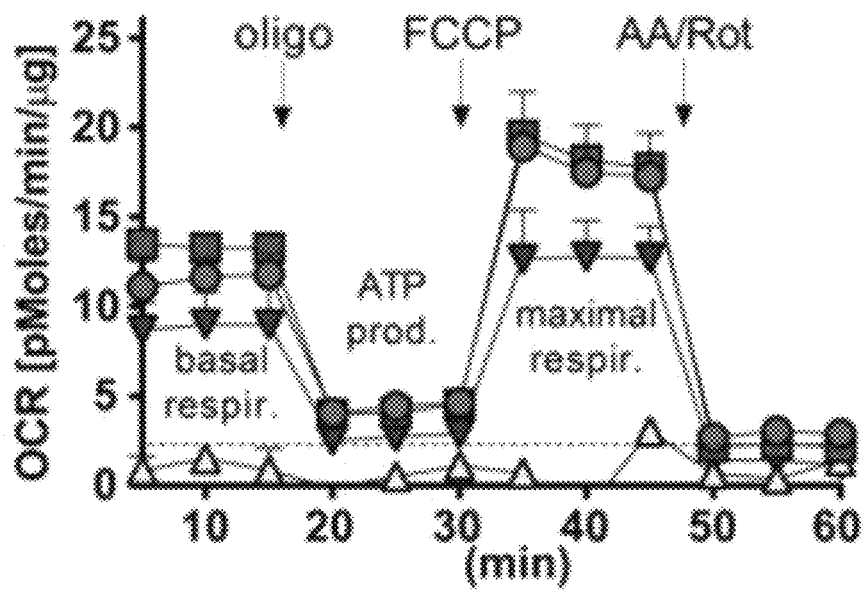

are control compound 6, and bars labeled "1508" are control compound 7, as described herein; for FIGS. 15D-F, circles are controls, open triangles pointing upward are donor compound 5, squares are control compound 6, and dark triangles pointing downward are control compound 7; "oligo" refers to oligomycin, "FCCP" refers to carbonyl cyanide 4-(trifluoromethoxy)phenylhydrazone, "AA/Rot" refers to antimycin and rotenone; and for FIGS. 15G-I, open bars are for AP39 and solid bars are for GYY4137.

Figure 16:
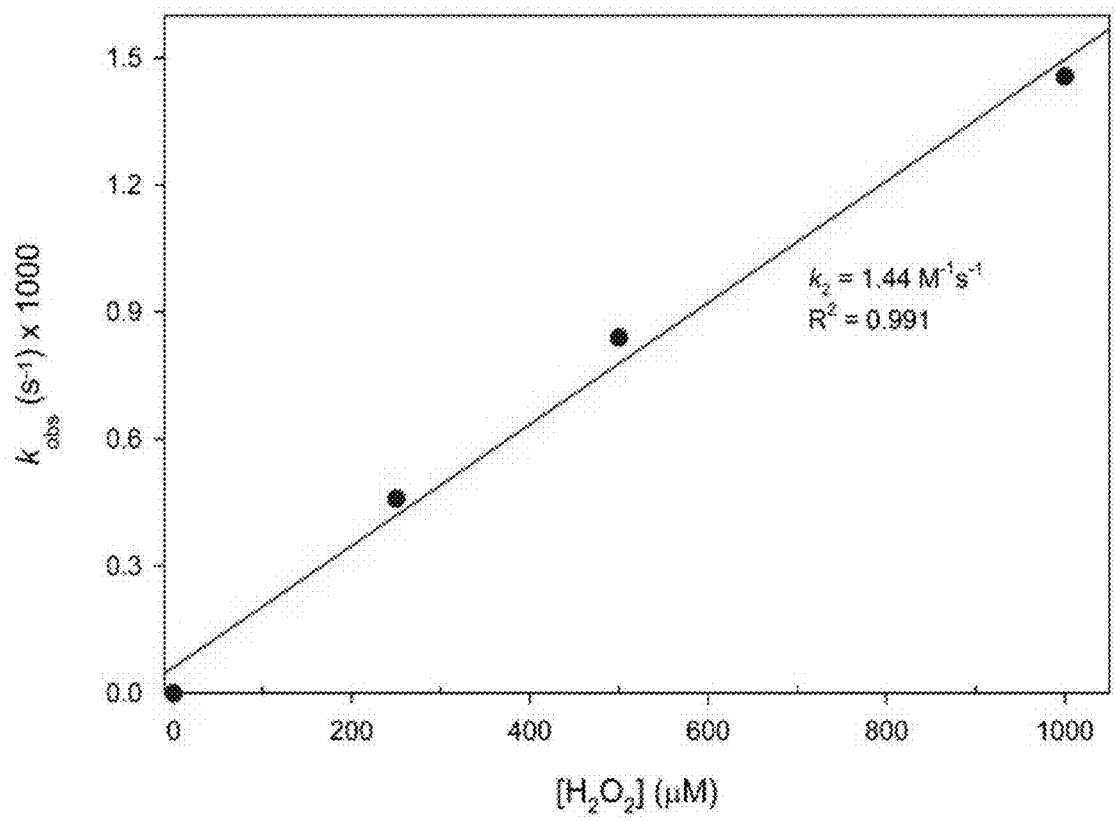

FIG. 16 is a graph showing the kinetics of $H_2S$ release from a representative donor compound disclosed herein (at a 50 micromolar concentration): the observed rate of $H_2S$ release ($K_{obs}$ in inverse seconds) is graphed as a function of concentration of hydrogen peroxide (micromolar).

Figure 17A:
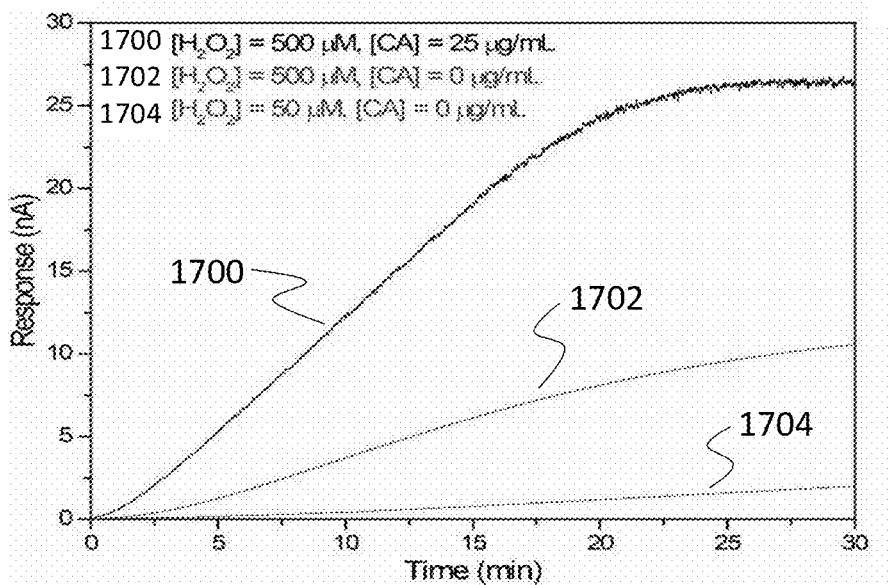
Figure 17B:
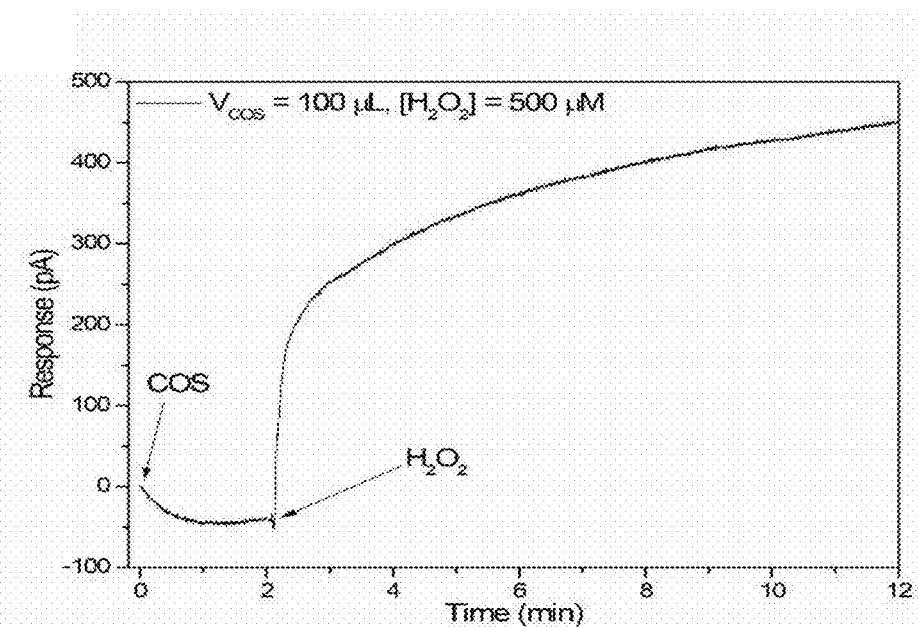

FIGS. 17A and 17B show the conversion of COS to $H_2S$ mediated by hydrogen peroxide from a representative donor compound disclosed herein (at a 50 micromolar concentration); FIG. 17A is a graph of response (nA) as a function of time (minutes) showing $H_2S$ release from a representative donor compound in the presence or absence of an enzyme; FIG. 17B is a graph of response (nA) as a function of time (minutes) showing the release of $H_2S$ from a COS gas prior to and after addition of hydrogen peroxide.

Figure 18:
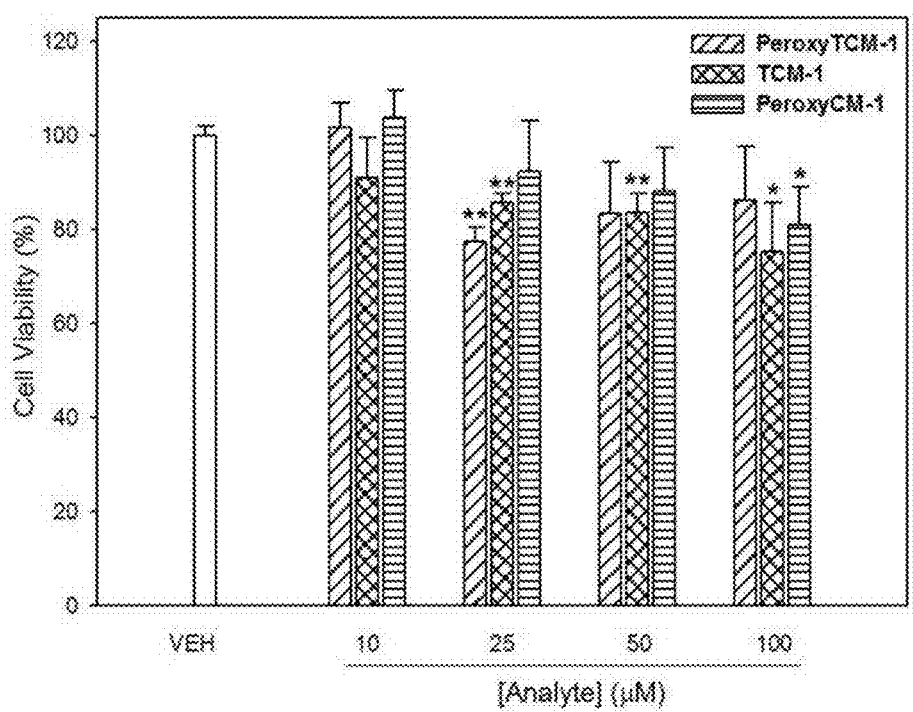

FIG. 18 is a graph of cell viability (as a percentage of vehicle response) as a function of concentration for one representative donor compound and two control compounds disclosed herein (at 10, 25, 50 and 100 micromolar concentrations).

Figure 19:
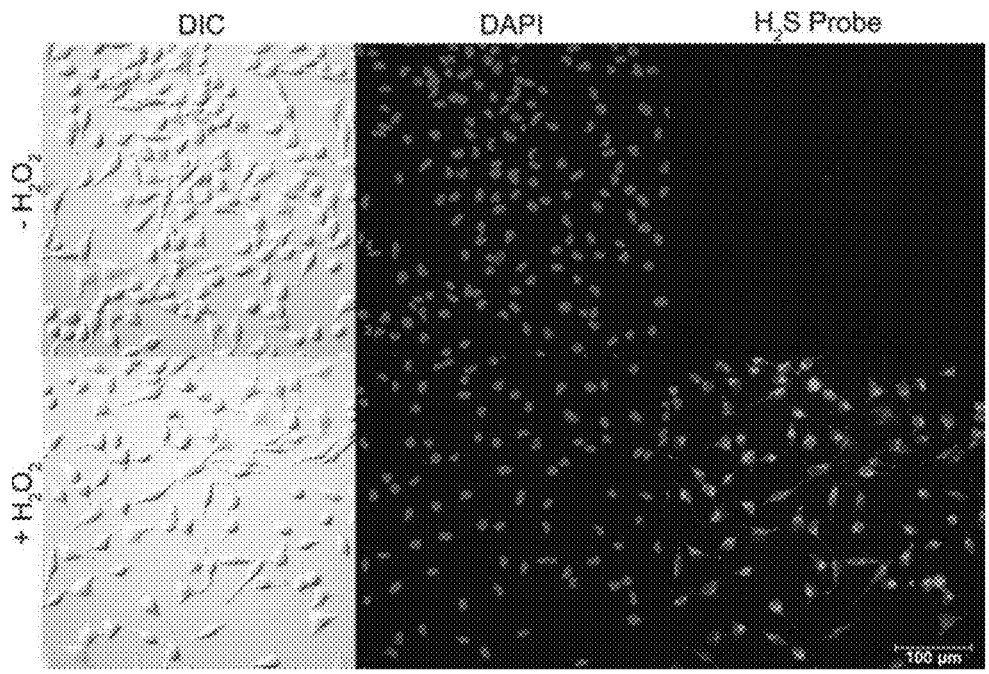

FIG. 19 shows fluorescence microscopy images of HeLa cells incubated with a representative donor compound disclosed herein (at a 50 micromolar concentration) in the presence and absence of hydrogen peroxide; the upper row of three images are in the absence of hydrogen peroxide, and the bottom row is in the presence of 50 micromolar hydrogen peroxide.

Figure 20:
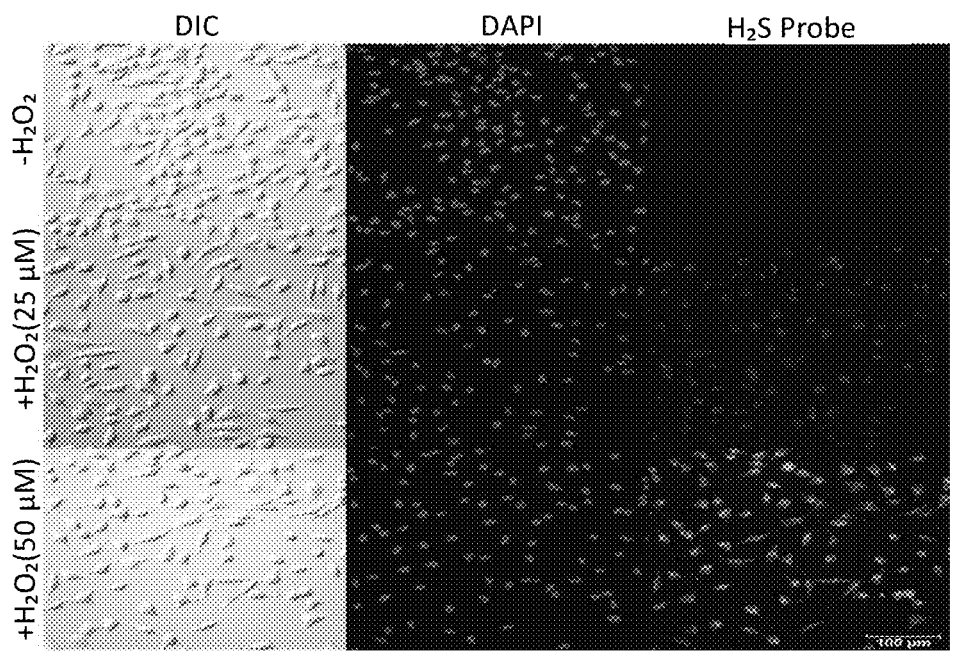

FIG. 20 shows fluorescence microscopy images of HeLa cells incubated with a representative donor compound disclosed herein (at a 50 micromolar concentration) in the presence and absence of hydrogen peroxide; the upper row of three images are in the absence of hydrogen peroxide, the middle row is in the presence of 25 micromolar hydrogen peroxide, and the lower row is in the presence of 50 micromolar hydrogen peroxide.

Figure 21:
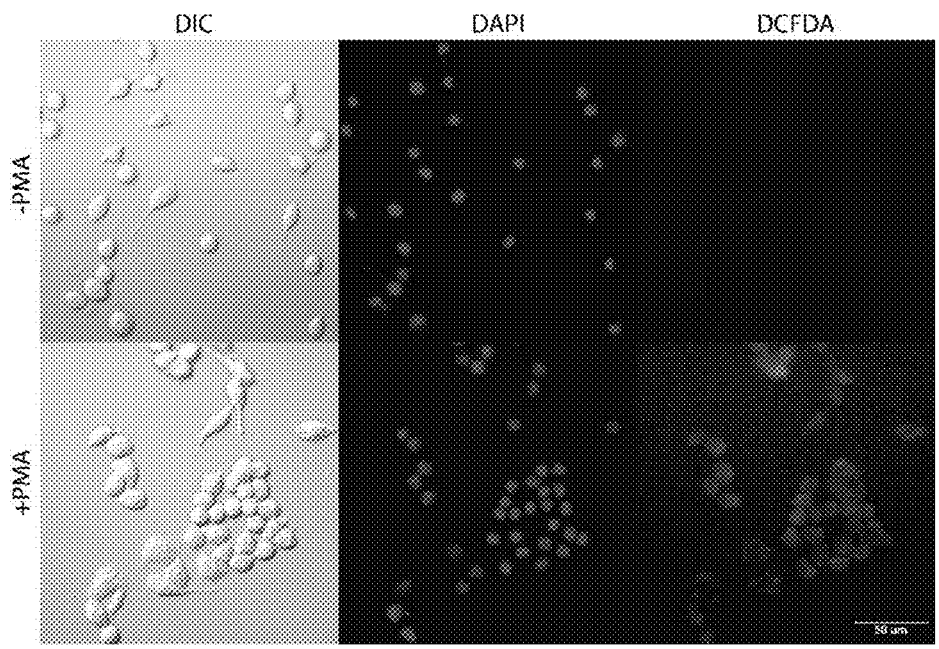

FIG. 21 shows fluorescence microscopy images of RAW 264.7 cells incubated with dichlorofluorescin diacetate (DFCDA) at a 10 micromolar concentration in the presence and absence of phorbol 12-myristate 13-acetate (PMA), showing induced endogenous reactive oxygen species (ROS) generation; the upper row of three images are in the absence of PMA, and the bottom row is in the presence of 500 nanomolar PMA.

Figure 22:
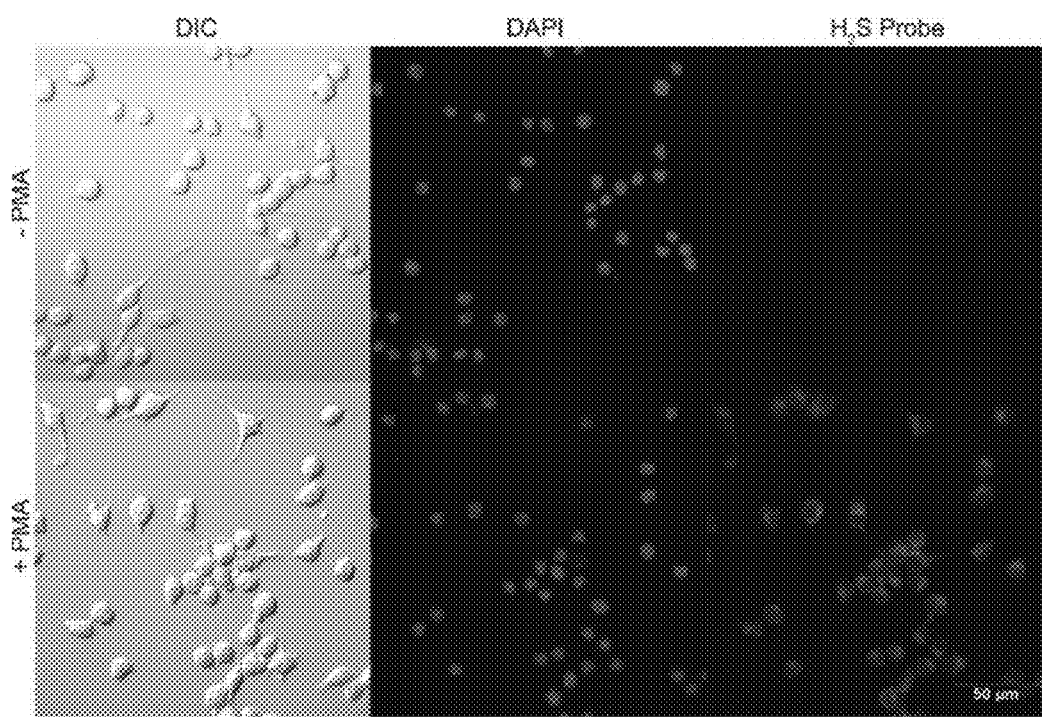

FIG. 22 shows fluorescence microscopy images of RAW 264.7 cells incubated with a representative donor compound disclosed herein (at a 50 micromolar concentration) in the presence and absence of PMA, showing induced endogenous ROS generation; the upper row of three images are in the absence of PMA, and the bottom row is in the presence of 500 nanomolar PMA.

Figure 23A:
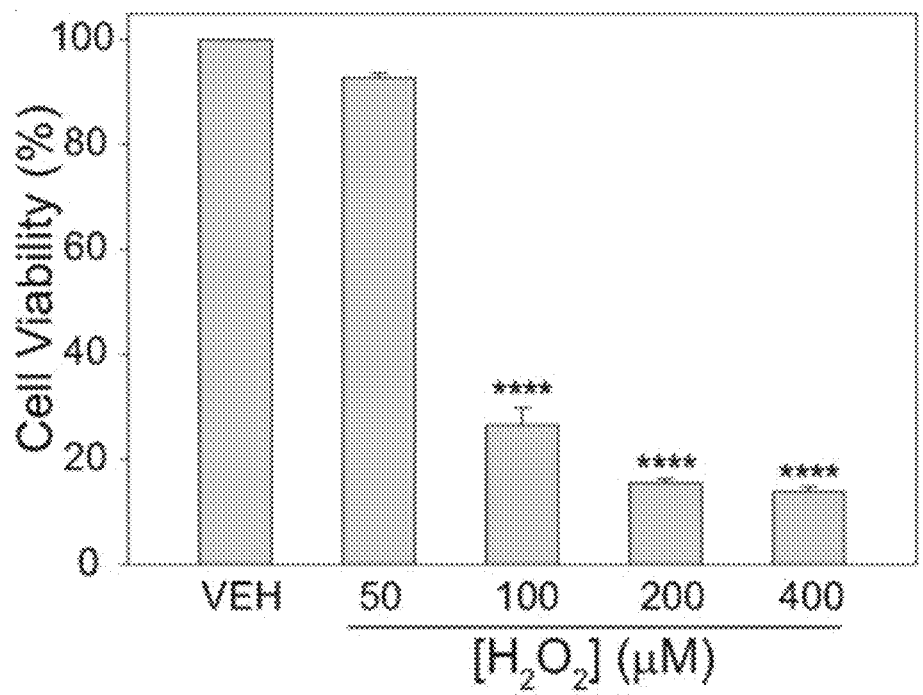
Figure 23B:
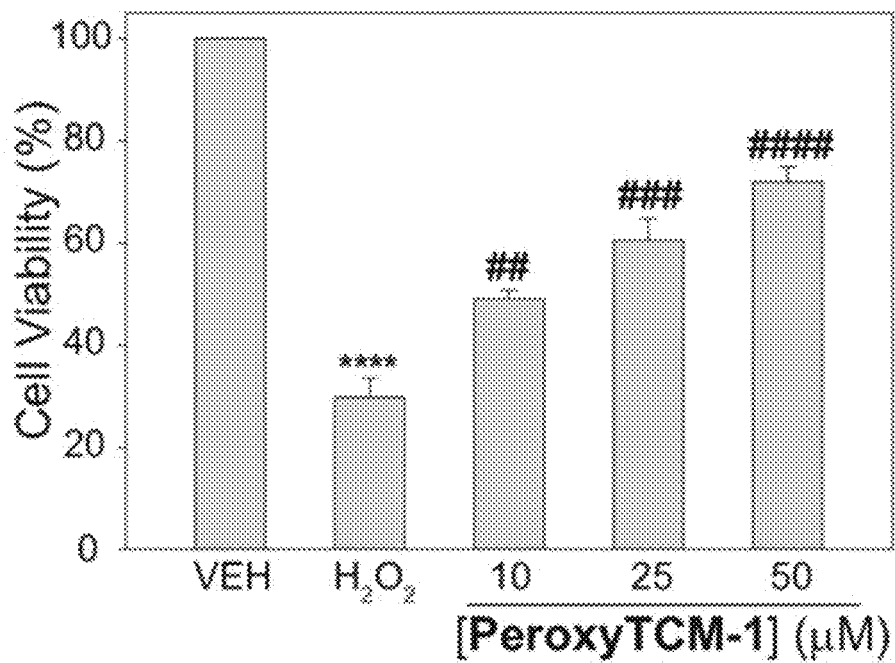
Figure 23C:
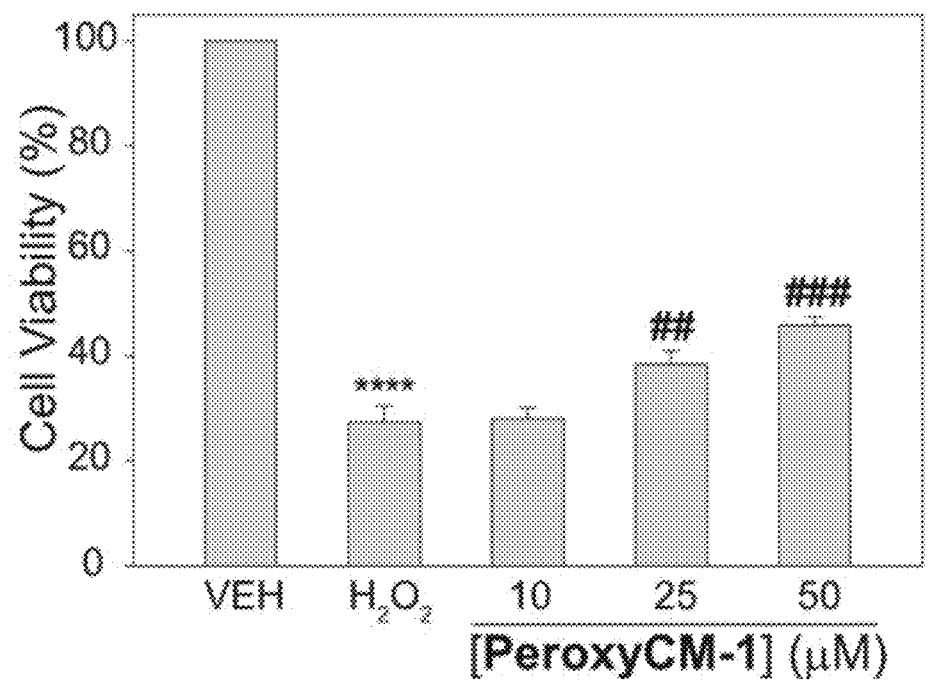
Figure 23D:
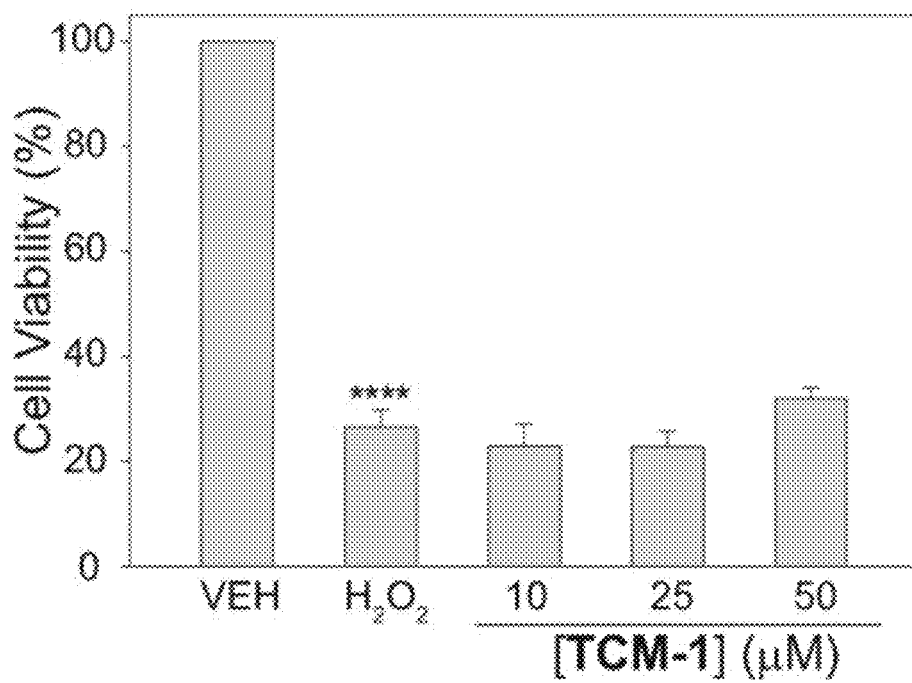

FIGS. 23A-23D are graphs of cell viability (as a percentage of vehicle) as a function of concentration for hydrogen peroxide and one representative donor compound and two representative control compounds disclosed herein; FIG. 23A shows the cytotoxicity of hydrogen peroxide at concentrations of 50, 100, 200 and 400 micromolar; FIG. 23B shows cytoprotection by PeroxyTCM-1 at concentrations of 10, 25 and 50 micromolar; FIG. 23C shows cytoprotection by PeroxyCM-1 at concentrations of 10, 25 and 50 micromolar; and FIG. 23D shows cytoprotection by TCM-1 at concentrations of 10, 25 and 50 micromolar.

Figure 24:
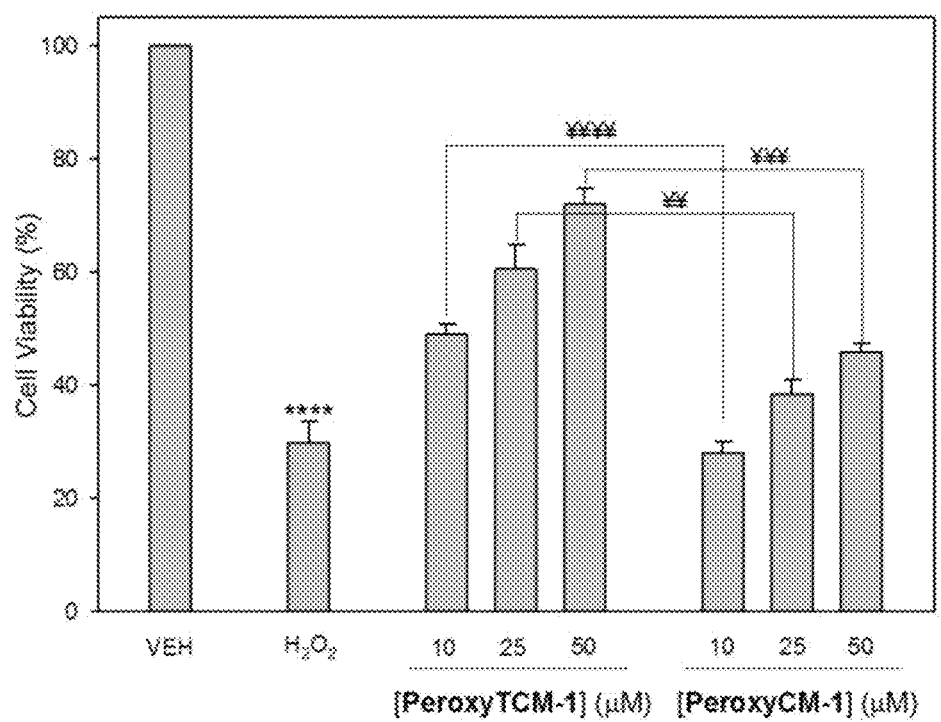

FIG. 24 is a graph showing the effects of one representative donor compound disclosed herein and one control compound; PeroxyTCM-1 and PeroxyCM-1 were tested at concentrations of 10, 25 and 50 micromolar in hydrogen peroxide-treated HeLa cells.

DETAILED DESCRIPTION

I. Explanation of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include an $R^a$ group that, though not part of the defined functional group, indicates how the functional group attaches to the donor compound to which it is bound. Also, a dashed bond (i.e., "---") as used in certain formulas described herein indicates an optional bond (that is, a bond that may or may not be present). A person of ordinary skill in the art would recognize that the definitions provided below and the donor compounds and formulas included herein are not intended to include impermissible substitution patterns (e.g., methyl substituted with 5 different groups, and the like). Such impermissible substitution patterns are easily recognized by a person of ordinary skill in the art. In formulas and donor compounds disclosed herein, a hydrogen atom is present and completes any formal valency requirements (but may not necessarily be illustrated) wherever a functional group or other atom is not illustrated. For example, a phenyl ring that is drawn as

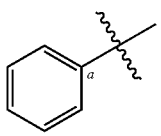 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyloxy: $R^aOC(O)R^b$, wherein $R^a$ is the atom of the formulas disclosed herein to which the acyloxy group is attached and $R^b$ is selected from hydrogen, alkyl, alkenyl, alkynyl, aryl, heteroalkyl, heteroalkenyl, heteroalkynyl, or heteroaryl.

Acyl Halide: $R^aC(O)X$, wherein $R^a$ is the atom of the formulas disclosed herein to which the acyl halide group is attached and X is a halogen, such as Br, F, I, or Cl.

Aldehyde: $R^aC(O)H$, wherein $R^a$ is the atom of the formulas disclosed herein to which the aldehyde group is attached.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Alkoxy: $R^a$O-alkyl, $R^a$O-alkenyl, or $R^a$O-alkynyl, wherein $R^a$ is the atom of the formulas disclosed herein to which the alkoxy is attached with exemplary embodiments including, but not limited to, methoxy, ethoxy, n-propoxy, isopropoxy, n-butoxy, t-butoxy, sec-butoxy, n-pentoxy.

Amide: $R^aC(O)NR^bR^c$ wherein $R^a$ is the atom of the formulas disclosed herein to which the amide is attached, and each of $R^b$ and $R^c$ independently is selected from hydrogen, aliphatic, heteroaliphatic, aryl, heteroaryl, or any combination thereof.

Amine: $R^aNR^bR^c$, wherein $R^a$ is the atom of the formulas disclosed herein to which the amine is attached, and each of $R^b$ and $R^c$ independently is selected from hydrogen, alkyl, alkenyl, alkynyl, aryl, heteroalkyl, heteroalkenyl, heteroalkynyl, heteroaryl, and any combination thereof.

Amine-terminated Compound: A compound produced by a reaction between a reactive component and a donor compound contemplated by the present disclosure. Amine-terminated compounds comprise a terminal amine group that is obtained from the fragmentation or bond breaking of the carbon-nitrogen bond present in a "—WC(=Y)V—" group wherein V is nitrogen.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Boronate Ester: A functional group comprising a boron atom covalently bound to two oxygen atoms that are in turn bound to one another through an aliphatic, aryl, heteroaliphatic, or heteroaryl group.

Boronic acid: A functional group comprising a boron atom covalently bound to two hydroxyl groups.

Carbamodithioate: A functional group satisfying a formula "—WC(=Y)V—" of the donor compounds described herein, wherein W is sulfur, C is carbon, Y is sulfur, and V is nitrogen connected to an $R^1$ group (i.e., —S(C=S)NR$^1$—).

Carbonodithioate: A functional group satisfying a formula "—WC(=Y)V—" of the donor compounds described herein, wherein W is sulfur, C is carbon, Y is sulfur, and V is oxygen (i.e., —S(C=S)O—).

Carbonothioate: A functional group satisfying a formula "—WC(=Y)V—" of the donor compounds described herein, wherein W is oxygen, C is carbon, Y is sulfur, and V is oxygen (i.e., —O(C=S)O—).

Carbonotrithioate: A functional group satisfying a formula "—WC(=Y)V—" of the donor compounds described herein, wherein W is sulfur, C is carbon, Y is sulfur, and V is sulfur (i.e., —S(C=S)S—).

Carboxyl: $R^aC(O)OR^b$, wherein $R^a$ is the atom of the formulas disclosed herein to which the carboxyl group is attached and wherein $R^b$ is alkyl, alkenyl, alkynyl, aryl, heteroalkyl, heteroalkenyl, heteroalkynyl, heteroaryl, hydrogen, and any combination thereof.

Cyclic By-Product: A compound having a cyclic core that is formed by a reaction between a reactive component and a donor compound contemplated by the present disclosure. In particular disclosed embodiments, the cyclic by-product has a structure meeting any one or more of the following formulas:

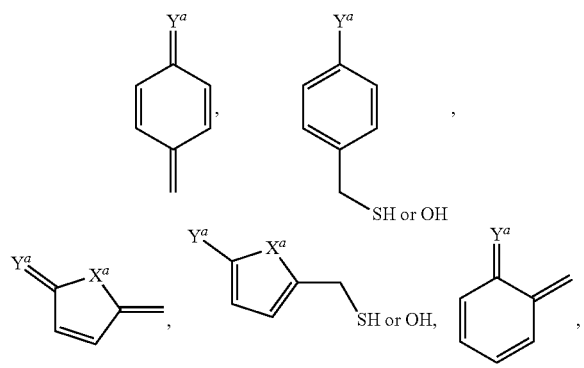

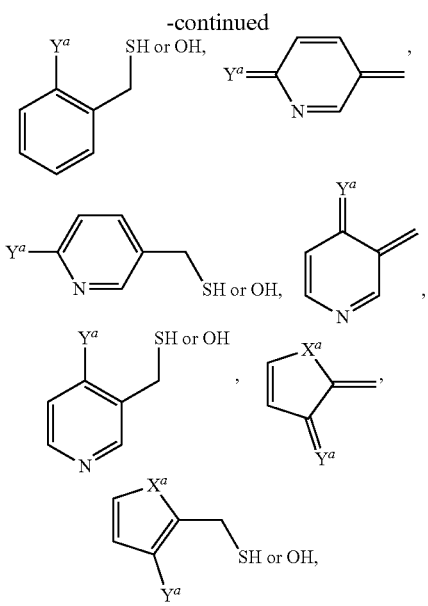

wherein $Y^a$ and $X^a$ independently is selected from oxygen, NR (wherein R is selected from hydrogen, aliphatic, or aryl), or sulfur.

Detectable signal: A color change that occurs when a donor compound disclosed herein comprising a detectable moiety (e.g., a fluorophore or a dye) reacts with a reactive component to release the detectable moiety.

Disulfide: $R^aSSR^b$, wherein $R^a$ is the atom of the formulas disclosed herein to which the disulfide group is attached and wherein $R^b$ is selected from hydrogen, aliphatic, aryl, heteroaliphatic, or heteroaryl.

Donor Compound: A compound having a structure satisfying any one or more of the formulas described herein, such as Formulas 1, 2A-2I, 3A-3I, 4-7, 4A-4I, 5A-5I, 6A-6I, or 7A-7K as disclosed herein. In some embodiments, a "donor compound" is also called a "compound contemplated by the present disclosure," or "donor compound contemplated by the present disclosure."

Ester: $R^aC(O)OR^b$, wherein $R^a$ is the atom of the formulas disclosed herein to which the aldehyde group is attached and $R^b$ is selected from hydrogen, alkyl, alkenyl, alkynyl, aryl, heteroalkyl, heteroalkenyl, heteroalkynyl, or heteroaryl.

Fluorophore: A functional group, or portion, of a donor compound disclosed herein that causes the donor compound or a part of the donor compound (e.g., an amine-terminated group) to fluoresce when exposed to an excitation source. Exemplary fluorophores are selected from, but not limited to, methylrhodol, 2-(2-methoxyethyl)-1H-benzo[de]isoquinoline-1,3(2H)-dione, 4-methyl-2H-chromen-2-one, coumarin, naphthalimide, fluorescein, rhodamine, rhodol, Cy3, or Cy5.

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a CX3 group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Ketone: $R^aC(O)R^b$, wherein $R^a$ is the atom of the formulas disclosed herein to which the ketone is attached, and $R^b$ is selected from aliphatic, heteroaliphatic, aryl, heteroaryl, and any combination thereof.

Reactive Component: A compound that reacts (e.g., via reduction, oxidation, nucleophilic attack, photolysis, or enzymatic cleavage) with the donor compounds contemplated by the present disclosure so as to initiate COS or $CS_2$ release from the donor compound. Exemplary precursor compounds include, but are not limited to, donor compounds comprising a thiocarbamate, a carbamodithioate, a carbonothioate, a carbonodithioate, a carbonotrithioate, or a thiocarbonate. Exemplary reactive components include, but are not limited to oxidants (e.g., $H_2O_2$, benzoyl peroxide, and other peroxides, $F_2$, $Cl_2$, $Br_2$, $I_2$, or the like), reductants (e.g., formic acid, ascorbic acid, dithiothreitol, tris(2-carboxyethyl)phosphine (TCEP), oxalic acid, hydrazine, hydride-based reductants, hydrogen sulfide, and the like), enzymes (e.g., esterases, such as acetylesterases, thioesterases, phosphatases, sulfatases, and the like), acids (e.g., mineral acids, such as sulfuric acid, fluorosulfuric acid, phosphoric acid; sulfonic acids, such as methanesulfonic acid, ethanesulfonic acid, benzenesulfonic acid, tosylic acid, and triflic acid; carboxylic acids, such as acetic acid, citric acid, formic acid, gluconic acid, ascorbic acid, lactic acid, oxalic acid, and tartaric acid; halogenated carboxylic acids, such as fluoroacetic acid and trifluoroacetic acid; or combinations thereof), bases (e.g., lithium hydroxide, sodium hydroxide, potassium hydroxide, cesium hydroxide, and amine-containing bases), nucleophiles (e.g., fluoride ($F^-$) sources, such as tetra-n-butylammonium fluoride (TBAF) or tris(dimethylamino)sulfonium difluorotrimethylsilicate (TASF), or hydrogen sulfide), light (e.g., UV light) or a combination thereof. In particular disclosed embodiments, the reactive component can also be hydrogen sulfide, or other reactive sulfur, oxygen, or nitrogen species (e.g., cysteine, homocysteine, thiosulfate, sulfite, sulfate, or nitrogen oxide).

Saccharide: A sugar that can be selected from monosaccharides, disaccharides, oligosaccharides, and/or polysaccharides.

Silyl Ether: A functional group comprising a silicon atom covalently bound to an alkoxy group.

Solubilizing Agent: An agent that increases the solubility of a donor compound disclosed herein in aqueous media. Solubilizing agents can be selected from, but are not limited to, sodium bicarbonate, glucose, polyalkylene ethers or glycols (e.g., polyethylene glycol, polypropylene glycol, and the like), surfactants (e.g., sorbitan esters), and other solubilizing agents known in the art.

Sulfonyl/Sulfonate: A functional group having a formula $R^aSO_2R^b$, wherein $R^a$ is the atom of the formulas disclosed herein to which the sulfonyl or sulfonate is attached, and $R^b$ is selected from hydrogen, aliphatic, heteroaliphatic, aryl, heteroaryl, and any combination thereof.

Targeting Group: A group that is capable of targeting a cell, an organelle, or the like and thereby directing the donor compound comprising the targeting group to the cell, organelle, or the like. In some embodiments, a targeting group can be a morpholine, a phosphonium or phosphine group, a quaternary amine, or the like. Other targeting components can include thiol or hydroxyl functional groups, which can be used to target surfaces or monolayers.

Thiocarbamate: A functional group satisfying a formula "—WC(=Y)V—" of the donor compounds described herein, wherein W is sulfur or oxygen, C is carbon, Y is sulfur, and V is nitrogen attached to an $R^1$ group. In embodiments where W is sulfur, the functional group is an S-thiocarbamate having a structure —S(C=S)NR$^1$—. In embodiments where W is oxygen, the functional group is an O-thiocarbamate having a structure —O(C=S)NR$^1$—. As used herein, the term "thiocarbamate" includes S-thiocarbamate and O-thiocarbamate, unless expressly indicated otherwise.

Thiocarbonate: A functional group satisfying a formula "—WC(=Y)V—" of the donor compounds described herein, wherein W is sulfur, C is carbon, Y is oxygen, and V is oxygen (i.e., —S(C=O)O—).

II. Introduction

Figure 1A:
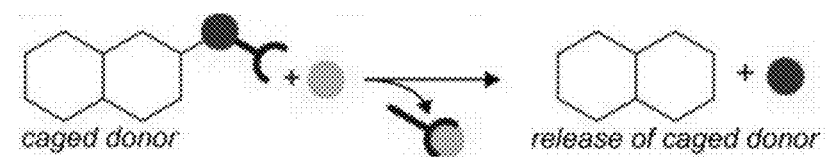
FIGS. 1A-1C illustrate different types of analyte replacement-based probes.
Figure 1B:
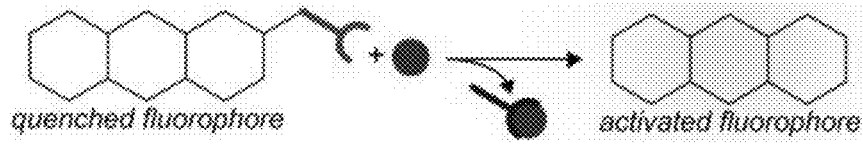

Conventional tools for analyte donation and reaction-based detection has provided significant insights into the roles of reactive sulfur, oxygen, and nitrogen species ("RSONs") in biology; however, there are challenges associated with conventional methods used for both of these processes. For example, most donor constructs require consumption of other RSONs to release the caged analyte, thus shifting the RSON landscape as a consequence of caged analyte release. Donor constructs that can be triggered to release H$_2$S by readily-modifiable triggers would provide a versatile platform for H$_2$S donation in different contexts (FIG. 1A). A related challenge in reaction-based sensing techniques is that these platforms react irreversibly with the analyte during probe activation, which not only results in analyte consumption, but also significantly alters its cellular homeostasis (FIG. 1B).

Figure 1C:
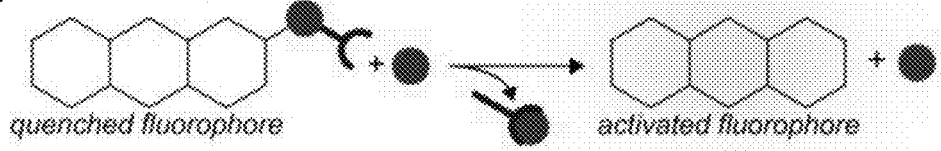

To address these limitations, the present inventors have developed novel compounds and methods to access caged, triggerable COS/H$_2$S donor motifs and CS$_2$/H$_2$S donor motifs that have direct applications in both caged analyte release and analyte-replacement probe development. In some embodiments, self-immolative H$_2$S donors have been made to provide a new class of easily-modifiable H$_2$S donors that can be triggered by external stimuli, and translate this caged H$_2$S motif to address the issue of analyte consumption in reaction-based fluorescent probe design. Analyte replacement fluorescent probes, which upon reaction with H$_2$S activate a fluorescence response and also release H$_2$S, also are described herein and can provide a significant advance in addressing the problem of analyte homeostasis in reaction-based probe development (FIG. 1C).

The donor compounds and methods described herein are not only useful research tools, but also have many potential therapeutic applications, such as providing a platform for protection in patients with high, eminent MI markers. The donor compounds described herein can be used as a modular donation platform in which the 'trigger' can readily be modified to respond to different events, including biological (such as enzymatic), chemical (such as peroxy), and photolytic (such as UV irradiation) events. In some embodiments, the donor compounds described herein contain a 'caged' molecule of H$_2$S, which is released upon donor activation. In these systems, the donor compounds can release carbonyl sulfide (COS), which is rapidly converted to H$_2$S by the ubiquitous enzyme carbonic anhydrase (CA), or by water. In yet additional embodiments, the donor compounds can release carbon disulfide (CS$_2$), which can be converted to H$_2$S using water or enzymes such as nitrogenase, RuBisCO, CO dehydrogenase, COSase, CS$_2$ hydrolase, or a combination thereof. The inventive H$_2$S-releasing compounds described herein are highly modular, allowing for both the triggering moieties and the rate of H$_2$S release from the platform to be readily modified. There are a number of diseases, such as glaucoma, that are characterized by an over-expression of CA but which can also be treated by H$_2$S addition. Such diseases are particularly attractive platforms for the disclosed COS/H$_2$S donor motifs and the disclosed CS$_2$/H$_2$S donor motifs.

III. Compounds

Disclosed herein are donor compounds that can be used to trigger production of H$_2$S and/or to detect the presence of H$_2$S while further regenerating H$_2$S. Such donor compounds react with a reactive component to produce COS or CS$_2$, which can be further converted to H$_2$S. In some embodiments, the donor compounds described herein can have structures meeting Formula 1.

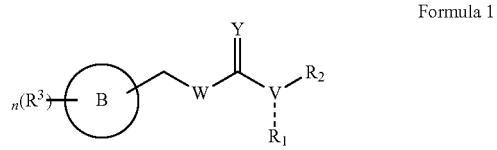

Formula 1

With reference to Formula 1, each of W and Y independently can be selected from oxygen or sulfur; V can be selected from oxygen, sulfur, or nitrogen (wherein if V is nitrogen, then the dashed bond of Formula 1 represents a bond between $R^1$ and the nitrogen atom; or if V is oxygen or sulfur, then the dashed bond and $R^1$ are not present); $R^3$ can be a functional group selected to provide donor compounds responsive to oxidative stress, intracellular esterases, endogenous stimuli, light, or external biorthogonal stimuli; and n can be an integer selected from 0 to 5. Solely by way of example, $R^3$ can be an ester group, a heteroaliphatic ester group (e.g., —O(CH$_2$)$_r$OCOR$^b$, —S(CH$_2$)$_r$OCOR$^b$, or —NH(CH$_2$)$_r$OCOR$^b$, wherein $R^b$ is aliphatic and r is 1-4), phosphoric esters, sulfuric esters, azo groups, nitro groups, or thioesters that can be hydrolyzed by enzymes. In yet other embodiments, $R^3$ can be a boronate ester or boronic acid that reacts with H$_2$O$_2$ to generate a phenol. In additional disclosed embodiments, $R^3$ can be a biorthogonal functional group, such as a silyl ether that can be converted to a phenol upon exposure to a fluoride (F$^-$) source, or a silyl ester.

In particular disclosed embodiments, ring B can be an aryl group or a heteroaryl group; $R^1$ can be selected from hydrogen, aliphatic, heteroaliphatic, aryl, or heteroaryl; $R^2$ can be selected from aliphatic, heteroaliphatic, aryl, heteroaryl, halogen, sugars, organelle targeting groups, fluorophores, drug molecules, or combinations thereof; each $R^3$ independently can be selected from aliphatic, heteroaliphatic, aryl, heteroaryl, halogen, hydroxyl, thiol, amine, azide, a boronate ester, a boronic acid, a disulfide, an ester, a heteroaliphatic ester group (e.g., —O(CH$_2$)$_r$OCOR$^b$, —S(CH$_2$)$_r$OCOR$^b$, or —NH(CH$_2$)$_r$OCOR$^b$, wherein $R^b$ is aliphatic and r is 1-4), nitro, a silyl ether, 3,5-dinitrobenzenesulfonic acid, or a combination thereof; and n can be 1-5. In some embodiments, ring B is selected from furan, thiophene, phenyl, pyridyl, or pyrrole. In some embodiments, $R^1$ is hydrogen. In some embodiments, $R^2$ is -phenyl-(R$^4$)$_m$, (wherein m can be 0-5 and $R^4$ is as described below), or a fluorophore, such as methylrhodol, 2-(2-methoxyethyl)-1H-benzo[de]isoquinoline-1,3(2H)-dione, 4-methyl-2H-chromen-2-one, or a combination thereof.

In some embodiments, the donor compounds can have structures satisfying any one of Formulas 2A-2I.

Formula 2A
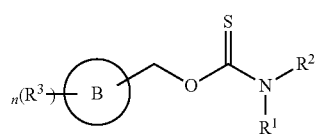

Formula 2B
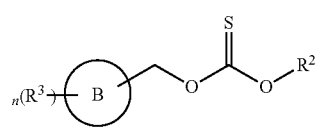

Formula 2C
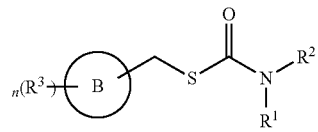

Formula 2D
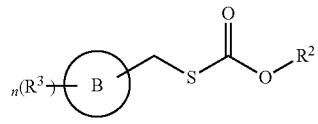

Formula 2E
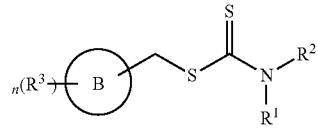

Formula 2F
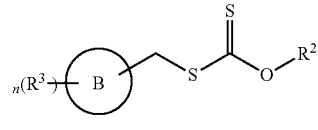

Formula 2G
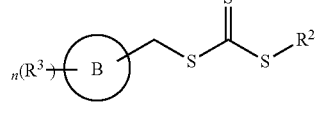

Formula 2H
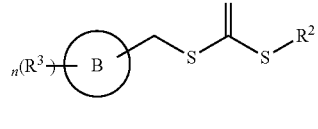

-continued

Formula 2I
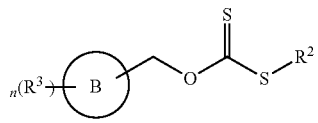

With reference to Formulas 2A-2I, $R^3$ can be as described above for Formula 1. For example, $R^3$ can be a functional group selected to provide donor compounds responsive to oxidative stress, intracellular esterases, endogenous stimuli, or external biorthogonal stimuli. In some embodiments, $R^3$ can be a group that can be hydrolyzed by esterases, such as an ester group, phosphoric esters, sulfuric esters, a heteroaliphatic ester group (e.g., —O(CH$_2$)$_r$OCOR$^b$, —S(CH$_2$)$_r$OCOR$^b$, or —NH(CH$_2$)$_r$OCOR$^b$, wherein $R^b$ is aliphatic and r is 1-4), or thioesters. In yet other embodiments, $R^3$ can be a boronate ester or boronic acid that reacts with $H_2O_2$ to generate a phenol. In additional disclosed embodiments, $R^3$ can be a biorthogonal functional group, such as a silyl ether that can be converted to a phenol upon exposure to a fluoride ($F^-$) source. In yet additional embodiments, $R^3$ can be a light triggerable group (e.g., nitro). In particular disclosed embodiments, ring B can be an aryl group or a heteroaryl group; $R^1$ can be selected from hydrogen, aliphatic, heteroaliphatic, aryl, or heteroaryl; $R^2$ can be selected from aliphatic, heteroaliphatic, aryl, heteroaryl, halogen, sugars, organelle targeting groups, fluorophores, drug molecules, or combinations thereof; each $R^3$ independently can be selected from aliphatic, heteroaliphatic, aryl, heteroaryl, halogen, hydroxyl, thiol, amine, azide, a boronate ester, a boronic acid, a disulfide, an ester, —OCH$_2$OCOR$^b$ (wherein $R^b$ is aliphatic), nitro, a silyl ether, 3,5-dinitrobenzenesulfonic acid, or a combination thereof; and n can be 0-5. In some embodiments, ring B is selected from furan, thiophene, phenyl, pyridyl, or pyrrole. In some embodiments, $R^1$ is hydrogen. In some embodiments, $R^2$ is -phenyl-(R$^4$)m (wherein m can be 0-5 and $R^4$ is as described below), or a fluorophore, such as methylrhodol, 2-(2-methoxyethyl)-1H-benzo[de]isoquinoline-1,3(2H)-dione, 4-methyl-2H-chromen-2-one, or a combination thereof.

In some embodiments, the donor compounds can have structures satisfying Formula 3A-3I.

Formula 3A
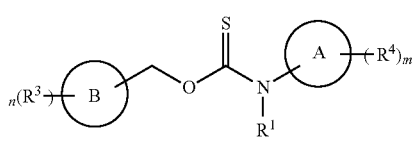

Formula 3B
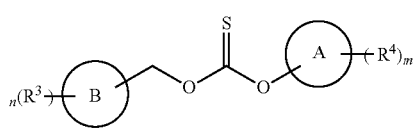

Formula 3C
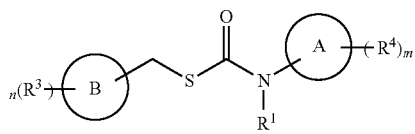

Formula 3D
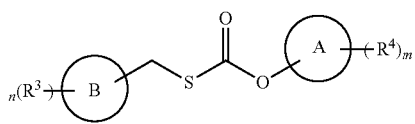

Formula 3E
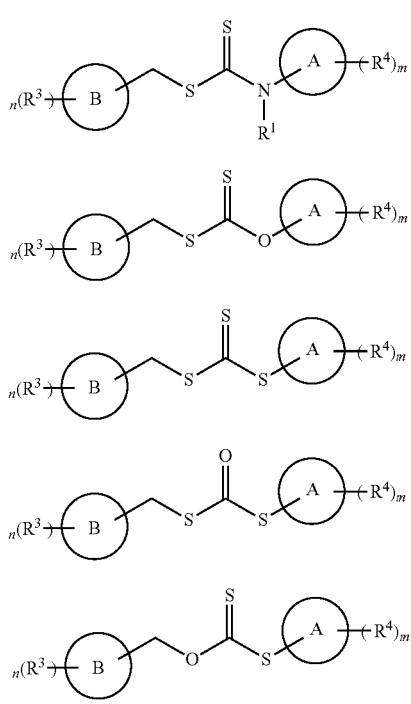
Formula 3F

Formula 3G

Formula 3H

Formula 3I

With reference to Formulas 3A-3I, each of ring B, $R^1$, $R^3$, and n can be as recited above for Formulas 1 and 2A-2I; ring A can be aryl or heteroaryl; each $R^4$ independently can be selected from aliphatic, aryl, heteroaliphatic, heteroaryl, or a combination thereof; and m can be 0 to 5. In particular disclosed embodiments, $R^4$ can be selected to control the rate of COS or $CS_2$ (and as such the rate of $H_2S$) released from the donor compound. For example, selecting electron-withdrawing groups or electron-donating groups for $R^4$ can result in the ability to control/tune the rate of COS or $CS_2$ release. As such, $R^4$ can be selected from electron-donating groups (e.g., alkoxy, thioether, amide, amine, hydroxyl, thiol, acyloxy, azide, aliphatic [e.g., alkyl, alkenyl, alkynyl)], aryl) or from electron-withdrawing groups (e.g., aldehyde, ketone, ester, carboxylic acid, acyl, acyl halide, cyano, sulfonate, nitro, quaternary amine, pyridinyl [or pyridinyl wherein the nitrogen atom is functionalized with an aliphatic or aryl group], alkyl halide, heterocyclyl, or halogen). In some embodiments, two or more $R^4$ groups can be joined to form a multicyclic fused ring system with Ring A. Exemplary fused ring systems formed when two $R^4$ groups join together include, but are not limited to methylrhodol, 2-(2-methoxyethyl)-1H-benzo[de]isoquinoline-1,3(2H)-dione, 4-methyl-2H-chromen-2-one.

In particular disclosed embodiments, the donor compounds can have structures satisfying any one or more of Formulas 4-7 and/or Formulas 4A-4I, 5A-5I, 6A-6I, and 7A-7K.

Formua 4
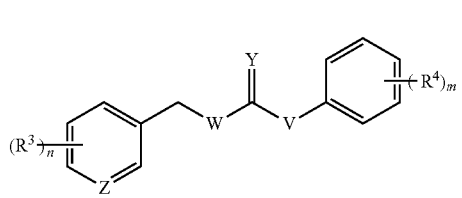

Formula 4A
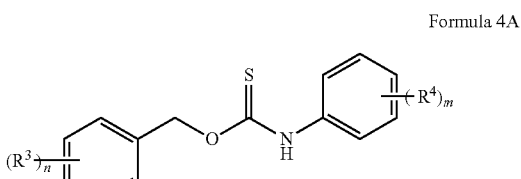

Formula 4B
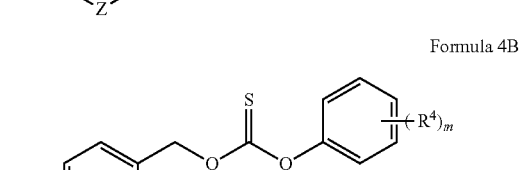

Formula 4C
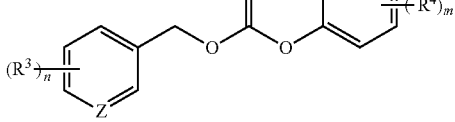

Formula 4D
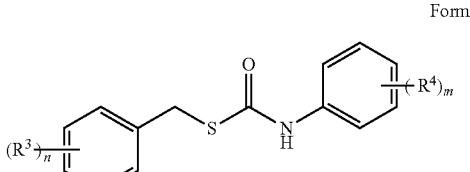

Formula 4E
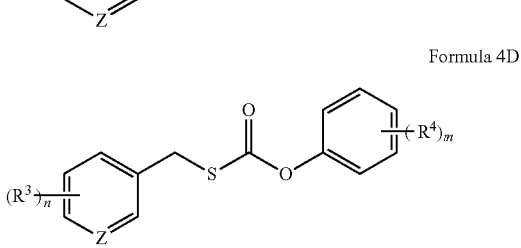

Formula 4F
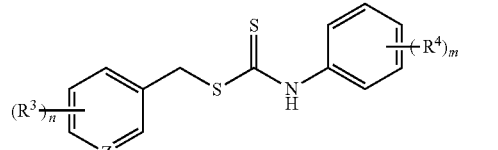

Formula 4G
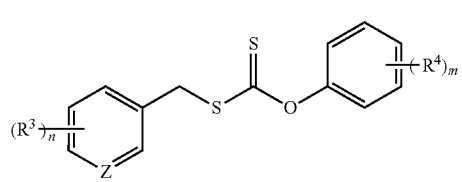

Formula 4H
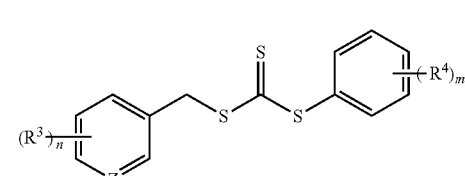

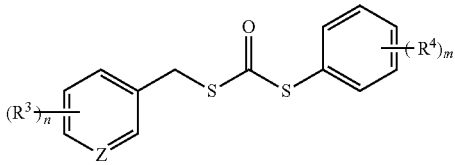

Formula 4I
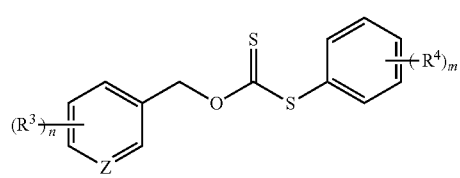
Formula 5
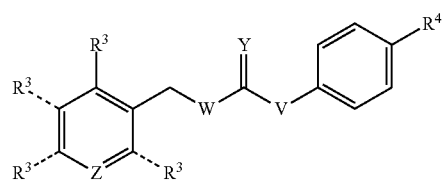
Formula 5A
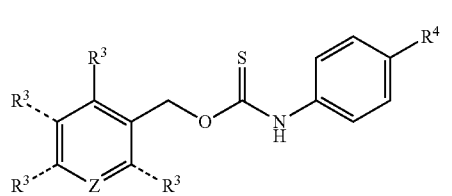
Formula 5B
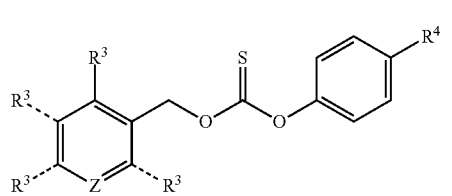
Formula 5C
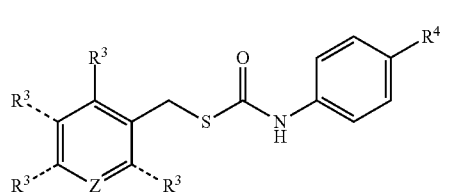
Formula 5D
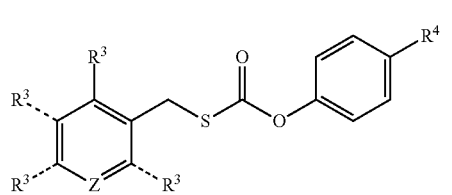
Formula 5E
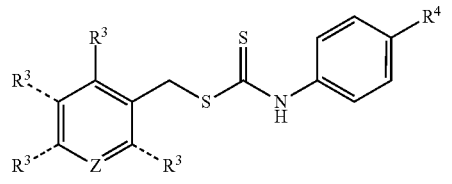
Formula 5F
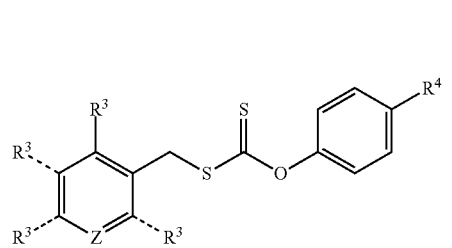
Formula 5G
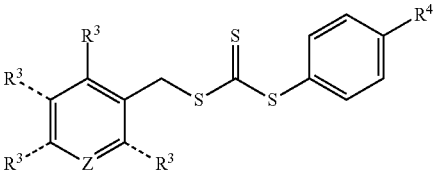
Formula 5H
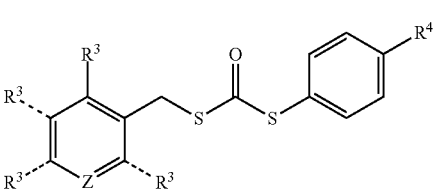
Formula 5I
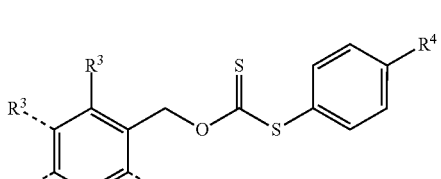
Formula 6
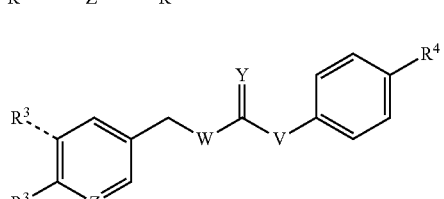
Formula 6A
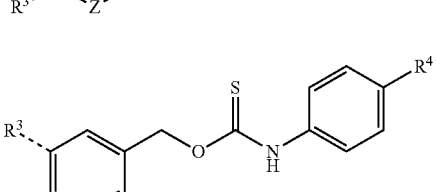
Formula 6B
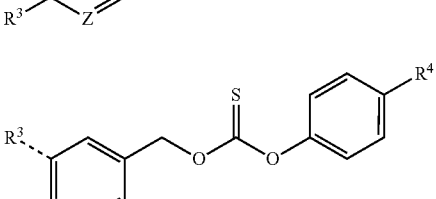
Formula 6C
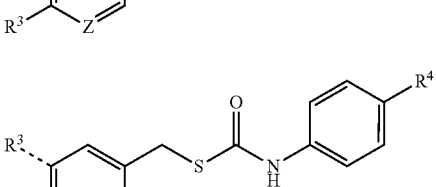
Formula 6D
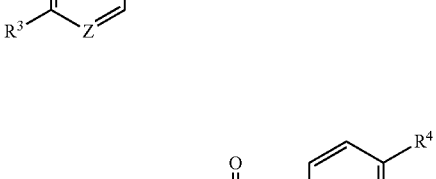
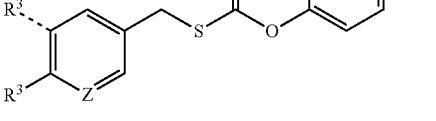

Formula 6E
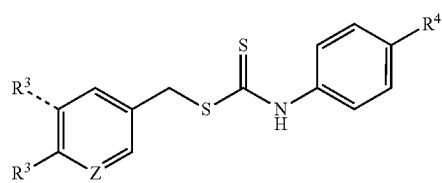

Formula 6F
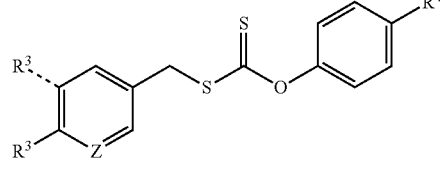

Formula 6G
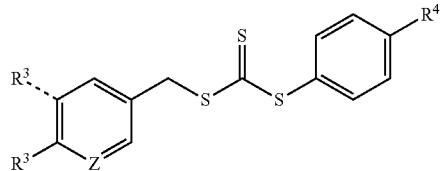

Formula 6H
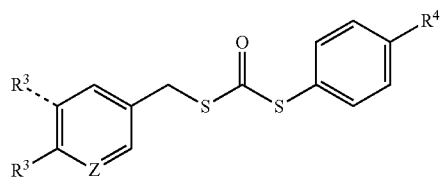

Formula 6I
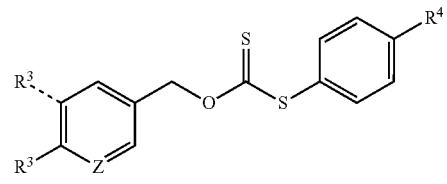

Formula 7
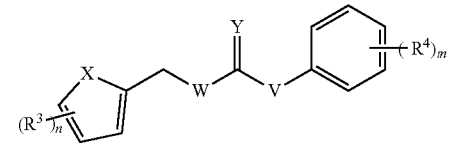

Formula 7A
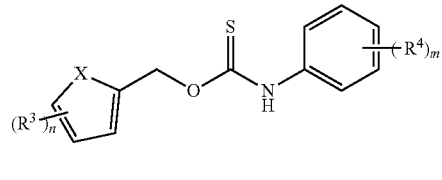

Formula 7B
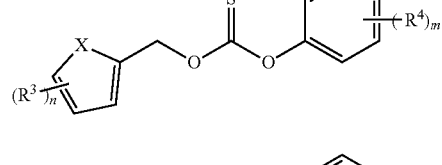

Formula 7C
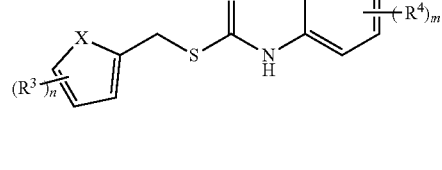

Formula 7D
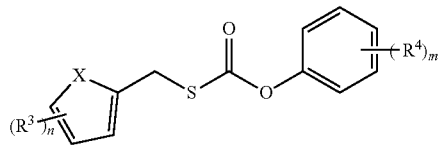

Formula 7E
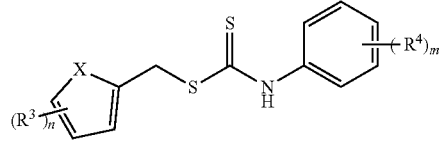

Formula 7F
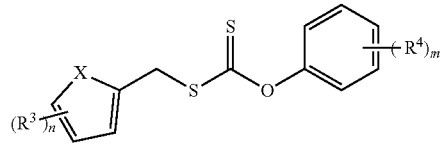

Formula 7G
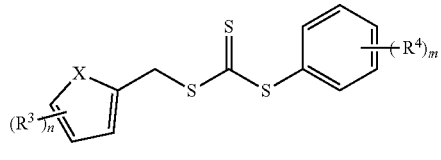

Formula 7H
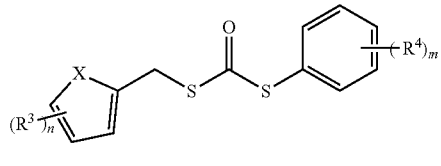

Formula 7I
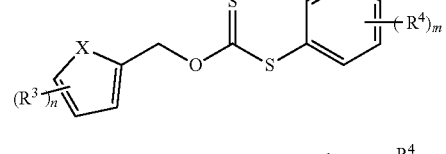

Formula 7J
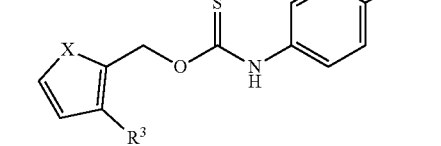

Formula 7K
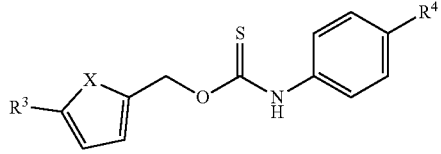

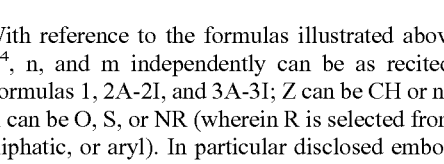

With reference to the formulas illustrated above, each $R^3$, $R^4$, n, and m independently can be as recited above for Formulas 1, 2A-2I, and 3A-3I; Z can be CH or nitrogen; and X can be O, S, or NR (wherein R is selected from hydrogen, aliphatic, or aryl). In particular disclosed embodiments, $R^3$ can be selected from pinocol boronate, —N=C(H)$_2$, —N=C(alkyl)$_2$, —OC(O)(CH$_2$)$_p$CH$_3$ (wherein p is 0-20), alkoxy (e.g., methoxy, ethoxy, propoxy, butoxy), ester (e.g., —OC(O)aliphatic, such as —OC(O)methyl, —OC(O)ethyl, —OC(O)propyl, —OC(O)i-propyl, —OC(O)butyl, —OC(O)t-butyl, —OC(O)i-butyl, and the like), heteroaliphatic ester (e.g., O(CH$_2$)$_r$OCOR$^b$, —S(CH$_2$)$_r$OCOR$^b$, or —NH (CH$_2$)$_r$OCOR$^b$, wherein R$^b$ is aliphatic and r is 1-4), —N$_3$, —F, —Cl, —I, —Br, —NO$_2$, —OTBS, —OTMS, and —SS-pyridyl; and R$^4$ can be selected from —F, —Cl, —Br, —I, morpholinyl (wherein the morpholine group is attached via the nitrogen atom of the morpholine group), alkyl (e.g., methyl, ethyl, propyl, butyl, and the like), and hydrogen. In some embodiments, two or more R$^4$ groups can be joined to form a multicyclic ring system with the phenyl group to which it is attached. Exemplary fused ring systems formed when two R$^4$ groups join together include, but are not limited to methylrhodol, 2-(2-methoxyethyl)-1H-benzo[de]isoquinoline-1,3(2H)-dione, 4-methyl-2H-chromen-2-one.

Exemplary donor compound embodiments are provided below.

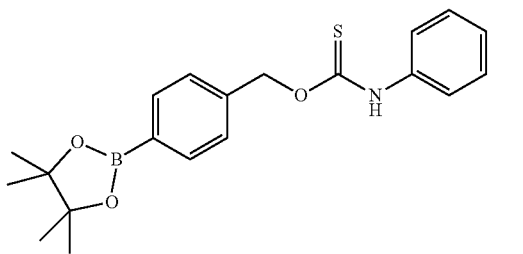
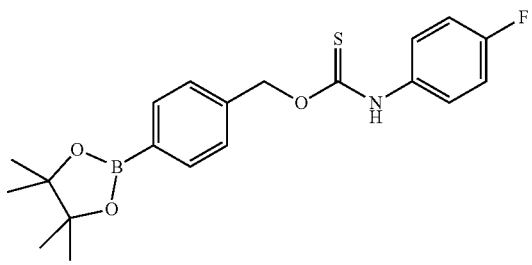
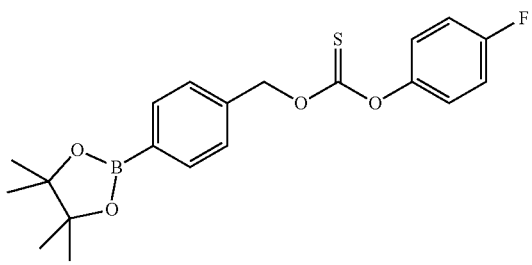
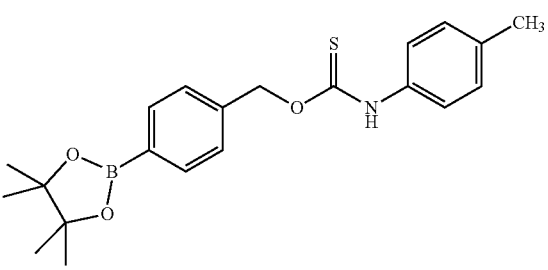
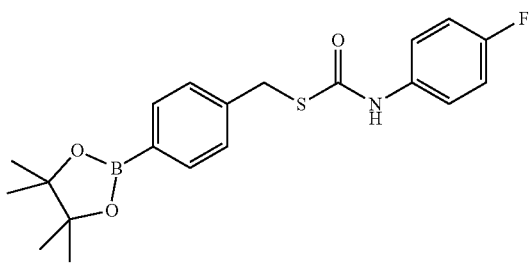
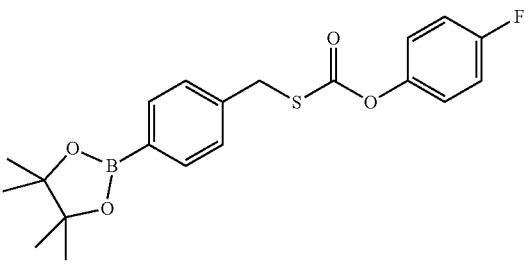
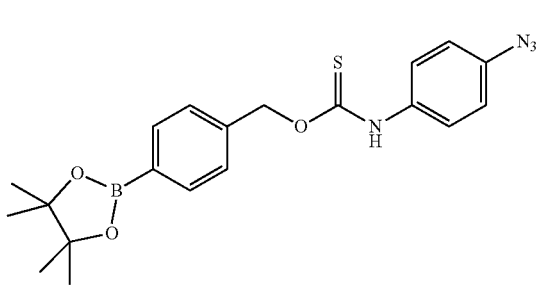
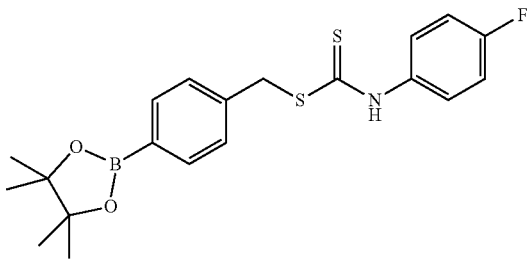
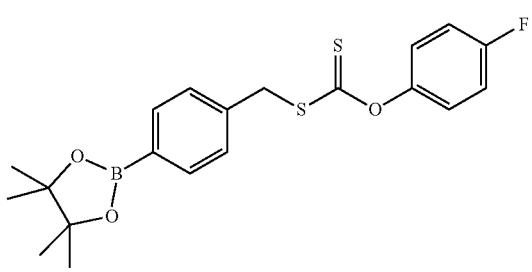
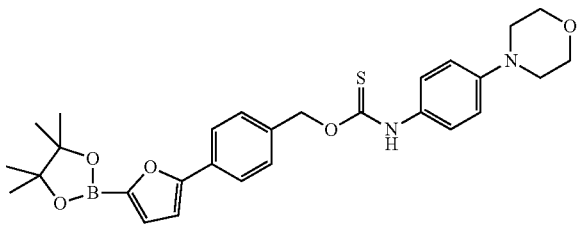

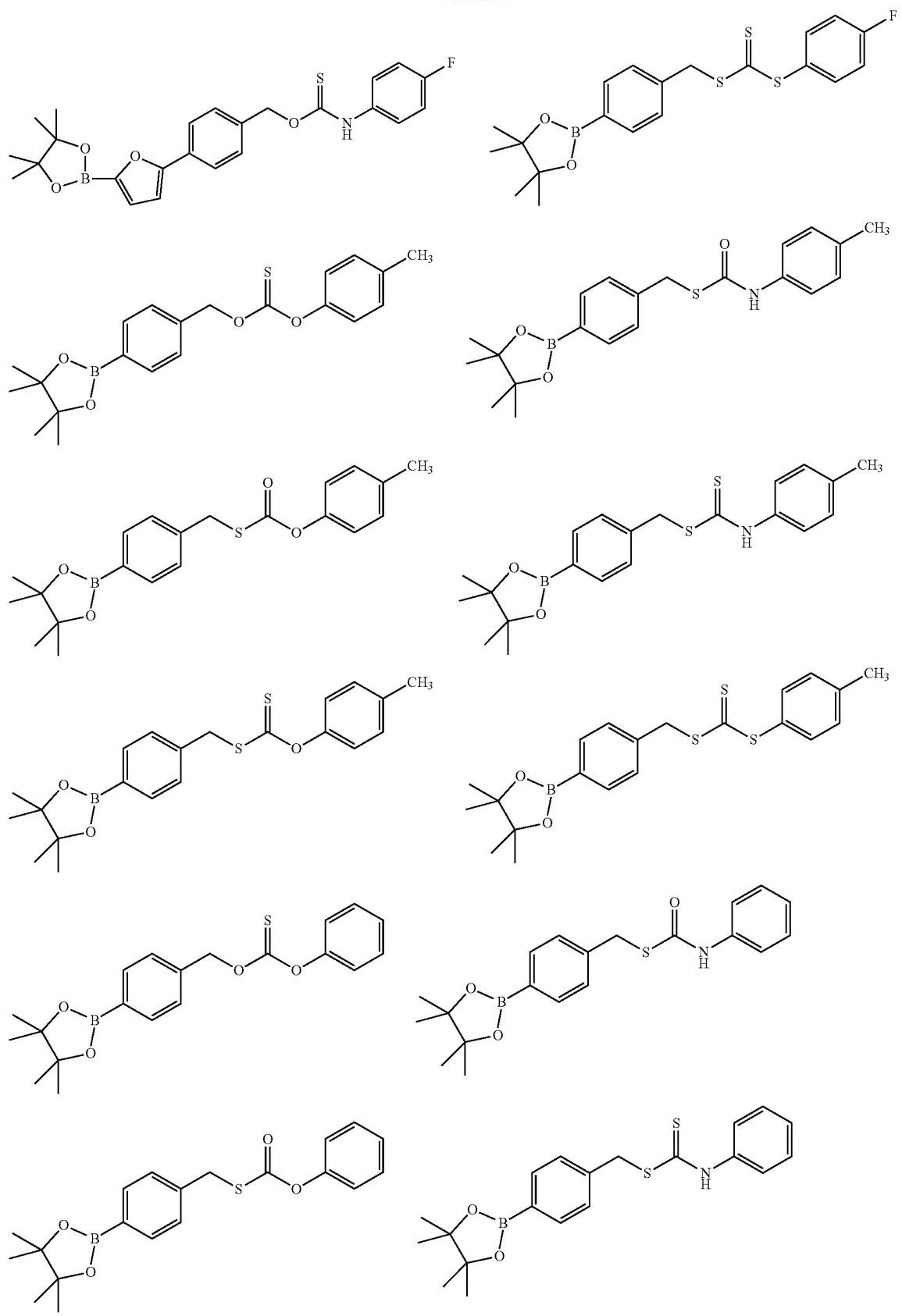

-continued
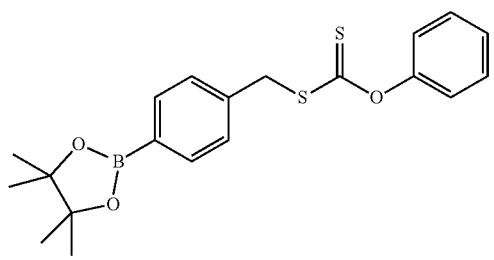
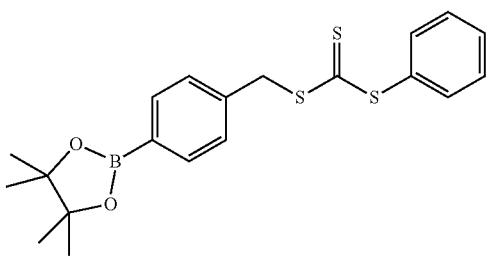
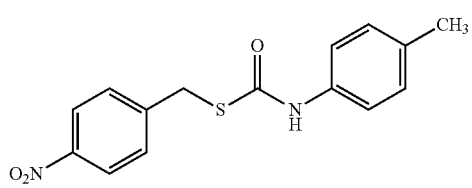
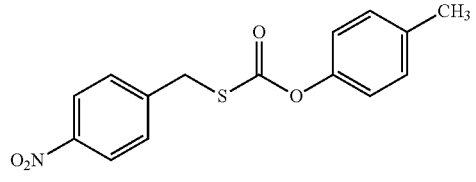
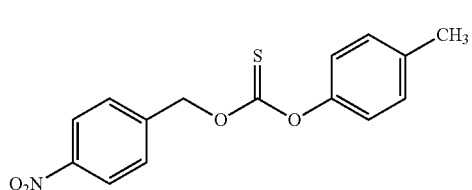
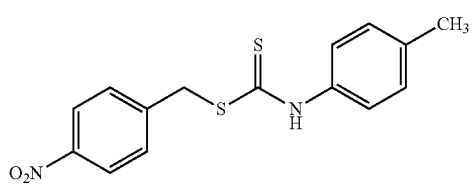
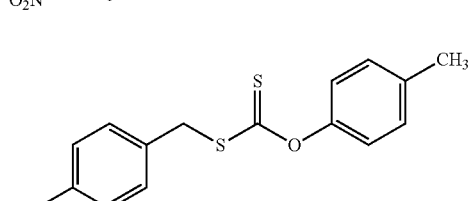
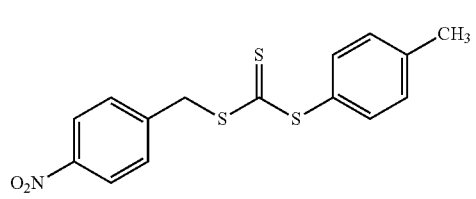
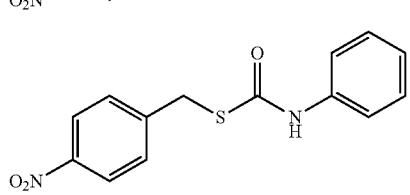
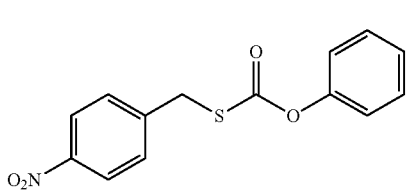
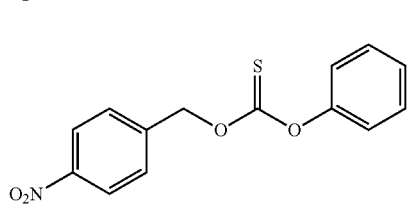
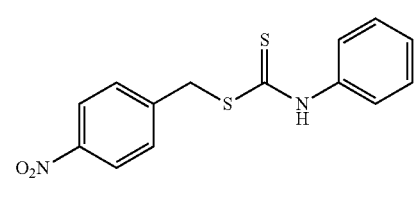
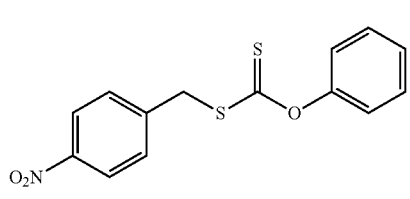
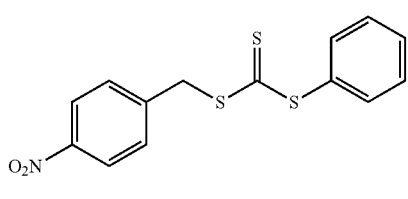
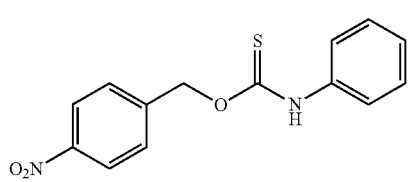
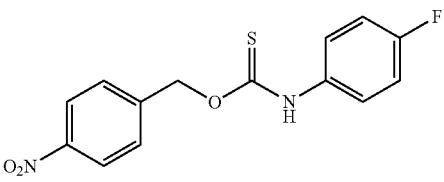

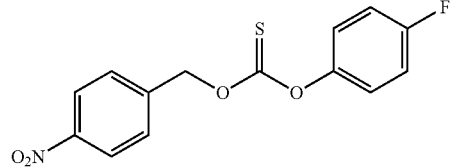
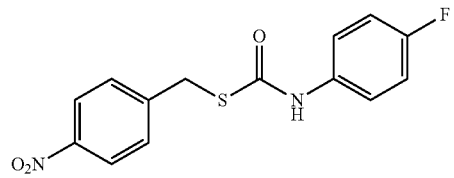
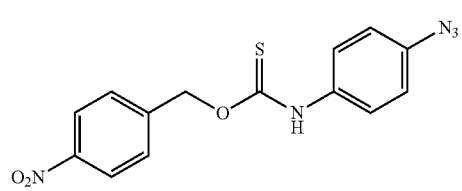
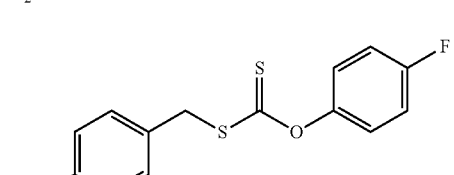
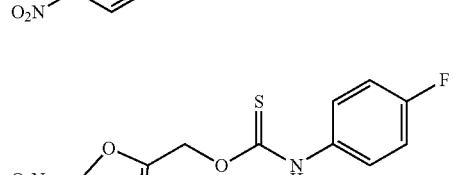
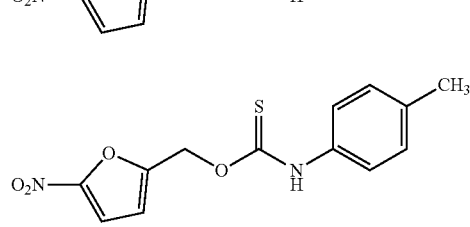
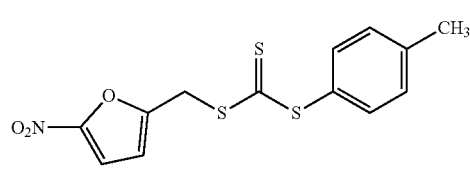
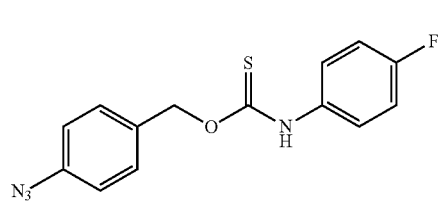
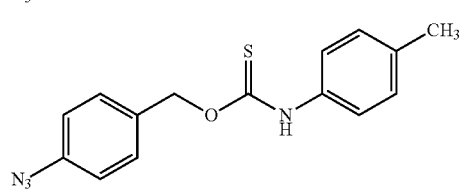
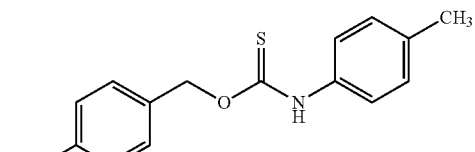
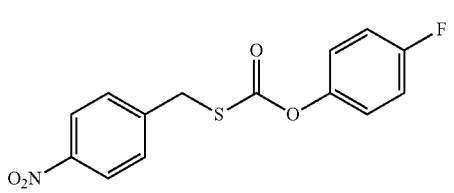
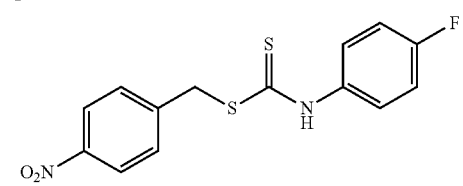
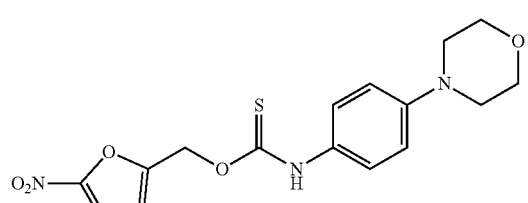
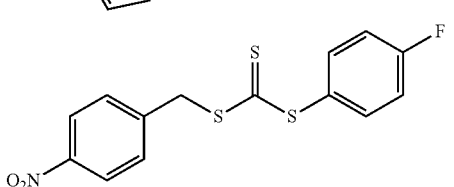
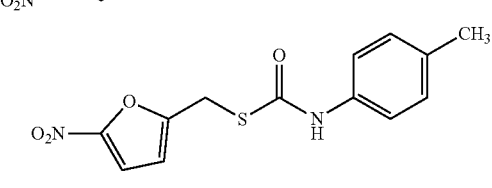
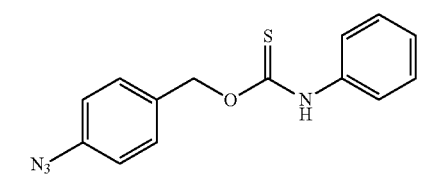
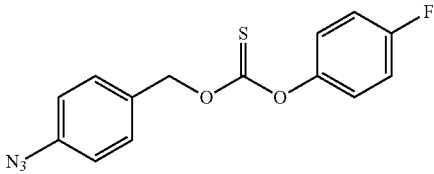
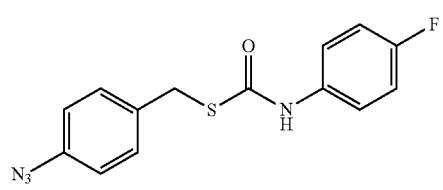

-continued
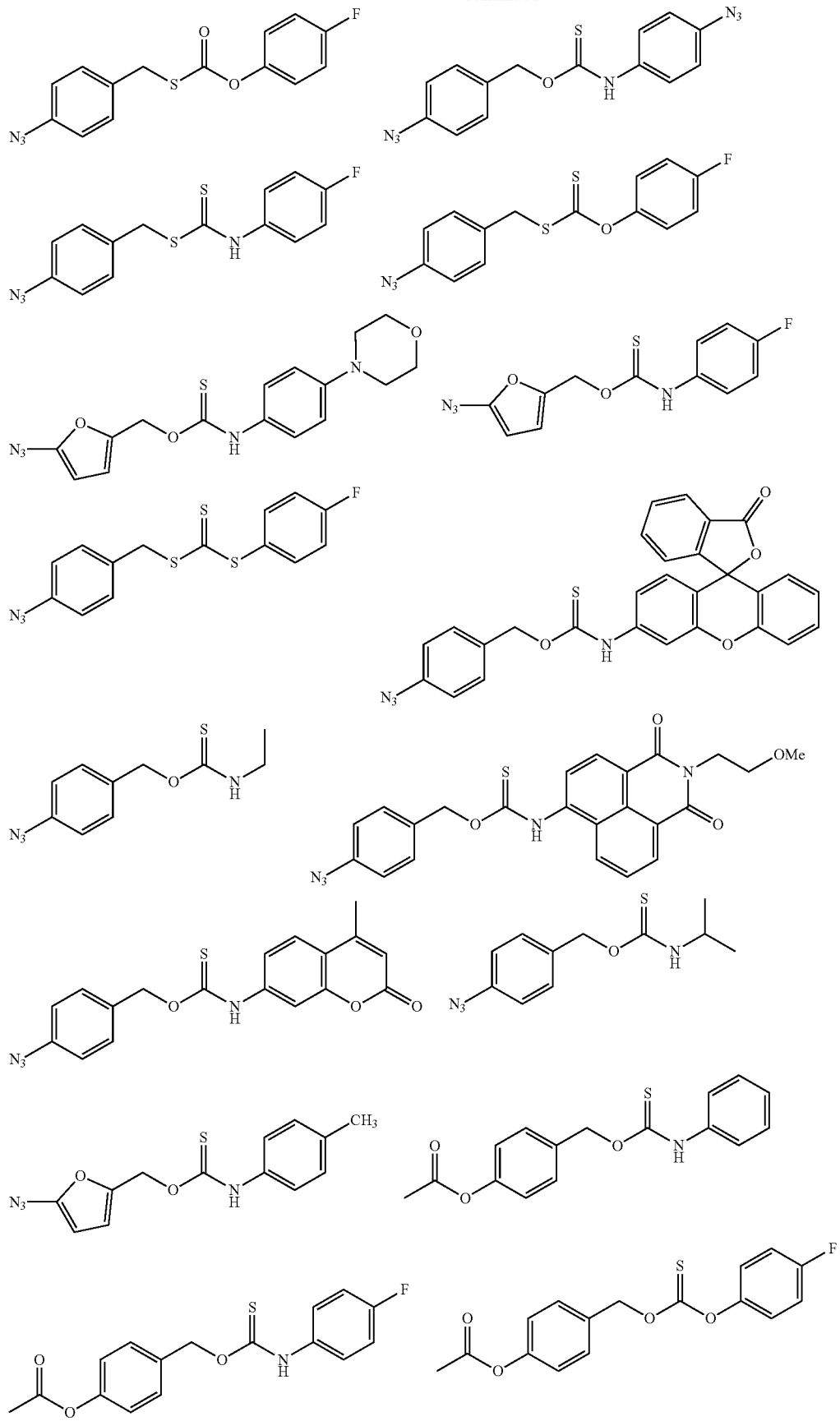

31
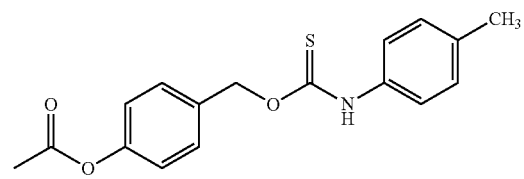
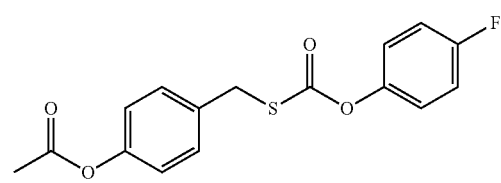
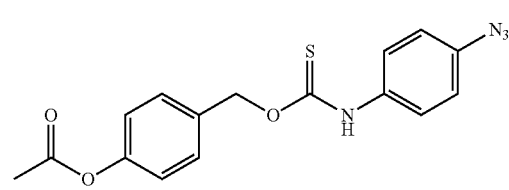
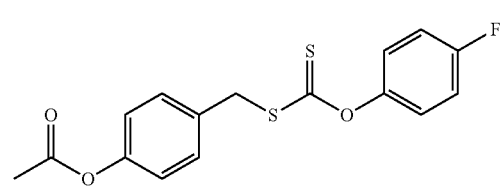
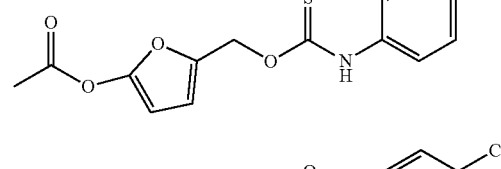
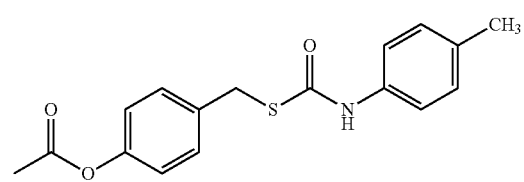
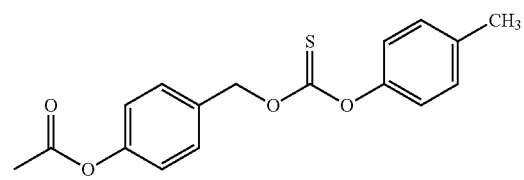
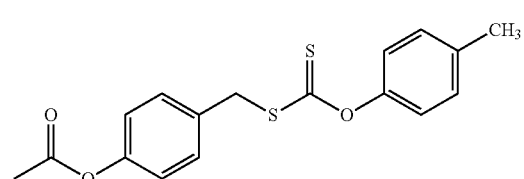
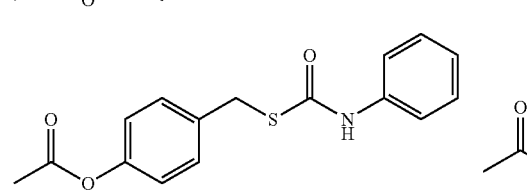
32
-continued
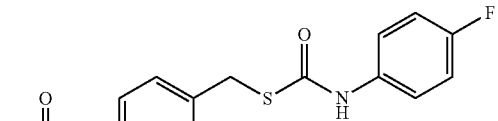
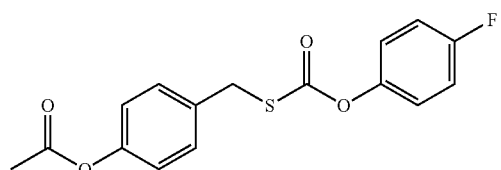
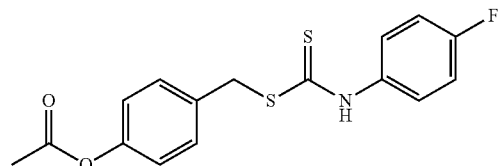
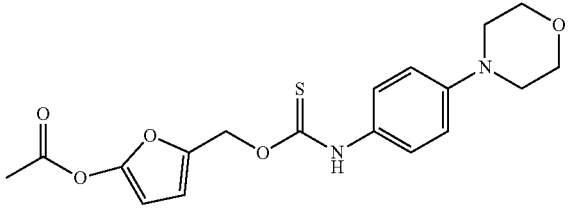
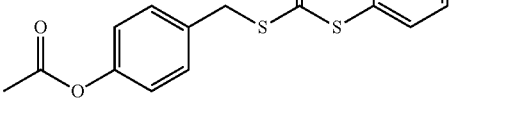
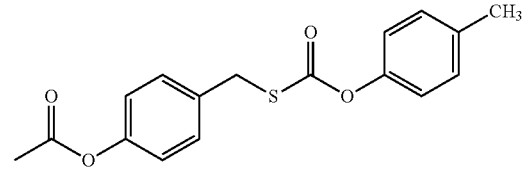
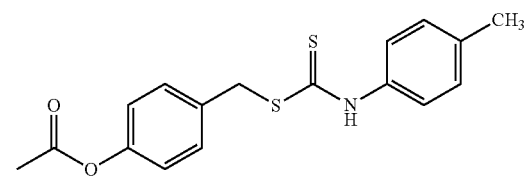
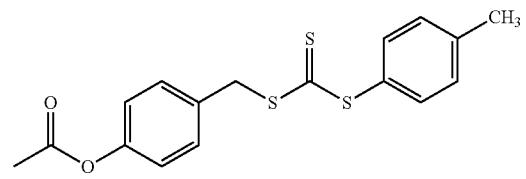
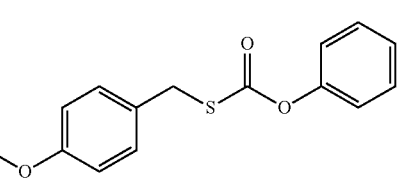

-continued
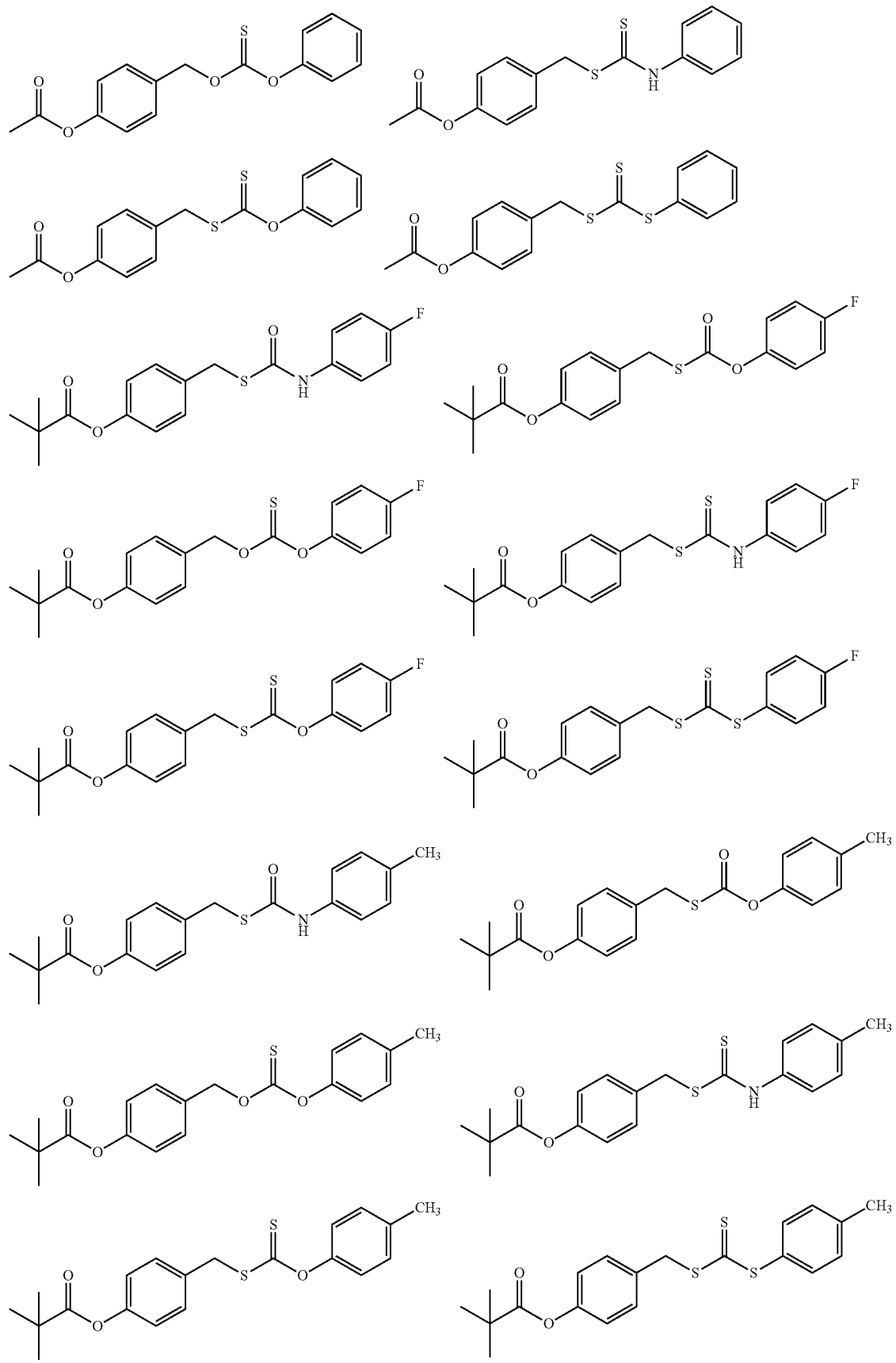

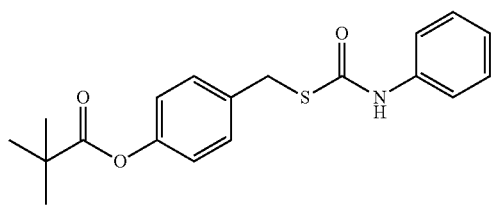
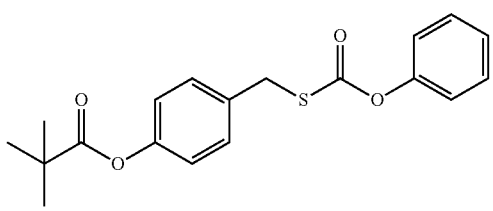
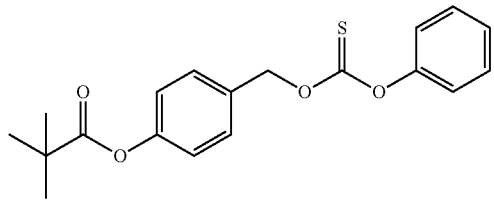
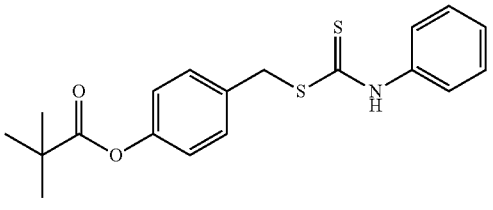
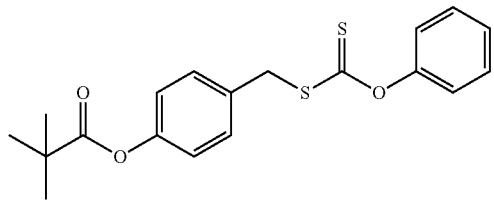
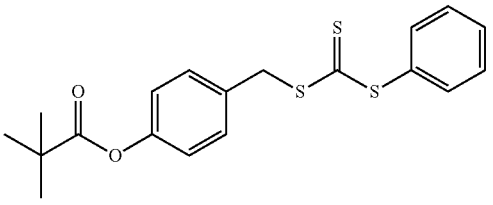
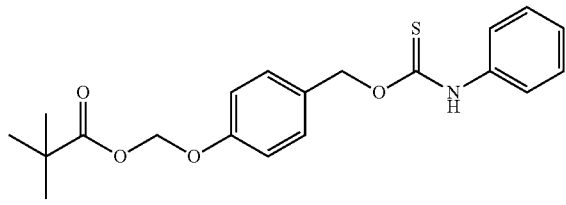
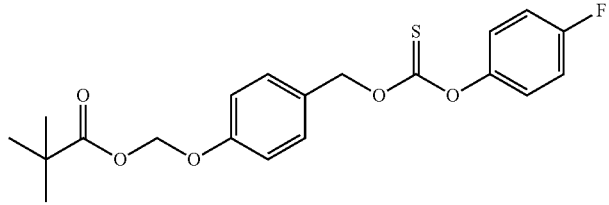
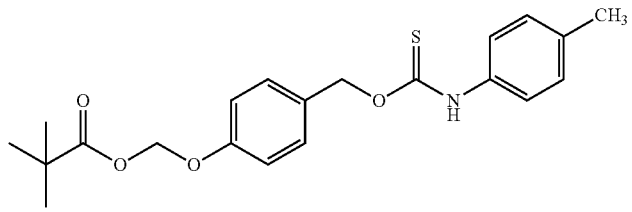
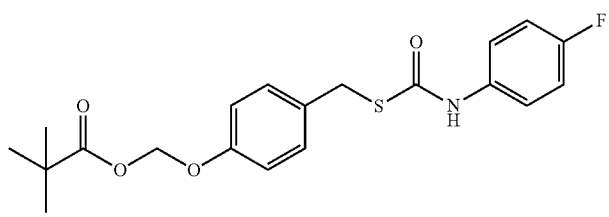
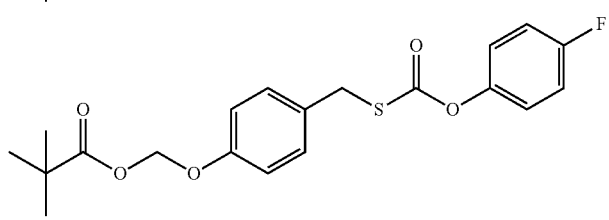

-continued
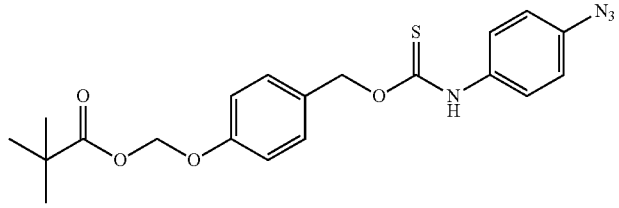
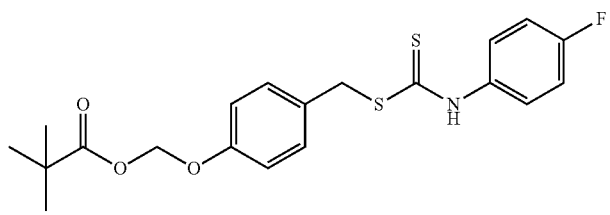
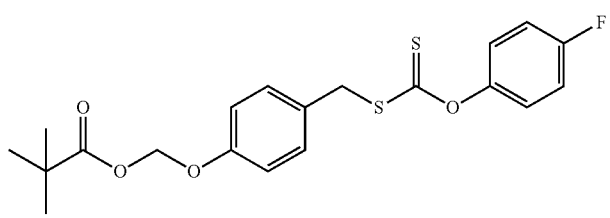
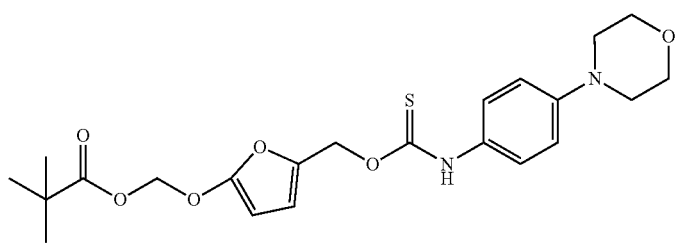
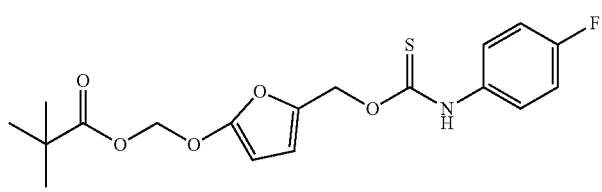
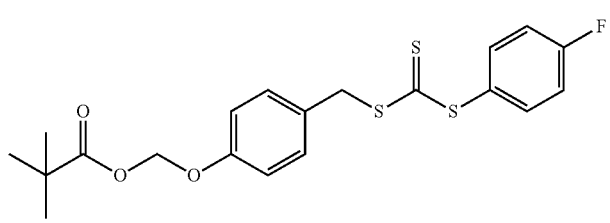
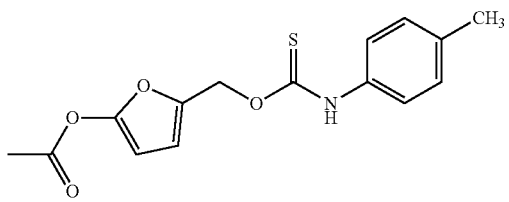
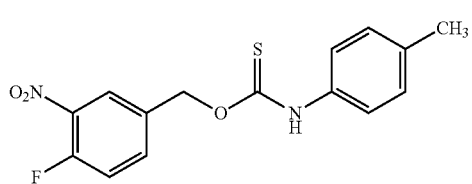
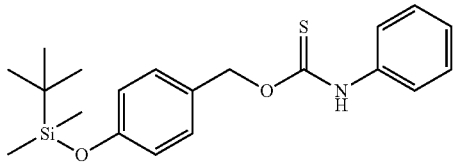
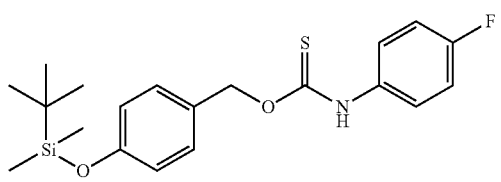
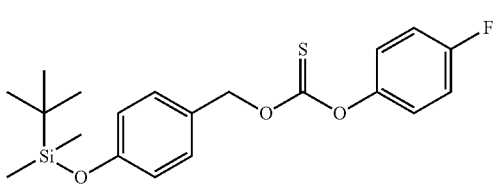

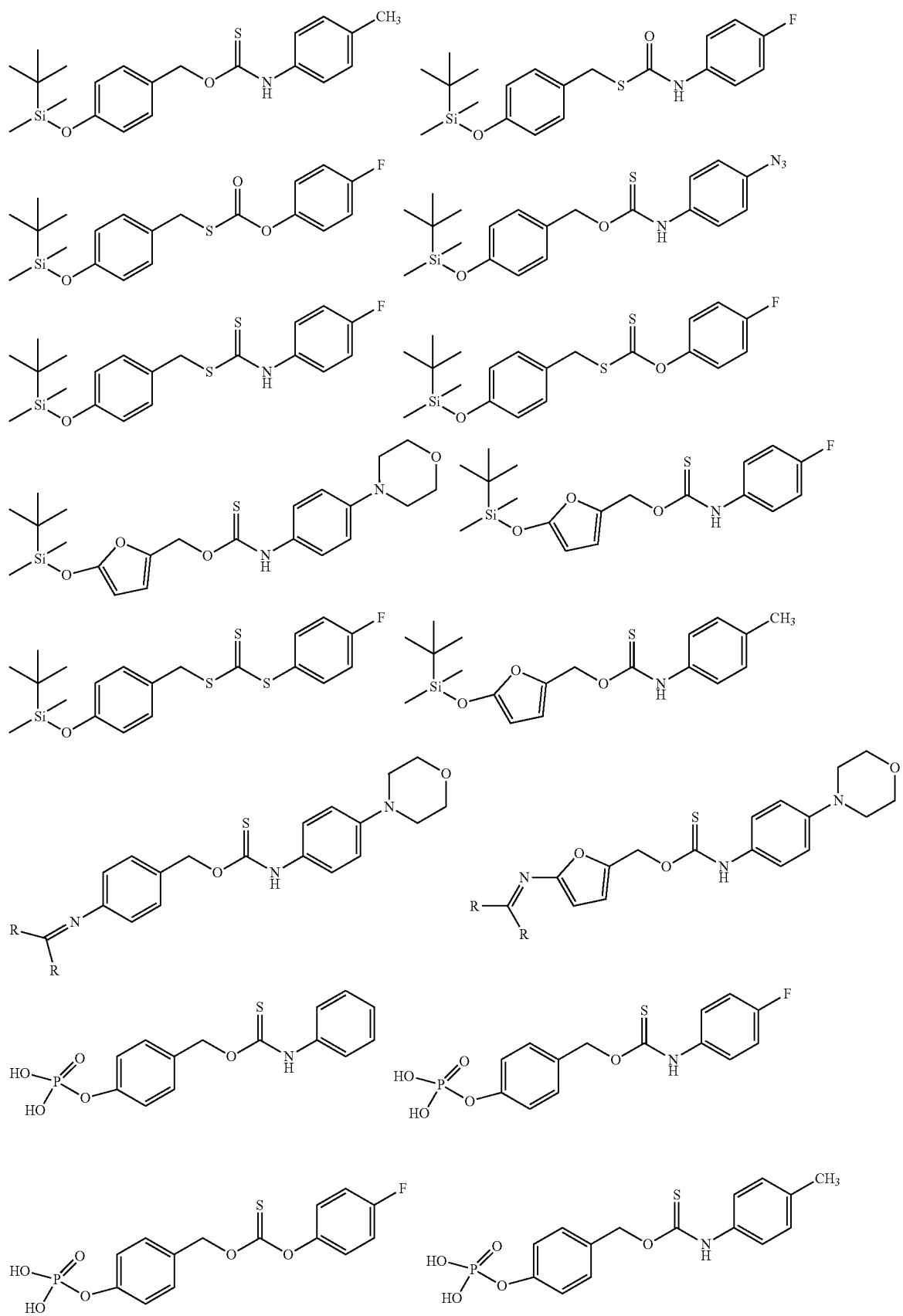

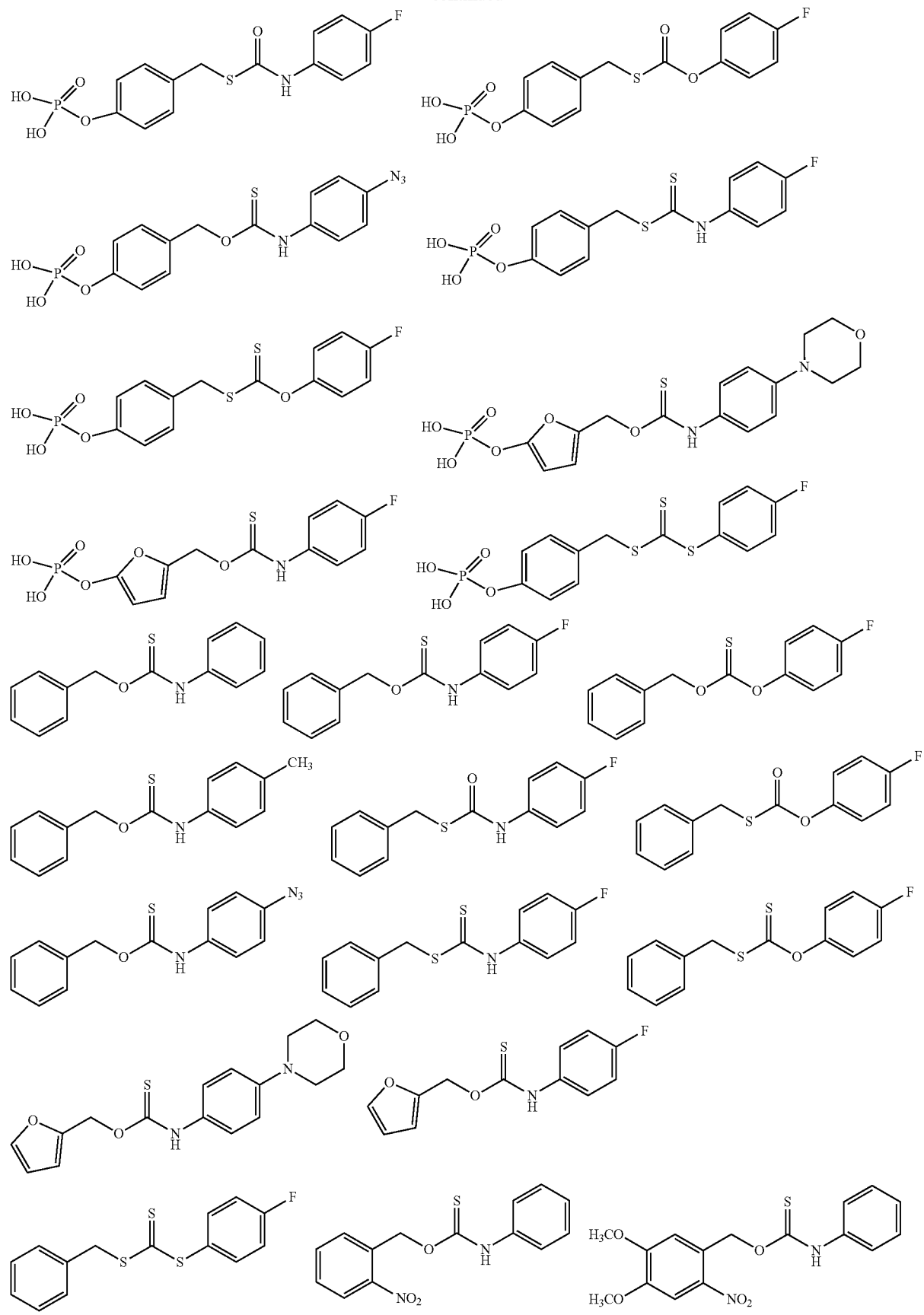

-continued
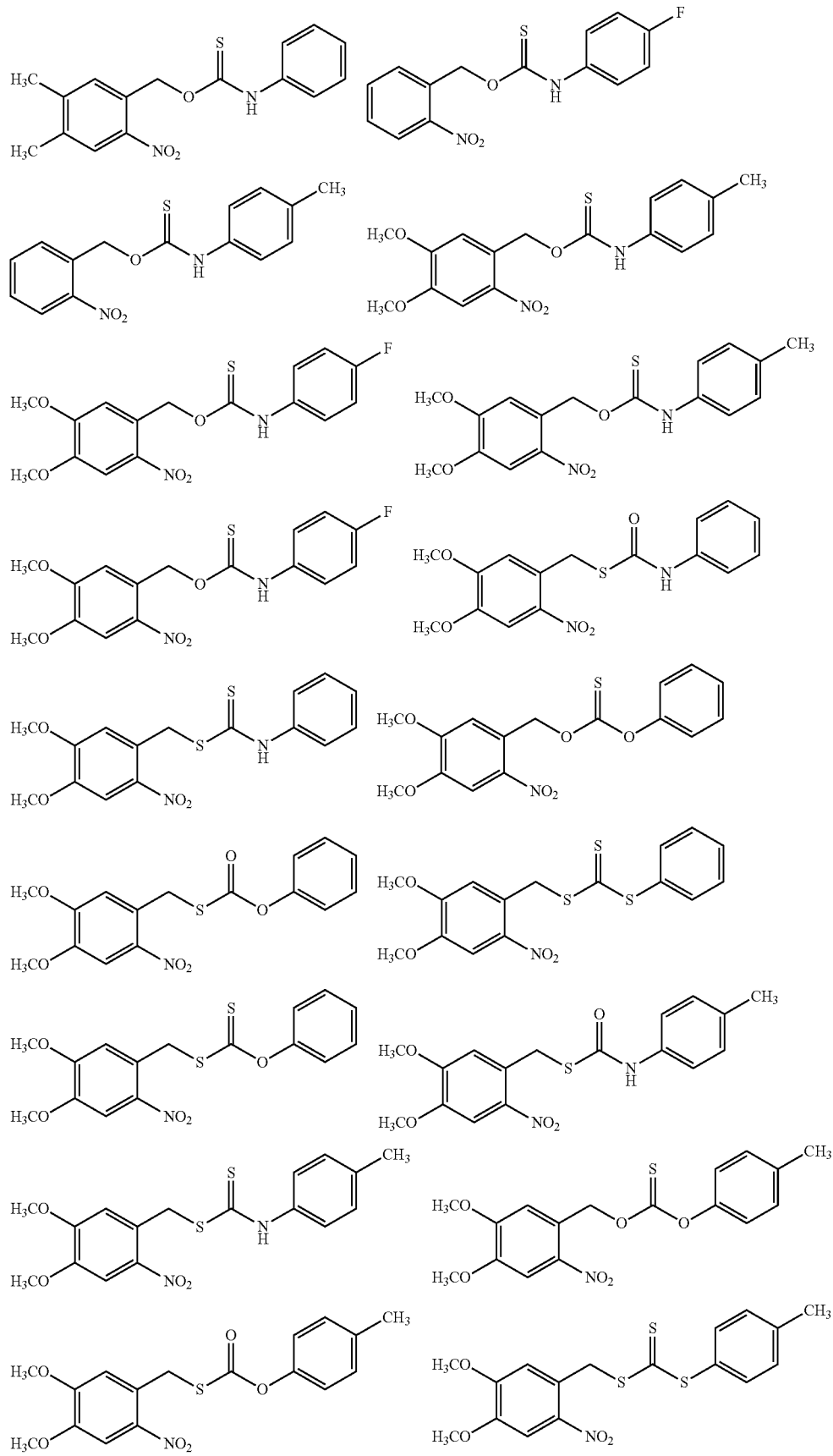

-continued
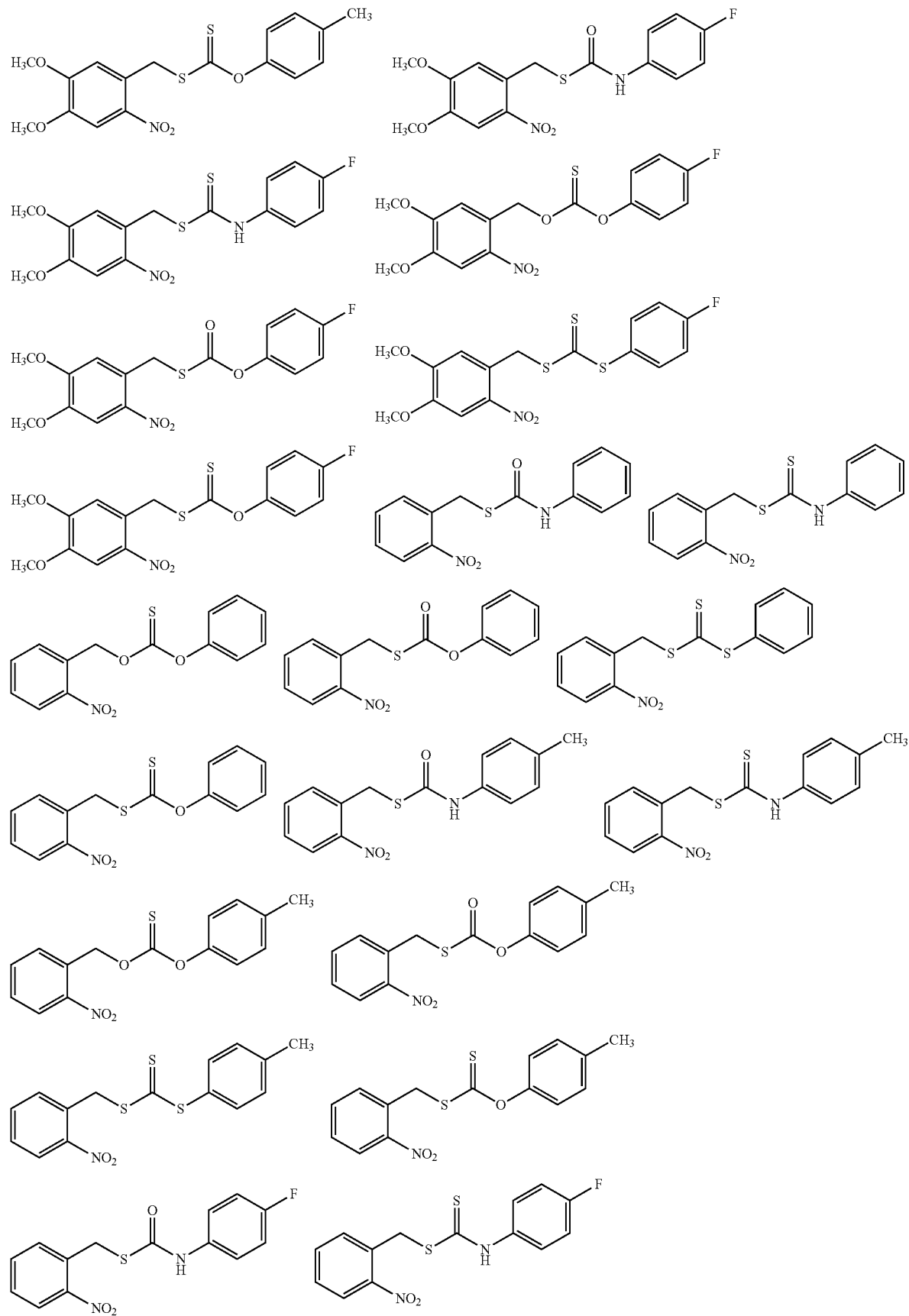

-continued
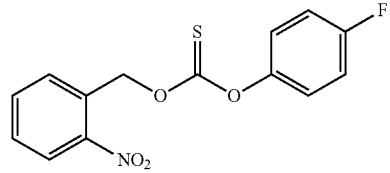
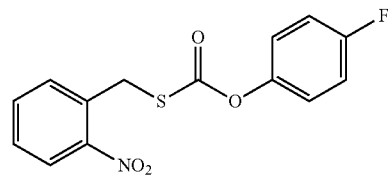
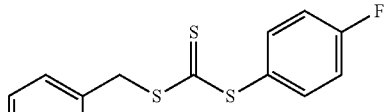
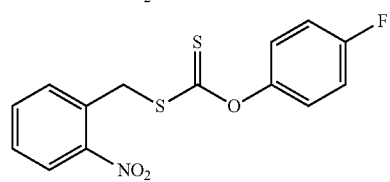
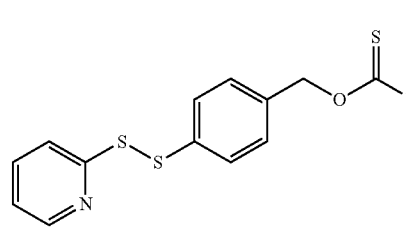
In an independent embodiment, the donor compounds are not, or are other than any of the following:

-continued
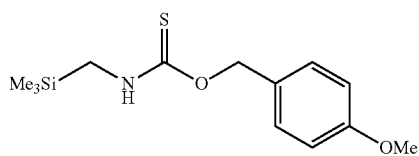
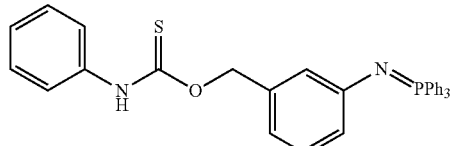
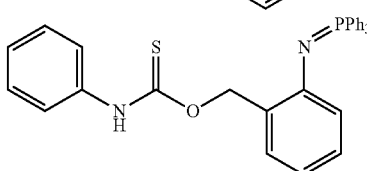
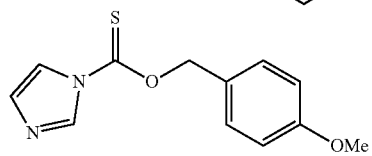
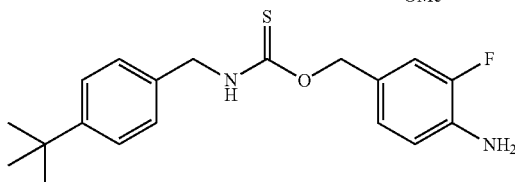
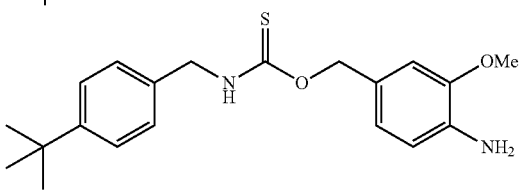
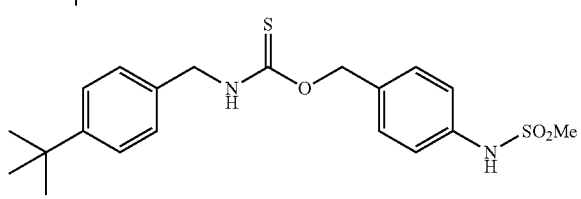
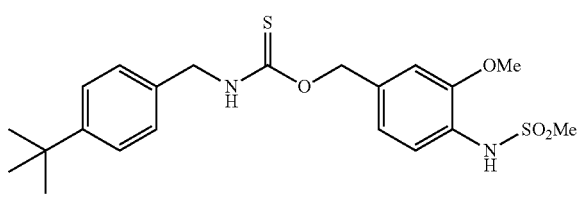
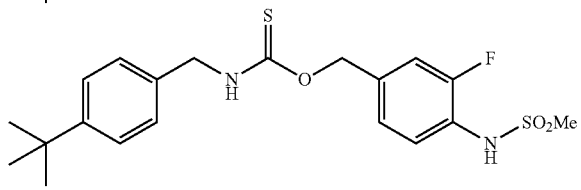
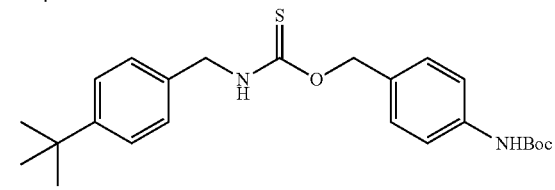
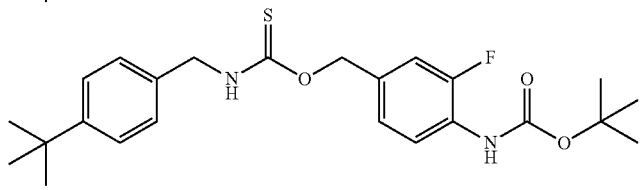
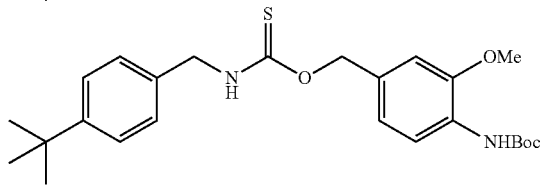
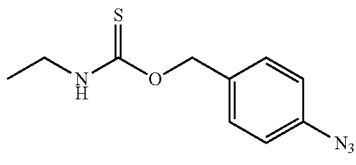

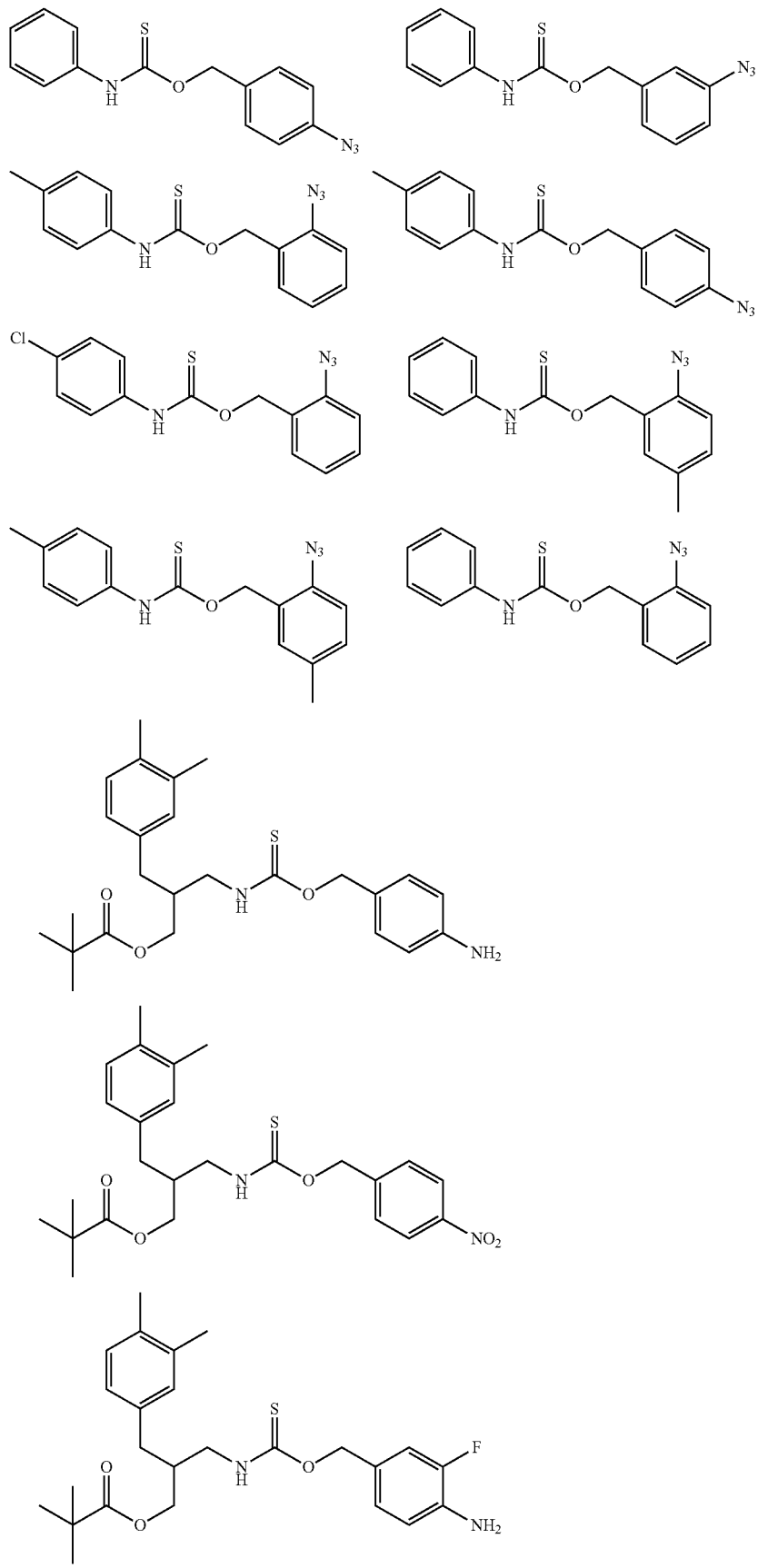

-continued
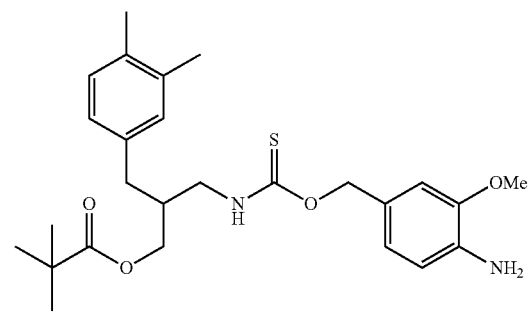
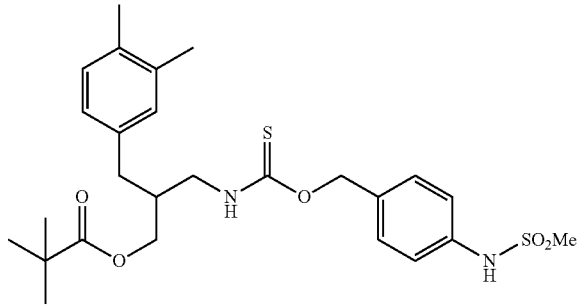
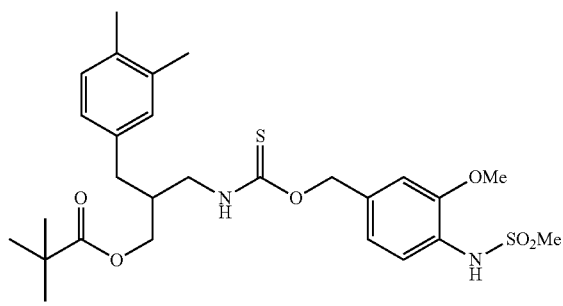
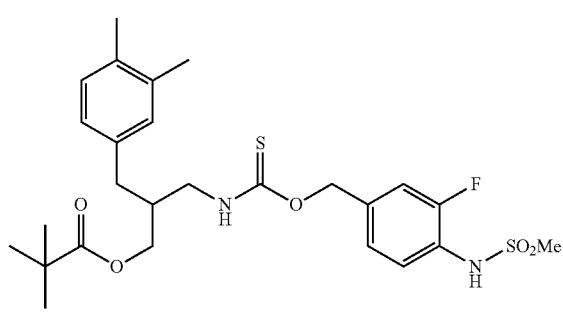
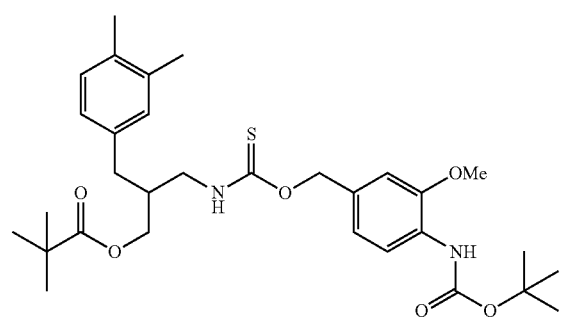

-continued
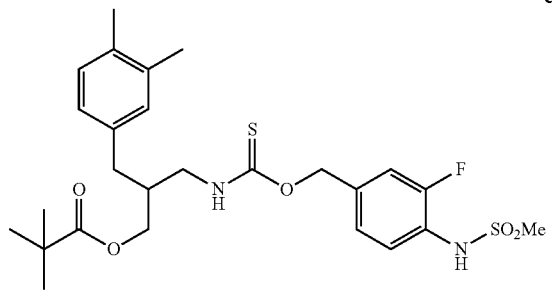
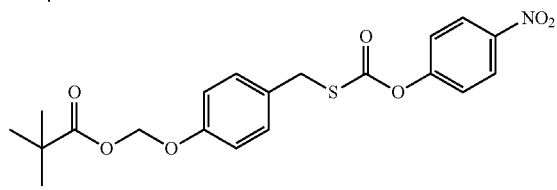
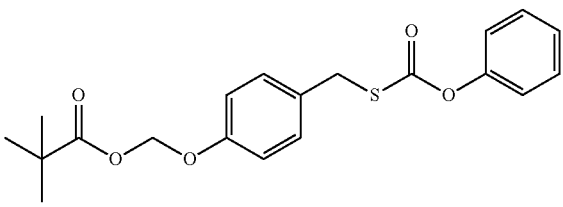
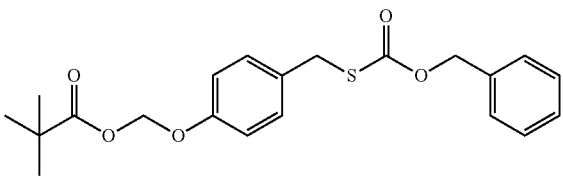
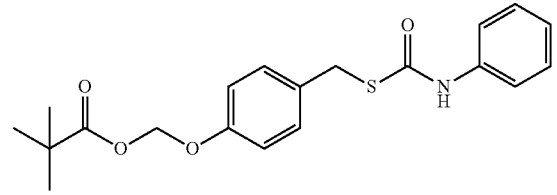
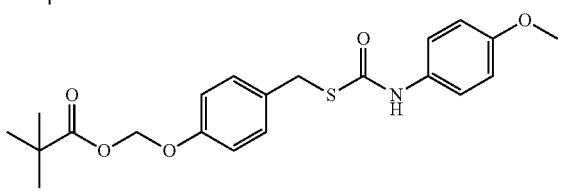
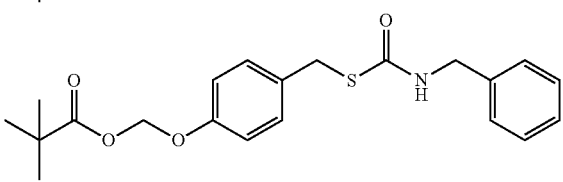
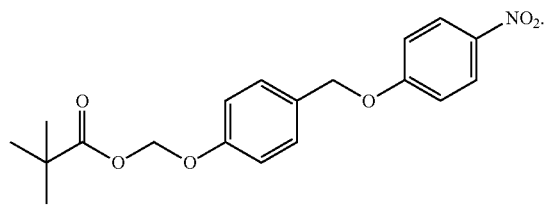

IV. Methods of Making and Using COS/H$_2$S and CS$_2$/H$_2$S Donor/Regenerating Compounds The donor compounds disclosed herein can be made using coupling reactions between hydroxyl-containing compounds (e.g., benzyl phenols, hydroxyl-containing furan, thiophene, or pyrrole compounds) and isothiocyanate-containing compounds (e.g., isothiocyanate-substituted phenyl compounds, isothiocyanate-substituted fluorophores or dyes, or isothiocyanate-substituted aliphatic compounds). Exemplary methods of making donor compounds disclosed herein are provided below in Schemes 1A and 1B. With reference to Schemes 1A and 1B, each of Y, W, V, R$^1$, R$^2$, R$^3$, R$^4$, and n can be as recited herein for the formulas described above.

Scheme 1A

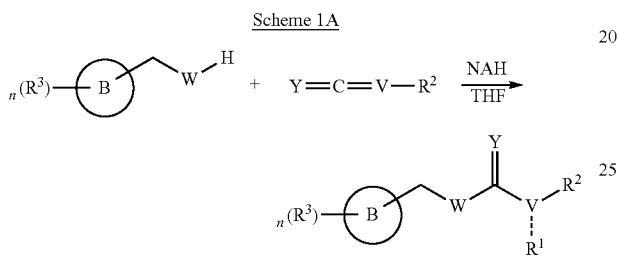

Scheme 1B

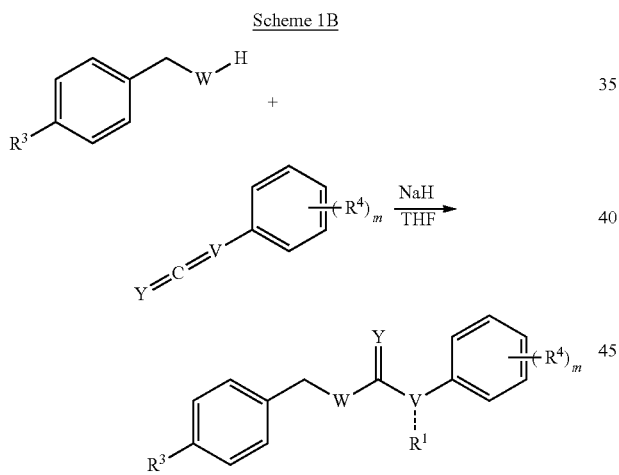

Another exemplary embodiment of a method for making the donor compounds disclosed herein is provided in Schemes 2A and 2B. As shown in Scheme 2B, a fluorophore can be coupled to a phenol starting material to provide the fluorophore-coupled thiocarbamate compound. The method illustrated in Scheme 2B can be used for other fluorophores and/or dyes comprising an amine functional group.

Scheme 2A

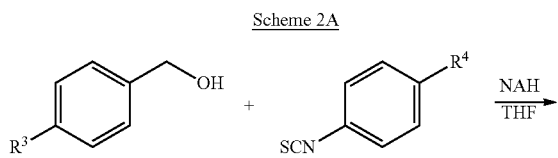

-continued

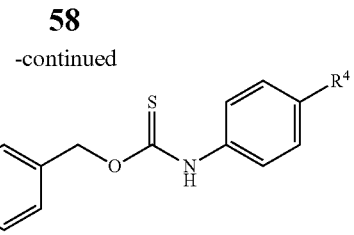

Scheme 2B

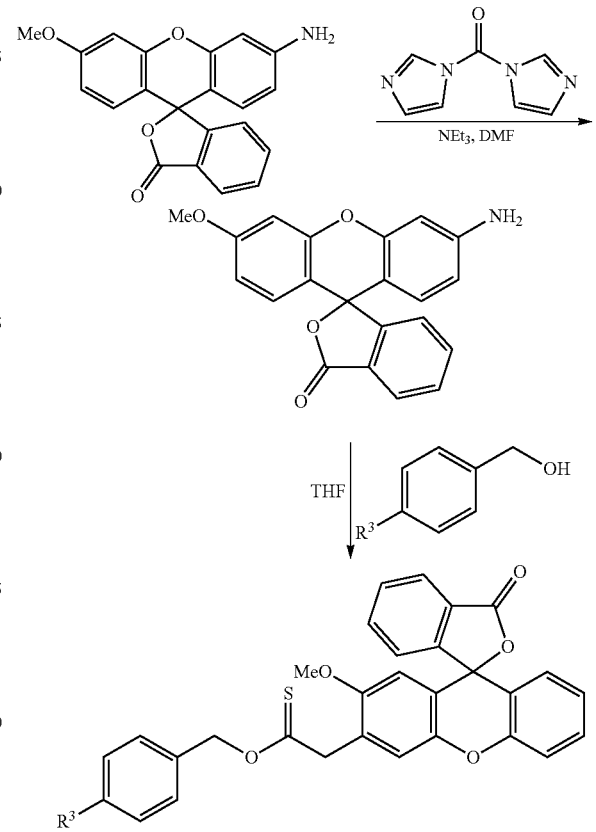

The donor compounds disclosed herein can be used to detect the presence of H$_2$S and/or produce H$_2$S. In contrast to conventional H$_2$S detection/release probes, the donor compounds disclosed herein are capable of releasing COS or CS$_2$, which can then be converted to H$_2$S. As such, the disclosed donor compounds can be used for controlled release of H$_2$S (from COS or CS$_2$ produced from the disclosed donor compounds), which can be triggered by external chemical stimuli. In particular disclosed embodiments, the donor compounds, which can act as COS or CS$_2$ donors, can be used to target diseases in which carbonic anhydrase is overexpressed and/or as therapeutics for diseases associated with H$_2$S misregulation, and therefore are useful in targeted therapy. In such embodiments, a therapeutically effective amount of the donor compound, or a sample comprising the donor compound, can be administered. The donor compounds also can be used as pro-drug conjugates. In yet additional embodiments, the donor compounds disclosed herein can be used to generate a detectable (e.g., fluorescent or colorimetric) signal upon COS or CS$_2$ (or H$_2$S) donation. As such, the rates and quantities of H$_2$S can be measured by evaluating the detectable signal produced by the donor compounds after COS/$H_2S$ release or $CS_2$/$H_2S$ release. The intensity of the detectable signal can be modified to thereby provide the ability to produce different functional donor concentration ranges with the same reaction platform. For example, the intensity can be modified by changing the brightness of the fluorophore or dye attached to the donor compound (e.g., by modifying the fluorophore/dye species and/or by changing the concentration of the donor compound comprising the fluorophore). In yet additional embodiments, the donor compounds disclosed herein can be used to replenish supplies of $H_2S$ as the donor compounds can be chemical tuned to release $H_2S$ upon reaction with $H_2S$ that activates the donor compound, thereby regenerating the $H_2S$.

In particular disclosed embodiments, methods contemplated by the present disclosure can include administering to a sample (or providing) one or more donor compounds having a structure satisfying any one of the formulas described herein and exposing the sample or the donor compound to a reactive compound to release COS, $CS_2$, $H_2S$, or a combination thereof. In some embodiments, exposing the sample or the donor compound to different pH environments can further facilitate COS/$H_2S$ or $CS_2$/$H_2S$ release. In such embodiments, the pH of the sample can be controlled (such as by adding a reactive component selected from an acid or base) to effect COS or $CS_2$ release from the COS/$H_2S$ donor compound or $CS_2$/$H_2S$ donor compound used in the method. Exemplary reactive components include, but are not limited to an oxidant (e.g., $H_2O_2$ and other peroxides, $F_2$, $Cl_2$, $Br_2$, $I_2$, or the like), a reductant (e.g., formic acid, ascorbic acid, dithiothreitol, tris(2-carboxyethyl)phosphine (TCEP), oxalic acid, hydrazine, hydride-based reductants, and the like), an enzyme (e.g., esterases, such as acetylesterases, thioesterases, phosphatases, sulfatases, and the like), a fluoride ($F^-$) source, an acid (e.g., mineral acid, such as sulfuric acid, fluorosulfuric acid, phosphoric acid; sulfonic acids, such as methanesulfonic acid, ethanesulfonic acid, benzenesulfonic acid, tosylic acid, and triflic acid; carboxylic acids, such as acetic acid, citric acid, formic acid, gluconic acid, ascorbic acid, lactic acid, oxalic acid, and tartaric acid; halogenated carboxylic acids, such as fluoroacetic acid and trifluoroacetic acid; or combinations thereof), a base (e.g., lithium hydroxide, sodium hydroxide, potassium hydroxide, cesium hydroxide, and amine-containing bases), a nucleophile, light, or a combination thereof.

In particular disclosed embodiments, an ester group (or a heteroaliphatic ester group) can be used as the triggering group, providing slow-release COS/$H_2S$ donor compounds or $CS_2$/$H_2S$ donor compounds upon ester cleavage by intracellular esterases that do not require consumption of cellular nucleophiles for activation (Scheme 3). By using intracellular esterases to promote cleavage, it is possible to impart cellular trappability, improve membrane permeability, and in the activation of caged pro-drugs and other biological payload. Additionally, activation by intracellular esterases eliminates the consumption of cellular nucleophiles for activation.

Scheme 3

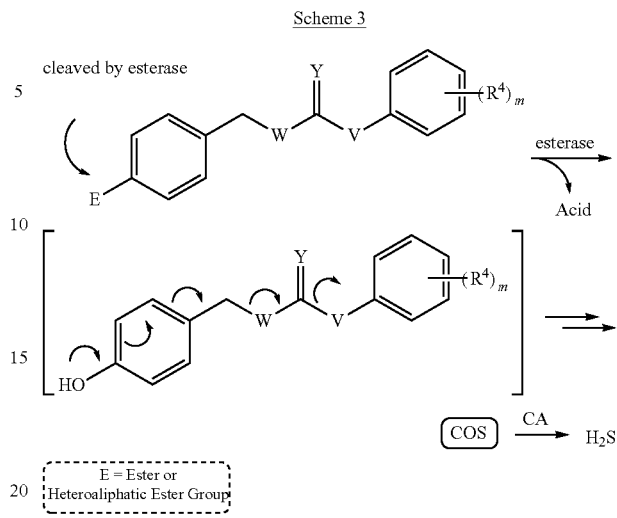

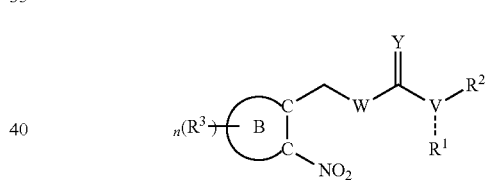

In additional embodiments, light can be used to initiate COS or $CS_2$ and $H_2S$ formation from donor compounds disclosed herein. In such embodiments, the donor compounds can comprise functional group capable of being activated by exposure to light. For example, the donor compounds can comprise a nitro group, ketone group, or other photoactivatable groups. In particular disclosed embodiments, the donor compounds comprise at least one $R^3$ group that is a nitro functional group and that is located at a position on Ring B that is ortho to Ring B's connection to a "W" group (as illustrated below).

By exposing the donor compounds to light, the nitro group, ketone group, or other photoactivatable group will promote cleavage of Ring B to provide intermediate 400, which can then react to provide COS or $CS_2$, as illustrated below in Scheme 4. The COS or $CS_2$ can then be exposed to a reactive component to provide $H_2S$ as illustrated and discussed below. In particular disclosed embodiments, UV light can be used to trigger COS or $CS_2$ release from the donor compounds described herein. For example, light having wavelengths ranging from 250 nm to 450 nm can be used, such as 300 nm to 400 nm, or 325 nm to 350 nm.

Scheme 4

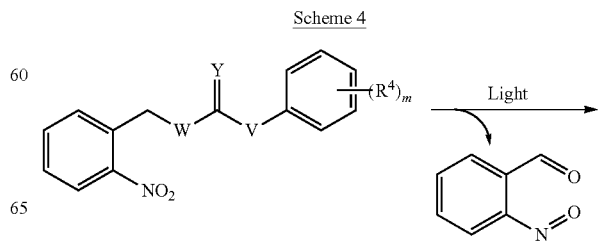

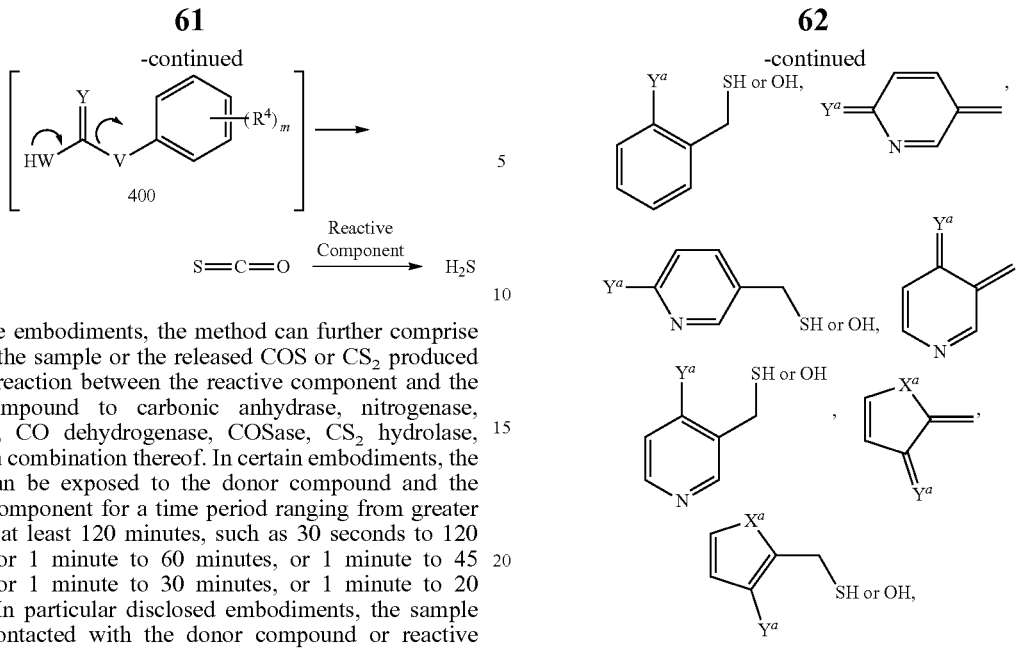

$$S{=}C{=}O \xrightarrow{\text{Reactive Component}} H_2S$$

In some embodiments, the method can further comprise exposing the sample or the released COS or $CS_2$ produced from the reaction between the reactive component and the donor compound to carbonic anhydrase, nitrogenase, RuBisCO, CO dehydrogenase, COSase, $CS_2$ hydrolase, water, or a combination thereof. In certain embodiments, the sample can be exposed to the donor compound and the reactive component for a time period ranging from greater than 0 to at least 120 minutes, such as 30 seconds to 120 minutes, or 1 minute to 60 minutes, or 1 minute to 45 minutes, or 1 minute to 30 minutes, or 1 minute to 20 minutes. In particular disclosed embodiments, the sample can be contacted with the donor compound or reactive component at a certain pH, such as greater than 0 to at least 12, such as 3 to 12, or 6 to 9, or 7 to 7.8, or 7 to 7.4. The pH can be maintained using an appropriate buffer, such as a phosphate buffer (e.g., 3-{[tris(hydroxymethyl)methyl]amino} propanesulfonic acid, tris(hydroxymethyl)methylamine, 4-2-hydroxyethyl-1-piperazineethanesulfonic acid, 2-{[tris(hydroxymethyl)methyl]amino}ethanesulfonic acid, piperazine-N,N'-bis(2-ethanesulfonic acid), or the like). In some embodiments, the sample can be further analyzed to determine the progress or completion of the reaction between the donor compound and the reactive component and/or to measure the amount of COS or $CS_2$ or $H_2S$ produced by the reaction. Such embodiments can comprise detecting a color change or fluorescent signal produced by a reaction product formed from the reaction, such as an amine-terminated fluorophore or amine-terminated dye. Such embodiments also can further comprise exposing the sample to a reagent that facilitates analytical measurement of sulfide, such as monobromobimane (mBB) or methylene blue (MB).

In some embodiments, the method of using the donor compounds described herein can comprise administering to a sample one or more donor compounds having a structure satisfying any of the formulas described herein, exposing the sample to $H_2S$ or another type of RSON species to form a composition comprising an amine-terminated by-product, COS or $CS_2$, a cyclic by-product having a formula selected from:

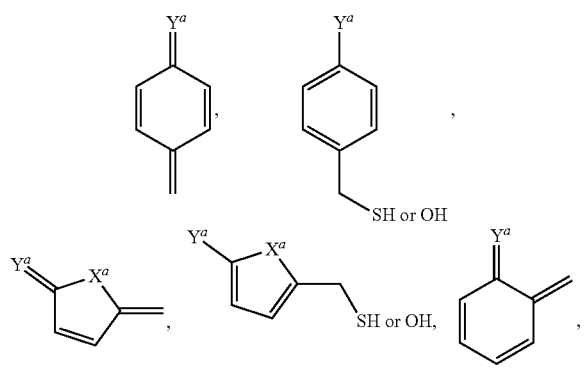

or any combination thereof, wherein each $Y^a$ and $X^a$ independently is selected from oxygen, NH, or sulfur; or any combination of the amine-terminated by-product, the COS or $CS_2$, and the cyclic by-product. In some embodiments, the method can further comprise exposing the composition to $H_2O$ or carbonic anhydrase to regenerate $H_2S$. In some embodiments, the donor compounds, when exposed to $H_2S$ (or another RSON species) or other reactive component, such as those described herein, can produce a mixture of by-products. The mixture of by-products, in some embodiments, can comprise one or more of an amine-terminated by-product, COS or $CS_2$, or a cyclic by-product as described herein (or a combination of two or more cyclic by-products). In some embodiments, the composition comprises two or more of an amine-terminated by-product, COS or $CS_2$, or a cyclic by-product as described herein (or a combination of two or more cyclic by-products).

An exemplary embodiment of using the disclosed donor compounds to produce $H_2S$ using oxidative stress activation is shown below in Scheme 5.

Scheme 5

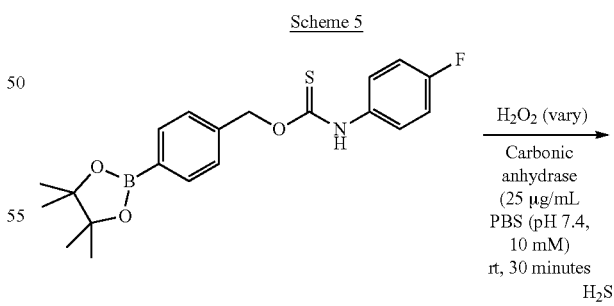

In particular disclosed embodiments, the donor compounds disclosed herein can be converted to various by-products. In some embodiments, the donor compounds can be converted to a mixture of any of these by-products. Exemplary methods and mechanisms for the reaction process are illustrated below in Schemes 6A, 6B, 7A, 7B, 8, and 9. Schemes 6A, 6B, 7A, 7B, 8, and 9 also illustrate the types of by-products that can be obtained using the donor compounds and methods described herein. The presence of such by-products can be determined using, for example, an $H_2S$ electrode, NMR ($^1H$, $^{13}O$, or $^{19}F$ NMR), and/or fluorescent or colorimetric detection methods.
Scheme 6A
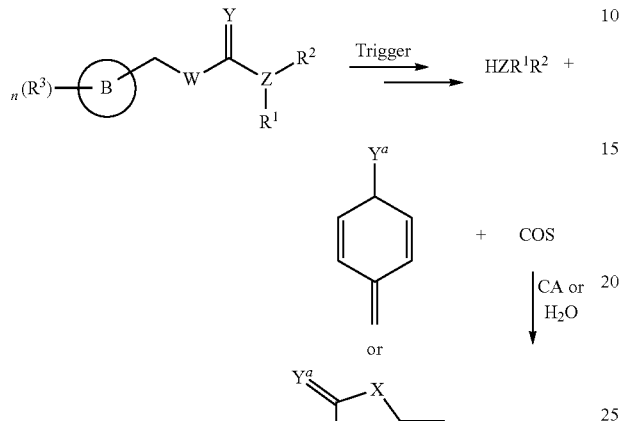
Scheme 6B
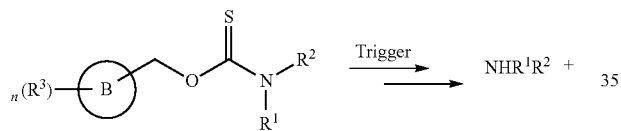
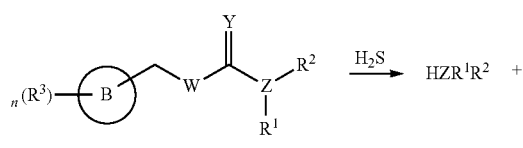
Scheme 7A
Scheme 7B
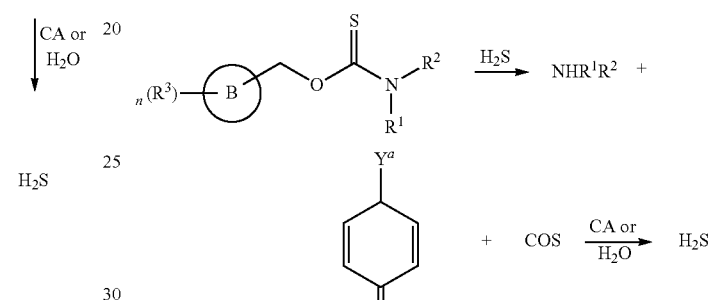
Scheme 8
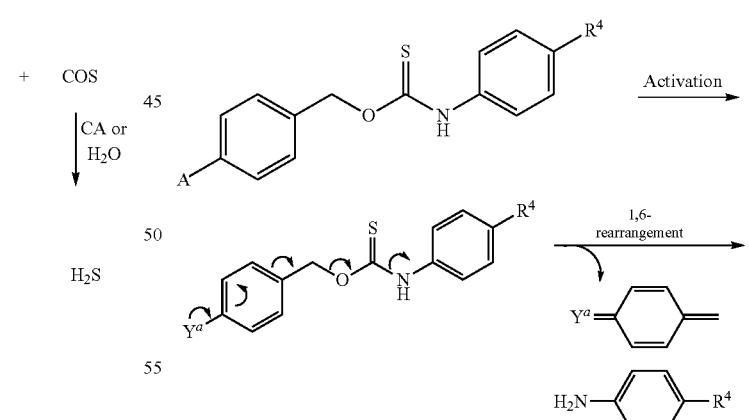
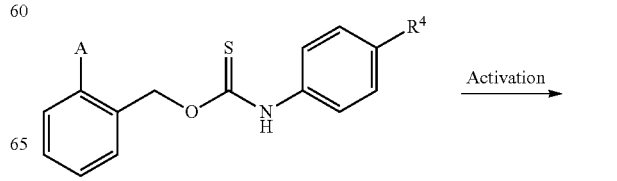

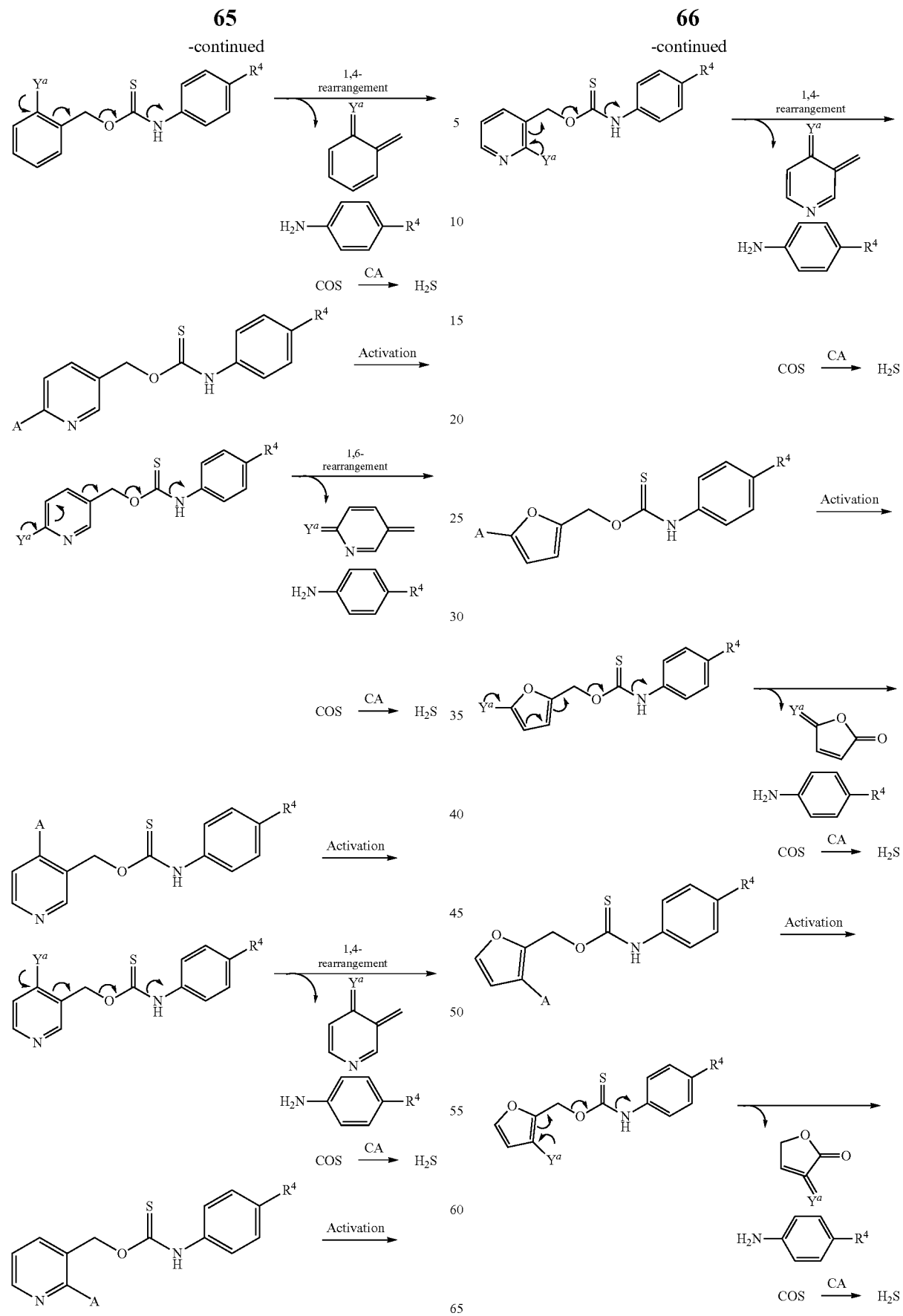

Scheme 9

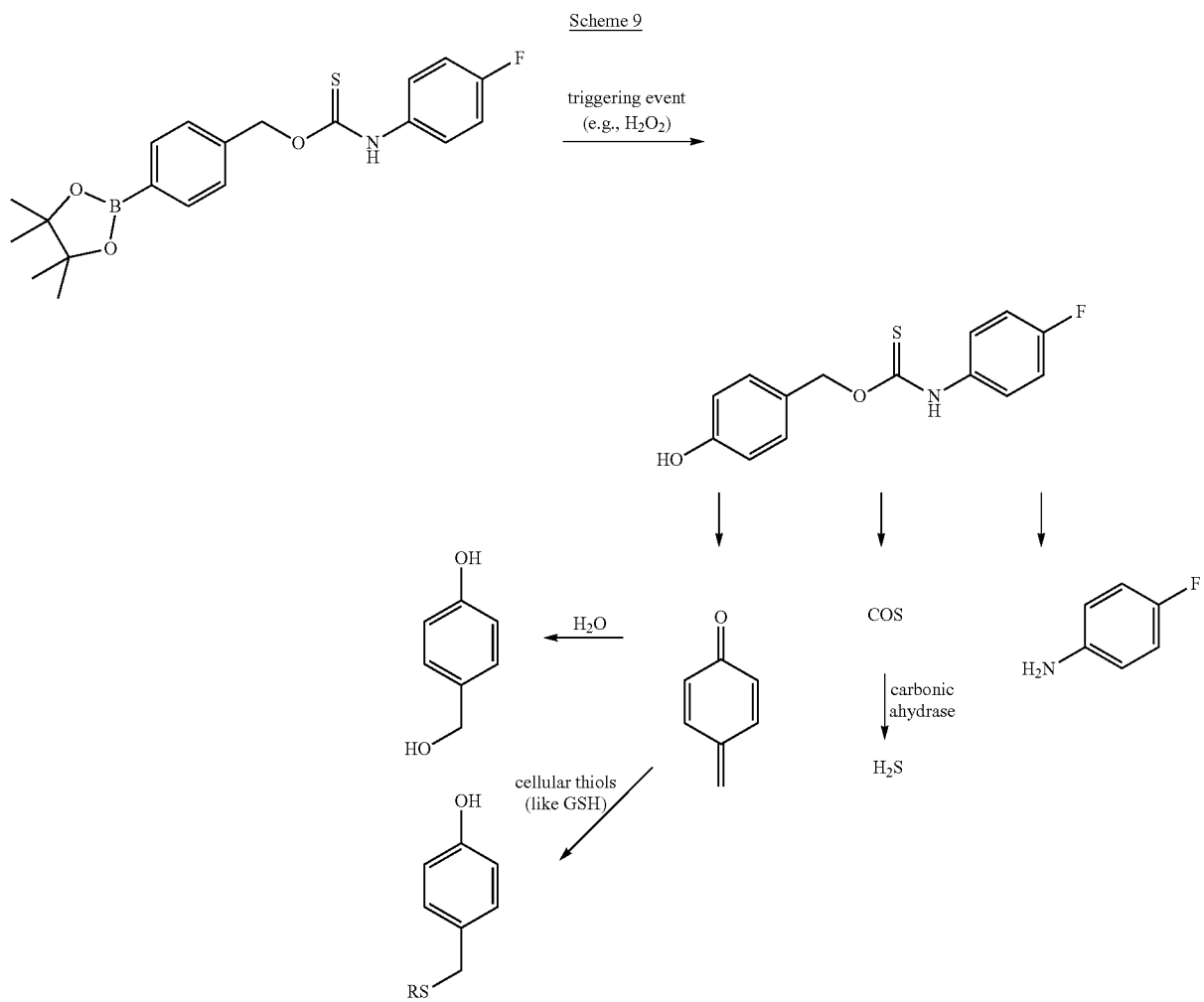

Also disclosed herein are kits comprising the donor compounds described herein. In some embodiments, the kit comprises a donor compound having a structure satisfying any of the formulas provided herein and a filter, a multi-well plate, a test strip, a slide, a disc, a container, or combination thereof. In some embodiments, the kit can further comprise an enzyme, carbonic anhydrase, water, solubilizing agents, or a combination thereof.

V. Examples

Materials and Methods.

Reagents were purchased from Sigma-Aldrich or Tokyo Chemical Industry (TCI) and used as received. p-Azidobenzylalcohol, O-(4-azidobenzyl)-N-tolylthiocarbamate, methylrhodol, and COS gas were synthesized as previously reported. Spectroscopic grade, inhibitor-free THF was deoxygenated by sparging with argon followed by passage through a Pure Process Technologies solvent purification system to remove water and then stored over 4 Å molecular sieves in an inert atmosphere glove box. Deuterated solvents were purchased from Cambridge Isotope Laboratories and used as received. Silica gel (SiliaFlash F60, Silicycle, 230-400 mesh) was used for column chromatography. Preparatory chromatography was performed on Silicycle SiliaPlates (1 mm thickness). $^1$H, $^{13}$C{$^1$H}, and $^{19}$F NMR spectra were recorded on a Bruker 600 MHz instrument. Chemical shifts are reported in ppm relative to residual protic solvent resonances. $H_2S$ electrode data were acquired with a World Precision Instruments (WPI) ISO-$H_2$S-2 sensor connected to a TBR4100 Free Radical Analyzer. Fluorescence spectra were obtained on a Quanta Master 40 spectrofluorometer (Photon Technology International) equipped with a Quantum Northwest TLC-50 temperature controller at 37.0±0.05° C. UV-visible spectra were acquired on a Cary 100 spectrometer equipped with a Quantum Northwest TLC-42 dual cuvette temperature controller at 37.00±0.05° C. All air-free manipulations were performed under an inert atmosphere using standard Schlenk techniques or an Innovative Atmospheres N2-filled glove box.

Spectroscopic Materials and Methods.

Phosphate buffered saline (PBS) tablets (1X, CalBioChem) and cetyl trimethylammonium bromide (CTAB) were used to make buffered solutions (PBS, 140 mM NaCl, 3 mM KCl, 10 mM phosphate, 1 mM CTAB, pH 7.4) in Millipore water. Buffer solutions were sparged with $N_2$ to remove dissolved oxygen and stored in an $N_2$-filled glovebox. Anhydrous sodium hydrosulfide (NaSH) was purchased from Strem Chemicals and handled under nitrogen. Aqueous stock solutions of NaSH were prepared in buffer in an $N_2$-filled glovebox immediately prior to use. Stock solutions of MeRho-TCA were prepared in an $N_2$-filled glovebox in DMSO and stored at −25° C. until immediately before use. Septum-sealed cuvettes from Starna Scientific were used to obtain spectroscopic measurements under anaerobic conditions.

$H_2S$ Electrode Materials and Methods.

Phosphate buffered saline (PBS) tablets (1X, CalBioChem) either with or without cetyl trimethylammonium bromide (CTAB) were used to make buffered solutions (PBS, 140 mM NaCl, 3 mM KCl, 10 mM phosphate, 1 mM CTAB, pH 7.4) in Millipore water. Buffer solutions were sparged with $N_2$ to remove dissolved oxygen and stored in an $N_2$-filled glovebox. Carbonic anhydrase (CA) from bovine erythrocytes (3,500 W/A units/mg) was obtained from Sigma Aldrich and a 1% CA stock solution was prepared in deoxygenated buffer (50 mM PIPES, 100 mM KCl, pH 7.4) in a glovebox, and the absorbance at 280 nm (1 cm path length cuvette) at 37° C. was measured to be 3.825. The concentration of the stock solution was calculated to be 67 μM using ε1%=19 for CA. The stock solution was stored under nitrogen at 4° C. and warmed to room temperature immediately before use. Stock solutions of tris(2-carboxyethyl)phosphine (TCEP) and acetazolamide (AAA) were prepared under $N_2$ with degassed buffer (PBS, pH 7.4) immediately prior to use. Thiocarbamate and carbamate stock solutions were prepared in an $N_2$-filled glovebox in DMSO and stored at −25° C. until immediately before use.

General Procedure for $H_2S$ Electrode Examples.

Scintillation vials containing 20.00 mL of phosphate buffer (140 mM NaCl, 3 mM KCl, 10 mM phosphate, 1 mM CTAB, pH 7.4) were prepared in an $N_2$-filled glovebox. A split-top septum cap was placed on the vial after probe insertion and the headspace was sparged with $N_2$. The WPI electrode was then inserted into the vial and the measured current was allowed to equilibrate before starting. With moderate stirring, the CA stock solution (50 μL, 67 μM) was injected, followed by subsequent injections of acetazolamide (10-50 μL of a 10 mM stock solution in PBS buffer), COS gas (10 μL, 0.345 μmol), TCA stock solution (10 mM in DMSO), or TCEP stock solution (10 mM in PBS buffer).

General Procedure for Fluorescence Measurements.

In an $N_2$-filled glovebox, a septum-sealed cuvette was charged with 3.00 mL of buffer (140 mM NaCl, 3 mM KCl, 10 mM phosphate, 1 mM CTAB, pH 7.4). The cuvette was removed from the glovebox and MeRho-TCA (60 μL of a 1 mM stock solution) was injected into the vial, after which a background spectrum was recorded. The desired analytes were then introduced, and the fluorescence spectrum was measured at designated time points.

General Procedure for Measurement of Total Sulfide in Mouse Blood.

Mice were maintained at the association for assessment and accreditation of laboratory animal care international-accredited Louisiana State University Health Science Center-Shreveport animal resource facility and maintained in accordance with the National Research Council's guide for care and use of laboratory animals. All animal studies were approved by the institutional animal care and use committee (protocol P-12-011) and conformed to the guide for the care and use of laboratory animals published by the National Institutes of Health. Mice were anesthetized by IP injection with 150 mg/kg ketamine and 10 mg/kg xylazine. Mouse whole blood was collected from the retroorbital capillary plexus from three C57BL/6J male mice and diluted 1:50 in PBS (phosphate buffered saline pH 7.4) or red blood cell lysing buffer (Sigma, St Louis). Samples were treated with either 3 or 4 (see FIG. 2) at a final concentration of 25 μM. A separate set of blood samples were left untreated and used for baseline sulfide measurements. Once mixed with either compound 3 or 4 (see FIG. 2), half of each sample was treated with 10 mM TCEP (tris(2-carboxyethyl)phosphine hydrochloride) for 30 minutes while the other half remained untreated. Sulfide bioavailability was subsequently measured in all samples using the MBB method.

$H_2S$ Calibration Curve

To 1.5 mL-UV cuvettes were added 0.5 mL of MB cocktail (vide infra) and 0.5 mL PBS buffer (pH 7.4, 10 mM). The resultant solution was mixed thoroughly, followed by the addition of an NaSH stock solution (1 mM) to make the final $H_2S$ concentrations of 1, 3, 5, 10, 15, and 20 μM. The MB solution was allowed to react with $H_2S$ for 1 hour before measuring the absorbance at 670 nm.

$H_2S$ Release from PhotoTCM in PBS

A PhotoTCM stock solution (50 μL, 20 mM in DMSO) was added to 20 mL of PBS (pH 7.4, 10 mM) containing CA (25 μg/mL) in a 25-mL Pyrex round bottom flask. One high power LED bulb (800 mW) was placed 1 cm away from the flask. After stirring the reaction solution at room temperature for 2 min, the LED bulb was turned on and 0.5 mL of the reaction aliquots were taken to UV cuvettes containing 0.5 mL of MB cocktail (0.1 mL zinc acetate (1% w/v), 0.2 mL $FeCl_3$ (30 mM in 1.2 M HCl), and 0.2 mL N,N-dimethyl-p-phenylene diamine (20 mM in 7.2 M HCl)) periodically. The absorbance at 670 nm was then measured after 1 hour and was converted to $H_2S$ concentration by using a $H_2S$ calibration curve.

A PeroxyTCM or TCM stock solution (50 μL, 20 mM in DMSO) was added to 20 mL of PBS (pH 7.4, 10 mM) containing CA (25 μg/mL) in a scintillation vial. After stirring at room temperature for 5 min, the $H_2O_2$ stock solution (1.0 M in $H_2O$) was added to reach the desired final $H_2O_2$ concentration, and the $H_2S$ release was monitored using an $H_2S$ electrode.

Figure 11A:
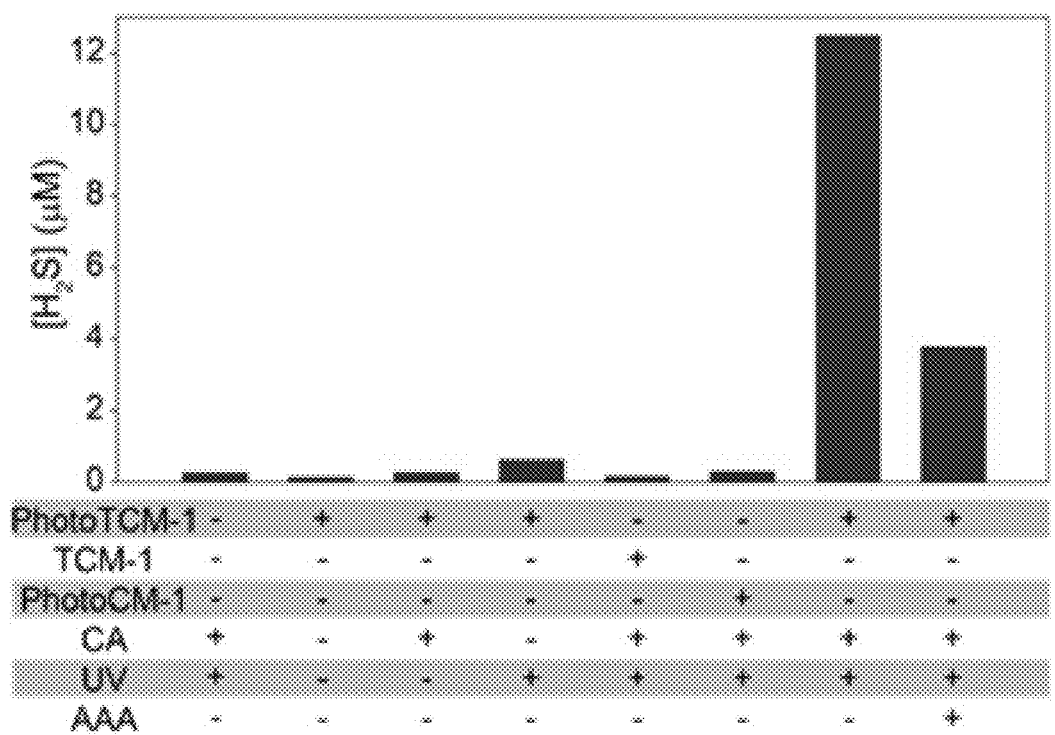
FIGS. 11A and 11B show $H_2S$ release results from analyzing representative donor compounds disclosed herein.

Effects of CA, UV and Acetazolamide (AAA) on $H_2S$ Release from PhotoTCM-1 and $H_2S$ Release from PhotoCM-1 and TCM-1 (FIG. 11A)

Bar #1: 10 mL of PBS containing CA (25 μg/mL) was irradiated by UV light in a 25-mL Pyrex round bottom flask for 10 min and 0.5 mL of the reaction aliquot was taken to a UV cuvette containing 0.5 mL of MB cocktail. The absorbance at 670 nm was then measured after 1 hour by the MB assay.

Bar #2: The PhotoTCM-1 stock solution (25 μL, 20 mM in DMSO) was added to 10 mL of PBS (pH 7.4, 10 mM) in a 25-mL Pyrex round bottom flask and the solution was stirred for 10 min. Then 0.5 mL of the reaction aliquot was taken to a UV cuvette containing 0.5 mL of MB cocktail. The absorbance at 670 nm was then measured after 1 hour by the MB assay.

Bar #3: The PhotoTCM-1 stock solution (25 μL, 20 mM in DMSO) was added to 10 mL of PBS (pH 7.4, 10 mM) containing CA (25 μg/mL) in a 25-mL Pyrex round bottom flask and the solution was stirred for 10 min. Then 0.5 mL of the reaction aliquot was taken to a UV cuvette containing 0.5 mL of MB cocktail. The absorbance at 670 nm was then measured after 1 hour by the MB assay.

Bar #4: The PhotoTCM-1 stock solution (25 μL, 20 mM in DMSO) was added to 10 mL of PBS (pH 7.4, 10 mM) in a 25-mL Pyrex round bottom flask and the solution was irradiated by UV light for 10 min. Then 0.5 mL of the reaction aliquot was taken to a UV cuvette containing 0.5 mL of MB cocktail. The absorbance at 670 nm was then measured after 1 hour by the MB assay.

Bar #5: The TCM-1 stock solution (25 μL, 20 mM in DMSO) was added to 10 mL of PBS (pH 7.4, 10 mM) containing CA (25 μg/mL) in a 25-mL Pyrex round bottom flask and the solution was irradiated by UV light for 10 min. Then 0.5 mL of the reaction aliquot was taken to a UV cuvette containing 0.5 mL of MB cocktail. The absorbance at 670 nm was then measured after 1 hour by the MB assay.
Bar #6: The PhotoCM-1 stock solution (25 μL, 20 mM in DMSO) was added to 10 mL of PBS (pH 7.4, 10 mM) containing CA (25 μg/mL) in a 25-mL Pyrex round bottom flask and the solution was irradiated by UV light for 10 min. Then 0.5 mL of the reaction aliquot was taken to a UV cuvette containing 0.5 mL of MB cocktail. The absorbance at 670 nm was then measured after 1 hour by the MB assay.
Bar #7: The PhotoTCM-1 stock solution (25 μL, 20 mM in DMSO) was added to 10 mL of PBS (pH 7.4, 10 mM) containing CA (25 μg/mL) in a 25-mL Pyrex round bottom flask and the solution was irradiated by UV light for 10 min. Then 0.5 mL of the reaction aliquot was taken to a UV cuvette containing 0.5 mL of MB cocktail. The absorbance at 670 nm was then measured after 1 hour by the MB assay.
Bar #8: The PhotoTCM-1 stock solution (25 μL, 20 mM in DMSO) was added to 10 mL of PBS (pH 7.4, 10 mM) containing CA (25 μg/mL) and AAA (10 μM) in a 25-mL Pyrex round bottom flask and the solution was irradiated by UV light for 10 min. Then 0.5 mL of the reaction aliquot was taken to a UV cuvette containing 0.5 mL of MB cocktail. The absorbance at 670 nm was then measured after 1 hour by the MB assay.
Effects of Amino Acids on $H_2S$ Release from PhotoTCM-1 (FIG. 11B)
A PhotoTCM-1 stock solution (25 μL, 20 mM in DMSO) was added to 10 mL of PBS (pH 7.4, 10 mM) containing CA (25 μg/mL) in a 25-mL Pyrex round bottom flask. After stirring at room temperature for 5 minutes, the amino acid stock solution was added to reach the final concentration of 500 μM (5 mM for GSH). The resultant solution was irradiated under UV light for 10 min and the absorbance at 670 nm was then measured after 1 hour by the MB assay.
Initial Mechanistic Insights into $H_2S$ Release from PhotoTCM-1
PhotoTCM-1 (15 mg) was dissolved in 4 mL of DMSO, followed by the addition of 2 mL of PBS (pH 7.4). The resultant solution was irradiated under UV light at 365 nm for 2 hours. $H_2O$ (15 mL) was then added and the aqueous solution was extracted with ethyl acetate (15 mL×3). The organic layers were combined, washed with brine (15 mL×3), dried over MgSO4, and removed under vacuum. The solid residue was dissolved in DMSO and injected into the Mass Spectrometer for product analysis.
MTT assay.
The MTT assay was performed as reported. Briefly, BEAS 2B cells were incubated with vehicle (DMSO), 1 (0.3, 1, 3, 10 μM) or 2 (0.3, 1, 3, 10 μM) for 24 hours, then 3-(4,5-dimethyl-2-thiazolyl)-2,5-diphenyl-2H-tetrazolium bromide (MTT) was added to the cells at a final concentration of 0.5 mg/mL and cells were cultured at 37° C. for 1 hour. The cells were washed with PBS and the formazan dye was dissolved in isopropyl alcohol. The amount of converted formazan dye was measured at 570 nm with background measurement at 690 nm on a Powerwave reader (Biotek).
LDH Assay.
Lactate dehydrogenase (LDH) release was determined as a cytotoxicity assay, a measurement of necrotic cell death, as described previously. Briefly, 30 μL of supernatant was saved before addition of MTT and mixed with 100 μL of freshly prepared LDH assay reagent to reach final concentrations of 85 mM lactic acid, 1040 mM nicotinamide adenine dinucleotide (NAD+), 224 mM N-methylphenazonium methyl sulfate (PMS), 528 mM 2-(4-lodophenyl)-3-(4-nitrophenyl)-5-phenyl-2H-tetrazolium chloride (INT) and 200 mM Tris (pH 8.2). The changes in absorbance were read kinetically at 492 nm for 15 min (kinetic LDH assay) on a monochromator-based reader (Powerwave HT, Biotek) at 37° C. LDH activity values are shown as $V_{max}$ for the kinetic assays in mOD/min.
Bioenergetic Analysis in Cultured Cells.
The XF24 Extracellular Flux Analyzer (Seahorse Bioscience, Billerica, Mass.) was used to measure bioenergetic function as described previously. Briefly, BEAS 2B cells were incubated with vehicle (DMSO), 1 (1, 3, 10 μM) or 2 (1, 3, 10 μM) for 24h. Oxygen consumption rate (OCR) after oligomycin (1.5 μg/mL) was used to assess ATP production rate and OCR after FCCP (0.5 μM) to assess maximal mitochondrial respiratory capacity. Antimycin A (2 μg/mL) and rotenone (2 μM) were used to inhibit the flux of electrons through complex III and I, to detect residual non-mitochondrial oxygen consumption rate, which is considered to be due to cytosolic oxidase enzymes.
$H_2O_2$-Mediated COS-to-$H_2S$ Conversion
$H_2O_2$ was injected to PBS (pH 7.4, 10 mM, 20 mL) containing PeroxyTCM-1 in the presence or absence of CA. $H_2S$ release was monitored by using an $H_2S$ electrode (FIG. 17A). COS (100 μL) was injected to PBS (pH 7.4, 10 mM, 20 mL) at r.t. $H_2O_2$ (1 M, 10 μL) was added at the time indicated in FIG. 17B. $H_2S$ release was monitored by using an $H_2S$ electrode.
Preparation of RSONS Solutions
Hydrogen peroxide ($H_2O_2$): $H_2O_2$ was delivered from 30% aqueous solutions. The concentration of $H_2O_2$ was determined using the absorption at 240 nm (c=43.6 $M^{-1}$ $cm^{-1}$).
Superoxide ($O_2^-$): $O_2^-$ was prepared by dissolving $KO_2$ in $H_2O$.
Hypochlorite ($OCl^-$): $OCl^-$ was delivered from 5% aqueous solutions. The concentration of $ClO^-$ was determined using the absorption at 292 nm (c=360 $M^{-1}$ $cm^{-1}$).
Hydroxy radical (.OH): .OH was generated by reaction of $FeSO_4$ (5 equiv.) with $H_2O_2$ (1 equiv.). The .OH concentration was equal to $H_2O_2$ concentration.
Singlet oxygen ($^1O_2$):$^1O_2$ was generated by mixing NaClO (3 equiv.) and $H_2O_2$ (1 equiv.). The $^1O_2$ concentration was equal to $H_2O_2$ concentration.
Peroxynitrite ($ONOO^-$): A mixture of $NaNO_2$ (0.6 M) and $H_2O_2$ (0.7 M) was acidified with HCl (0.6 M) and KOH (1.5 M) was added immediately to make the solution alkaline. Manganese dioxide ($MnO_2$) was added and the resultant mixture was stirring vigorously at r.t. for 20 min to remove excess $H_2O_2$. The concentration of $ONOO^-$ was determined using the absorption at 302 nm (ε=1670 $M^{-1}$ $cm^{-1}$).
tert-Butyl hydroperoxide (TBHP): TBHP was delivered from 70% aqueous solutions.
tert-Butoxy radical (.OtBu): .OtBu was generated by reacting FeSO4 (5 equiv.) with TBHP (1 equiv.). The .OtBu concentration was equal to TBHP concentration.
S-Nitrosoglutathione (GSNO): Glutathione (0.2 M in $H_2O$) was mixed with HCl (0.2 M), followed by the addition of $NaNO_2$ (0.2 M in $H_2O$). The reaction solution was stirred in dark for 30 min. The concentration of GSNO was determined using the absorption at 335 nm (ε=922 $M^{-1}$ $cm^{-1}$).
Nitric oxide (NO): NO was delivered by using DEA-Nonoate as a NO donor.
Nitroxyl (HNO): HNO was delivered by using Angeli's salt as an HNO donor.

RSONS Effects on H$_2$S Release from PeroxyTCM-1

A PeroxyTCM-1 stock solution (50 µL, 20 mM in DMSO) was added to 20 mL of PBS (pH 7.4, 10 mM) containing CA (25 µg/mL) in a scintillation vial. After stirring at room temperature for 5 minutes, the RSONS stock solution was added to reach the final concentration to 500 µM (5 mM for GSH). The H$_2$S release was monitored using an H$_2$S electrode for 20 min. The experiments were repeated in triplicate, and the results are reported as mean±SD (n=3).

Cell Culture and Cytotoxicity of PeroxyTCM-1, PeroxyCM-1, and TCM-1

HeLa cells were cultured in high glucose Dulbecco's modified Eagle's medium (DMEM) supplemented with 10% fetal bovine serum (FBS) and 1% penicillin/streptomycin at 37° C. under 5% CO$_2$. Confluent HeLa cells were incubated in FBS-free DMEM containing vehicle (0.5% DMSO), PeroxyTCM-1, PeroxyCM-1, or TCM-1 (10-100 µM) for 2 hours in a 96-well plate. After the indicated treatment, 100 µL of FBS-free DMEM containing 10% CCK-8 solution was added to each well, and cells were incubated for 3 hours at 37° C. The absorbance at 450 nm was measured by using a microplate reader. The cell viability was measured and normalized to the vehicle group. The results are expressed as mean±SEM (n=6).

Cell Imaging of Exogenous H$_2$O$_2$-Induced H$_2$S Release from PeroxyTCM-1

HeLa cells were plated in poly-D-lysine coated plates (MatTek) containing 2 mL of DMEM and incubated at 37° C. under 5% CO$_2$ for 24 h. The confluent cells were washed with PBS and then co-incubated with PeroxyTCM-1 (50 µM), HSN$_2$ (5 µM) and NucBlue nuclear dye (2 drops) in FBS-free DMEM for 30 min. After removal of extracellular PeroxyTCM-1 and HSN$_2$ by washing with PBS, cells were incubated in FBS-free DMEM in the presence or absence of H$_2$O$_2$ (25 or 50 µM) for 30 min. Prior to imaging, cells were washed with PBS and bathed in 2 mL of PBS. Cell imaging was performed on a Leica DMi8 fluorescent microscope.

Cell Imaging of PMA-Induced Endogenous ROS Generation

RAW 264.7 cells were plated in poly-D-lysine coated plates (MatTek) containing 2 mL of DMEM and incubated at 37° C. under 5% CO$_2$ for 24 h. The confluent cells were washed with PBS and then co-incubated with DCFDA (10 µM) and NucBlue nuclear dye (2 drops) in FBS-free DMEM for 30 min. After removal of extracellular DCFDA by washing with PBS, cells were incubated in FBS-free DMEM in the presence or absence of PMA (500 nM) for 3 h. Prior to imaging, cells were washed with PBS and bathed in 2 mL of PBS. Cell imaging was performed on a Leica DMi8 fluorescent microscope.

Cell Imaging of Endogenous ROS-Induced H$_2$S Release from PeroxyTCM-1

RAW 264.7 cells were plated in poly-D-lysine coated plates (MatTek) containing 2 mL of DMEM and incubated at 37° C. under 5% CO$_2$ for 24 h. The confluent cells were washed with PBS and then co-incubated with PeroxyTCM-1 (50 µM), HSN2 (5 µM), and NucBlue nuclear dye (2 drops) in FBS-free DMEM for 30 min. After removal of extracellular PeroxyTCM-1 and HSN$_2$ by washing with PBS, cells were incubated in FBS-free DMEM in the presence or absence of PMA (500 nM) for 3 h. Prior to imaging, cells were washed with PBS and bathed in 2 mL of PBS. Cell imaging was performed on a Leica DMi8 fluorescent microscope.

Cytotoxicity of H$_2$O$_2$ in HeLa Cells

Confluent HeLa cells were incubated in FBS-free DMEM containing H$_2$O$_2$ (50-400 µM) for 1 h. Cells were then washed with PBS. Cell viability was evaluated by using CCK-8 assay, and the results are expressed as mean±SEM (n=5).

Cytoprotection of PeroxyTCM-1, PeroxyCM-1, and TCM-1 against H$_2$O$_2$-Induced Oxidative Stress Confluent HeLa cells were incubated in FBS-free DMEM containing H$_2$O$_2$ (100 µM) in the absence or presence of PeroxyTCM-1, PeroxyCM-1, or TCM-1 (10-50 µM) for 1 hour in a 96-well plate. Cells were then washed with PBS, and 100 µL of FBS-free DMEM containing 10% CCK-8 solution was added to each well. Cells were incubated for 3 hours at 37° C. The absorbance at 450 nm was measured by using a microplate reader. The cell viability was evaluated, and the results are expressed as mean±SEM (n=5).

Representative Syntheses

General Procedure for the Preparation of Thiocarbamates.

Sodium hydride (60% in oil, 1.25 mmol) was added to a solution of the isothiocyanate (1 mmol) and the benzyl alcohol (1 mmol) in anhydrous THF (6-12 mL). The reaction mixture was stirred at room temperature under nitrogen for 18 hours. After the solvent was removed under reduced pressure, CH$_2$Cl2 was added, and the resulting solution was washed with water and brine. The organic layer was dried over sodium sulfate and filtered. The solvent was removed by rotary evaporation and the crude product was purified using either column chromatography (hexanes:EtOAc gradient) or silica gel preparatory thin layer chromatography (3:2 hexanes:EtOAc).

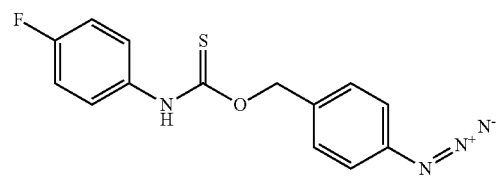

O-(4-Azidobenzyl)-N-(4-fluorophenyl)thiocarbamate
(1)

Purification via preparatory TLC (3:2 hexanes/EtOAc) yielded the product as a pure white solid (107.9 mg, 35% yield). $^1$H NMR (600 MHz, DMSO-d6) δ (ppm): 7.23-7.50 (m, 4H), 7.06-7.13 (m, 4H), 7.44-7.48 (br s, 2H). Two rotomers were observable by $^{13}$C{$^1$H} and $^{19}$F NMR: $^{13}$C{$^1$H} NMR (150 MHz, DMSO) δ (ppm): 189.4 (187.9 minor), 161.3 (159.7 minor), 140.6 (d, J=15.4 Hz), 135.4 (134.3 minor), 133.7 (133.0 minor), 126.8 (125.5 minor), 120.1 (130.9 minor), 116.5 (m), 71.0 (72.7 minor). $^{19}$F NMR (470 MHz, DMSO-d6) δ (ppm): −115.9 (−116.4 minor). FTIR (ATR, cm-1): 3199, 3039, 2109, 1607, 1543, 1503, 1404, 1339, 1280, 1220, 1168, 1014, 857, 787, 658.

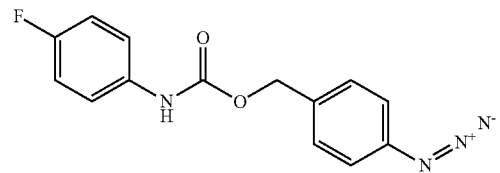

O-(4-Azidobenzyl)-N-(4-fluorophenyl)carbamate (2)

p-Azidobenzyl alcohol (57.5 mg, 0.386 mmol) and NEt3 (54 µL, 0.39 mmol) were combined in dry THF (2 mL), and 4-fluorophenylisocyanate (44 µL, 0.39 mmol) was added dropwise. The reaction mixture was stirred under nitrogen at room temperature and shielded from light for 24 hours. The solvent was evaporated under reduced pressure, and the crude product was purified by preparatory TLC (2:1 hexanes/EtOAc) to yield the pure product as a white solid (61.8 mg, 56%). $^1$H NMR (600 MHz, DMSO-d6) δ (ppm): 9.79 (s, 1H), 7.48-7.44 (m, 4H), 7.10-7.15 (m, 4H), 5.12 (s, 2H). $^{13}$C{$^1$H} NMR (150 MHz, DMSO-d6) δ (ppm): 158.4, 156.9, 153.4, 139.2, 135.4, 133.5, 130.0, 119.2, 115.4 (d, J=22.2 Hz), 65.2. $^{19}$F NMR (470 MHz, DMSO-d6) δ (ppm): −120.82. HRMS (m/z): [M+Na]+ calcd for [C$_{14}$H$_{11}$FN$_4$O$_2$Na]$^+$ 309.0764, found 309.0601.

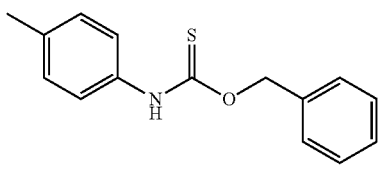

O-(4-Benzyl)-N-tolylthiocarbamate (3)

Purification via column chromatography (hexanes/EtOAc gradient) yielded the product as a pure white solid (173.7 mg, 68%). $^1$H NMR (600 MHz, DMSO-d6) δ (ppm): 11.11 (s, 1H), 7.57-7.44 (m, 2H), 7.43-7.32 (m, 4H), 7.23-7.06 (m, 3H), 5.49-5.58 (br s, 2H), 2.26 (s, 3H). $^{13}$C{$^1$H} NMR (150 MHz, DMSO-d6) δ (ppm): 187.4, 186.8, 136.0, 135.6, 135.1, 134.4, 134.0, 129.2, 128.8, 128.4, 128.3, 128.2, 128, 122.9, 121.2, 72.0, 70.3, 20.4. HRMS (m/z): [M+H]+ calcd for [C$_{15}$H$_{16}$NOS]$^+$ 258.0953, found 258.0948.

Methylrhodol-isothiocyanate (MeRho-NCS)

Methylrhodol (200 mg, 0.577 mmol) and NEt3 (480 µL, 3.46 mmol) were combined in dry DMF (2 mL) in oven-dried glassware. Thiocarbonyldiimidazole (TCDI, 211 mg, 1.16 mmol) was dissolved in dry DMF (6 mL) and added dropwise to the solution. The reaction mixture was stirred under nitrogen at room temperature for 24 hours then quenched with water. The organic layer was extracted with EtOAc, washed three times with aqueous LiCl (5%, 20 mL), dried over MgSO4, and the solvent was evaporated under reduced pressure. The crude product was purified using preparatory TLC on an oven-dried prep plate using dry hexanes:EtOAc (1:1) and isolated as a white solid (134 mg, 60%). $^1$H NMR (600 MHz, CDCl$_3$) δ (ppm): 8.03 (d, J=7.5 Hz, 1H), 7.68 (t, J=7.4 Hz, 1H), 7.63 (t, J=7.5 Hz, 1H), 7.15-7.12 (m, 2H), 6.89 (dd, J1=8.5, J2=2.1 Hz, 1H), 6.80-6.76 (m, 2H), 6.70 (d, J=8.8 Hz, 1H), 6.64 (dd, J1=8.9, J2=2.5 Hz, 1H), 3.84 (s, 3H). $^{13}$C{$^1$H} NMR (150 MHz, CDCl$_3$) δ (ppm): 169.3, 161.7, 153.0, 152.1, 151.9, 137.8, 135.4, 133.4, 130.2, 129.5, 129.2, 126.5, 125.4, 123.9, 121.4, 118.5, 114.2, 112.4, 110.8, 101.1, 82.2, 55.8. FTIR (ATR, cm-1): 2922, 2852, 2017, 1761, 1607, 1563, 1495, 1416, 1324, 1247, 1099, 1079, 941. HRMS (m/z): [M+H]+ calcd for [C$_{22}$H$_{13}$NO$_4$SH]$^+$ 388.0644, found 388.0471.

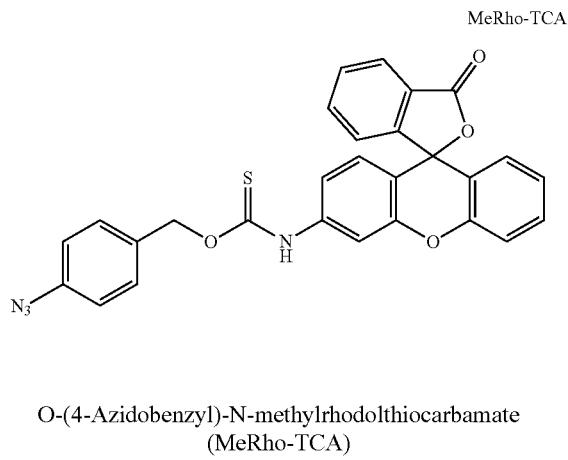

O-(4-Azidobenzyl)-N-methylrhodolthiocarbamate (MeRho-TCA)

In oven-dried glassware, MeRho-NCS (134 mg, 0.346 mmol) was dissolved in dry THF (5 mL). p-Azidobenzyl-alcohol (150 mg, 1.00 mmol) was dissolved in dry THF (5 mL) and added to the solution of MeRho-NCS. Sodium hydride (60% in mineral oil, 18 mg, 0.45 mmol) was added and the reaction mixture was stirred at room temperature under nitrogen and protected from light for 24 hours. The solvent was evaporated under reduced pressure and the crude product was dissolved in EtOAc. The organic layer was washed with water and brine and dried over sodium sulfate. The product was purified by preparatory TLC (5% MeOH in DCM) while protected from light, to yield the pure product as a pale yellow solid (65 mg, 35%). $^1$H NMR (600 MHz, CDCl$_3$) δ (ppm): 8.26 (br s, 1H), 8.02 (d, J=7.6 Hz, 1H), 7.67 (td, J1=7.5, J2=1.3 Hz, 1H), 7.62 (td, J1=7.5, J2=1.0 Hz, 1H), 7.43 (d, J=8.4 Hz, 2H), 7.14 (d, J=7.5 Hz, 1H), 7.05 (d, J=8.4 Hz, 2H), 6.78 (d, J=2.5 Hz, 1H), 6.73 (d, J=8.2 Hz, 1H), 6.69 (d, J=8.8 Hz, 1H), 6.62 (dd, J1=8.8, J2=2.5 Hz, 1H), 5.59 (br s, 2H), 3.84 (s, 3H). $^{13}$C{$^1$H} NMR (150 MHz, CDCl$_3$) δ (ppm): 206.9, 169.3, 161.5, 152.9, 152.3, 151.7, 140.6, 135.1, 130.3, 129.9, 129.0, 128.8, 126.6, 125.1, 123.9, 119.3, 116.9, 115.9, 112.0, 110.9, 109.2, 100.9, 82.5, 55.6, 53.5, 30.9, 29.7, 29.3. HRMS (m/z): [M+H]+ calcd for [C$_{29}$H$_{20}$N$_4$O$_5$SH]$^+$ 537.1233, found 537.0827.

General Procedure for the Synthesis of Photolabile Compounds.

The o-nitrobenzyl alcohol species (1.0 equiv.) was combined with p-fluorophenyl isothiocyanate (1.0 equiv.) in anhydrous THF (15 mL) at 0° C., followed by the addition of NaH (60% in paraffin liquid, 1.25 equiv.). The resultant mixture was stirred at 0° C. for 20 min, after which the ice bath was removed, and the reaction mixture was stirred at room temperature until the completion of the reaction indicated by TLC. The reaction was quenched by adding brine (30 mL), and the aqueous solution was extracted with ethyl acetate (3×15 mL). The organic layers were combined, dried over MgSO4, and evaporated under vacuum. The crude product was purified by column chromatography. NMR spectra were obtained at 60° C. because thiocarbamates show two sets of NMR resonances at room temperature due to slow rotation around the thiocarbamate functional group at room temperature.

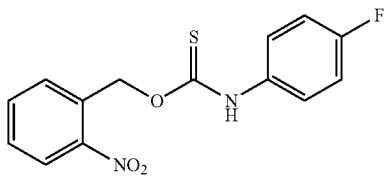

PhotoTCM-1

PhotoTCM-1 was prepared from o-nitrobenzyl alcohol and p-fluorophenyl isothiocyanate using the general synthetic procedure described above (520 mg, 85% yield). $^1$H NMR (500 MHz, DMSO-d$_6$ at 60° C.) δ (ppm): 11.20 (s, 1H), 8.13 (d, J=5.0 Hz, 1H), 7.64 (m, 5H), 7.18 (t, J=10.0 Hz, 2H), 5.89 (s, 2H). $^{19}$F NMR (470 MHz, DMSO-ds at 60° C.) δ (ppm): −116.9. $^{13}$C{$^1$H} NMR (150 MHz, DMSO-d$_6$ at 60° C.) δ (ppm): 187.8, 160.7, 159.1, 148.0, 134.5, 132.0, 130.0, 129.8, 125.4, 125.2, 115.8, 67.5.1R (cm$^{-1}$): 3170, 3007, 1521, 1501, 1332, 1207, 1185, 1154, 1057, 1046, 791, 727, 561. HRMS m/z [M+H]$^+$ calcd. for [C$_{14}$H$_{12}$FN$_2$O$_3$S]+ 307.0553; found 307.0558. M. P. (° C.): 120-122.

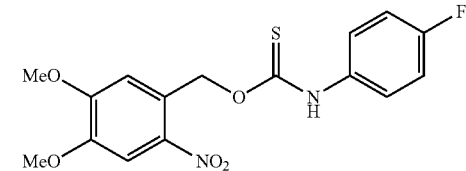

PhotoTCM-2

PhotoTCM-2 was prepared from 4,5-dimethoxy-2-nitrobenzyl alcohol and p-fluorophenyl isothiocyanate using the general synthetic procedure described above (626 mg, 86% yield). $^1$H NMR (500 MHz, DMSO-d$_6$ at 60° C.) δ (ppm): 11.6 (s, 1H), 7.72 (s, 1H), 7.56 (m, 2H), 7.18 (t, J=10.0 Hz, 3H), 5.83 (s, 2H), 3.90 (s, 6H). $^{19}$F NMR (470 MHz, DMSO-d$_6$ at 60° C.) δ (ppm): −116.9. $^{13}$C{$^1$H} NMR (150 MHz, DMSO-ds at 60° C.) δ (ppm): 188.0, 160.7, 159.1, 153.8, 148.7, 140.4, 134.9, 125.6, 115.9, 112.3, 109.0, 69.4, 68.0, 56.7. IR (cm$^{-1}$): 3170, 3007, 1521, 1502, 1406, 1333, 1235, 1208, 1185, 1154, 1056, 1046, 791, 778, 726, 703, 681. HRMS m/z [M+H]$^+$ calcd. for [C$_{16}$H$_{16}$FN$_2$O$_5$S]+ 367.0764; found 367.0755. M. P. (° C.): 156-158.

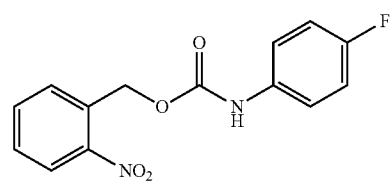

PhotoCM-1 o-Nitrobenzyl alcohol (153 mg, 1.0 mmol, 1.0 equiv.) was combined with p-fluorophenyl isocyanate (137 mg, 1.0 mmol, 1.0 equiv.) in anhydrous toluene (30 mL) at room temperature, followed by the addition of triethylamine (101 mg, 1.0 mmol, 1.0 equiv.). The resultant mixture was stirred at 110° C. for 20 h, after which the oil bath was removed, and the reaction solution was cooled to room temperature. The reaction mixture was quenched by adding brine (30 mL), and the aqueous solution was extracted with ethyl acetate (3×15 mL). The organic layers were combined, dried over MgSO$_4$, and evaporated under vacuum. The crude product was purified by using column chromatography to afford pure PhotoCM-1 as white solid (220 mg, 76%). $^1$H NMR (500 MHz, CDCl$_3$) δ (ppm): 9.95 (s, 1H), 8.14 (d, J=10.0 Hz, 1H), 7.83 (t, J=5.0 Hz, 1H), 7.75 (t, J=10.0 Hz, 1H), 7.64 (t, J=5.0 Hz, 1H), 7.49 (m, 2H), 7.14 (t, J=10.0 Hz, 2H), 5.50 (s, 2H). $^{19}$F NMR (470 MHz, CDCl$_3$) δ (ppm): −120.6. $^{13}$C{$^1$H} NMR (125 MHz, CDCl$_3$) δ (ppm): 159.2, 157.3, 153.5, 147.8, 135.7, 134.6, 132.7, 129.8, 125.3, 120.4, 115.9, 63.0. IR (cm$^{-1}$): 3170, 3007, 1521, 1502, 1406, 1333, 1235, 1208, 1185, 1154, 1056, 846, 791, 778, 726, 703, 681, 561. HRMS m/z [M+H]$^+$ calcd. for [C$_{14}$H$_{12}$FN$_2$O$_4$]$^+$ 291.0781; found 291.0786. M. P. (° C.): 146-148.

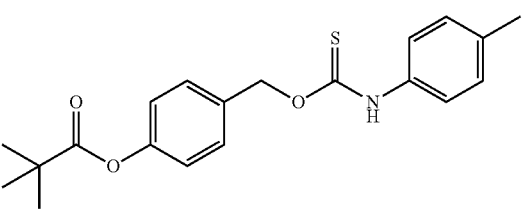

5

O-(4-pivaloylbenzyl)-N-(p-tolyl)thiocarbamate (5)

4-Pivaloylbenzyl alcohol (131 mg, 0.668 mmol) and p-tolylisothiocyanate (107 mg, 0.717 mmol) were combined in anhydrous THF (3 mL) and DBU (125 µL, 0.835 mmol) was added dropwise. The reaction mixture was stirred under nitrogen at room temperature for 4 hours. The solvent was removed under reduced pressure and the crude mixture was purified using column chromatography (hexanes:EtOAc gradient) to yield the pure product as a white solid (123 mg, 52%). Note: The resonances of thiocarbamates are doubled as a result of slow rotation and the peaks associated with these rotamers are denoted with "major" and "minor" when delineation is possible. $^1$H NMR (600 MHz, DMSO-d$_6$) δ(ppm): 11.13 (s, 1H), 7.54-7.42 (m, 3H), 7.21-7.07 (m, 5H), 5.57 (minor); 5.48 (major) (s, 2H), 2.28 (major); 2.23 (minor) (s, 3H), 1.30 (s, 9H). $^{13}$C{$^1$H} NMR (150 MHz, DMSO-d$_6$) δ (ppm): 187.8, 187.2, 176.9, 151.1, 136.5, 135.5, 134.9, 134.6, 134.0, 133.6, 130.2, 129.9, 129.7, 129.4, 123.4, 122.5, 122.3, 71.9, 70.3, 39.0, 27.2, 20.9. FTIR (ATR, cm$^{-1}$): 3207, 2972, 1750, 1704, 1541, 1423, 1107, 1043, 810. HRMS (m/z): [M+N]$^+$ calcd for [C$_{20}$H$_{23}$NO$_3$SNa]$^+$ 380.1296, found 380.1299.

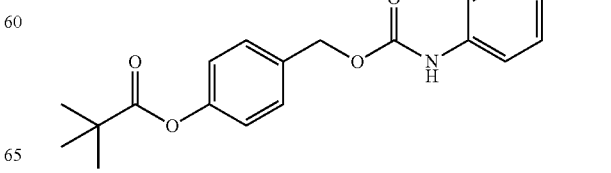

6

O-(4-pivaloylbenzyl)-N-(p-tolyl)carbamate (6)

4-Pivaloyl benzyl alcohol (100 mg, 0.480 mmol) was dissolved in anhydrous THF (4 mL) and DBU (89.6 μL, 0.600 mmol) was added. p-Tolylisocyanate (64.3 mg, 0.480 mmol) was added dropwise in anhydrous THF (1 mL). The reaction mixture was stirred under nitrogen at room temperature for 18 hours. The solvent was removed under reduced pressure and the crude mixture was purified using column chromatography (hexanes:EtOAc gradient) to yield the pure product as a clear oil (119 mg, 73%). $^1$H NMR (600 MHz, DMSO-$d_6$) δ (ppm): 9.65 (s, 1H), 7.47 (d, J=8.2 Hz, 2H), 7.32 (d, J=8.8 Hz, 2H), 7.07 (d, J=8.1 Hz, 2H), 6.85 (d, J=8.7 Hz, 2H), 5.05 (s, 2H), 2.23 (s, 3H), 1.30 (s, 9H). $^{13}$C{$^1$H} NMR (150 MHz, DMSO-$d_6$) δ(ppm): 176.9, 153.8, 150.9, 137.1, 134.8, 131.9, 129.9, 129.6, 122.2, 118.6, 65.5, 39.0, 27.3, 20.8. FTIR (ATR, cm$^{-1}$): 3364, 2974, 1725, 1595, 1524, 1508, 1192, 1111, 1015, 812, 785, 766. HRMS (m/z): [M+Na]$^+$ calcd for [$C_{20}H_{23}NO_4Na$]$^+$ 364.1525, found 364.1525.

General Procedure for the Synthesis of Boronate Ester Compounds.

The benzyl alcohol species (1.0 equiv.) was combined with substituted phenyl isothiocyanate (1.0 equiv.) in anhydrous THF (15 mL) at 0° C., followed by the addition of NaH (60% in paraffin liquid, 1.25 equiv.). The resultant mixture was stirred at 0° C. for 20 min, after which the ice bath was removed, and the reaction mixture was stirred at r.t. until the completion of the reaction indicated by TLC. The reaction was quenched by adding brine (30 mL), and the aqueous solution was extracted with ethyl acetate (3×15 mL). The organic layers were combined, dried over MgSO$_4$, and evaporated under vacuum. The crude product was purified by column chromatography. Certain compounds show two sets of NMR resonances at room temperature due to slow rotation around thiocarbamate functional groups.

PeroxyTCM-1

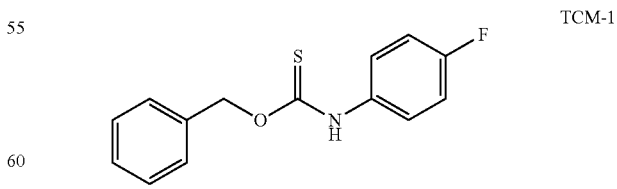

PeroxyTCM-1 was prepared from 4-(hydroxymethyl)phenylboronic acid pinacol ester and 4-fluorophenyl isothiocyanate using the general synthetic procedure described above (245 mg, 32% yield). $^1$H NMR (500 MHz, CDCl$_3$) δ (ppm): 8.59 (s, 1H), 7.84 (s, 2H), 7.55 (s, 1H), 7.38 (br, 2H), 7.20 (br, 1H), 7.02 (br, 2H), 5.65 (br, 2H), 1.38 (s, 12H). $^{19}$F NMR (470 MHz, CDCl$_3$) δ (ppm): −115.3, −115.9. $^{13}$C{$^1$H} NMR (125 MHz, CDCl$_3$) δ (ppm): 188.5, 137.8, 135.1, 132.8, 127.3, 125.9, 124.0, 116.0, 115.8, 84.0, 74.0, 24.9. IR (cm$^{-1}$): 3196, 2978, 1736, 1612, 1541, 1507, 1451, 1391, 1357, 1210, 1194, 1140, 1087, 1059, 1020, 964, 859, 817, 724, 652. HRMS m/z [M+Na]$^+$ calcd. for [$C_{20}H_{23}BFNNaO_3S$]$^+$ 410.1377; found 410.1367.

PeroxyTCM-2

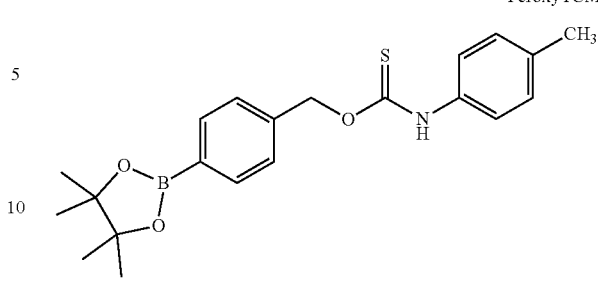

PeroxyTCM-2 was prepared from 4-(hydroxymethyl)phenylboronic acid pinacol ester and 4-tolyl isothiocyanate using the general synthetic procedure described above (251 mg, 34% yield). $^1$H NMR (500 MHz, CDCl$_3$) δ (ppm): 8.53 (s, 1H), 7.84 (s, 2H), 7.41 (s, 3H), 7.12 (m, 3H), 5.66 (s, 2H), 2.34, (s, 3H), 1.38 (s, 12H). $^{13}$C{$^1$H} NMR (125 MHz, CDCl$_3$) δ (ppm): 188.4, 135.0, 129.6, 127.3, 127.2, 121.8, 83.9, 73.9, 24.9, 20.9. IR (cm$^{-1}$): 3279, 2973, 2924, 1613, 1596, 1530, 1515, 1442, 1339, 1318, 1274, 1212, 1168, 1141, 1085, 1042, 1021, 962, 856, 818, 787, 728, 652. HRMS m/z [M+N]$^+$ calcd. for [$C_{21}H_{26}BNNaO_3S$]$^+$ 406.1628; found 406.1632.

PeroxyTCM-3

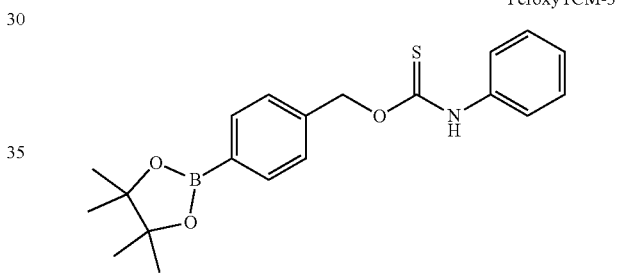

PeroxyTCM-3 was prepared from 4-(hydroxymethyl)phenylboronic acid pinacol ester and phenyl isothiocyanate using the general synthetic procedure described above (157 mg, 21% yield). $^1$H NMR (500 MHz, CDCl$_3$) δ (ppm): 8.56 (s, 1H), 7.85 (s, 2H), 7.30 (m, 7H), 5.67 (s, 2H), 1.38 (s, 12H). $^{13}$C{$^1$H} NMR (125 MHz, CDCl$_3$) δ (ppm): 188.4, 138.0, 136.8, 135.1, 129.1, 127.3, 125.6, 123.3, 121.7, 83.9, 74.0, 24.9.1R (cm$^{-1}$): 3177, 2981, 1616, 1593, 1535, 1491, 1449, 1401, 1367, 1332, 1223, 1176, 1144, 1094, 1027, 1018, 860, 842, 799, 747, 727. HRMS m/z [M+Na]$^+$ calcd. for [$C_{20}H_{24}BNNaO_3S$]+392.1472; found 392.1477.

TCM-1

TCM-1 was prepared from benzyl alcohol and 4-fluorophenyl isothiocyanate using the general synthetic procedure described above (205 mg, 79% yield). $^1$H NMR (500 MHz, CDCl$_3$) δ (ppm): 8.63 (s, 1H), 7.94 (s, 1H), 7.40 (br, 5H), 7.22 (s, 1H), 7.03 (br, 2H), 5.62 (br, 2H). $^{19}$F NMR (470

MHz, CDCl₃) δ (ppm): −115.2, −116.0. $^{13}C\{^1H\}$ NMR (125 MHz, CDCl₃) δ (ppm): 188.5, 134.9, 132.9, 128.7, 128.6, 128.2, 125.8, 123.9, 115.9, 74.1. IR (cm-1): 3204, 3039, 1610, 1550, 1497, 1450, 1401, 1344, 1301, 1289, 1233, 1208, 1192, 1049, 840, 815, 730, 693. HRMS m/z [M+Na]⁺ calcd. for [C₁₄H₁₂FNNaOS]⁺ 284.1521: found 284.0529.

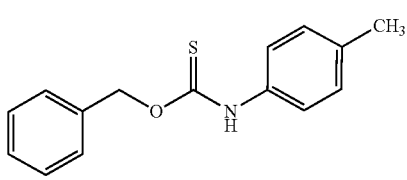

TCM-2

TCM-2 was prepared from benzyl alcohol and 4-tolyl isothiocyanate using the general synthetic procedure mentioned above (365 mg, 71% yield). $^1H$ NMR (500 MHz, CDCl₃) δ (ppm): 8.43 (s, 1H), 7.94 (s, 1H), 7.41 (br, 5H), 7.13 (br, 3H), 5.62 (br, 2H), 2.34 (s, 3H). $^{13}C\{^1H\}$ NMR (125 MHz, CDCl₃) δ (ppm): 188.4, 135.3, 134.4, 129.6, 128.6, 128.5, 128.2, 123.8, 121.7, 74.0, 21.0. IR (cm-1): 3197, 3028, 1593, 1545, 1498, 1451, 1401, 1346, 1309, 1288, 1207, 1186, 1081, 1055, 804, 692, 646. HRMS m/z [M+Na]⁺ calcd. for [C₁₅H₁₅NNaOS]⁺ 280.0772; found 280.0771.

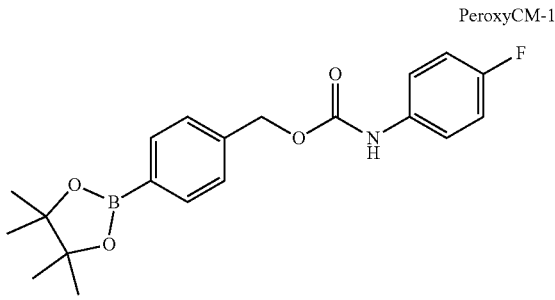 [SMILES: CC1(C)OB(c2ccc(COC(=O)Nc3ccc(F)cc3)cc2)OC1(C)C]

PeroxyCM-1

4-(Hydroxymethyl)phenylboronic acid pinacol ester (655 mg, 2.80 mmol, 1.4 equiv.) was combined with 4-fluorophenyl isocyanate (274 mg, 2.00 mmol, 1.0 equiv.) in anhydrous toluene (30 mL) at room temperature, followed by the addition of triethylamine (202 mg, 2.00 mmol, 1.0 equiv.). The resultant mixture was stirred at 110° C. for 16 h, after which the oil bath was removed, and the reaction solution was cooled to room temperature. The reaction mixture was quenched by adding brine (30 mL), and the aqueous solution was extracted with ethyl acetate (3×15 mL). The organic layers were combined, dried over MgSO₄, and evaporated under vacuum. The crude product was purified by using column chromatography to afford pure PeroxyCM-1 as white solid (571 mg, 77%). $^1H$ NMR (300 MHz, CDCl₃) δ (ppm): 7.84 (d, J=7.8 Hz, 2H), 7.35 (m, 4H), 7.01 (t, J=8.4 Hz, 2H), 6.79 (s, 1H), 5.22 (s, 2H), 1.37 (s, 12H). $^{19}F$ NMR (470 MHz, CDCl₃) δ (ppm): −119.4. $^{13}C\{^1H\}$ NMR (125 MHz, CDCl₃) δ (ppm): 160.0, 158.1, 153.5, 139.0, 135.1, 133.7, 127.3, 120.5, 115.8, 83.9, 67.0, 24.9. IR (cm⁻¹): 3326, 2971, 1734, 1614, 1538, 1511, 1407, 1373, 1308, 1278, 1204, 1139, 1084, 1037, 855, 833, 784, 740, 656. HRMS m/z [M+Na]⁺ calcd. for [C₂₀H₂₃BFNNaO₄]⁺ 394.1606; found 394.1602.

Example 1

In some embodiments, model thiocarbamates were made to confirm that the proposed decomposition cascade to release COS occurs efficiently and to demonstrate the biological compatibility of this new $H_2S$ donor motif. In some embodiments, an azide in the para position of the benzylthiocarbamate was used to function as the $H_2S$-responsive "trigger" for self-immolation and COS release. To facilitate NMR identification of the products, azidobenzylthiocarbamate (donor compound 1 of FIG. 2) was made with a p-fluoroaniline payload, and the corresponding carbamate (donor compound 2 of FIG. 2) as a control donor compound. Although donor compound 2 should undergo the same self-immolative decomposition upon azide reduction, it will release $CO_2$ rather than COS, and thus should not result in $H_2S$ donation upon reaction with CA. To monitor the reactivity of the model compounds under controlled reaction conditions, tris(2-carboxyethyl)phosphine) (TCEP), an azide-reducing agent, was used to trigger self-immolation, due to its near-instantaneous reduction of azides. In each case, $^1H$, $^{13}C\{^1H\}$, and $^{19}F$ NMR spectroscopy was used to monitor the reaction after reduction of the model complexes by TCEP. The disappearance of the benzylic peak, loss of the thiocarbonyl carbon peak, and formation of new resonances upon self-immolation by NMR spectroscopy (FIGS. 3A-3C) confirmed that self-immolation occurs. All such changes were observed within 5 minutes of TCEP addition, confirming the rapid self-immolation of the scaffold upon reduction, and were consistent with COS release from the thiocarbamate scaffold upon azide reduction.

Figure 2:
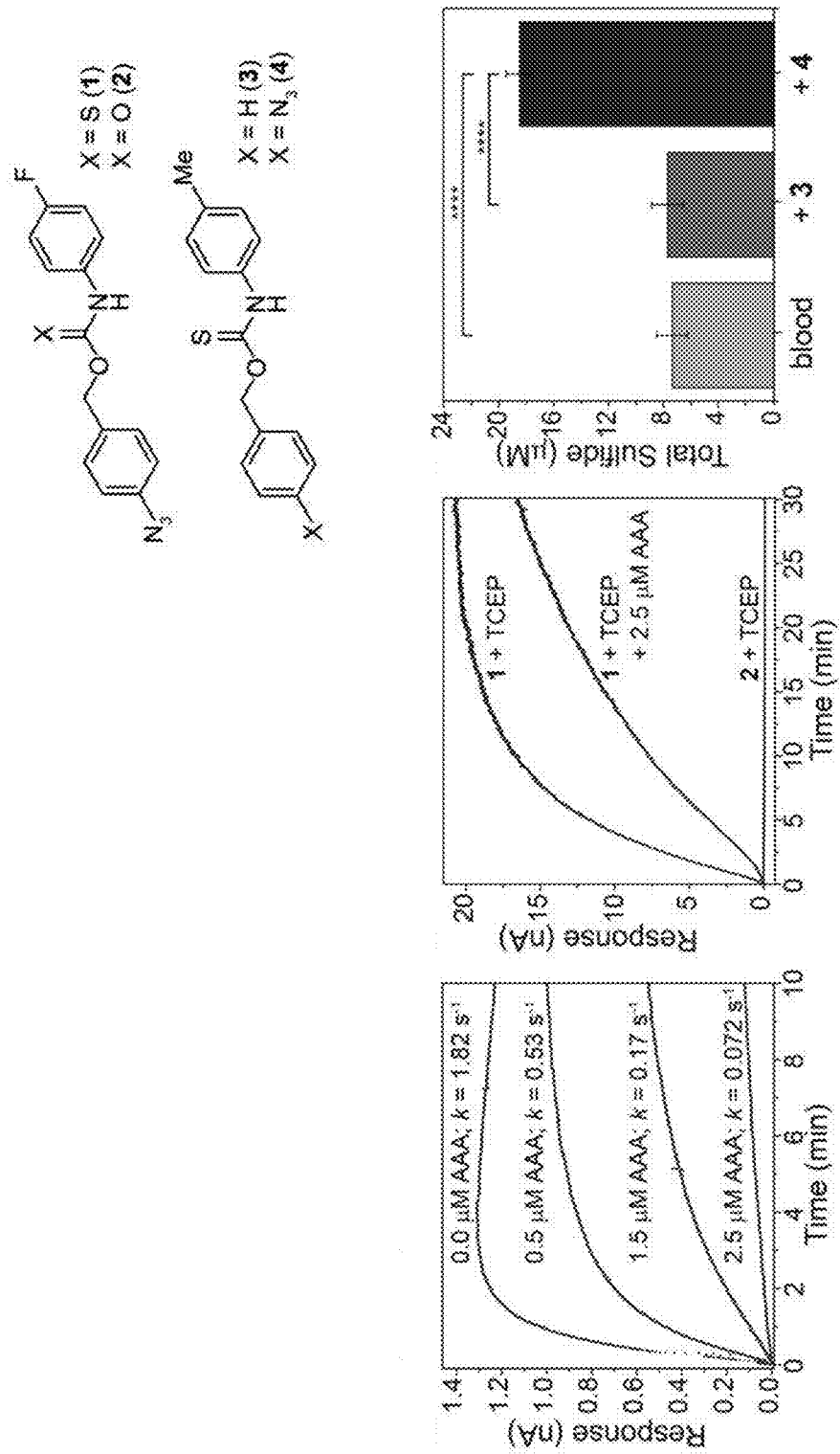
FIG. 2 shows results obtained from analyzing the behavior of representative donor compounds and control compounds when interacting with biological samples.
Figure 3A:
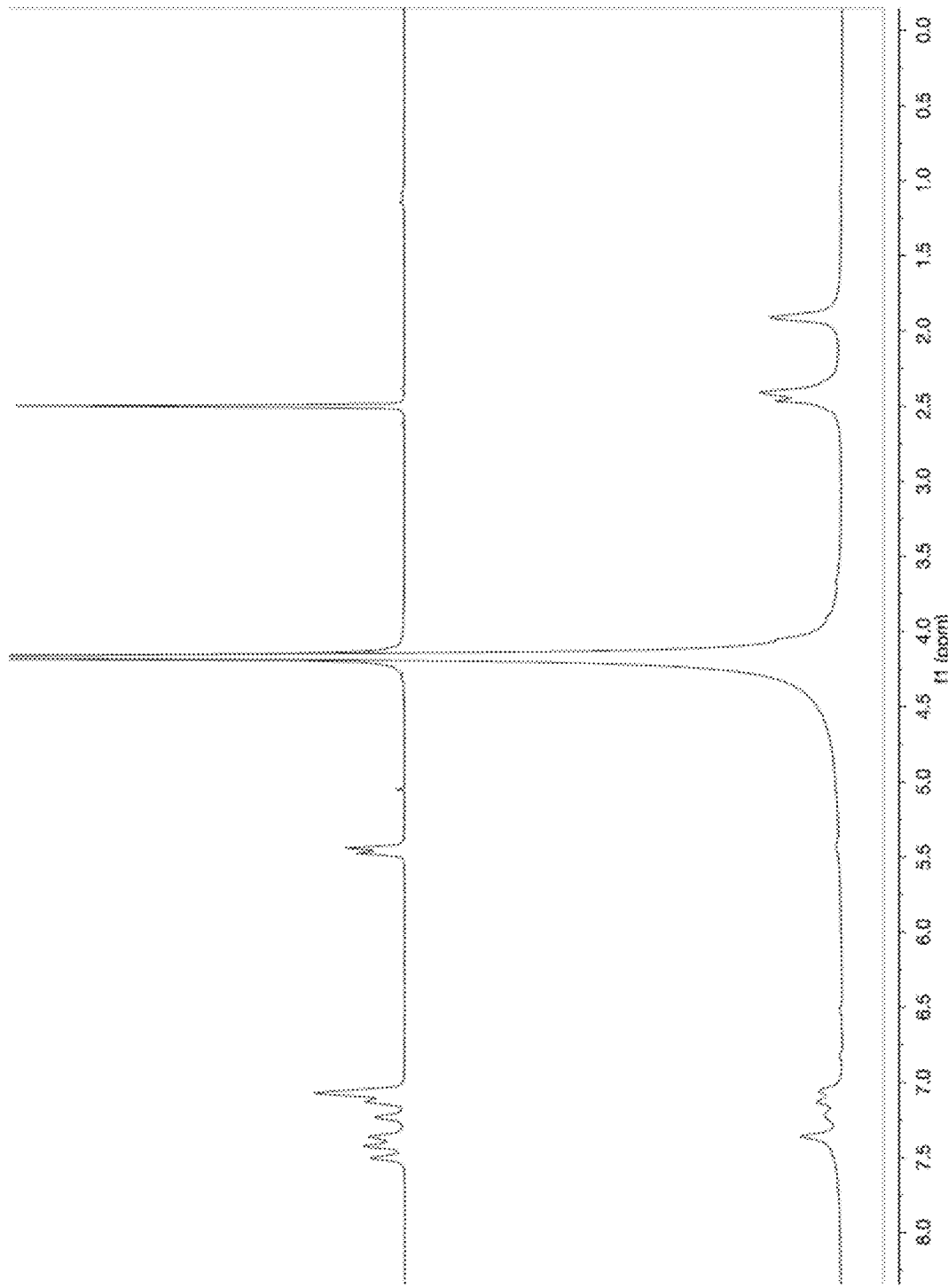
FIGS. 3A-3C are NMR spectra showing the progression of the break-down of donor compound 1 to various by-products.
Figure 3B:
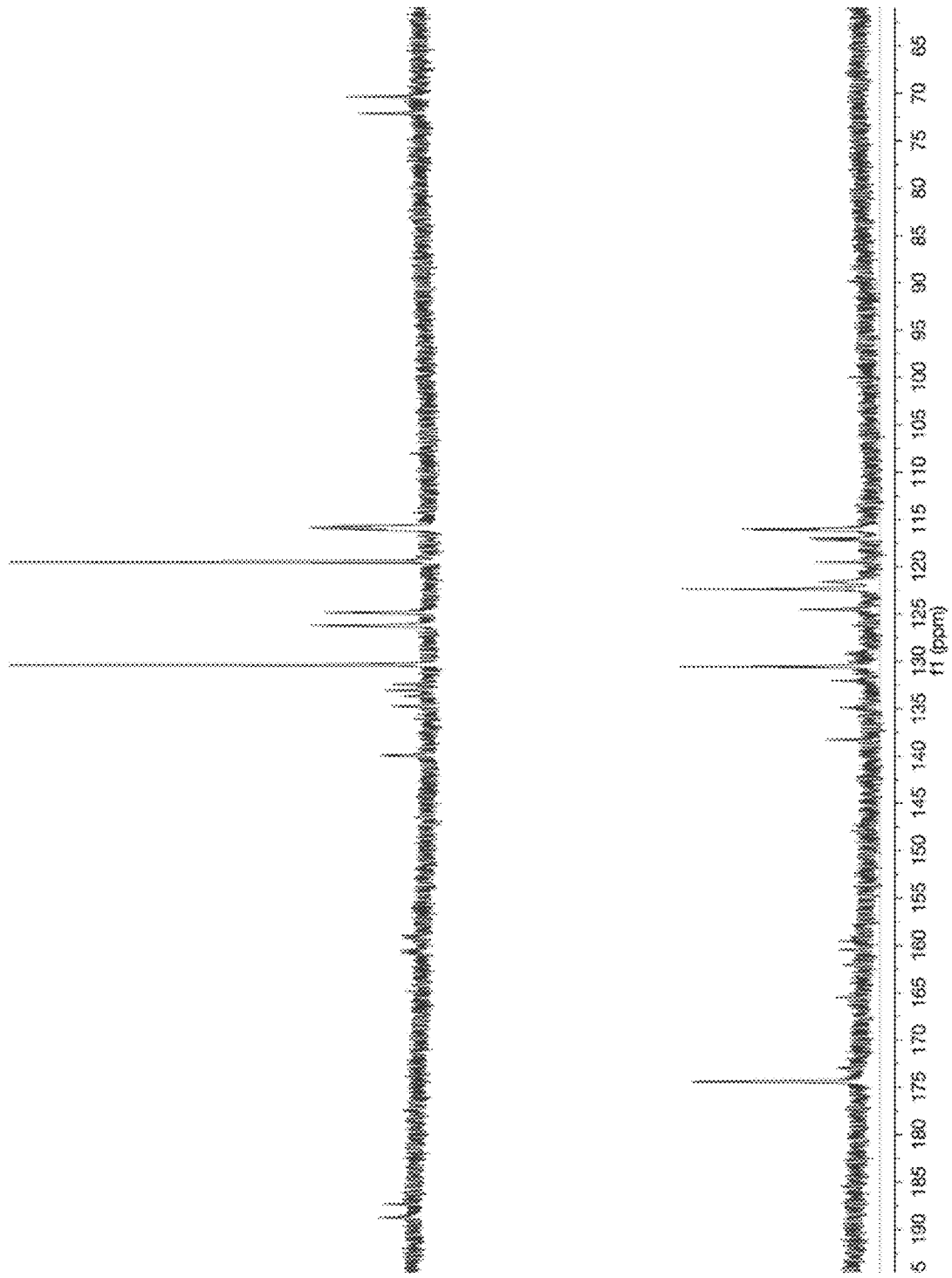
Figure 3C:
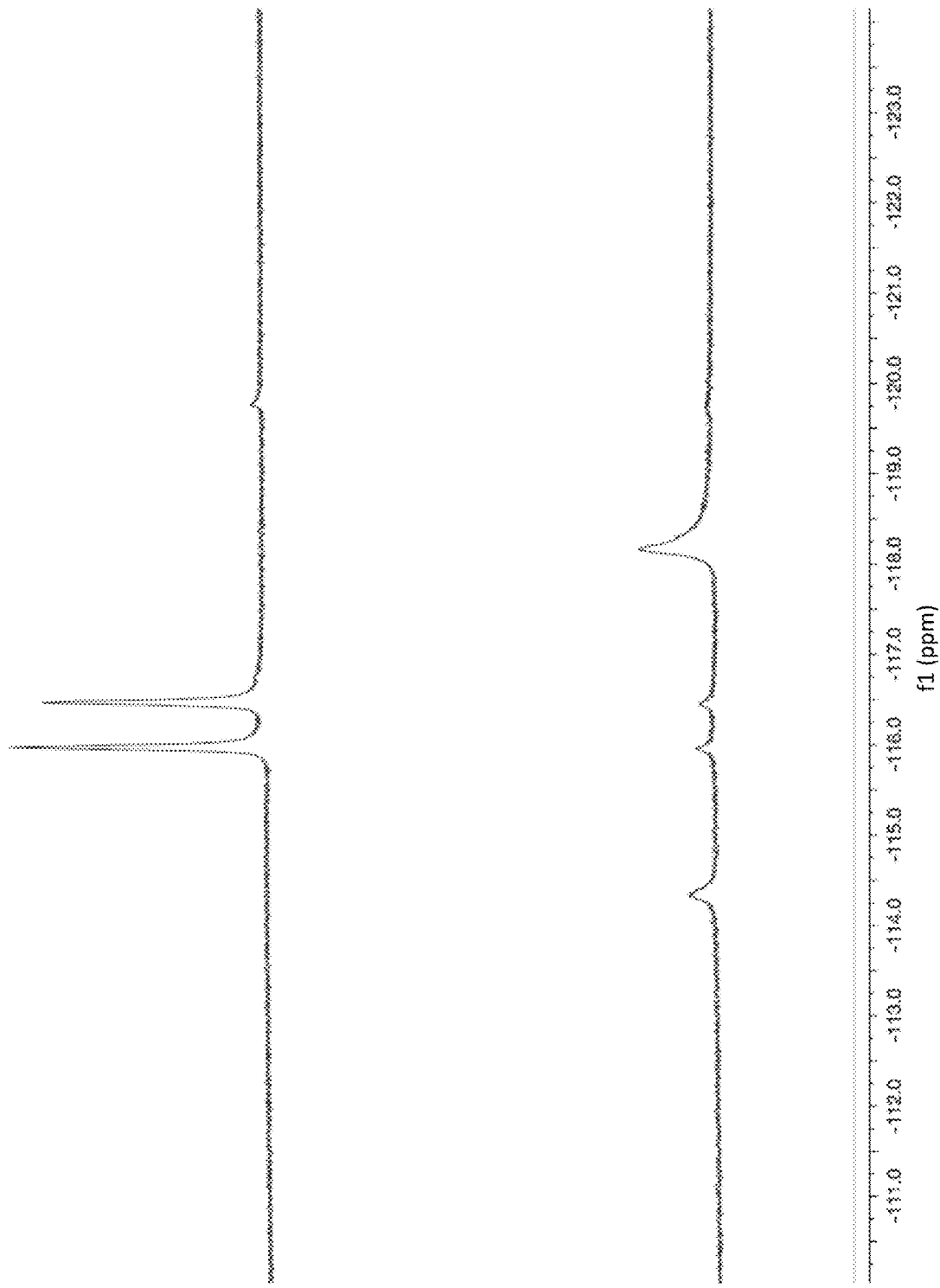
Figure 4:
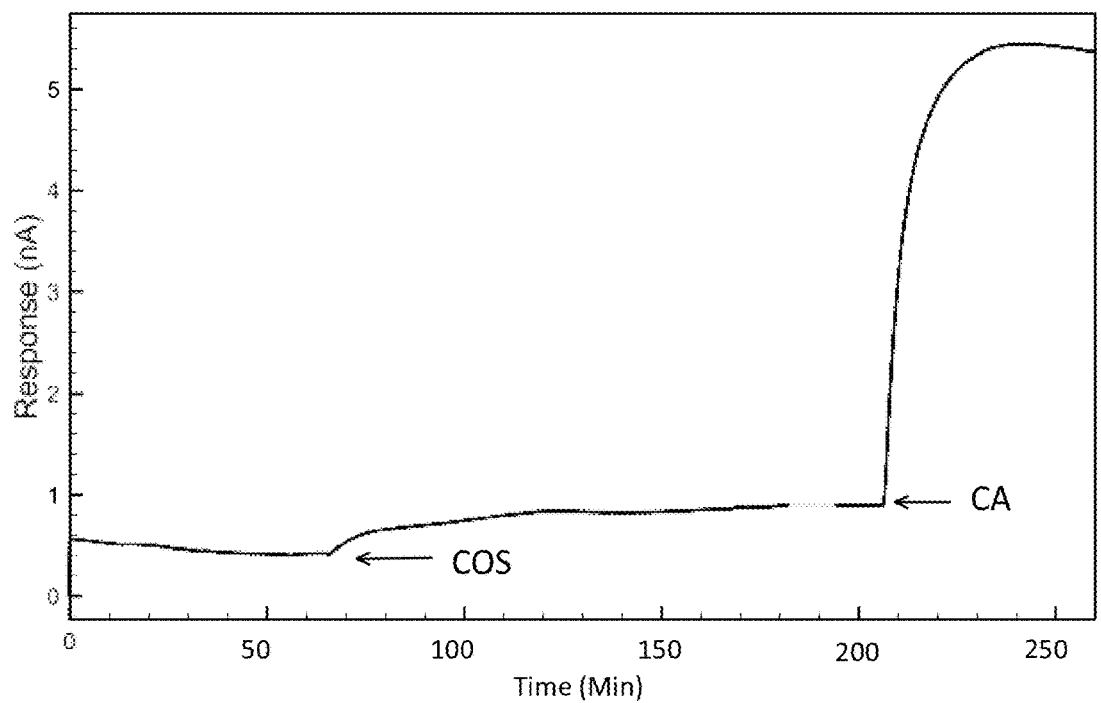
FIG. 4 is graph of response (nA) as a function of time (minutes), which shows that the addition of COS to PBS buffer results in minimal $H_2S$ formation until the addition of CA.
Figure 5:
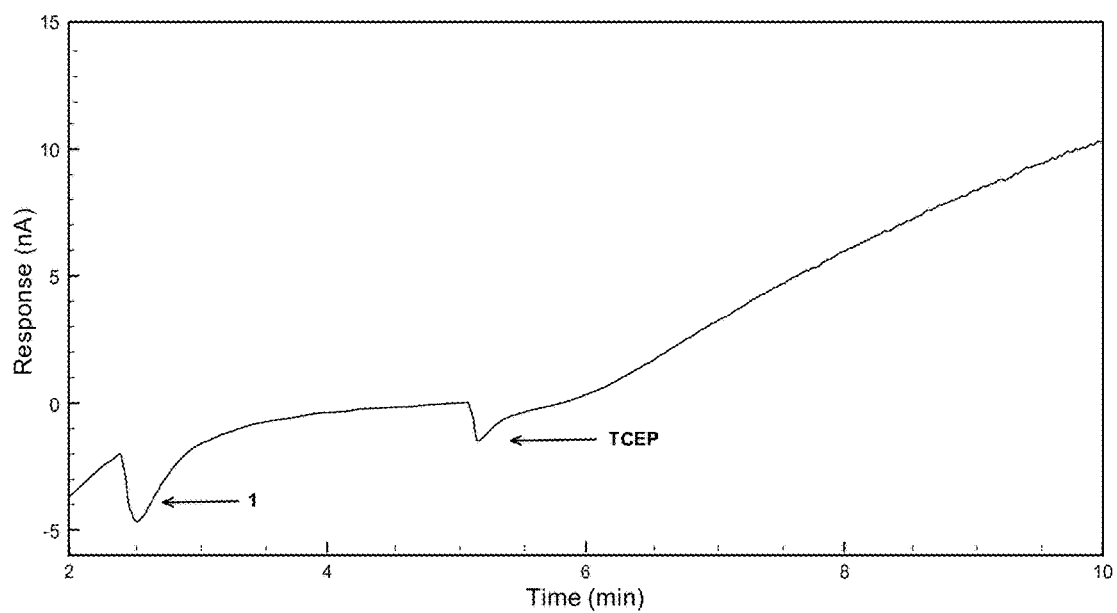
FIG. 5 is a graph of response (nA) as a function of time (minutes), which shows that no $H_2S$ is formed from donor compound 1 in PBS buffer until TCEP is added.

To confirm that the COS released from self-immolative thiocarbamates can serve as a potential source of $H_2S$ donation, it was established that independently prepared COS could be efficiently hydrolyzed to $H_2S$ by CA. Upon addition of COS gas to deoxygenated aqueous buffer (PBS, 1 mM CTAB, pH 7.4) containing CA from bovine erythrocytes, rapid $H_{2S}$ production was observed using an $H_2S$-responsive electrode. In the absence of CA, negligible current was observed from COS alone, which is consistent with slow and pH-dependent, nonenzymatic hydrolysis in water (FIG. 4). A dose-dependent reduction in $H_2S$ production also was observed upon addition of the CA inhibitor acetazolamide (AAA), which confirmed the enzymatic hydrolysis of COS by CA (FIG. 2). After confirming that CA rapidly catalyzes the hydrolysis of COS, the $H_2S$-donating ability of model compounds 1 and 2 under the same conditions were evaluated. Monitoring thiocarbamate 1 in buffer containing CA did not result in $H_2S$ formation, confirming that the thiocarbamates do not react directly with CA and that aryl azides are stable in the presence of CA (FIG. 5). Upon injection of TCEP, however, rapid release of $H_2S$ was observed, indicating that reduction of the azide to an amine triggers self-immolation and COS release. Additionally, repetition of this example with added AAA significantly reduced the rate of $H_2S$ production, confirming that uninhibited CA is used for significant $H_2S$ production from the triggered thiocarbamate scaffold (FIG. 2, bottom left). Finally, the analogous carbamate (2) was investigated under identical conditions, and no $H_2S$ was produced upon addition of TCEP, confirming that the sulfur-containing thiocarbamate is required for $H_2S$ formation. These examples establish the validity of using the thiocarbamate group as a triggerable source of $H_2S$ release in aqueous solution, which can prove fruitful for applications evaluating and/or using the pharmacological and physiological roles of sulfide donating molecules.

Example 2

Figure 6:
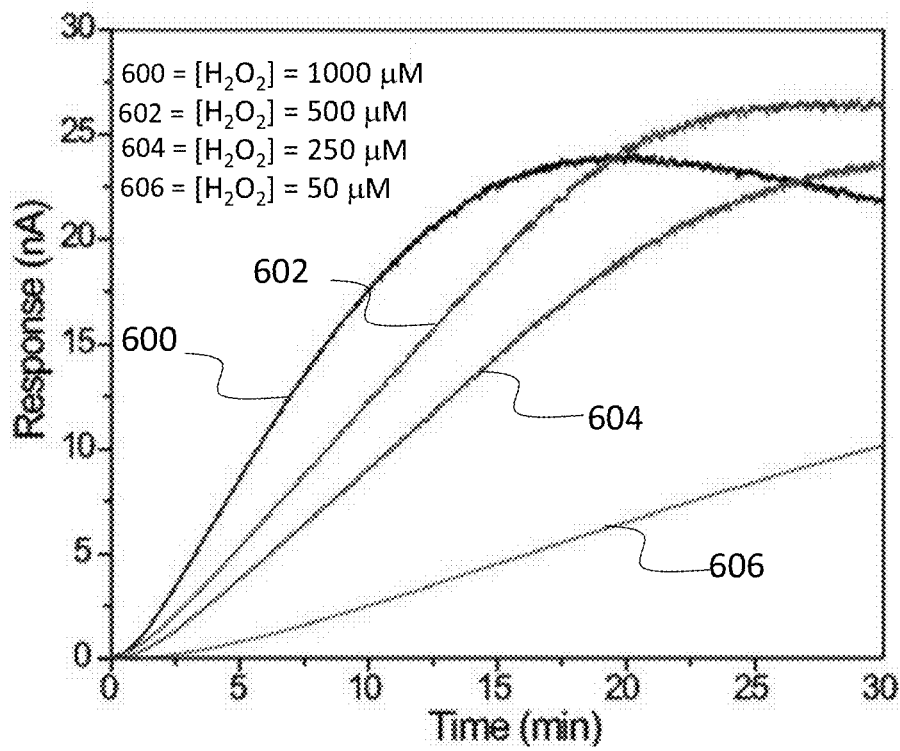
FIG. 6 is a graph of response (nA) as a function of time (minutes) showing $H_2S$ release from a representative donor compound in the presence of $H_2O_2$.
Figure 7:
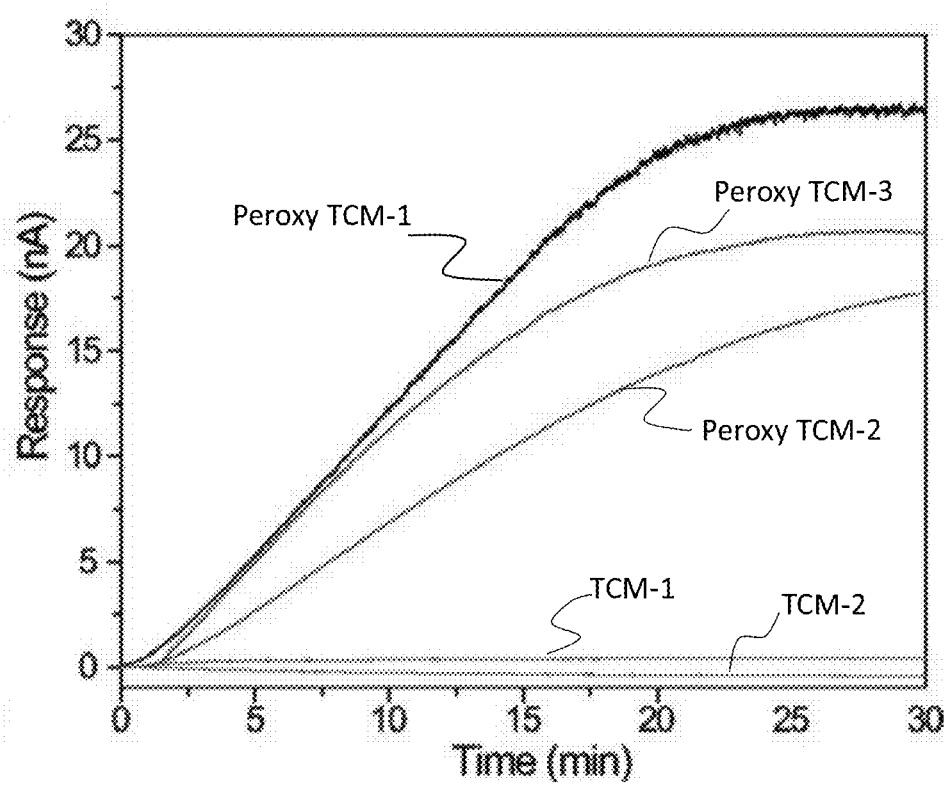
FIG. 7 is a graph of response (nA) as a function of time (minutes) showing $H_2S$ release from a control compound and two different representative donor compounds described herein in the presence of $H_2O_2$.

In some embodiments, H$_2$S release from model thiocarbamates in whole mouse blood was evaluated to expand on the efficacy of H$_2$S release from thiocarbamates in more biologically-relevant contexts. Although murine systems provide a convenient model, mice have among the lowest CA levels in mammals, with murine blood only containing about 15% of the CA present in human blood, and thus represent a challenging target for sulfide release mediated by CA. To quantify total sulfide levels, the monobromobimane (mBB) method was used, which allows for the analytical measurement of different sulfide pools and is compatible with many types of biological samples. Measurement of the total sulfide, which includes free sulfide as well as bound sulfane-sulfur, revealed background levels of 8 170 μM, which are higher than total sulfide levels commonly observed and reported in plasma, but are consistent with the high sulfane-sulfur content in red blood cells. Thiocarbamate 3 (FIG. 2), which lacks the azide trigger, was made to confirm that the thiocarbamate group was stable in whole blood and did not release COS without activation of the trigger group, and the results obtained with this model compound were compared with azide-functionalized 4 (FIG. 2). Total sulfide levels were measured for each compound, as well as the control, after 30 minutes of incubation with excess TCEP (FIG. 2, bottom right). Only samples containing donor 4 with the azide trigger increased total sulfide levels in blood (p 0.0001). These results establish the stability of the thiocarbamate in biological milieu, and confirm that endogenous CA, even in the low levels found in murine blood, is sufficient to hydrolyze the COS released from thiocarbamates after the self-immolation cascade is triggered, highlighting the efficacy of this H$_2$S-releasing strategy in biological environments. Additional examples of H$_2$S release results obtained from using donor compounds described herein are shown in FIGS. 6 and 7. FIG. 6 is a graph showing the response as a function of time of H$_2$S release from a donor compound embodiment using H$_2$O$_2$ as the reactive component. FIG. 7 is a graph showing the difference in reactivity between compound embodiments wherein R$^4$ is H, Me, or F.

Example 3

Figure 8A:
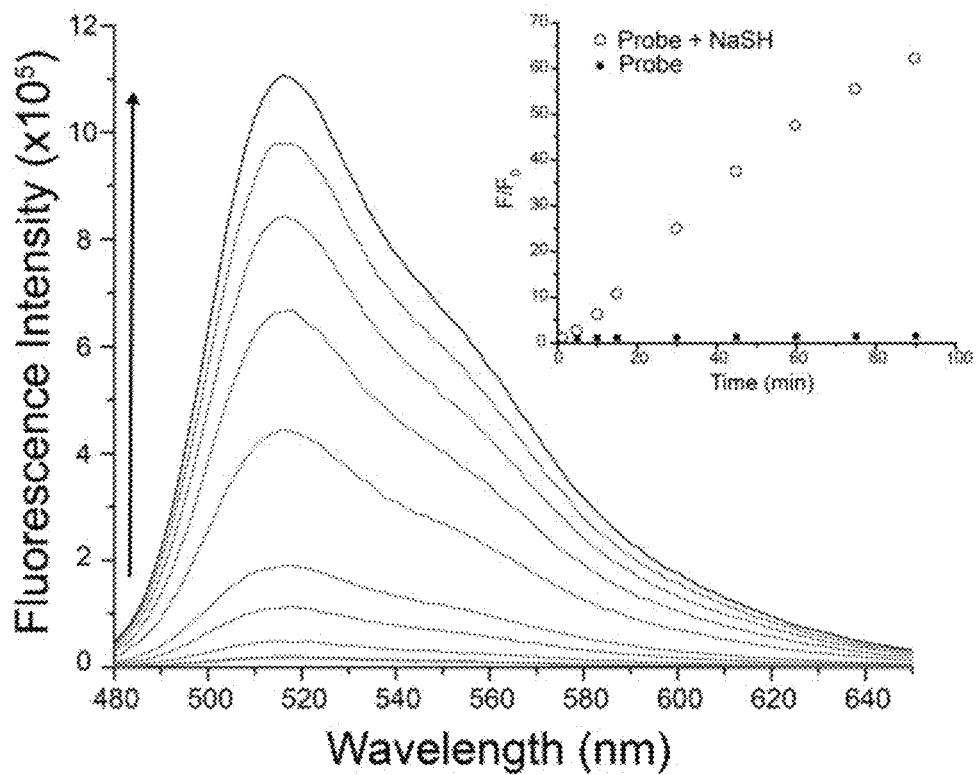
FIGS. 8A and 8B show fluorescence results obtained from analyzing a representative donor compound disclosed herein.
Figure 8B:
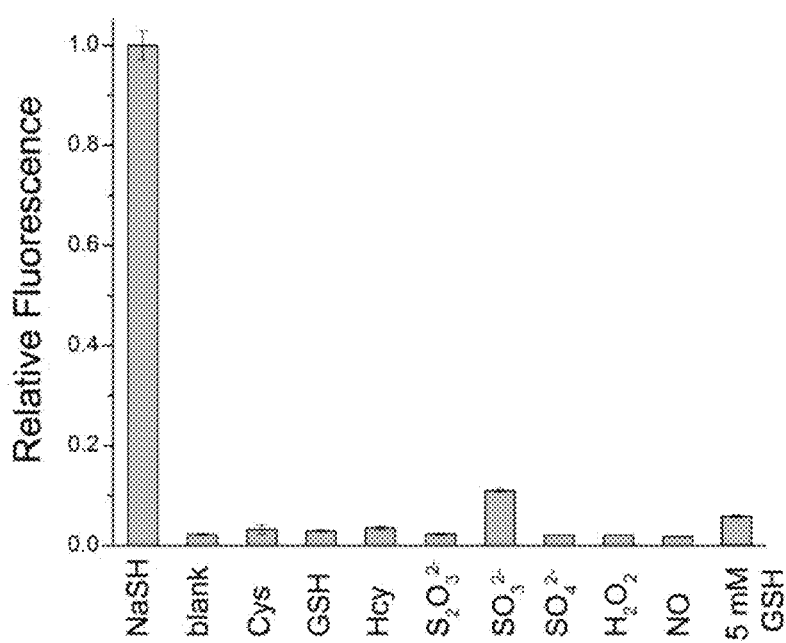
Figure 9:
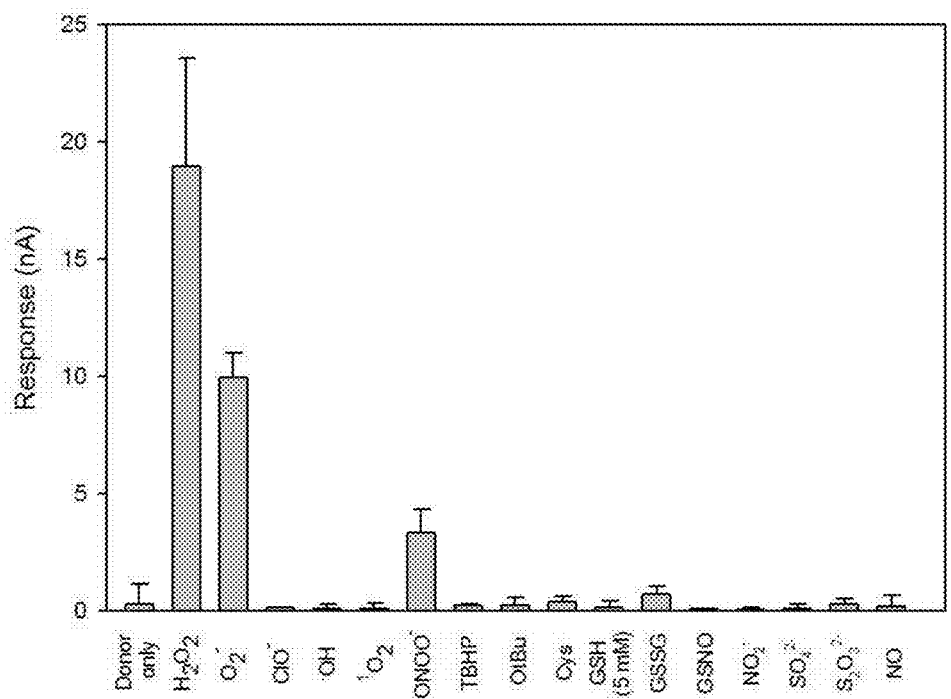
FIG. 9 is a graph of relative fluorescence that shows the $H_2S$ release of a representative donor compound disclosed herein in the presence of various reactive sulfur, oxygen, and nitrogen species (RSONS).

In additional embodiments, incorporating a fluorophore into the scaffold can be conducted to access an H$_2$S-responsive fluorescent probe that releases H$_2$S upon H$_2$S detection. In some embodiments, methylrhodol (MeRho) was used as the fluorophore due to its high quantum yield and single fluorogenic amine, which could be readily converted into the desired thiocarbamate. Since the azide-functionalized scaffold would be triggered by H$_2$S to release both MeRho and COS, this would function as a fluorescent H$_2$S probe that would replenish sulfide through the release of COS. To access the desired scaffold, MeRho was treated with thiocarbonyldiimidazole (TODI) and NEt$_3$ in DMF to afford methylrhodol isothiocyanate (MeRho-NCS) in 60% yield. Subsequent treatment with 4-azidobenzyl alcohol and NaH afforded the methylrhodol thiocarbamate azide (MeRho-TCA) in 35% yield. One benefit of this simple synthetic route is that almost any fluorophore containing a fluorogenic nitrogen can readily be functionalized with the benzylazide thiocarbamate group, thus providing access to a diverse library of fluorophores. With a sulfide-replenishing H$_2$S probe in hand, the fluorescence response upon addition of sulfide was evaluated. Treatment of MeRho-TCA with 50 equivalents of NaSH in aqueous buffer (PBS, 1 mM CTAB, pH 7.4) resulted in a 65-fold fluorescence turn-on over 90 minutes (FIG. 8A). Additionally, it was confirmed that the MeRho-TCA scaffold was selective for HS— over other RSONs, by measuring the fluorescence response to Cys, GSH, Hcy, S$_2$O$_3^{2-}$, SO$_3^{2-}$, SO$_4^{2-}$, H$_2$O$_2$, and NO (FIG. 8B). Results from an additional embodiment are shown in FIG. 9. The MeRho-TCA scaffold exhibited excellent selectivity for H$_2$S over other RSONs, demonstrating that the thiocarbamate linker group did not erode the selectivity of the azide trigger, and also establishing that the MeRho-TCA scaffold can function as a viable H$_2$S reporter.

Example 4

Figure 10:
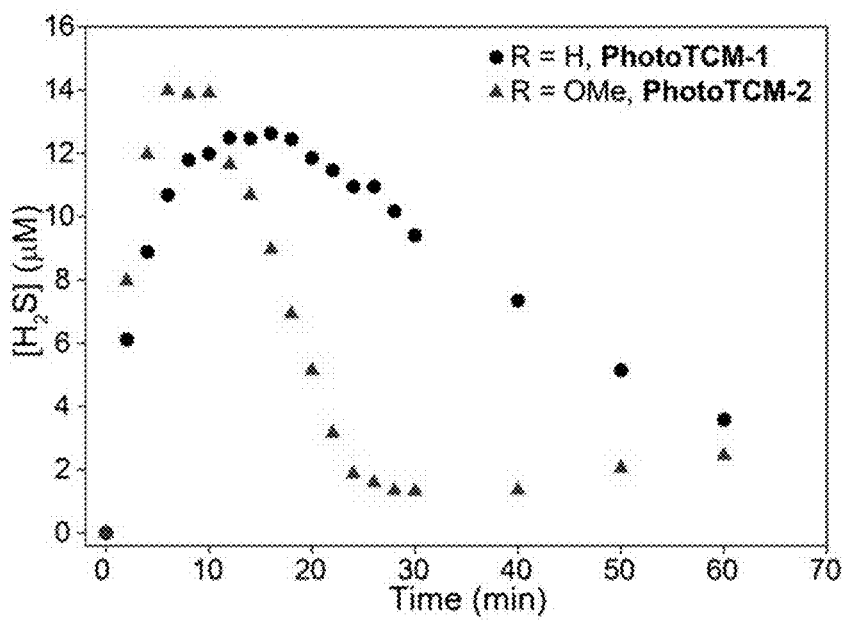
FIG. 10 is a graph of $H_2S$ release (micromolar) as a function of time (minutes) for two representative donor compounds described herein in the presence of UV light.

In this example, the H$_2$S releasing profiles of light-triggerable compounds were explored. A methylene blue (MB) assay was used to monitor H$_2$S release from representative photo-triggerable compounds (e.g., PhotoTCM-1 (50 μM) and PhotoTCM-2 (50 μM)) upon irradiation with an LED UV light (365 nm) in PBS buffer (pH 7.4, 10 mM) containing CA (25 μg/mL). A time-dependent H$_2$S release was observed from both PhotoTCM-1 and PhotoTCM-2, with a peaking time for H$_2$S release of ~10-minutes (FIG. 10).

Figure 11B:
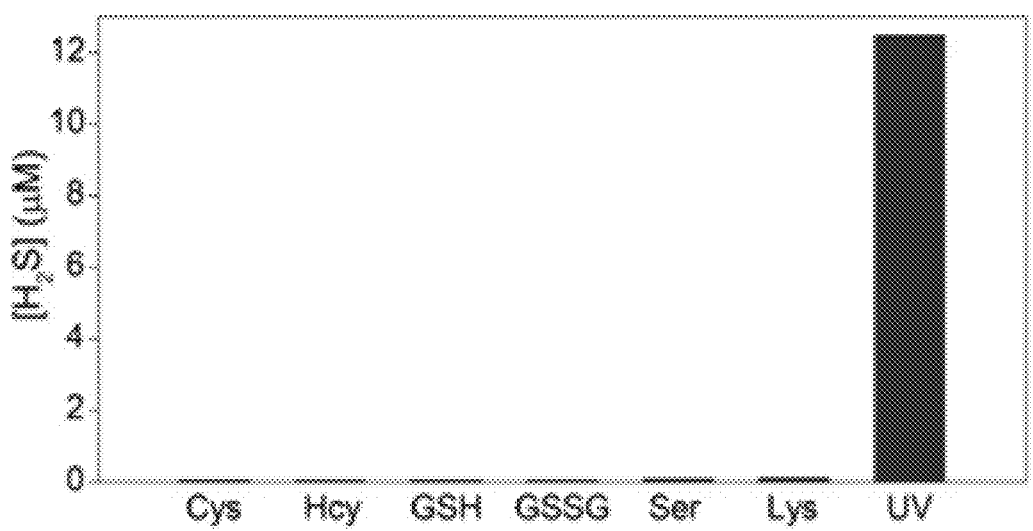

To confirm that the observed COS/H$_2$S release was due to photocleavage of the ONB protecting group (ortho-nitrobenzyl), a series of control embodiments were performed. As shown in FIG. 11A, UV-irradiation of a PBS solution containing CA does not generate H$_2$S. Similarly, PhotoTCM-1 did not generate H$_2$S in the absence of UV irradiation in these embodiments. Upon UV irradiation of PhotoTCM-1 in the absence of CA (bar 4 in FIG. 11A), low levels of H$_2$S were observed. Without being limited to a particular theory, it is currently believed that this result may be a result of the slow background hydrolysis of COS to H$_2$S in the absence of CA. In this example, TCM-1, which lacks an ONB group, did not release H$_2$S upon the treatment of UV light. In this example, this established that the thiocarbamate linkage is not photodegraded to generate H$_2$S. Similarly, no H$_2$S release was observed from the carbamate control compound PhotoCM-1 in this example. Incubation of PhotoTCM-1 with CA under UV exposure results in a significant enhancement of H$_2$S concentration, indicating UV irradiation is a sufficient trigger to promote H$_2$S release. Moreover, the measured H$_2$S is significantly reduced in the presence of acetazolamide (AAA), a well-known CA inhibitor. In addition, incubation of PhotoTCM-1 with cellular nucleophiles, such as cysteine, homocysteine, reduced glutathione, oxidized glutathione, serine, and lysine, in the presence of CA does not generate H$_2$S, demonstrating PhotoTCM-1 is stable towards cellular nucleophiles (FIG. 11B). Taken together, these studies demonstrate that ONB-functionalized compounds provide a functional platform to access photo-labile H$_2$S donors and that H$_2$S production can be triggered and tuned by UV irradiation.

The cleavage mechanism of the photolabile groups is compatible with a thiocarbamate linking group and other "—WC(=Y)V—" groups illustrated in the formulas described herein, resulting in generation of intermediates that decompose to produce COS and the by-products disclosed herein (e.g., 4-fluoroaniline). Consistent with this reaction mechanism, mass spectrometric analysis of the reaction mixture after UV irradiation clearly shows formation of 4-fluoroaniline (m/z: 106.1) and 2-nitrosobenzylaldehyde (m/z: 136.0). Additionally, this COS/H$_2$S release does not proceed through an electrophilic quinone methide intermediate often required in self-immolative cascade reactions, thus increasing the biological compatibility of this bioorthogonal delivery approach.

In summary, this example demonstrates that photolysis of photolabile groups is compatible with the "—WC(=Y)V—" groups of the formulas described herein and thus provides a broad platform for reactivity. The time-dependent $H_2S$ release after UV-activation suggests that the donor compounds disclosed herein can be used as new efficacious photo-labile COS/$H_2S$ donors.

Example 5

Figure 12A:
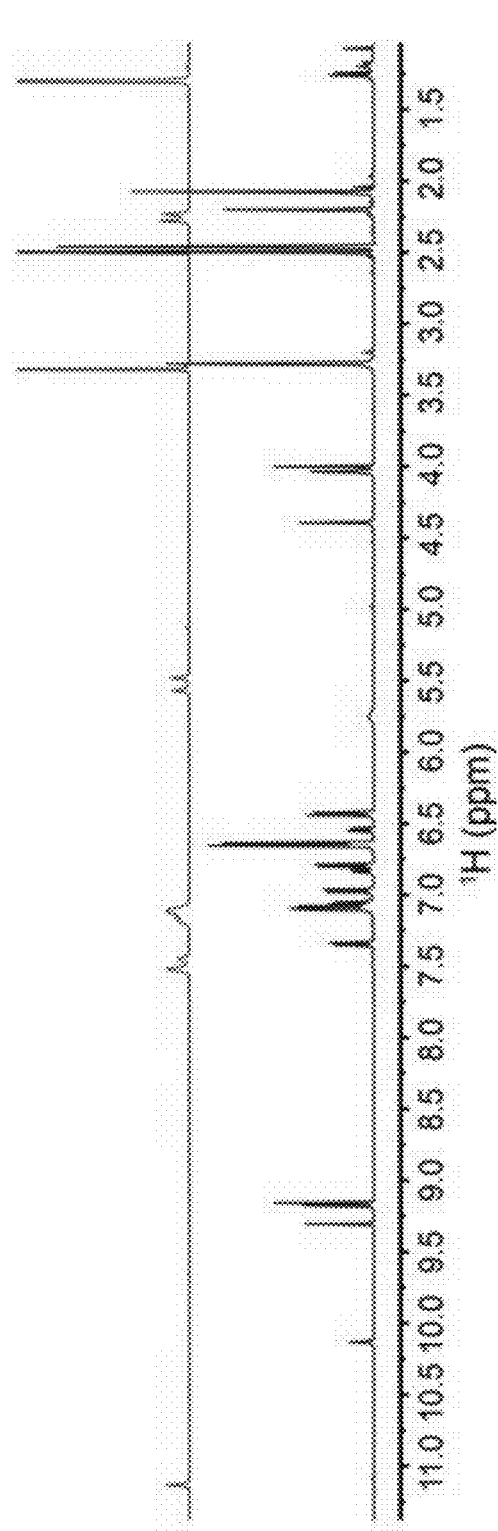
FIGS. 12A and 12B are NMR spectra showing the progression of the break-down of a representative donor compound disclosed herein to various by-products.
Figure 12B:
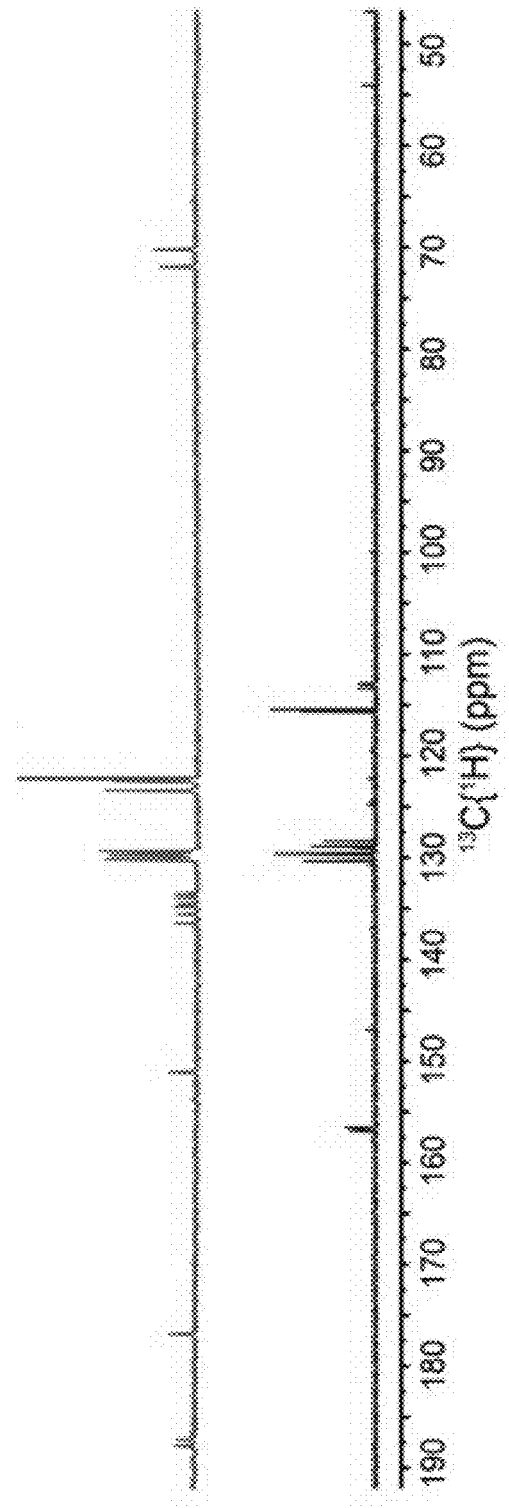

In this example, porcine liver esterase (PLE) is used to initiate a self-immolative decomposition reaction. After stirring the donor (14 mM) with PLE (28 U/mL) in PBS (pH 7.4) with 10% DMSO for 48 hours, the organic layer was extracted and analyzed by NMR spectroscopy and mass spectrometry (FIGS. 12A and 12B). Loss of the benzylic and thiocarbamate N—H protons at ~5.5 ppm and 11.1 ppm, respectively, in the $^1$H NMR spectrum of the reaction mixture confirmed self-immolation (FIG. 12B). As further evidence of the triggered cascade decomposition, the broad NMR resonances characteristic of O-alkyl thiocarbamates, which is due to the slow rotation around the thiocarbamate moiety on the NMR time scale, sharpen significantly upon ester cleavage with PLE. Additionally, the $^{13}$C{$^1$H} NMR spectrum after treatment with PLE (FIG. 12B), clearly showed the loss of the C=S and benzylic carbon resonances at 185 and 70 ppm, respectively. Both the $^1$H and $^{13}$C{$^1$H} NMR spectra also show the formation of new aromatic species corresponding to several products, which were further characterized using mass spectrometry. Because the generated p-quinone methide is electrophilic, it was expected that it would be scavenged by biological nucleophiles, such as thiols, amines, or water, under physiological conditions. The mass spectrum acquired of the reaction mixture after treatment with PLE clearly showed formation of p-toluidine (m/z: 107.0) and the product corresponding to p-toluidine trapping of the o-quinone methide intermediate (m/z: 214.1). Taken together, the NMR spectroscopy and mass spectrometry studies confirm self-immolation of the scaffold, an embodiment of which is illustrated below in Scheme 10.

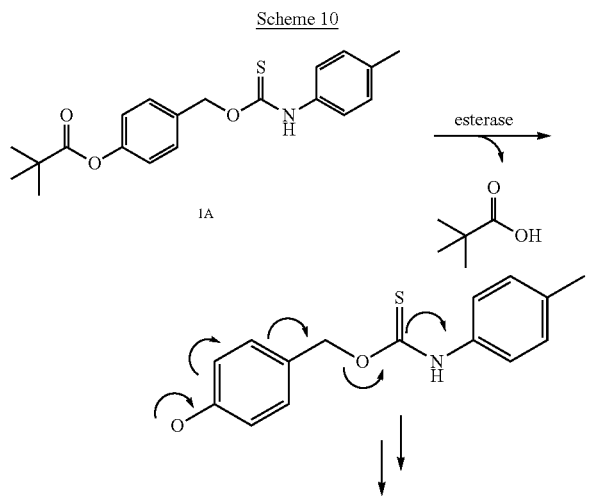

Scheme 10

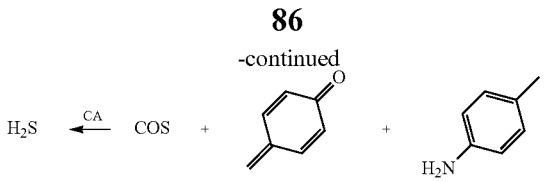

Example 6

Figure 13A:
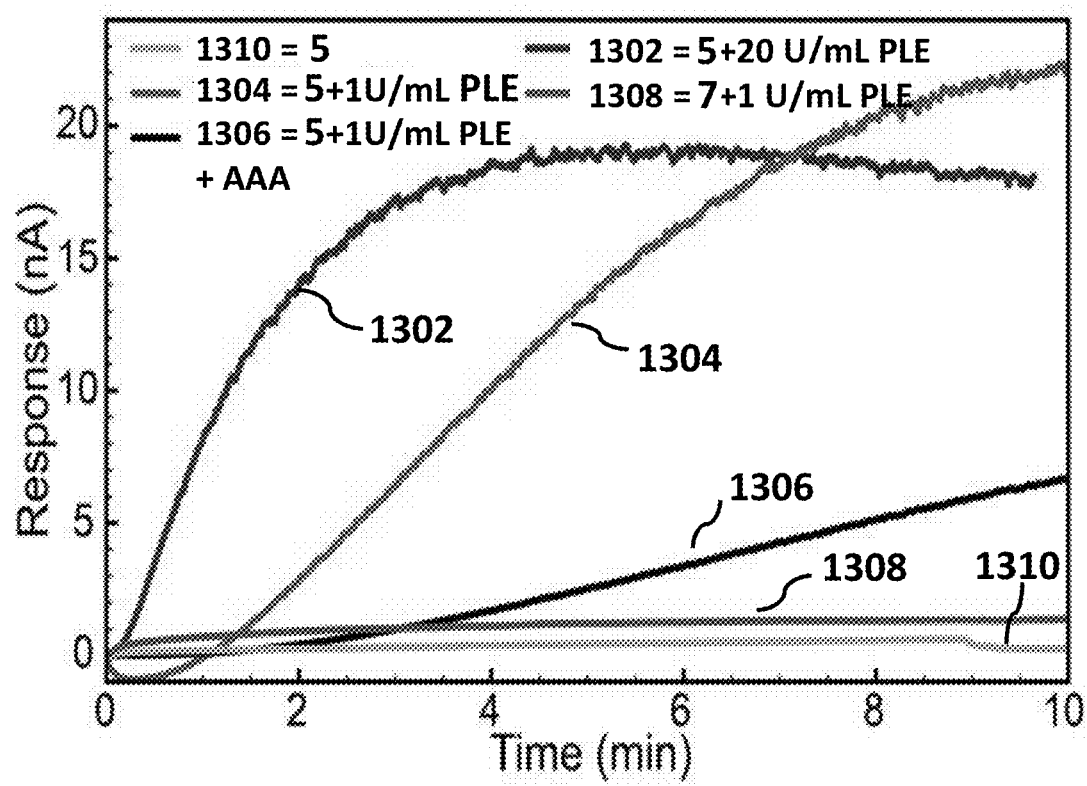
FIGS. 13A and 13B show the $H_2S$ release results for representative donor compounds disclosed herein.
Figure 13B:
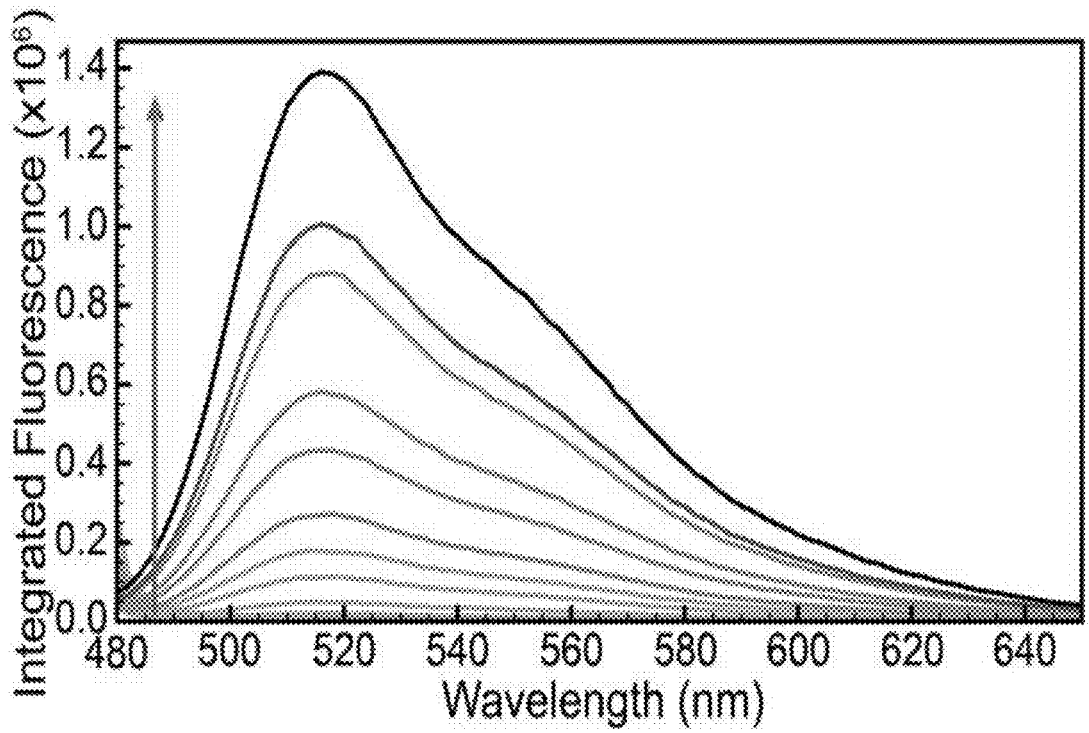

With esterase-triggered donors in hand, it was first confirmed that 5 was stable in aqueous solution in the absence of esterase. Next, it was verified that addition of 5 to pH 7.4 PBS buffer containing physiologically relevant levels of CA (25 µg/mL) did not result in $H_2S$ generation when monitored using an $H_2S$-selective electrode, confirming that the esterase does not cleave thiocarbamates directly (FIG. 13A). Further control examples using the parent benzyl thiocarbamate (7), which lacks the ester trigger, confirmed that the benzyl thiocarbamate moiety is not cleaved directly by PLE. Having confirmed the stability of the donor platform prior to activation, 5 was treated with 1 U/mL PLE in the presence of CA and observed immediate $H_2S$ release (FIG. 13B). Increasing the PLE concentration to 20 U/mL under otherwise identical conditions resulted in significantly faster $H_2S$ release. Additionally, treatment of 5 with acetazolamide (AAA), a known CA inhibitor, significantly reduced the rate of $H_2S$ production, confirming that CA is necessary for COS conversion to $H_2S$ under the reaction conditions. Supplementing the $H_2S$ electrode measurements, it also was confirmed that $H_2S$ was released from 5 using an $H_2S$-responsive fluorescent probe (FIG. 13B). Consistent with the electrode data, incubation of 50 µM 5 with 5 µM MeRho-Az in the presence of CA and 1 U/mL PLE resulted in a fluorescence turn-on consistent with $H_2S$ release. Fluorescent live cell images were attempted by incubating 5 in BEAS 2B cells with MeRho-Az, but the high cytotoxicity of 5 and limited permeability of MeRho-Az in BEAS 2B cells limited the ability to obtain high quality images. As a whole, these data demonstrate that the thiocarbamate donors are stable until activated by esterases and release $H_2S$ in a COS-dependent manner.

Example 7

Figure 14A:
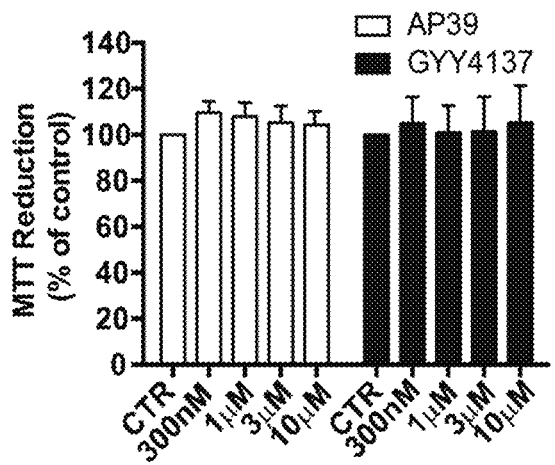
FIGS. 14A-14D show the results of cell viability studies of cells in the presence of varying concentrations of a representative donor compound disclosed herein and/or control compounds.
Figure 14B:
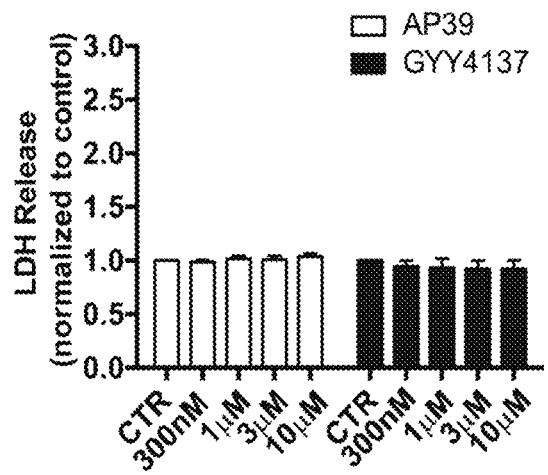
Figure 14C:
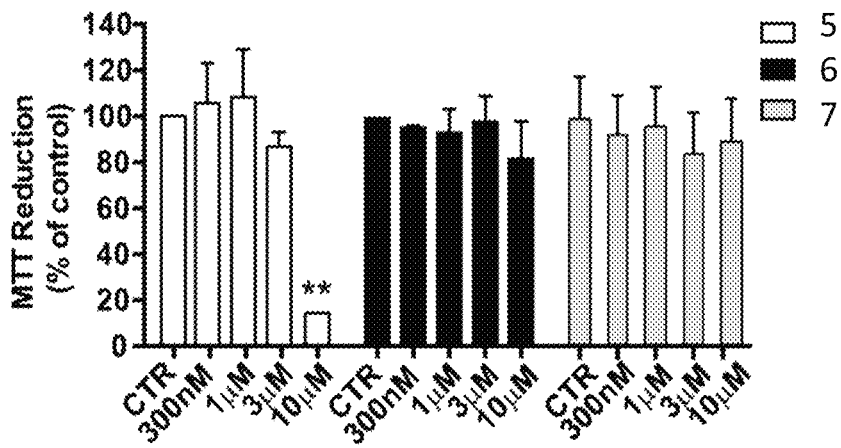
Figure 14D:
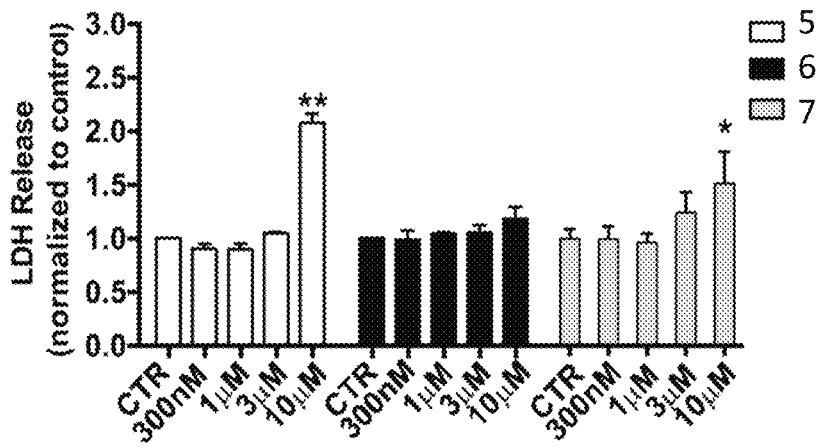

Next, the cytotoxicity of 5-7 on BEAS 2B cells was evaluated by measuring the reduction of a tetrazolium compound (MTT) to formazan by metabolically active cells, and by measuring the release of lactate dehydrogenase (LDH) due to permeability of the plasma membrane, which is a sign of necrotic cell death. BEAS 2B human lung epithelial cells exhibit low expression of all three canonical $H_2S$-producing enzymes, CBS, CSE, and 3-MST. To provide suitable comparisons with commonly-used synthetic donors, comparable cytotoxicity data for known $H_2S$ donors GYY4137, which does not localize in the mitochondria, was first obtained and also with mitochondrially-targeted AP39 (FIGS. 14A and 14B). When compared to the DMSO vehicle, GYY4137 showed no significant cytotoxicity up to 30 µM using either the MTT or LDH assay. Similarly, AP39 showed minimal cytotoxicity at 30 µM and none at lower concentrations, indicating that neither of these $H_2S$ donors are significantly cytotoxic. By contrast, 10 µM of 5 resulted a significant decrease cell viability and increase in LDH levels, which was not observed for control compounds 6 or 7 (FIGS. 14C and 14D). The lack of cytotoxicity of control compound 6 suggests that the mechanism of cytotoxicity does not result from the formation of the electrophilic p-quinone methide intermediate because this species is formed upon activation of both donor 5 and control compound 6. Similarly, 7 does not reduce cell viability, confirming that the observed cytotoxicity of 5 relies on triggering by cellular esterases and is not a result of the thiocarbamate scaffold itself. Importantly, the esterase-triggered COS/$H_2S$ donor 5 provides a significantly different toxicological profile from other commonly-used $H_2S$ donors.

Figure 15G:
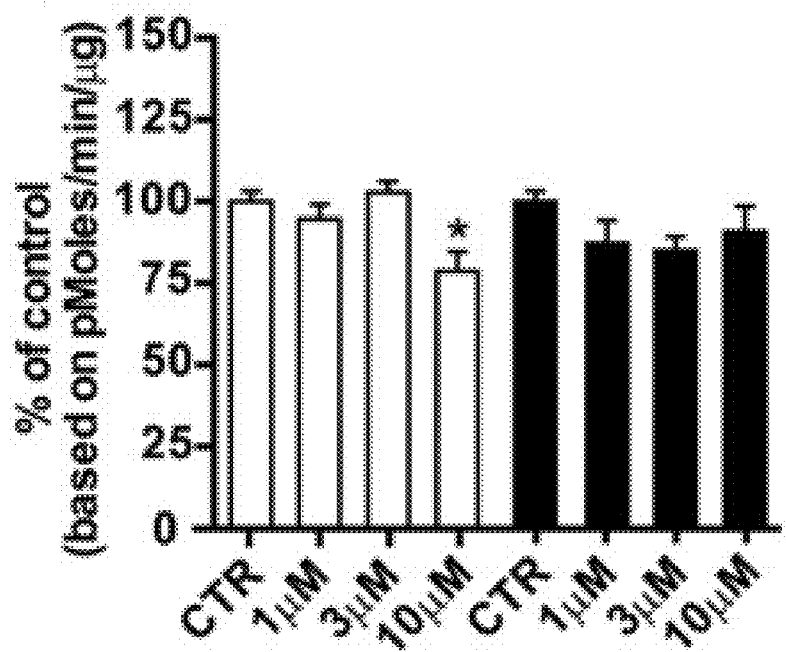
Figure 15H:
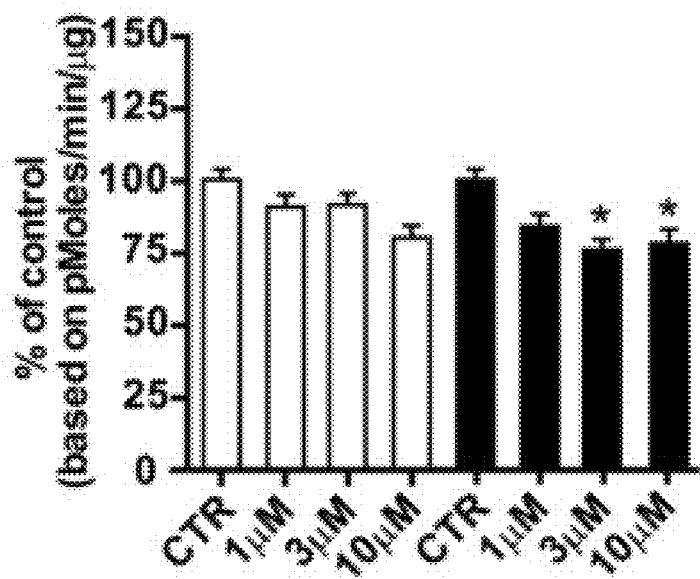
Figure 15I:
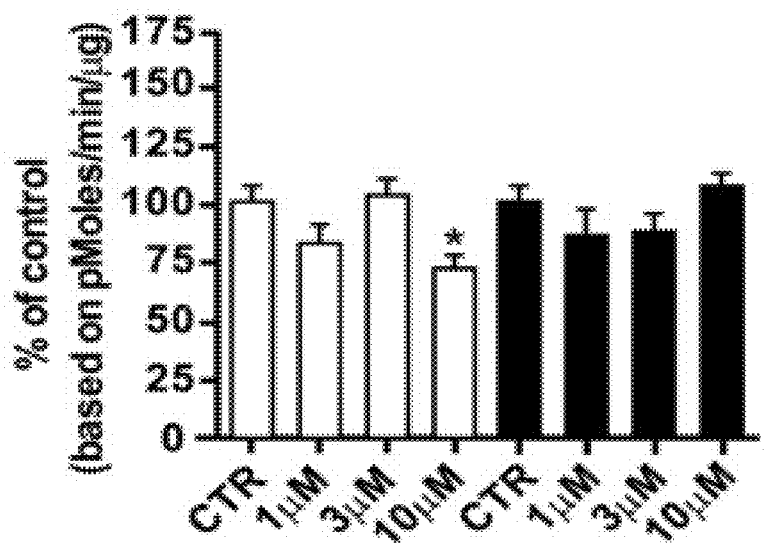

To investigate the underpinnings of the increased cytotoxicity of 5, and because $H_2S$ is a well-known inhibitor of mitochondrial cytochrome c oxidase, the mitochondrial respiration of BEAS 2B cells treated with 5-7 was evaluated using an Extracellular Flux Analyzer. This assay was selected because $H_2S$ is well known to impact mitochondrial respiration, even if the $H_2S$ is not delivered directly to the mitochondria, and because COS has been suggested to inhibit the mitochondrial respiratory chain. Incubation of BEAS 2B cells with increasing concentrations of 5 for 24 hours negatively affected all major bioenergetics parameters in this example, namely oxygen consumption linked with basal respiration, maximal respiration, and ATP synthesis (FIGS. 15A-15F). These reductions are consistent with known inhibitory effects of $H_2S$ on cellular bioenergetics, primarily through inhibition of mitochondrial cytochrome c oxidase (Complex IV). By contrast, control compound 6 did not negatively impact the measured bioenergetics parameters, but rather resulted in increases in basal respiration and ATP synthesis in this example. Compound 7 had no effect on basal respiration or ATP synthesis in this example, and only slightly decreased maximal respiration at 10 μM. To better compare these results with known $H_2S$ donors, the mitochondrial respiration of BEAS 2B cells incubated with AP39 and GYY4137 also was evaluated under the same conditions (FIGS. 15G-15I). No significant inhibition of cellular bioenergetics was observed at the observed concentrations, raising the possibility that the inhibitory effects of 5 may not be from $H_2S$ release alone, but could also be due to direct COS inhibition of cytochrome c oxidase. The observed cytotoxicity from 5 may be either specific to lung epithelial cells or may be amplified by preferential release in certain cellular locales that enable efficient interaction with the mitochondrial respiratory chain.

These examples illustrate that the easy-to-access, esterase-triggered COS/$H_2S$ donor compounds disclosed herein can be rapidly activated by esterases to generate $H_2S$ in vitro using isolated PLE.

Example 8

In this example, donor compounds comprising boronate groups were evaluated to determine their ability to function as ROS-triggered $H_2S$ donors. Three thiocarbamate donors (peroxythiocarbamate: PeroxyTCM-1, PeroxyTCM-2, and PeroxyTCM-3) and two carbamate control compounds (thiocarbamates: TCM-1 and TCM-2) were prepared. The PeroxyTCM compounds are stable in aqueous buffer (pH 5-9) and are not hydrolyzed by esterases. The parent carbamate (peroxycarbamate-1, PeroxyCM-1) also was used and can also be activated by ROS, but releases $CO_2/H_2O$ instead of COS/$H_2S$. Access to these simple control compounds provides useful tools to determine whether observed biological activities of the donors are $H_2S$-related or merely a product of the organic scaffold and/or byproducts.

To evaluate the $H_2S$ release from the donor constructs in the presence of ROS, an $H_2S$-selective electrode was used to monitor $H_2S$ release from PeroxyTCM-1 (50 μM) upon treatment with $H_2O_2$ (50-1000 μM) in PBS buffer (pH 7.4, 10 mM) containing CA (25 μg mL$^{-1}$). $H_2O_2$-dependent $H_2S$ release from PeroxyTCM-1 was observed with corresponding second-order rate constant of 1.44 M$^{-1}$ s$^{-1}$ (FIG. 6 and FIG. 16, respectively). Quantification of $H_2S$ release, 50 μM PeroxyTCM-1 using electrode data demonstrated $H_2S$ release efficiencies of 80% and 60% in the presence of 250 μM and 500 μM $H_2O_2$, respectively, which are consistent with increased $H_2O_2$ scavenging by $H_2S$ at higher ROS concentrations. Next, PeroxyTCM-2 and PeroxyTCM-3 were evaluated and demonstrated that the rate of $H_2S$ release can be tuned by electronic modulation of the thiocarbamate (FIG. 7). In contrast, TCM-1 and TCM-2, which lack the $H_2O_2$-reactive arylboronate trigger, did not release $H_2S$ upon treatment with $H_2O_2$ in this example (FIG. 7).

The role of CA in converting COS into $H_2S$ was evaluated by incubating PeroxyTCM-1 with $H_2O_2$ (10 equiv) in the absence of CA. Although COS can be hydrolyzed to $H_2S$ under both acidic and basic conditions, this hydrolysis is much slower at physiological pH. Unexpectedly, a positive $H_2S$ release response was observed, indicating that COS could react directly with $H_2O_2$ to generate $H_2S$ in a CA-independent pathway (FIG. 17A). To further investigate these observations, an aqueous solution (10 mM PBS, pH 7.4) of COS gas was treated with $H_2O_2$. No $H_2S$ was detected prior to $H_2O_2$ addition, whereas $H_2O_2$ addition resulted in rapid $H_2S$ generation (FIG. 17B). These embodiments demonstrate that $H_2O_2$ alone can convert COS into $H_2S$ directly, although this process was significantly slower than CA-catalyzed COS hydrolysis.

Specific reactive sulfur, oxygen, and nitrogen species (RSONS) were also evaluated to determine which RSONS could result in donor activation by measuring $H_2S$ release from PeroxyTCM-1 after incubation with different RSONS (FIG. 9). Incubation with $H_2O_2$, $O_2^{-1}$, or ONOO$^-$ resulted in $H_2S$ release, with $H_2O_2$ being the most active trigger. Other RSONS, such as hypochlorite ($C_{10}^-$), hydroxyl radical (HO), singlet oxygen ($^1O_2$), tert-butyl hydroperoxide (TBHP), tert-butoxy radical (tBuO$^-$) cysteine (Cys), reduced glutathione (GSH), oxidized glutathione (GSSG), S-nitrosoglutathione (GSNO), nitrite (NO$_2$), sulfate (SO$_4^{2-}$), thiosulfate (S$_2$O$_3^{2-}$), NO, or nitroxyl (HNO) failed to release $H_2S$. Taken together, this selectivity screening demonstrates that only specific ROS ($H_2O_2$, $O_2^-$, and ONOO$^-$) activate PeroxyTCM-1 to release $H_2S$.

Before investigating different potential biological applications of the PeroxyTCM compounds, the cytotoxicity of PeroxyTCM-1, PeroxyCM-1 and TCM1 (10-100 μM) in HeLa cells was evaluated. No significant decrease in cell viability was observed after a 2 hour incubation, indicating that none of the three compounds exhibited appreciable cytotoxicity at the tested concentrations (FIG. 18). Also evaluated was whether exogenous $H_2O_2$ could be used to release $H_2S$ in cellular environments by incubating HeLa cells with PeroxyTCM-1 (50 μM) followed by treatment with $H_2O_2$ (25 μM or 50 μM). HSN$_2$, a reaction-based $H_2S$ fluorescent probe, was used to monitor $H_2S$ accumulation by fluorescence microscopy. In the absence of $H_2O_2$, no HSN$_2$ fluorescence was observed, confirming that PeroxyTCM-1 was stable and did not release $H_2S$ in a normal cellular environment. By contrast, addition of $H_2O_2$ resulted in a $H_2O_2$ dose-dependent increase in HSN$_2$ fluorescence (FIGS. 19 and 20), confirming that PeroxyTCM-1 can be activated by exogenous ROS in a cellular environment to release $H_2S$.

The response of PeroxyTCM-1 to endogenous ROS generation also was evaluated. RAW 264.7 cells were incubated with phorbol 12-myristate 13-acetate (PMA), which is a well-established method to induce ROS and H₂O₂ production in macrophages. ROS generation was confirmed using 2',7'-dichlorofluorescin diacetate (DCFDA; FIG. 21). PeroxyTCM-1-treated cells were stimulated by PMA, and H₂S release was monitored using HSN₂. In the absence of PMA, no fluorescent signal from HSN₂ was observed. By contrast, addition of 500 nM PMA resulted in a significant increase in signal from HSN₂ corresponding to the released H₂S (FIG. 22). These embodiments confirm that peroxyTCM-1 is sensitive enough to be activated by endogenous ROS, suggesting that it may provide a viable platform for ROS-related H₂S investigations.

Also investigated was whether the developed ROS-activated donors could provide protection against ROS-related oxidative stress in simple cell culture models. ROS can play deleterious roles in various physiological and pathological systems ranging from aging to cardiovascular damage. In many cases, H₂S administration can provide partial protection or rescue from these different disease states. For example, ROS generated during mitochondrial dysfunction are responsible for a wide range of damage in the cardiovascular system, including MI/R injury, and that exogenous H₂S significantly preserved cardiac activity through a ROS scavenging pathways. On the basis of this H₂S /ROS relationship, embodiments of donor compounds disclosed herein were evaluated to determine if the donor compounds would exhibit similar cytoprotective effects toward ROS-induced damage due to H₂S release.

To simulate increased cellular oxidative stress, HeLa cells were incubated with H₂O₂ (50-400 μM) for 1 hour and observed a dose-dependent reduction of cell viability (FIG. 23A). Since 100 μM of H₂O₂ led to approximately 70% cell death, this dose was used to investigate protective activities of PeroxyTCMs. Although this dose of H₂O₂ is higher than physiological H₂O₂ concentrations, it falls into the range of H₂O₂ concentrations used to induce oxidative stress in previous studies. In subsequent examples, cells were treated with H₂O₂ (100 μM) in the presence or absence of PeroxyTCM-1, PeroxyCM-1, or TCM-1 (10-50 μM) for 1 hour. PeroxyTCM-1 exhibited a significant dose-dependent increase of cell viability, suggesting that the released H₂S provided rescue from H₂O₂-induced oxidative damage (FIG. 23B). PeroxyCM-1 showed an attenuated rescue from oxidative stress (FIG. 23C) as a result of H₂O₂ consumption by the arylboronate and antioxidant effects of 4-hydroxylbenzyl alcohol (HBA), one of the byproducts after H₂S generation, but the observed protection was significantly lower than that from PeroxyTCM-1 (FIG. 24). In contrast, TCM-1 provided no protection against H₂O₂-mediated oxidative stress (FIG. 23D). Taken together, these results provide strong evidence that PeroxyTCM-1 is a robust H₂S donor and provides cellular protection from oxidative stress. In addition, compared to other H₂S donors, specific ROS selectivity makes the targeting of ROS-triggered H₂S donors to different subcellular locations feasible, which would greatly benefit the H₂S-related biological investigations and H₂S-based therapeutics development.

In view of the many possible embodiments to which the principles of the present disclosure may be applied, it should be recognized that the illustrated embodiments are only preferred examples of the disclosure and should not be taken as limiting. Rather, the scope of the present disclosure is defined by the following claims. We therefore claim as our invention all that comes within the scope and spirit of these claims.

We claim:
1. A donor compound represented by Formula 1:

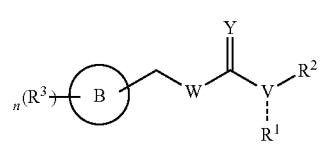

Formula 1 wherein ring B is an aryl group or a heteroaryl group selected from pyridyl, pyrrole, or thiophene; each of W and Y independently is oxygen or sulfur; V is oxygen, sulfur, or nitrogen; wherein each of W, Y, and V are selected to provide a carbamodithioate, a carbonodithioate, a carbonothioate, a carbonotrithioate, a thiocarbamate, or a thiocarbonate; or wherein W is oxygen and Y and V are both sulfur or Y is oxygen and W and V are both sulfur; R¹, if present, is hydrogen, aliphatic, heteroaliphatic, aryl, or heteroaryl; R² is heteroaliphatic, aryl, heteroaryl, a saccharide, a targeting group, a detectable moiety, a drug molecule, or combinations thereof; each R³ independently is aliphatic, heteroaliphatic, aryl, heteroaryl, halogen, hydroxyl, thiol, amine, imine, azide, a boronate ester, a boronic acid, a disulfide, an ester, a heteroaliphatic ester group, nitro, a silyl ether, a phosphoric ester, a sulfuric ester, 3,5-dinitrobenzenesulfonic acid, or a combination thereof; and n is an integer selected from 1 to 5; provided that when ring B is an aryl or heteroaryl group selected from pyridyl, pyrrole, or thiophene, the aryl or heteroaryl group comprises at least one ortho- or para-positioned R³ group, relative to the

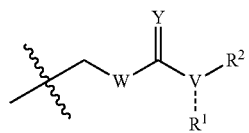

group, wherein the ortho-positioned R³ group is a thiol; an amine of formula —NRᵇRᶜ, wherein each of Rᵇ and Rᶜ independently is selected from hydrogen, alkenyl, alkynyl, aryl, heteroalkyl, heteroalkenyl, heteroalkynyl, heteroaryl, and any combination thereof; an imine; a boronate ester; a boronic acid; a disulfide; an ester; a heteroaliphatic ester group; a nitro group; a silyl ether; a phosphoric ester; a sulfuric ester; or 3,5-dinitrobenzenesulfonic acid; and/or wherein the para-positioned R³ group is a thiol; an amine, an imine, an azide, a boronate ester, a boronic acid, a disulfide, an ester, a heteroaliphatic ester group, a nitro group, a silyl ether, a phosphoric ester, a sulfuric ester, or 3,5-dinitrobenzenesulfonic acid;

if R¹ is hydrogen and R² is aryl, then the aryl group is -phenyl-(R⁴)ₘ wherein m is an integer selected from 0 to 5 and R⁴ is alkoxy, thioether, amide, amine, hydroxyl, thiol, acyloxy, azide, aliphatic, aryl, aldehyde, ketone, ester, carboxylic acid, acyl, acyl halide, cyano, sulfonate, nitro, quaternary amine, bromo, iodo, alkyl halide, heterocyclyl, pyridinyl, or pyridinyl wherein the nitrogen atom is functionalized with an aliphatic or aryl group;

if R¹ is hydrogen and V is N, then R² is heteroaliphatic, aryl, heteroaryl, a saccharide, a targeting group, a detectable moiety, a drug molecule, or a combination thereof; and the donor compound is not or is other than

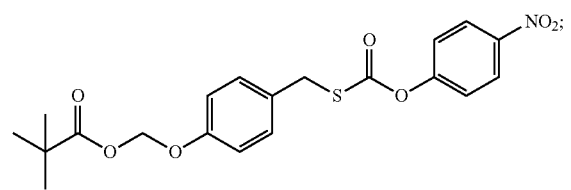

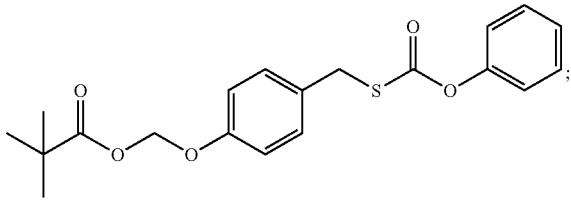

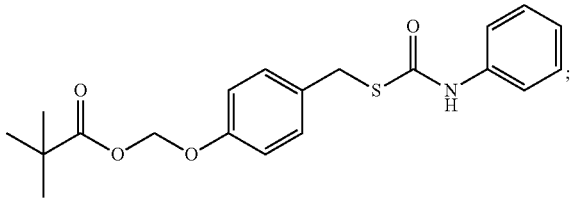

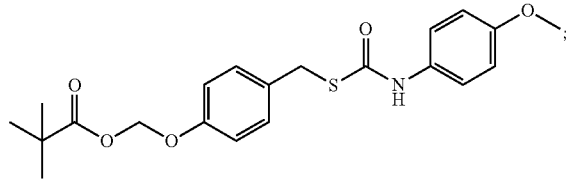

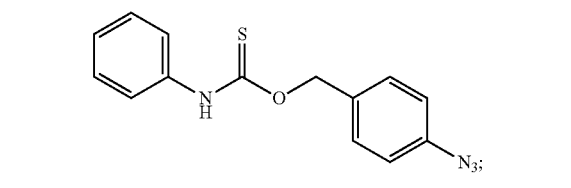

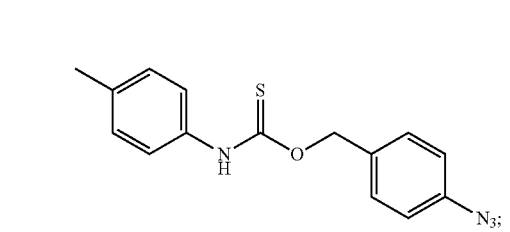

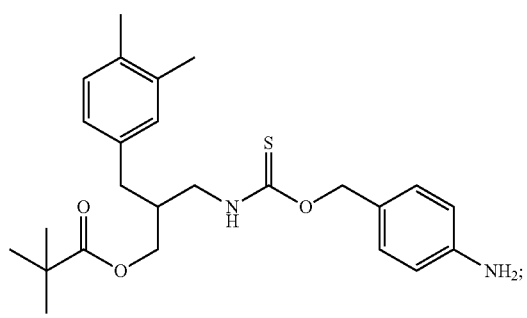

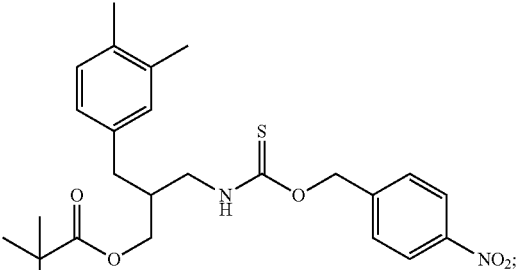

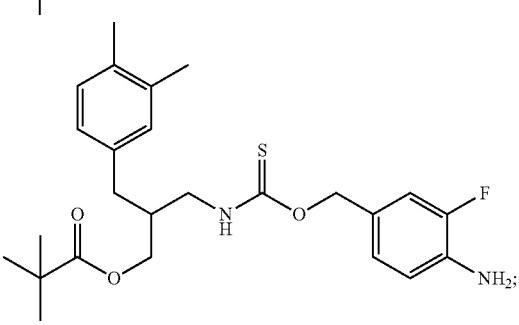

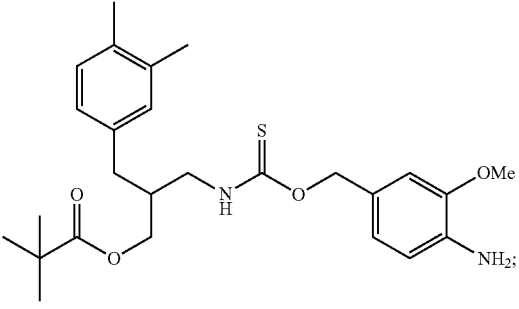

or

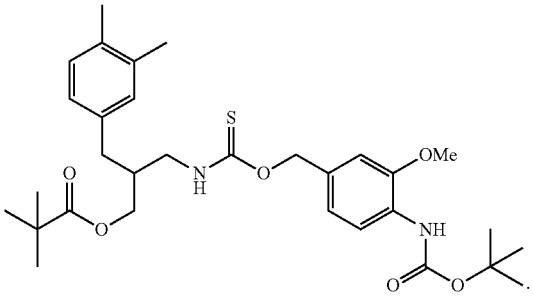

2. The donor compound of claim 1, wherein ring B is a phenyl group a pyridyl group, a thiophene group, or a pyrrole group; $R^2$ is phenyl or phenyl comprising one or more $R^4$ groups, wherein $R^4$ is alkoxy; thioether; amide; amine; hydroxyl; thiol; acyloxy; aliphatic; aryl; aldehyde; ketone; ester; carboxylic acid; acyl; acyl halide; cyano; sulfonate; nitro; quaternary amine; heterocyclyl; pyridinyl; pyridinyl comprising a nitrogen atom functionalized with an aliphatic or aryl group; alkyl halide; halogen; 3H-spiro[isobenzofuran-1,9'-xanthen]-3-one; 4-methyl-2H-chromen-2-one; or 2-(2-methoxyethyl)-1H-benzo[de]isoquinoline-1,3(2H)-dione; the ortho-positioned $R^3$ group, if present, is a methyl ester, a pinacol boronate ester, a nitro, —OCH$_2$OC(O)t-butyl, silyl ether, —SS-pyridinyl, or —SS-phenyl; the para-positioned $R^3$ group, if present, is a methyl ester, a pinacol boronate ester, an azide, a nitro, —OCH$_2$OC(O)t-butyl, silyl ether, —SS— pyridinyl, or —SS-phenyl;

and any other R³ groups are independently selected from aliphatic, heteroaliphatic, aryl, heteroaryl, halogen, hydroxyl, thiol, amine, imine, azide, a boronate ester, a boronic acid, a disulfide, an ester, a heteroaliphatic ester group, nitro, a silyl ether, a phosphoric ester, a sulfuric ester, 3,5-dinitrobenzenesulfonic acid, or a combination thereof.

3. The donor compound of claim 1, represented by any one or more of Formulas 2A-2I:

Formula 2A

Formula 2B

Formula 2C

Formula 2D

Formula 2E

Formula 2F

Formula 2G

Formula 2H

Formula 2I

4. The donor compound of claim 1, represented by any one of Formulas 3A-3I:

Formula 3A

Formula 3B

Formula 3C

Formula 3D

Formula 3E

Formula 3F

Formula 3G

Formula 3H

Formula 3I wherein ring A is aryl or heteroaryl; and each $R^4$ independently is alkoxy; thioether; amide; amine; hydroxyl; thiol; acyloxy; aliphatic; aryl; aldehyde; ketone; ester; carboxylic acid; acyl; acyl halide; cyano; sulfonate; nitro; quaternary amine; heterocyclyl; pyridinyl; pyridinyl comprising a nitrogen atom functionalized with an aliphatic or aryl group; alkyl halide; halogen; or together with one or more other $R^4$ groups and ring A forms a 4-methyl-2H-chromen-2-one group; a 2-(2-methoxyethyl)-1H-benzo[de]isoquinoline-1,3 (2H)-dione group, or a 3H-spiro[isobenzofuran-1,9'-xanthen]-3-one group; and m is an integer selected from 0 to 5.

5. The donor compound of claim 1, represented by having a structure satisfying any one of Formulas 4-7:

Formula 4
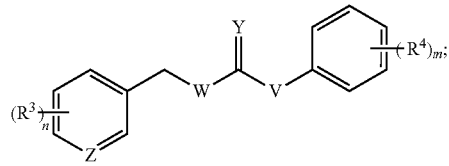

Formula 5
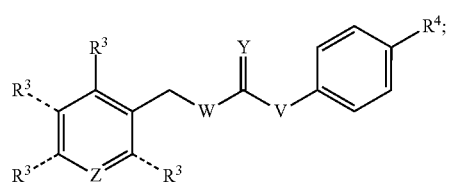

Formula 6
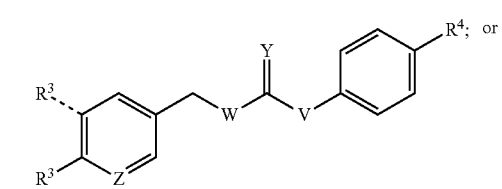

; or

Formula 7
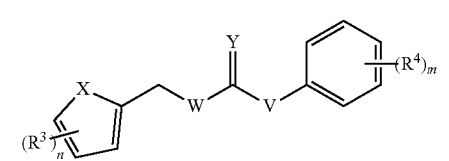

wherein
V is oxygen, sulfur, or $NR^1$
Z is CH or nitrogen;
X is S or NR, wherein R is selected from hydrogen, aliphatic, aryl, heteroaliphatic, or heteroaryl;
each $R^4$ independently is alkoxy; thioether; amide; amine; hydroxyl; thiol; acyloxy; aliphatic; aryl; aldehyde; ketone; ester; carboxylic acid; acyl; acyl halide; cyano; sulfonate; nitro; quaternary amine; heterocyclyl; pyridinyl; pyridinyl comprising a nitrogen atom functionalized with an aliphatic or aryl group; alkyl halide; halogen; or together with one or more other $R^4$ groups and ring A forms a 4-methyl-2H-chromen-2-one group; a 2-(2-methoxyethyl)-1H-benzo[de]isoquinoline-1,3 (2H)-dione group, or a 3H-spiro[isobenzofuran-1,9'-xanthen]-3-one group; and
m is an integer selected from 0 to 5.

6. The donor compound of claim 1, represented by any one of Formulas 4A-4I, 5A-5I, 6A-6I, or 7A-7K:

Formula 4A
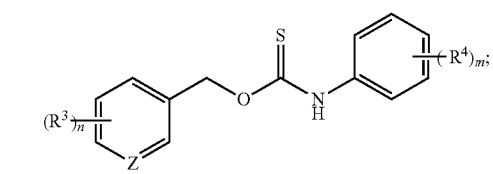

Formula 4B
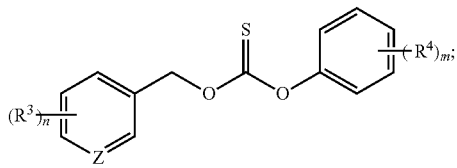

Formula 4C
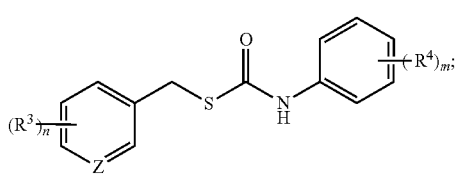

Formula 4D
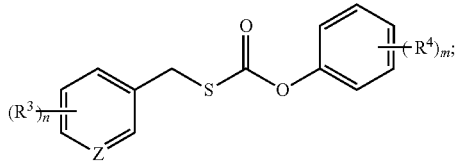

Formula 4E
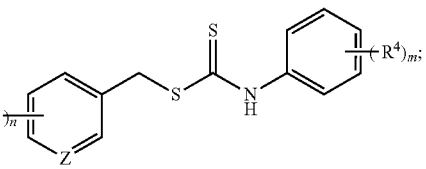

Formula 4F
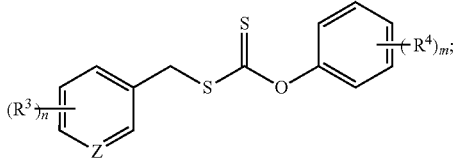

Formula 4G
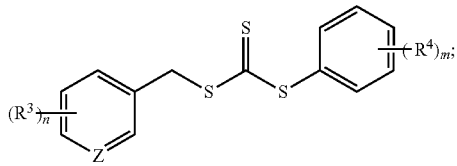

Formula 4H
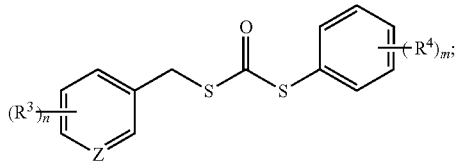

Formula 4I
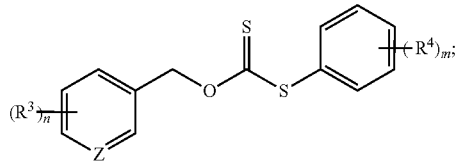

Formula 5A
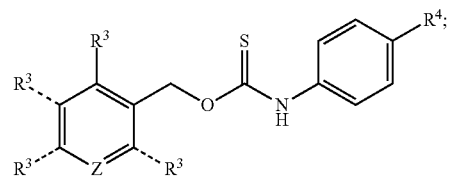
Formula 5B
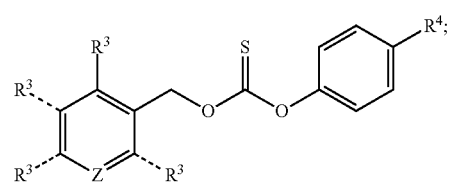
Formula 5C
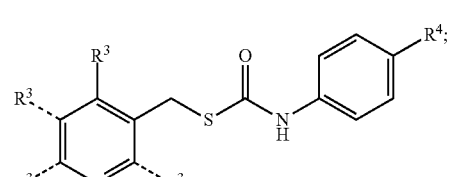
Formula 5D
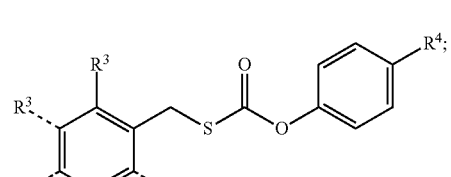
Formula 5E
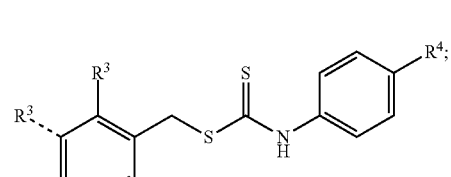
Formula 5F
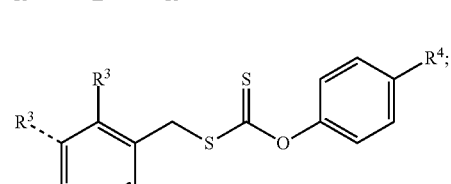
Formula 5G
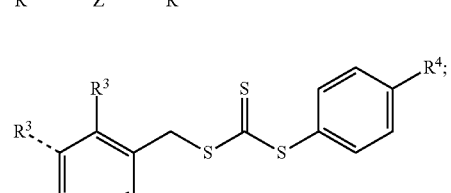
Formula 5H
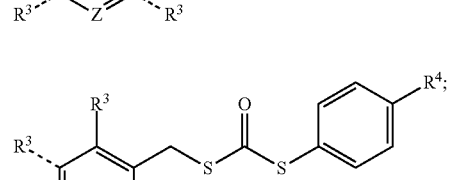
Formula 5I
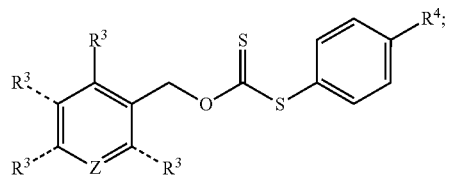
Formula 6A
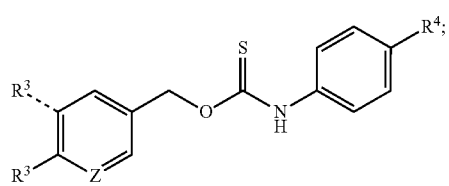
Formula 6B
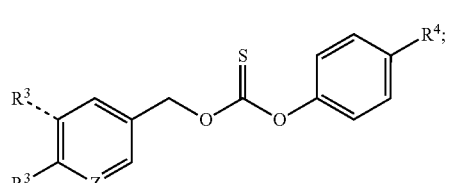
Formula 6C
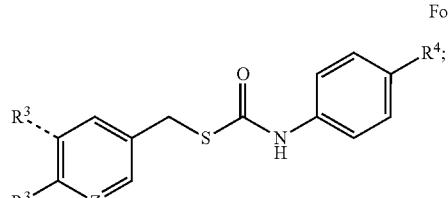
Formula 6D
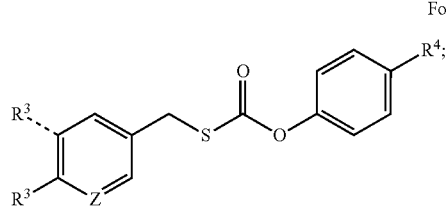
Formula 6E
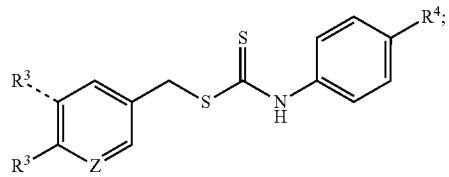
Formula 6F
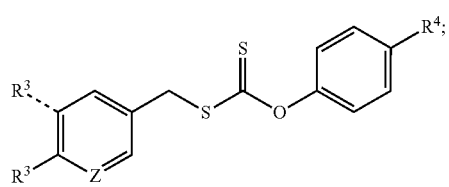
Formula 6G
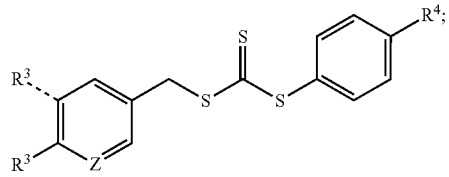

Formula 6H
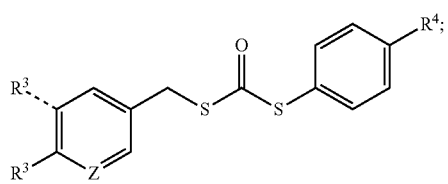

Formula 6I
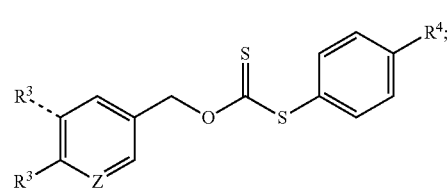

Formula 7A
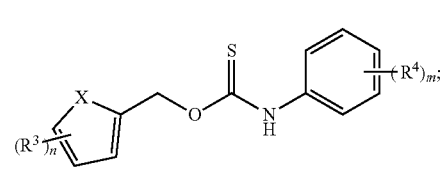

Formula 7B
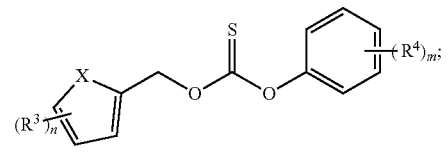

Formula 7C
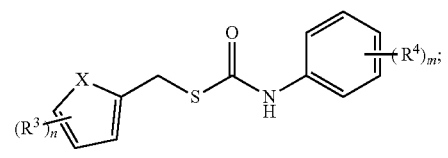

Formula 7D
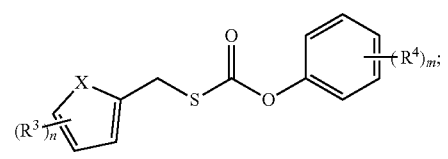

Formula 7E
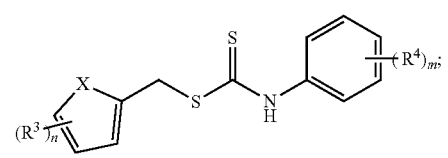

Formula 7F
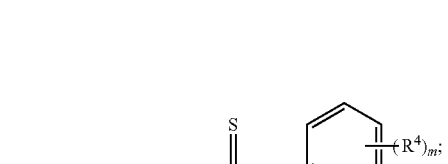
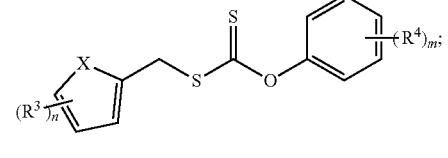

Formula 7G
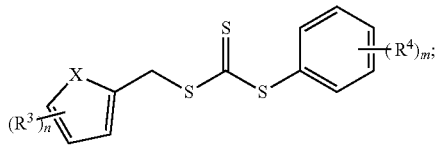

Formula 7H
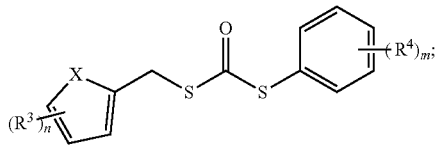

Formula 7I
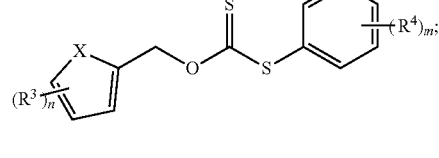

Formula 7J
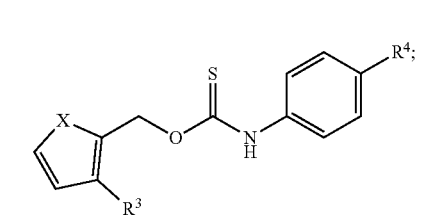

or

Formula 7K
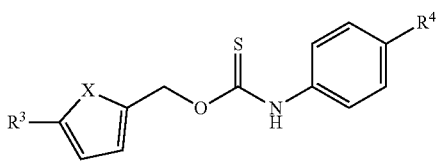

wherein

Z is CH or nitrogen;

X is S or NR, wherein R is selected from hydrogen, aliphatic, aryl, heteroaliphatic, or heteroaryl;

each $R^4$ independently is alkoxy; thioether; amide; amine; hydroxyl; thiol; acyloxy; aliphatic; aryl; aldehyde; ketone; ester; carboxylic acid; acyl; acyl halide; cyano; sulfonate; nitro; quaternary amine; heterocyclyl; pyridinyl; pyridinyl comprising a nitrogen atom functionalized with an aliphatic or aryl group; alkyl halide; halogen; or together with one or more other $R^4$ groups and ring A forms a 4-methyl-2H-chromen-2-one group; a 2-(2-methoxyethyl)-1H-benzo[de]isoquinoline-1,3 (2H)-dione group, or a 3H-spiro[isobenzofuran-1,9'-xanthen]-3-one group; and m is an integer selected from 0 to 5.

7. The donor compound of claim 6, wherein m is 0 or 1 and each $R^4$, if present, independently is selected from alkyl, azide, fluoro, bromo, chloro, iodo, or morpholinyl.

8. The donor compound of claim 1, wherein the donor compound is selected from
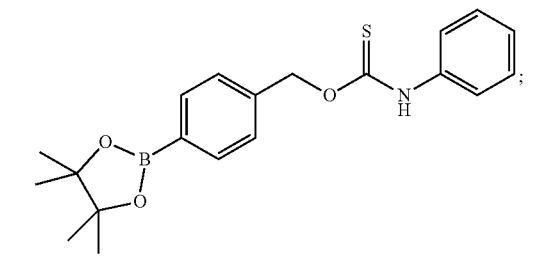
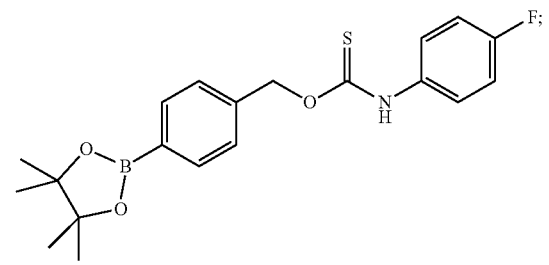
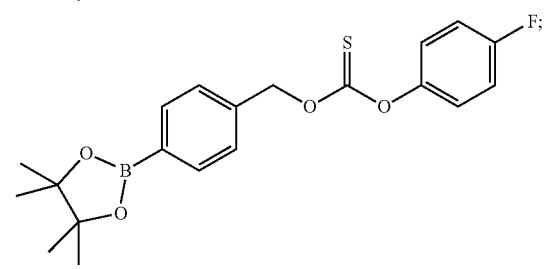
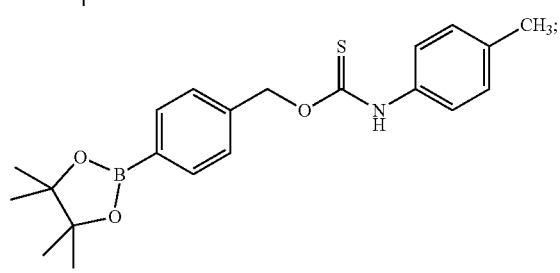
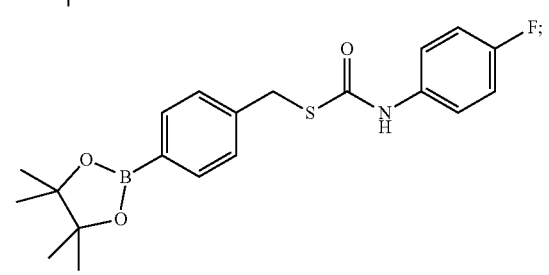
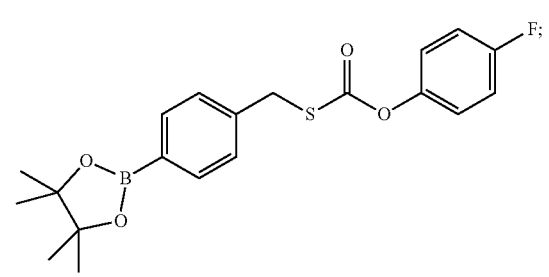

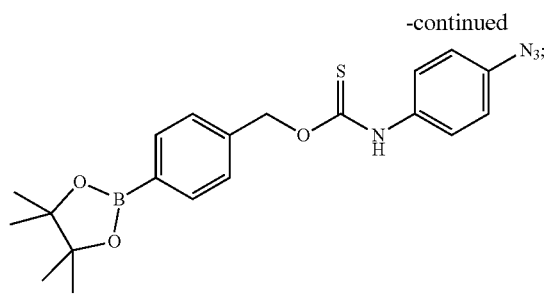
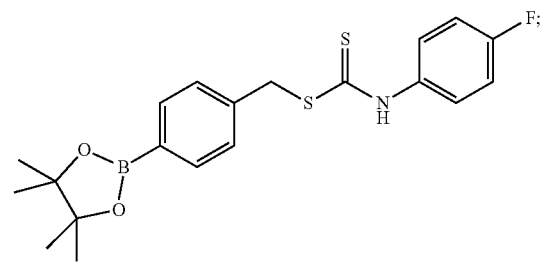
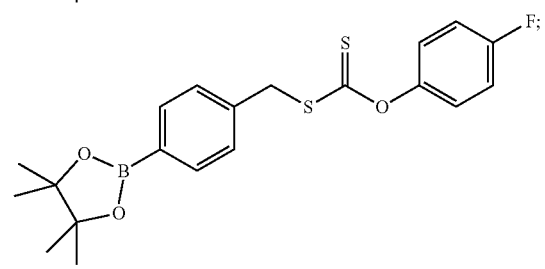
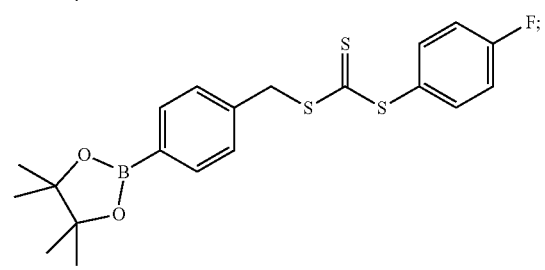
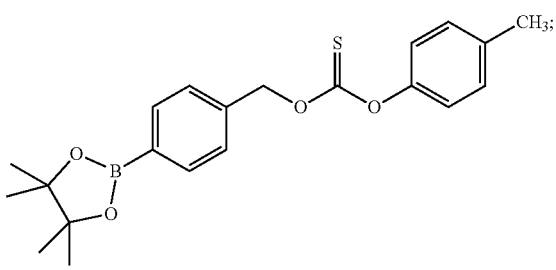
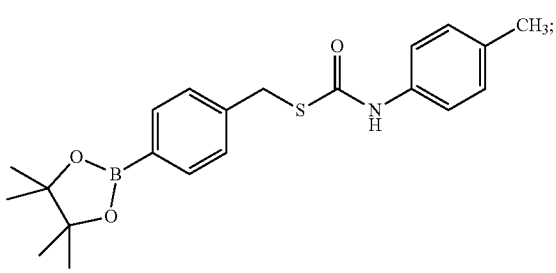

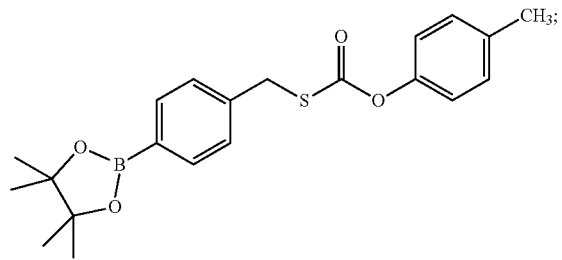
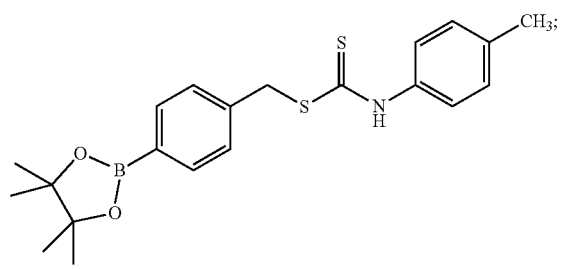
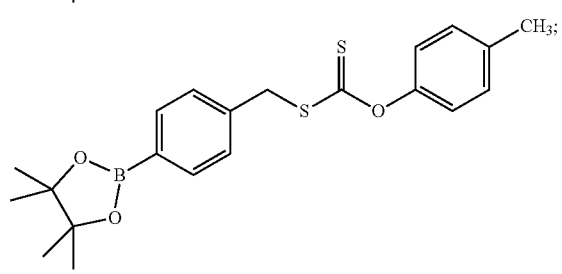
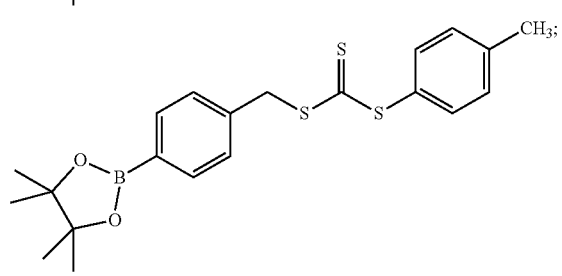
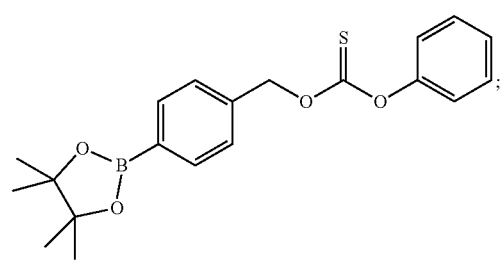
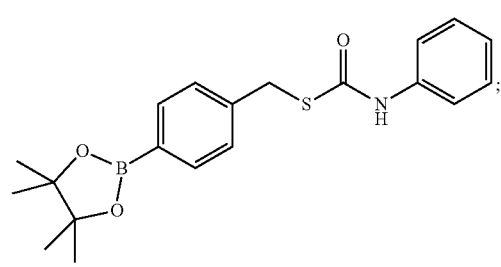

-continued
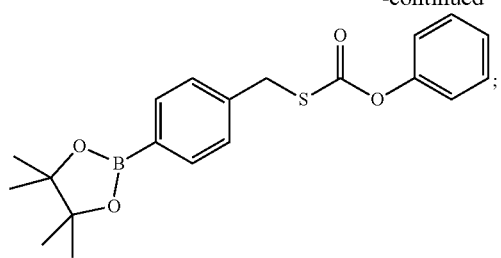
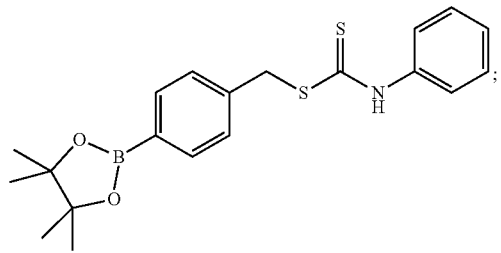
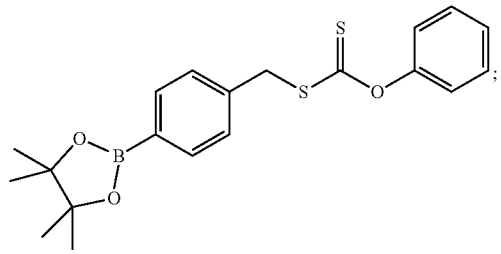
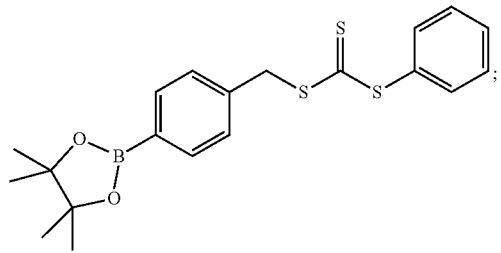
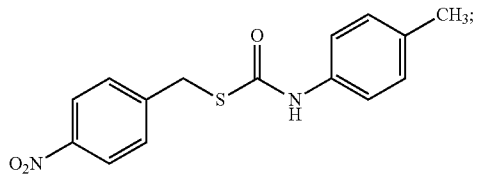
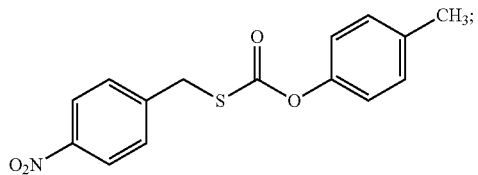
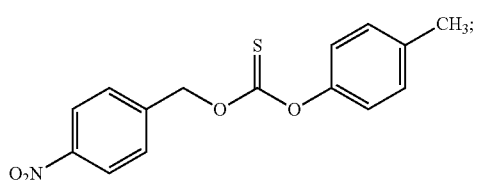
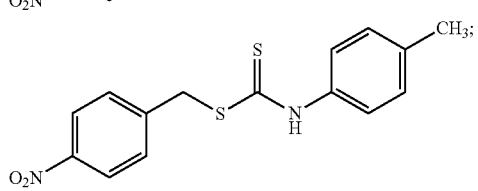

-continued
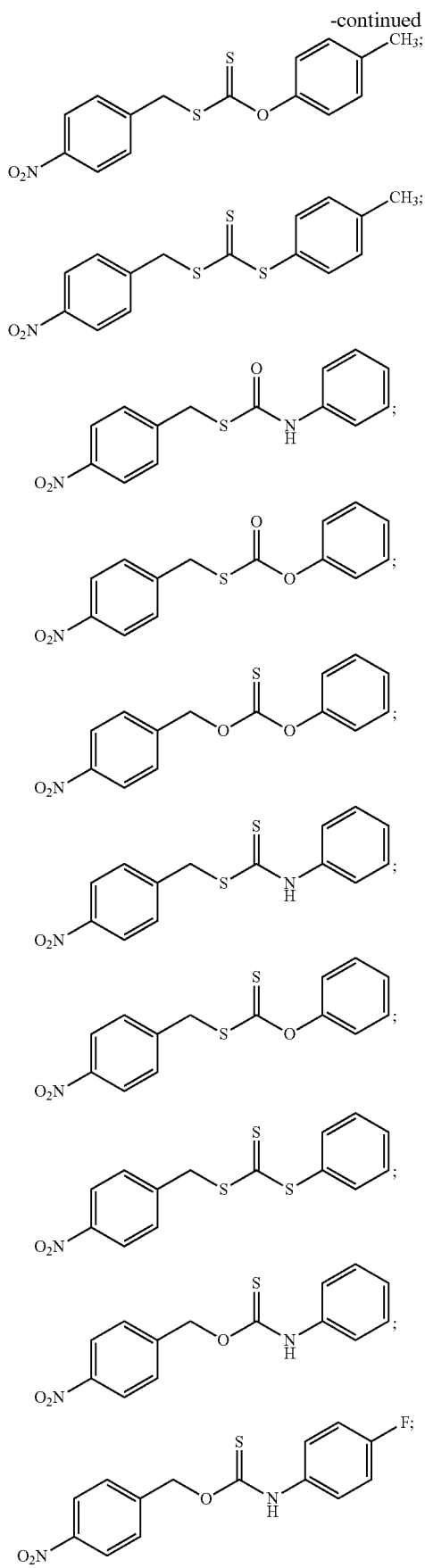

-continued
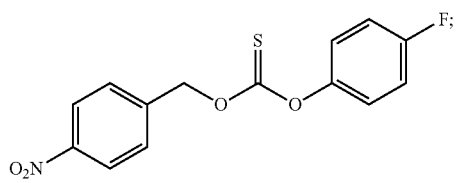
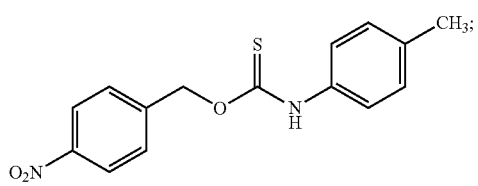
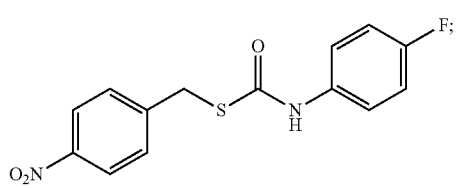
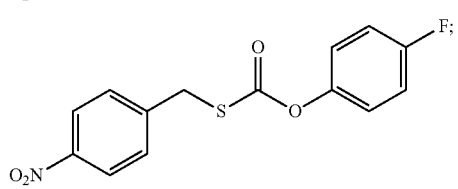
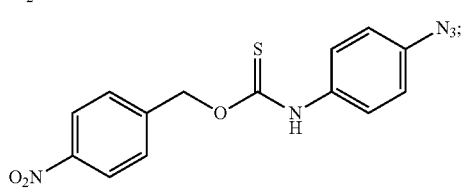
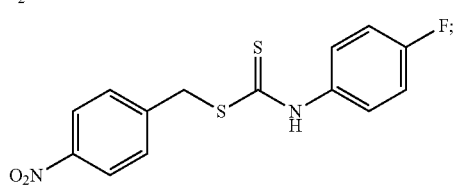
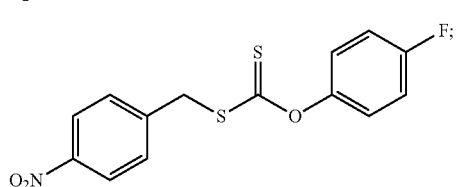
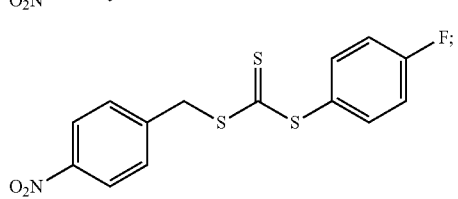
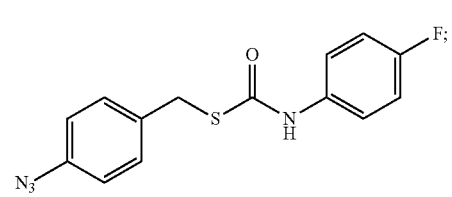

-continued
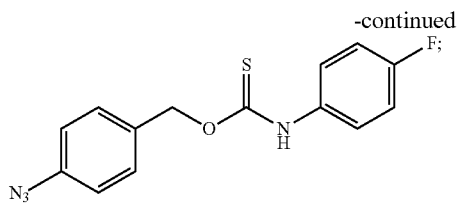
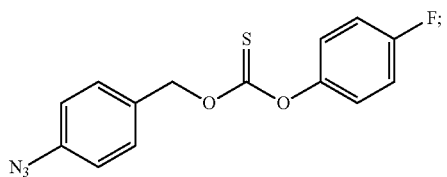
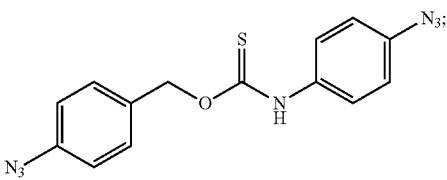
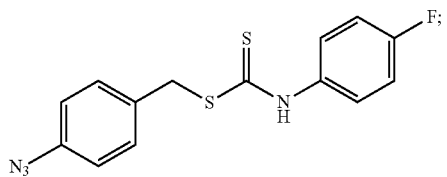
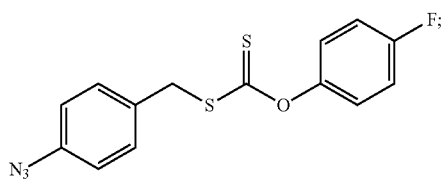
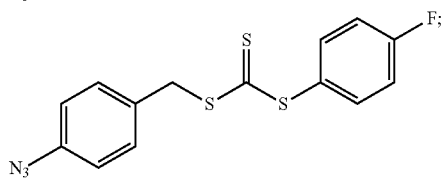
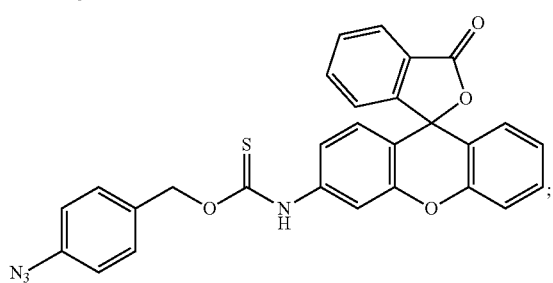
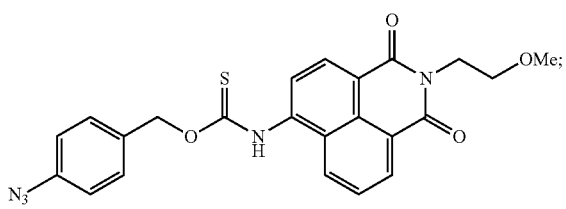
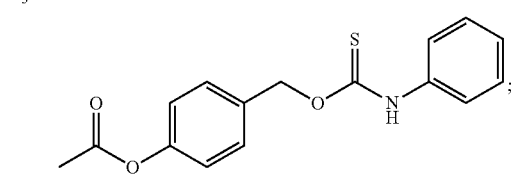

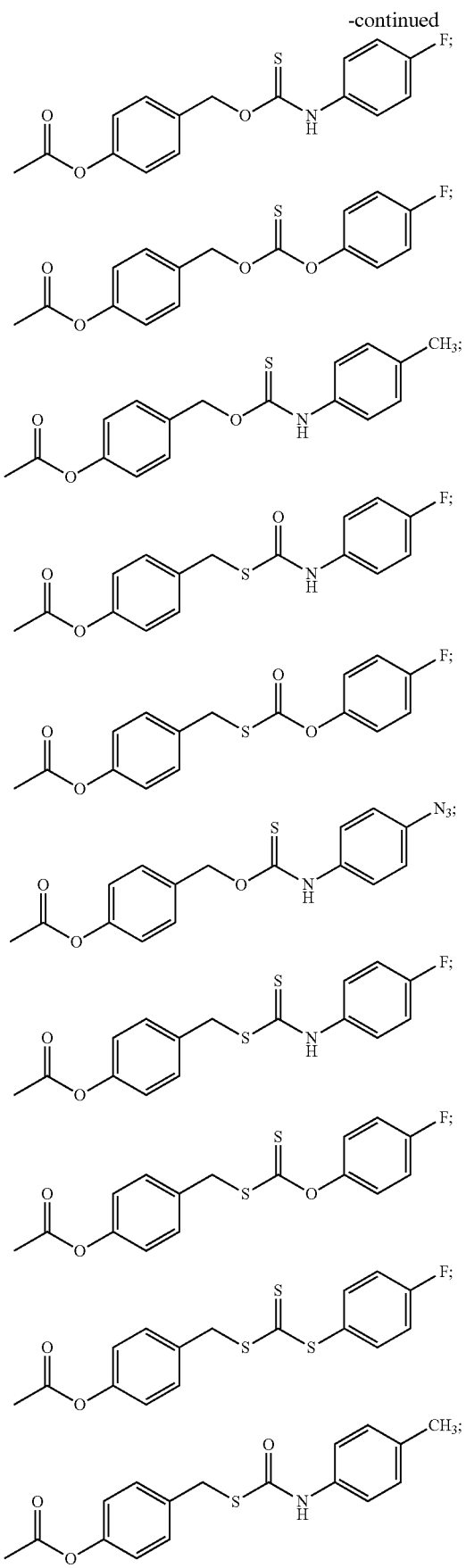

-continued
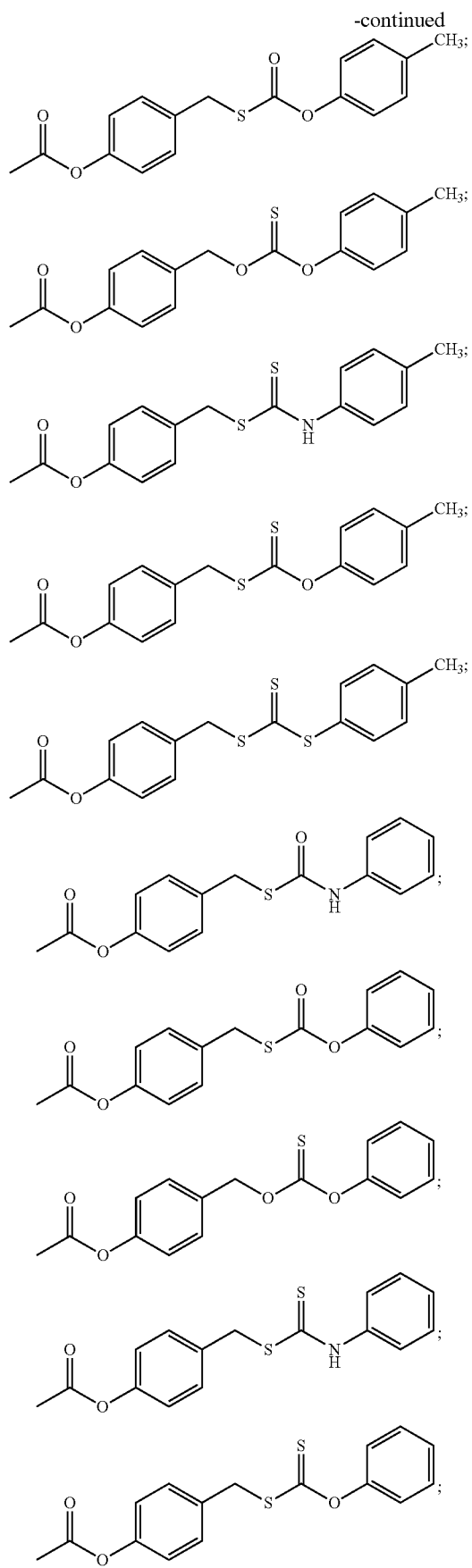

-continued
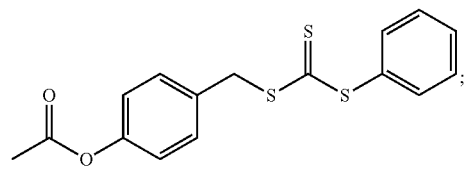
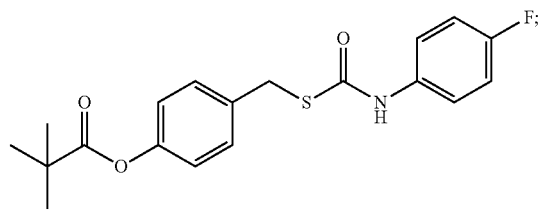
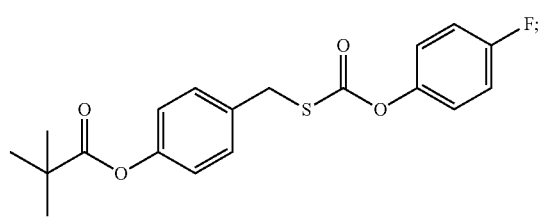
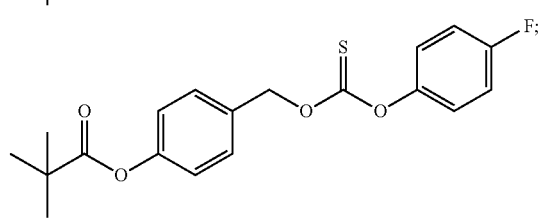
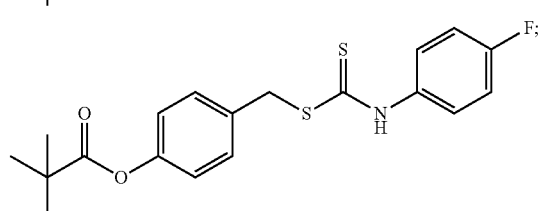
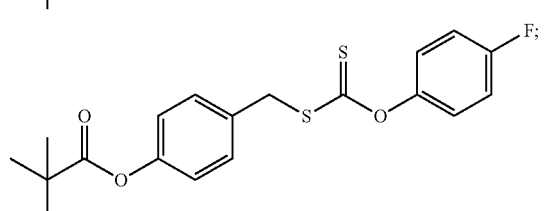
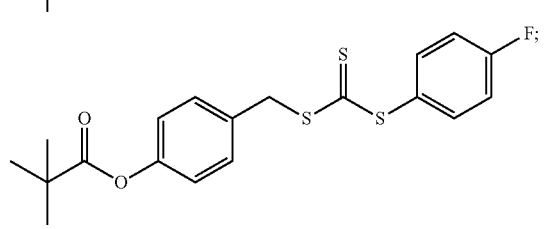
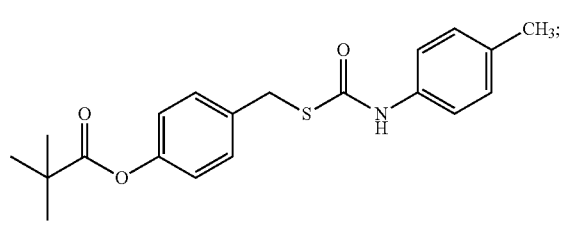

-continued
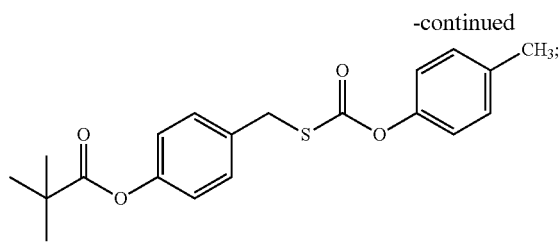
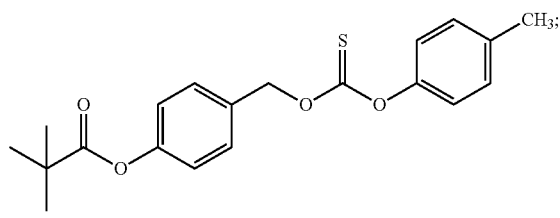
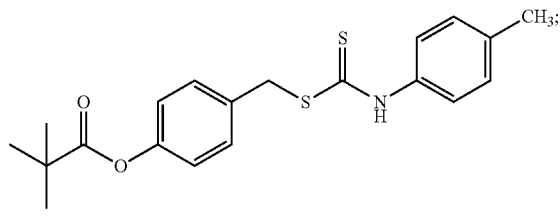
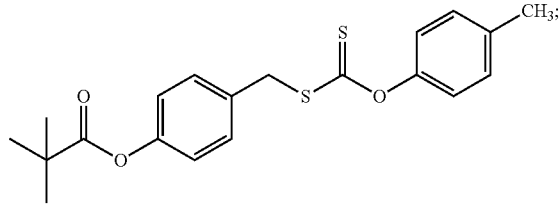
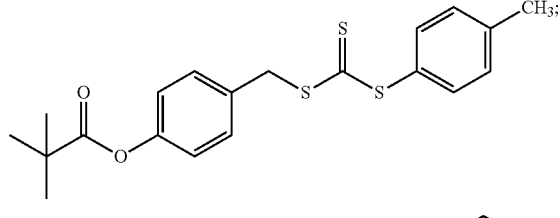
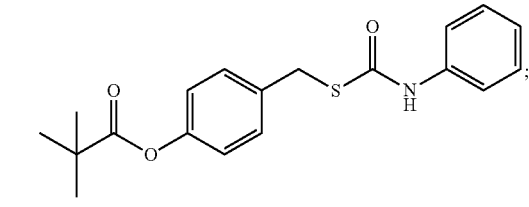
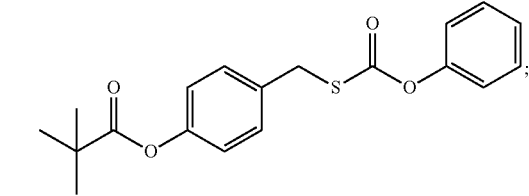
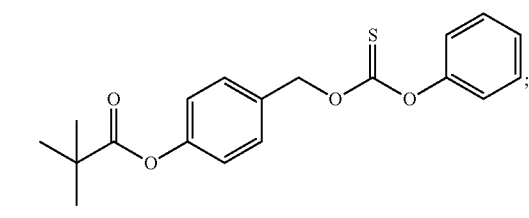

-continued
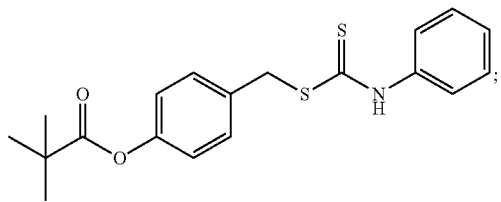
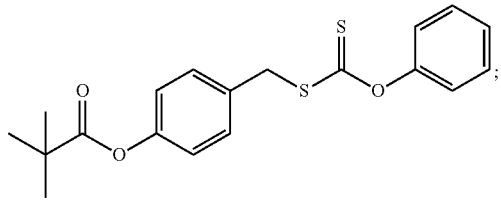
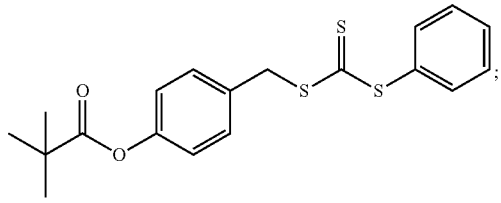
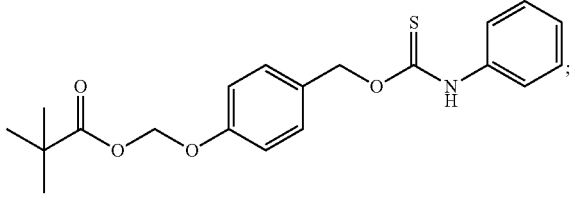
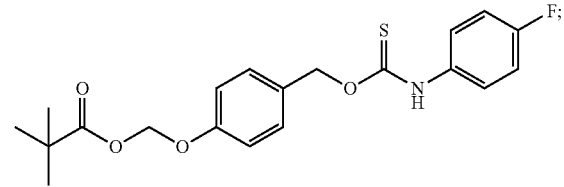
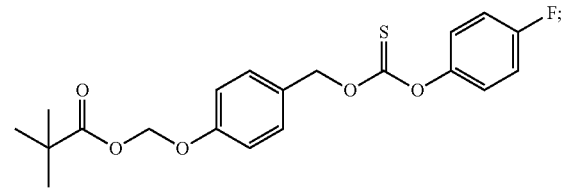
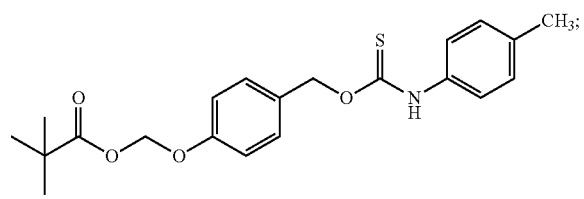
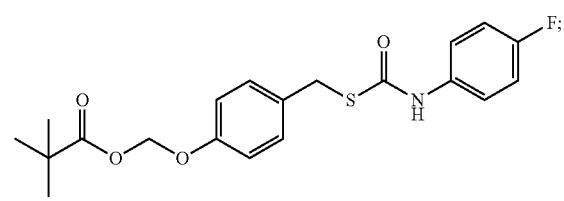

-continued
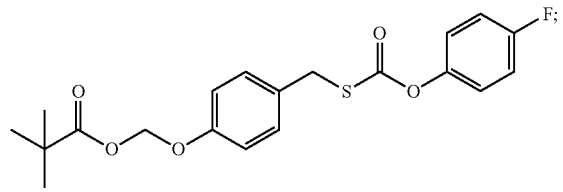
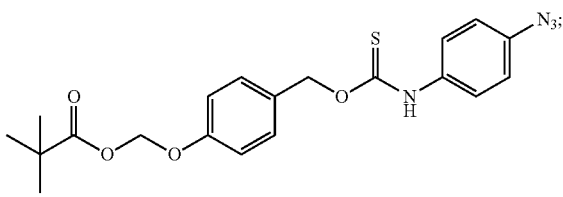
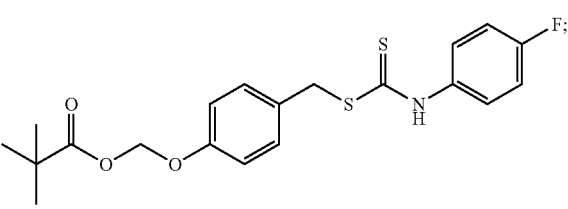
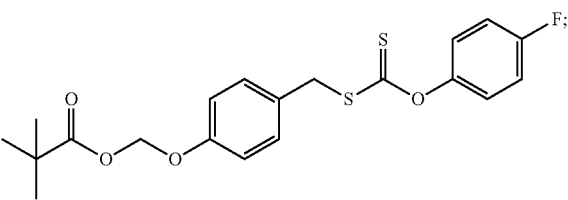
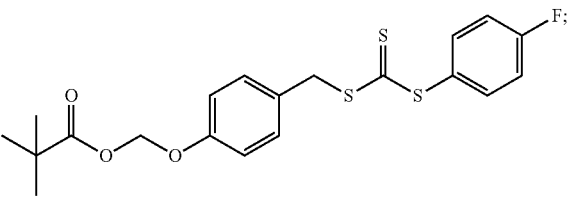
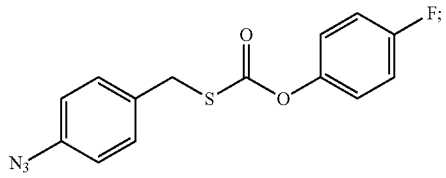
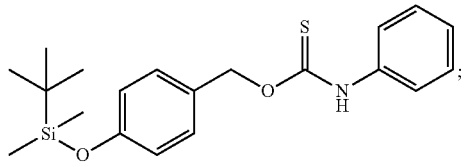
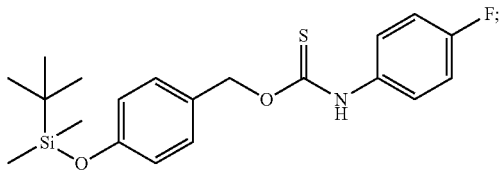
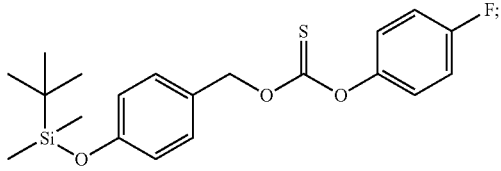

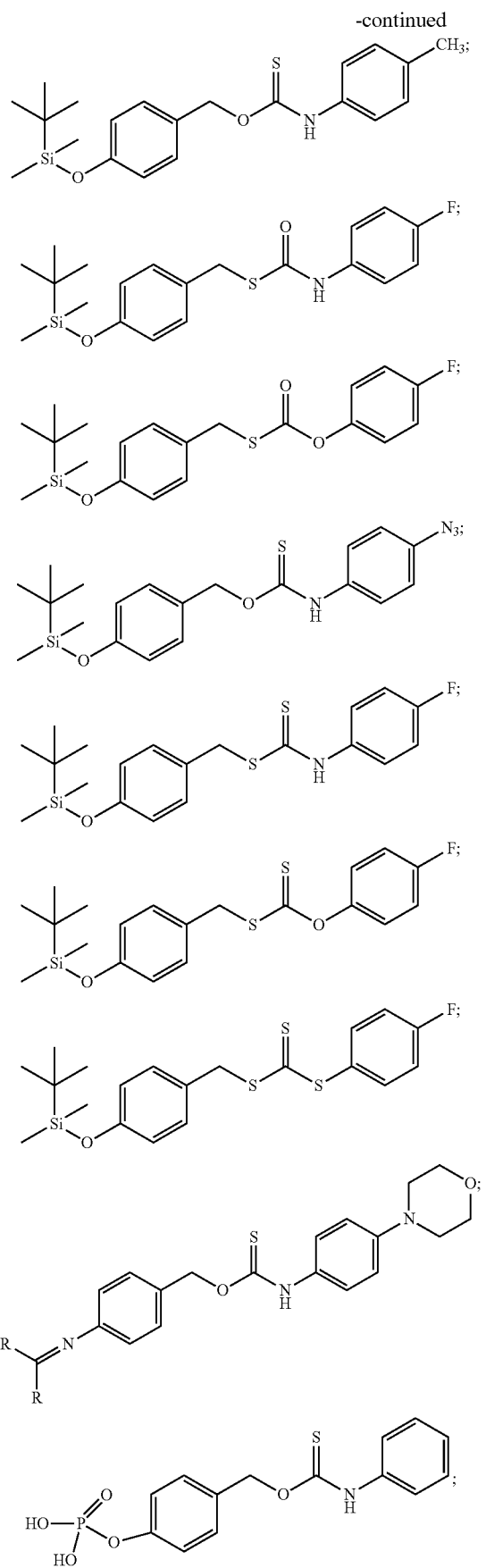

-continued
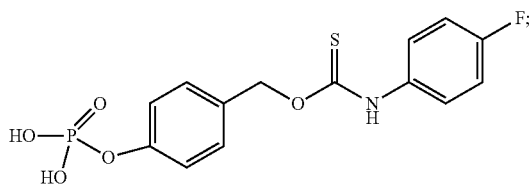
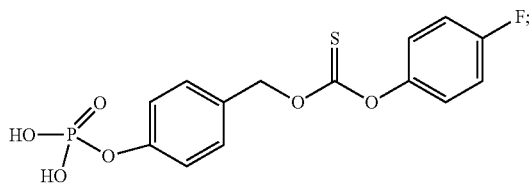
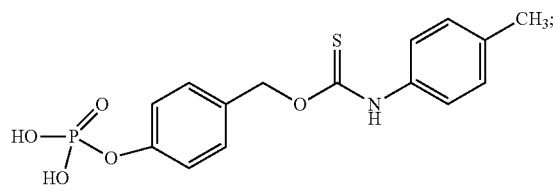
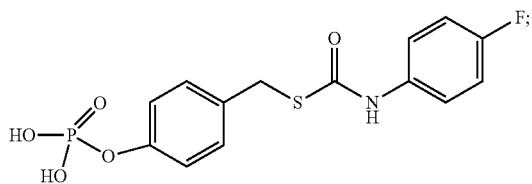
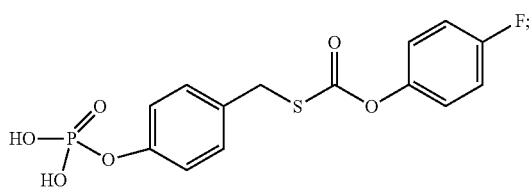
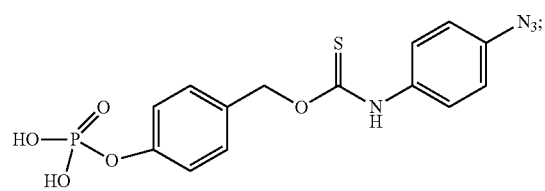
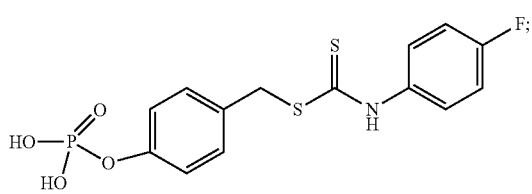
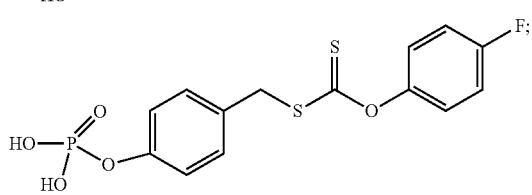
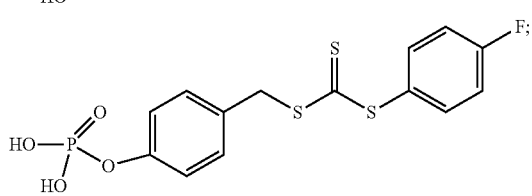

-continued
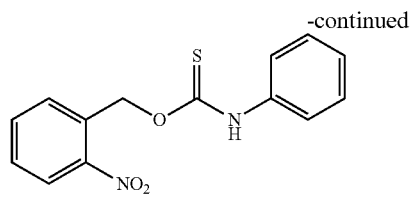
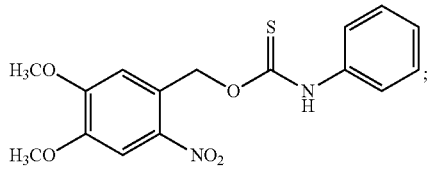
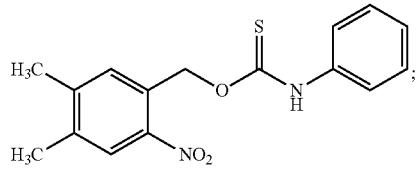
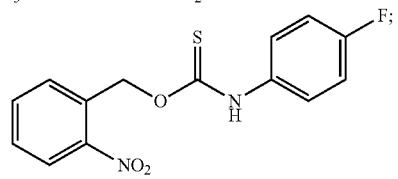
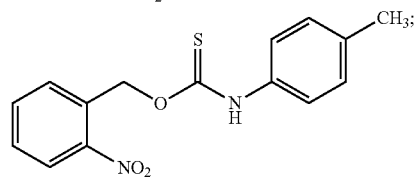
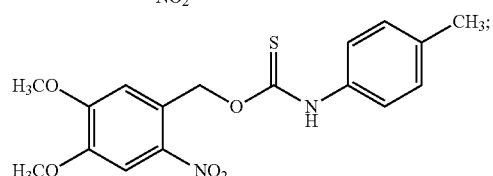
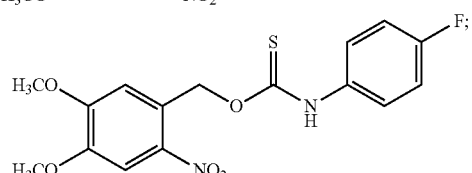
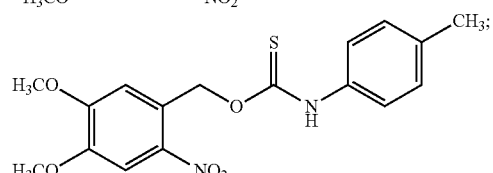
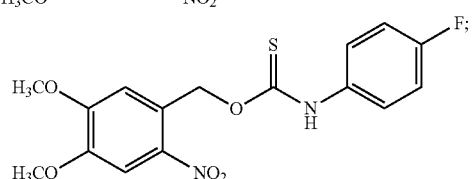
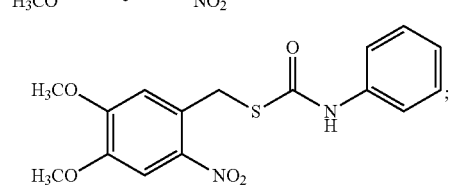

-continued
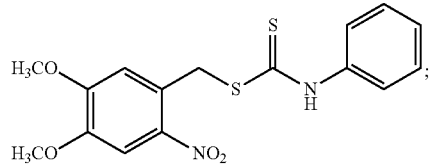
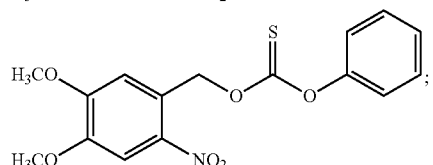
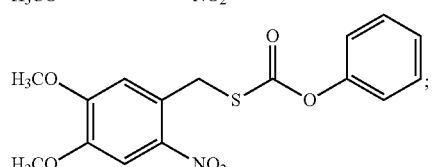
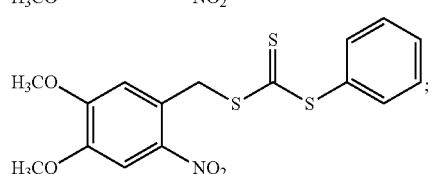
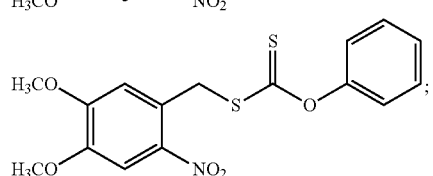
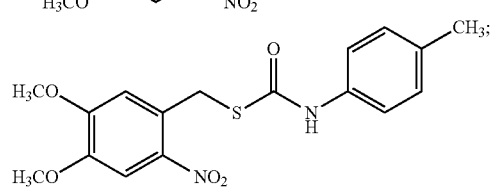
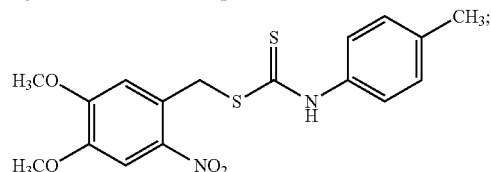
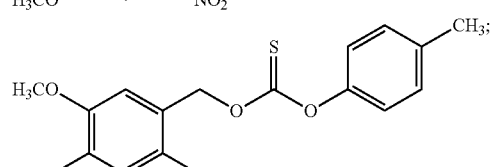
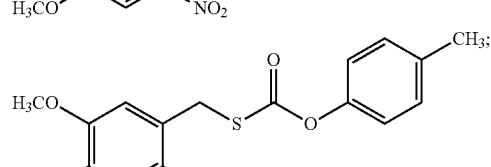
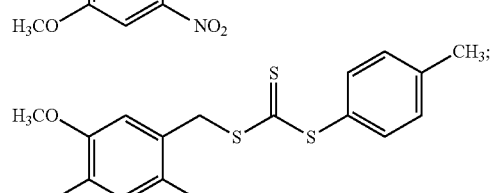

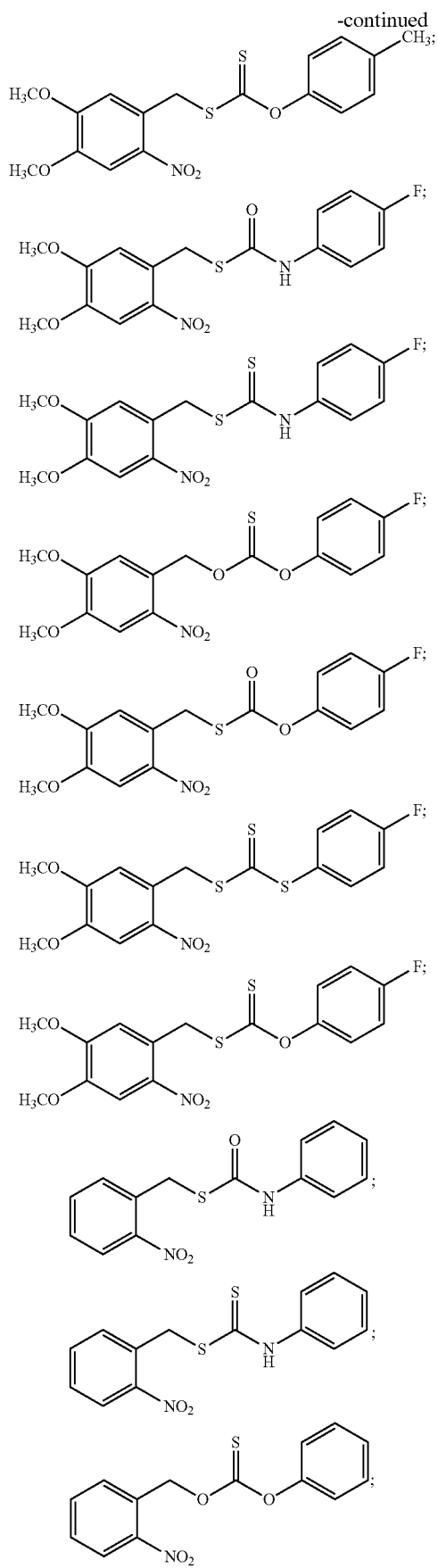

-continued
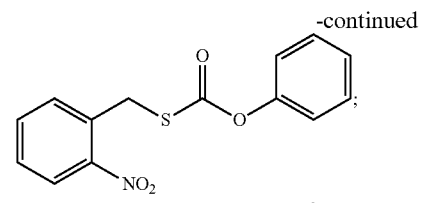
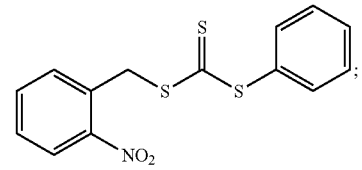
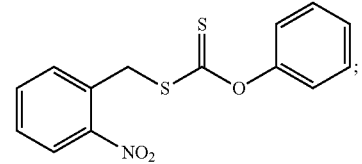
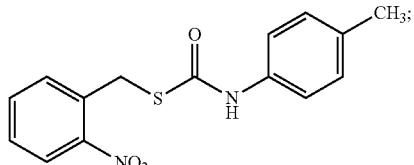
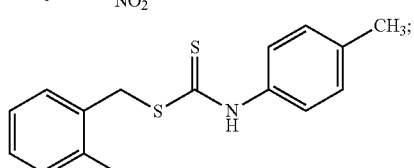
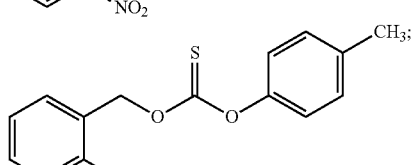
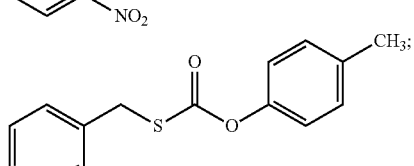
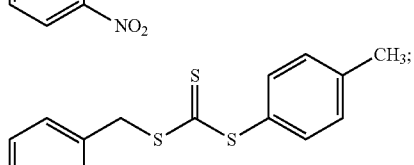
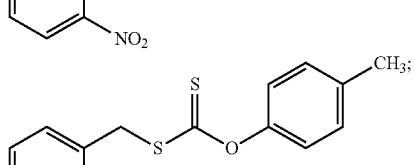
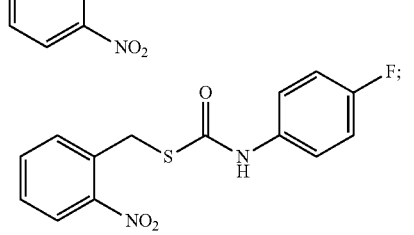

-continued
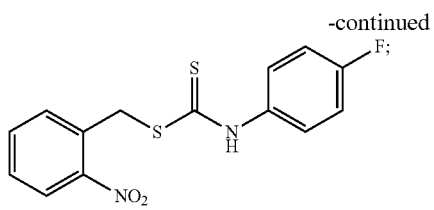
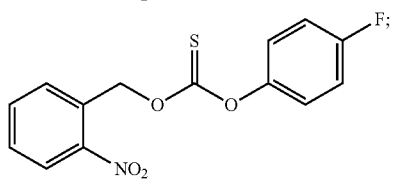
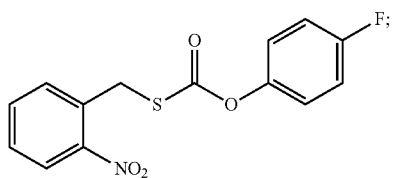
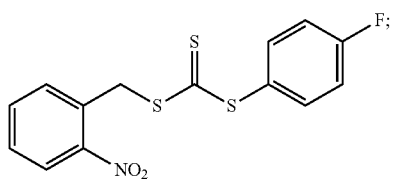
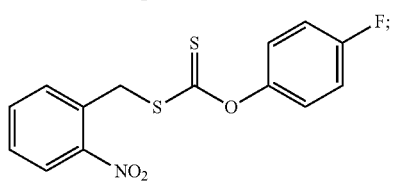
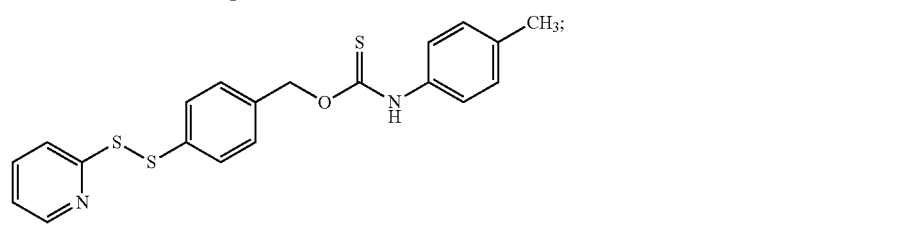
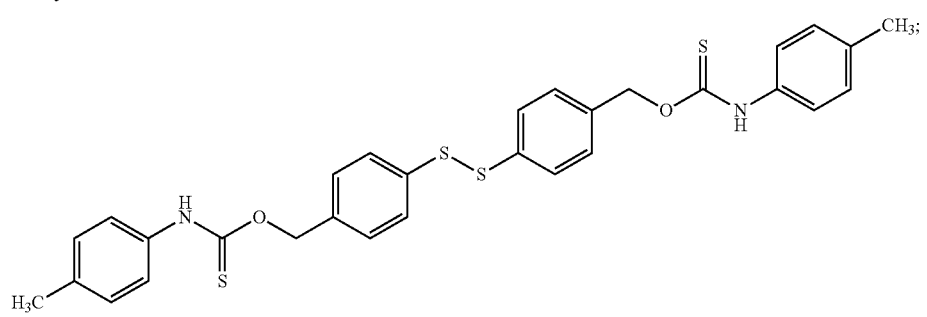
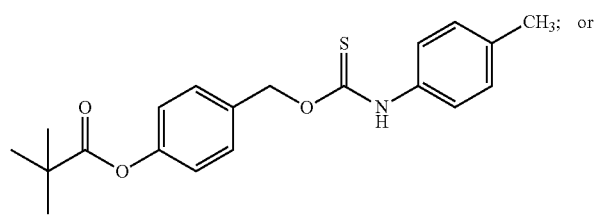

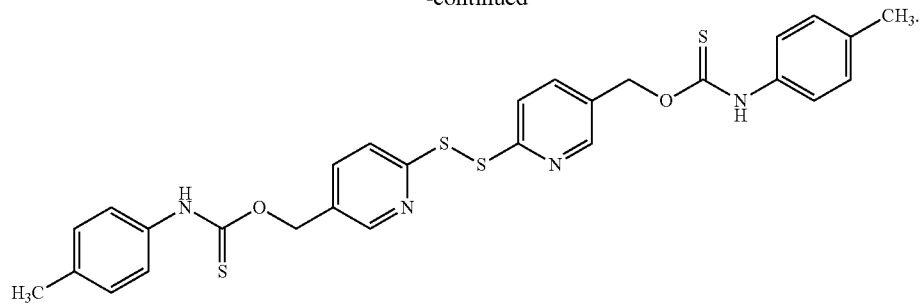

9. A method, comprising:
   administering to a sample a donor compound of claim 1, or a composition thereof; and
   exposing the donor compound to a reactive component to release COS, $CS_2$, $H_2S$, or any combination thereof.

10. The method of claim 9, wherein the reactive component is an oxidant, a reductant, an enzyme, a nucleophile, light, an acid, a base, or any combination thereof.

11. The method of claim 9, further comprising exposing the sample, released COS, $CS_2$, or a combination thereof to carbonic anhydrase, nitrogenase, RuBisCO, CO dehydrogenase, COSase, $CS_2$ hydrolase, water, or a combination thereof.

12. The method of claim 9, further comprising analyzing the sample to detect a reaction between the donor compound and the reactive component, measuring an amount of COS, $CS_2$, or $H_2S$ produced, or any combination thereof.

13. The method of claim 12, wherein analyzing the sample comprises detecting a color change and/or fluorescence change produced by a reaction product of the reaction between the donor compound and the reactive component.

14. The method of claim 9, wherein the sample is a biological sample selected from a cell, tissue, and/or bodily fluid.

15. A method, comprising:
    administering to a sample a donor compound of claim 1;
    exposing the sample to one or more of $H_2S$, reactive oxygen, sulfur, and nitrogen species, to form a composition comprising an amine-terminated compound, COS, $CS_2$, a cyclic by-product represented by a formula selected from:

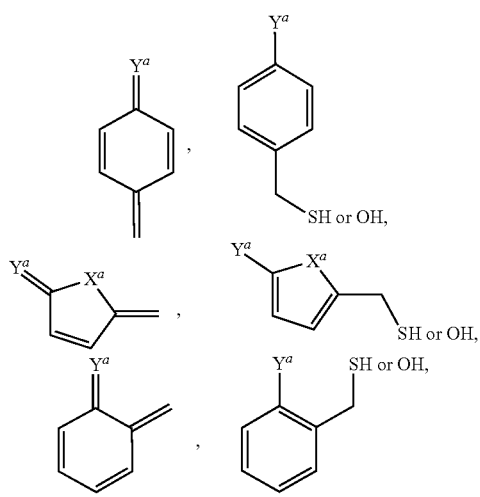

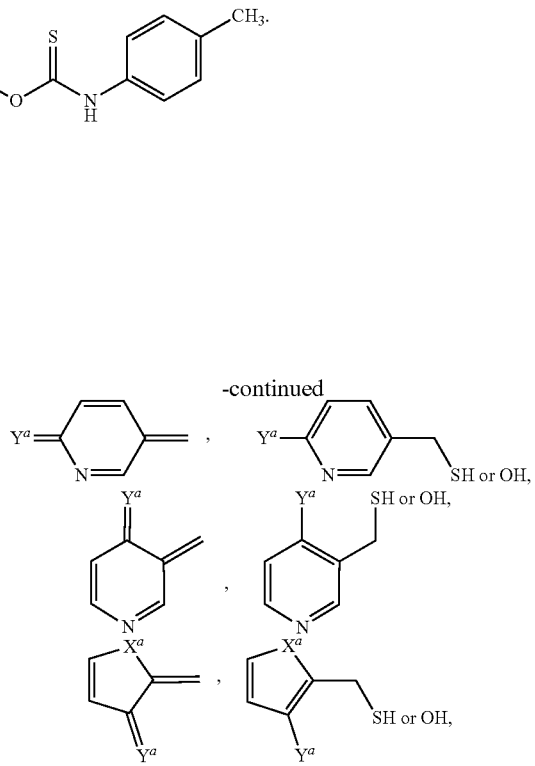

or any combination thereof, wherein each $Y^a$ independently is selected from oxygen, NH, or sulfur and each $X^a$ independently is selected from NH or sulfur; or any combination of the amine-terminated compound, the COS, $CS_2$, and the cyclic by-product; and
    regenerating $H_2S$ by exposing the composition to $H_2O$, carbonic anhydrase, nitrogenase, RuBisCO, CO dehydrogenase, COSase, $CS_2$ hydrolase, or a combination thereof.

16. The method of claim 15, further comprising detecting a reaction between the donor compound and the reactive component, measuring an amount of COS, $CS_2$, and/or $H_2S$ produced, or any combination thereof, wherein analyzing the sample comprises detecting a color change and/or fluorescence change produced by a reaction product of a reaction between the donor compound and one or more of the $H_2S$, other reactive oxygen, sulfur, and/or nitrogen species.

17. A method, comprising:
    administering to a sample from a subject a donor compound of claim 1;
    exposing the sample to a reactive component; and
    detecting a reaction in the sample between the donor compound and a reactive component and/or measuring an amount of COS, $CS_2$, and/or $H_2S$ produced by the reaction.

18. The method of claim 17, further comprising determining if a subject has a disease associated with $H_2S$ misregulation or a disease associated with carbonic anhydrase overexpression.

19. A kit, comprising:
    a donor compound of claim 1; and
    a filter, a multi-well plate, a test strip, a slide, a disc, a container, an enzyme, carbonic anhydrase, nitrogenase, RuBisCO, CO dehydrogenase, COSase, $CS_2$ hydrolase, water, a solubilizing agent, or a combination thereof.

20. A donor compound represented by Formula 2A:

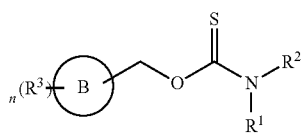

Formula 2A wherein ring B is an aryl group or a heteroaryl group; $R^1$ is hydrogen, aliphatic, heteroaliphatic, aryl, or heteroaryl; $R^2$ is aliphatic, heteroaliphatic, aryl, heteroaryl, halogen, a saccharide, a targeting group, a detectable moiety, a drug molecule, or combinations thereof; each $R^3$ independently is aliphatic, heteroaliphatic, aryl, heteroaryl, halogen, hydroxyl, thiol, amine, imine, azide, a boronate ester, a boronic acid, a disulfide, an ester, a phosphoric ester, a sulfuric ester, a heteroaliphatic ester group, nitro, a silyl ether, 3,5-dinitrobenzenesulfonic acid, or a combination thereof; and n is an integer selected from 1 to 5; provided that when ring B is an aryl or heteroaryl group, the aryl or heteroaryl group comprises at least one ortho- or para-positioned $R^3$ group, relative to the

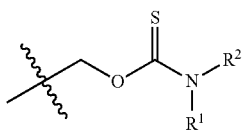

group, wherein the ortho-positioned $R^3$ group is a hydroxyl, a thiol, an amine, a heteroaliphatic group, an imine, a boronate ester, a boronic acid, a disulfide, an ester, a heteroaliphatic ester group, a nitro group, a silyl ether, a phosphoric ester, a sulfuric ester, or 3,5-dinitrobenzenesulfonic acid; and/or wherein the para-positioned $R^3$ group is a hydroxyl, a thiol, an amine, a heteroaliphatic group, an imine, an azide, a boronate ester, a boronic acid, a disulfide, an ester, a heteroaliphatic ester group, a nitro group, a silyl ether, a phosphoric ester, a sulfuric ester, or 3,5-dinitrobenzenesulfonic acid;

if $R^1$ is hydrogen and $R^2$ is aryl, then the aryl group is -phenyl-$(R^4)_m$ wherein m is an integer selected from 0 to 5 and $R^4$ is alkoxy, thioether, amide, amine, hydroxyl, thiol, acyloxy, azide, aliphatic, aryl, aldehyde, ketone, ester, carboxylic acid, acyl, acyl halide, cyano, sulfonate, nitro, quaternary amine, fluoro, bromo, iodo, alkyl halide, heterocyclyl, pyridinyl, or pyridinyl wherein the nitrogen atom is functionalized with an aliphatic or aryl group;

if $R^1$ is hydrogen then $R^2$ is non-aromatic aliphatic; or heteroaliphatic, aryl, heteroaryl, a saccharide, a targeting group, a detectable moiety, a drug molecule, or a combination thereof; and the donor compound is not or is other than

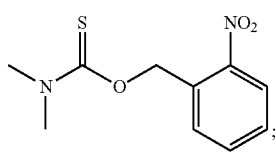

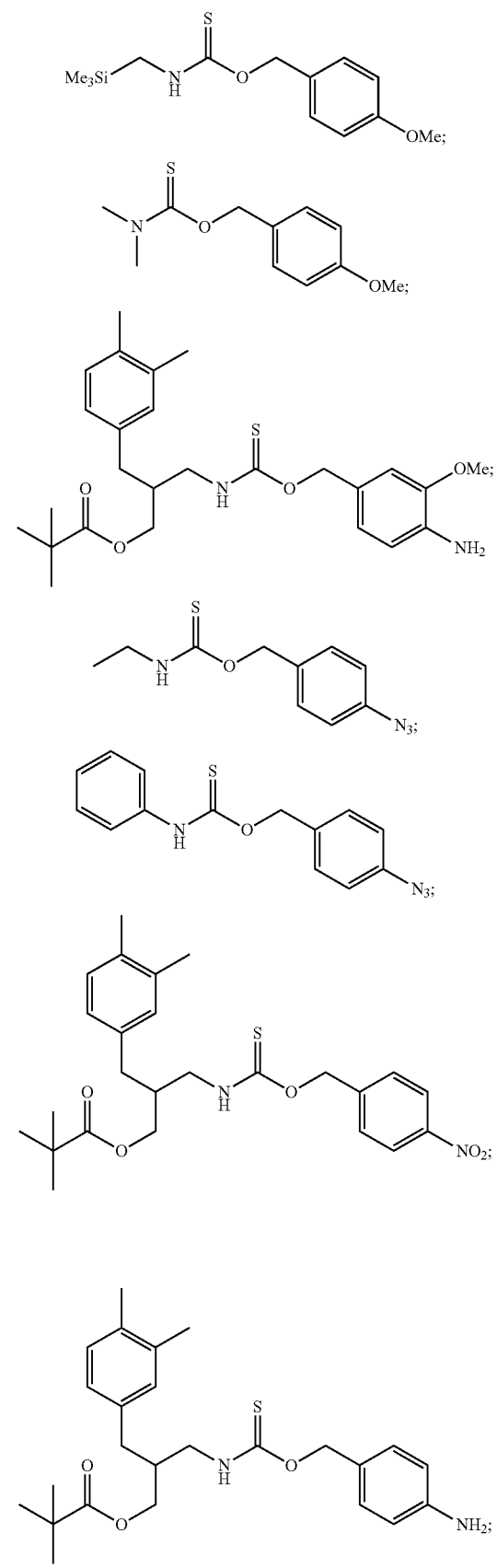

-continued

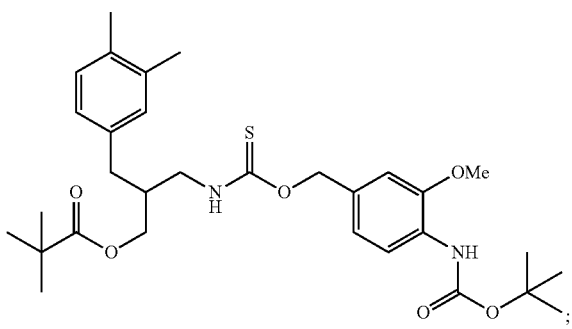

or

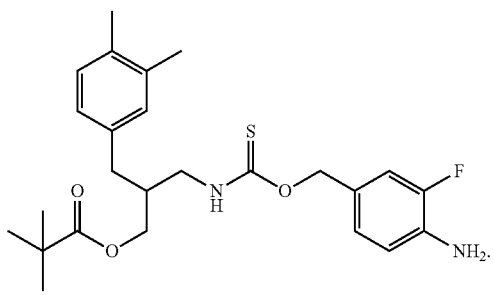

21. A donor compound represented by any one or more of the following formulas:

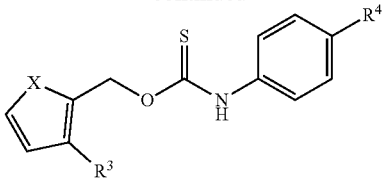

-continued

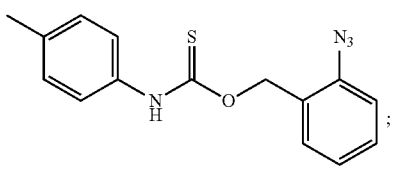

wherein
each Z independently is CH or nitrogen;
each X independently is O, S, or NR, wherein R is selected from hydrogen, aliphatic, aryl, heteroaliphatic, or heteroaryl;
each $R^3$ independently is aliphatic, heteroaliphatic, aryl, heteroaryl, halogen, hydroxyl, thiol, amine, azide, a boronate ester, a boronic acid, a disulfide, an ester, nitro, a phosphoric ester, a sulfuric ester, a silyl ether, 3,5-dinitrobenzenesulfonic acid, or a combination thereof;
$R^4$ is alkoxy, thioether, amide, amine, hydroxyl, thiol, acyloxy, aliphatic, aryl, aldehyde, ketone, ester, carboxylic acid, acyl, acyl halide, cyano, sulfonate, nitro, quaternary amine, fluoro, bromo, iodo, alkyl halide, pyridinyl, pyridinyl wherein the nitrogen atom is functionalized with an aliphatic or aryl group; and
n is an integer selected from 1 to 3; and provided that the donor compound is not

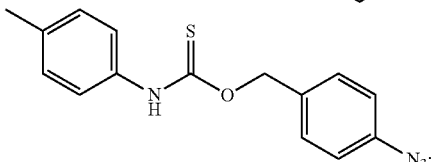

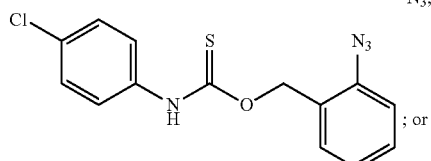

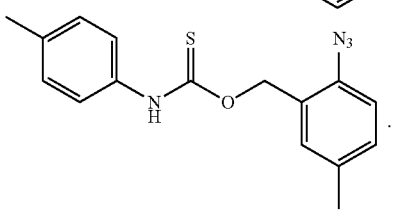

* * * * *